US012486293B2

(12) United States Patent
Wolf et al.

(10) Patent No.: US 12,486,293 B2
(45) Date of Patent: Dec. 2, 2025

(54) CHIRALITY SENSING WITH MOLECULAR CLICK CHEMISTRY PROBES

(71) Applicant: GEORGETOWN UNIVERSITY, Washington, DC (US)

(72) Inventors: Christian Wolf, Arlington, VA (US); Fathima Yushra Thanzeel, Washington, DC (US); Kaluvu Balaraman, Arlington, VA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 1235 days.

(21) Appl. No.: 17/265,147

(22) PCT Filed: Jul. 30, 2019

(86) PCT No.: PCT/US2019/044189

§ 371 (c)(1),
(2) Date: Feb. 1, 2021

(87) PCT Pub. No.: WO2020/028396

PCT Pub. Date: Feb. 6, 2020

(65) Prior Publication Data

US 2022/0380395 A1 Dec. 1, 2022

Related U.S. Application Data

(60) Provisional application No. 62/712,150, filed on Jul. 30, 2018.

(51) Int. Cl.

| | |
|---|---|
| ***C07F 9/00*** | (2006.01) |
| ***C07D 311/18*** | (2006.01) |

(Continued)

(52) U.S. Cl.

CPC ........ *C07F 9/65848* (2013.01); *C07D 311/18* (2013.01); *C07F 9/52* (2013.01); *C07F 9/65744* (2013.01); *G01N 21/33* (2013.01)

(58) Field of Classification Search

CPC .................................................. C07F 9/65848

(Continued)

(56) References Cited

U.S. PATENT DOCUMENTS

| | | | |
|---|---|---|---|
| 5,229,301 | A | 7/1993 | Spira-Solomon et al. |
| 5,763,679 | A | 6/1998 | Nicholson et al. |

(Continued)

FOREIGN PATENT DOCUMENTS

| | | | |
|---|---|---|---|
| CN | 104610960 | A | 5/2015 |
| WO | 2014144197 | A1 | 9/2014 |

(Continued)

OTHER PUBLICATIONS

Kazuo Nagasawa et al. "N-Coumarinyl-L-Proline, A Novel Chiral Derivatizing Agent for 1H NMR Determination of Enantiomeric Purities of Alcohols and Amines" Chem. Pharm. Bull. 43(2) 344-346 (1995) (Year: 1995).*

(Continued)

*Primary Examiner* — Elizabeth A Robinson
*Assistant Examiner* — Emily R. Berkeley
(74) *Attorney, Agent, or Firm* — Troutman Pepper Locke LLP (Rochester)

(57) ABSTRACT

The present invention relates to an analytical method that includes providing a sample potentially containing a chiral analyte that can exist in stereoisomeric forms, and providing a probe selected from the group consisting of coumarin-derived Michael acceptors, dinitrofluoroarenes and analogs thereof, arylsulfonyl chlorides and analogs thereof, arylchlorophosphines and analogs thereof, aryl halophosphites, and halodiazaphosphites. The sample is contacted with the probe under conditions to permit covalent binding of the probe to the analyte, if present in the sample; and, based on any binding that occurs, the absolute configuration of the analyte in the sample, and/or the concentration of the analyte in the (Continued)

sample, and/or the enantiomeric composition of the analyte in the sample is/are determined. The probe may be a coumarin-derived Michael acceptor, a di nitrofluoroarene or analog thereof, an arylsulfonyl chloride or analog thereof, an arylchlorophosphine or analog thereof, an aryl halophosphite, or a halodiazaphosphite.

25 Claims, 68 Drawing Sheets

(51) Int. Cl.
*C07F 9/52* (2006.01)
*C07F 9/6574* (2006.01)
*C07F 9/6584* (2006.01)
*G01N 21/33* (2006.01)

(58) Field of Classification Search
USPC .......................................................... 436/111
See application file for complete search history.

(56) References Cited

U.S. PATENT DOCUMENTS

| | | | |
|---|---|---|---|
| 6,875,877 | B2 | 4/2005 | Li et al. |
| 7,045,360 | B2 | 5/2006 | Shair et al. |
| 7,332,343 | B2 | 2/2008 | Anslyn et al. |
| 7,648,841 | B2 | 1/2010 | Inoue et al. |
| 7,670,847 | B2 | 3/2010 | Anslyn et al. |
| 7,736,902 | B2 | 6/2010 | Inoue et al. |
| 8,189,188 | B2 | 5/2012 | Busch et al. |
| 9,085,511 | B2 | 7/2015 | Wolf et al. |
| 9,815,746 | B2 | 11/2017 | Wolf et al. |
| 10,012,627 | B2 | 7/2018 | Wolf et al. |
| 10,788,471 | B2 | 9/2020 | Wolf et al. |
| 10,900,941 | B2 | 1/2021 | Wolf et al. |
| 2011/0045598 | A1 | 2/2011 | Busch et al. |
| 2012/0064632 | A1 | 3/2012 | Robinson et al. |
| 2015/0010938 | A1 | 1/2015 | Strongin et al. |
| 2016/0011156 | A1 | 1/2016 | Wolf et al. |
| 2016/0039792 | A1 | 2/2016 | Bogyo et al. |
| 2016/0195532 | A1 | 7/2016 | Carroll et al. |
| 2017/0261502 | A1 | 9/2017 | Karlsson |
| 2020/0150128 | A1 | 5/2020 | Wolf et al. |

FOREIGN PATENT DOCUMENTS

| | | | |
|---|---|---|---|
| WO | 2014145251 | A1 | 9/2014 |
| WO | 2017078570 | A1 | 5/2017 |
| WO | 2018200498 | A1 | 1/2018 |
| WO | 2020028396 | A1 | 2/2020 |
| WO | 2020056012 | A1 | 3/2020 |

OTHER PUBLICATIONS

"Principles of UV/Visible Spectrophotometry" in UV and Visible Absorption Techniques, in Schirmer, ed. Modern Methods of Pharmaceutical Analysis, vol. 1, CRC-Press, pp. 31-125 (1982).
Aikawa & Mikami, "Asymmetric Catalysis Based on Tropos Ligands," Chem. Commun. 48:11050-69 (2012).
Altun et al., "Structural and Spectroscopic (UV-VIS, IR, Raman, and NMR) Characteristics of Anisaldehyde That Are Flavoring Additives: A Density Functional Study in Comparison with Experiments," J. Mol. Struct. 1128:590-605 (2017).
Bentley et al., "Chirality Sensing of Amines, Diamines, Amino Acids, Amino Alcohols, and Alpha-Hydroxy Acids with a Single Probe," J. Am. Chem. Soc. 135:18052-55 (2013).
Bull et al., "Exploiting the Reversible Covalent Bonding of Boronic Acids: Recognition, Sensing, and Assembly," Acc. Chem. Res. 46(2):312-26 (2013).
Gajewy et al., "Asymmetric Hydrosilylation of Ketones Catalyzed by Complexes Formed from Trans-Diaminocyclohexane-Based Diamines and Diethylzinc," Monatsh Chem. 143:1045-54 (2012).
Gajewy et al., "Mechanism and Enantioselectivity of [Zinc(diamine)(diol)]-Catalyzed Asymmetric Hydrosilylation of Ketones: DFT, NMR and ECD Studies," Eur. J. Org. Chem. 2013(2):307-18 (2013).
Ghosn & Wolf, "Chiral Amplification with a Stereodynamic Triaryl Probe: Assignment of the Absolute Configuration and Enantiomeric Excess of Amino Alcohols," J. Am. Chem. Soc.131:16360-61 (2009).
Ghosn & Wolf "Synthesis, Conformational Stability, and Asymmetric Transformation of Atropisomeric 1,8-Bisphenolnapthalenes," J. Org. Chem. 76(10):3888-3897 (2011).
Iwaniuk & Wolf, "Chiroptical Sensing of Citronellal: Systematic Development of a Stereodynamic Probe Using the Concept of Isostericity," Chem. Commun. 48:11226-28 (2012).
Iwaniuk et al., "Enantioselective Sensing of Chiral Amino Alcohols with a Stereodynamic Arylacetylene-Based Probe," Chirality 24:584-89 (2012).
Joyce et al., "Enantio- and Chemoselective Differentiation of Protected Alpha-Amino Acids and Beta-Homoamino Acids with a Single Copper Host," Chemistry 18(26):8064-69 (2012).
Li et al., "Absolute Configuration for 1,n-Glycols: A Nonempirical Approach to Long-Range Stereochemical Determination," J. Am. Chem. Soc. 134:9026-29 (2012).
Lima et al., "Elucidating the Role of Aromatic Interactions in Rotational Barriers Involving Aromatic Systems," J. Org. Chem. 77(22): 10422-10426 (2012).
Lynch, et al., "Chiroptical Sensing of Unprotected Amino Acids, Hydroxy Acids, Amino Alcohols, Amines and Cabroxylic Acids with Metal Salts," Chem. Commun. 55:6297-6933 (2019).
Matyasovszky et al., "Kinetic Study of the Electrochemical Oxidation of Salicylic Acid and Salicylaldehyde Using UV/Vis Spectroscopy and Multivariate Calibration," J. Phys. Chem. A 113:9348-9353 (2009).
Meca et al., "Racemization Barriers of 1,1'-Binaphthyl and 1,1'-Binapthalene-2,2'-Diol: A DFT Study," J. Org. Chem. 68:5677-80 (2003).
Mikami & Aikawa, "Dynamic Asymmetric Catalysis by Diphenylphosphinoferrocene (DPPF)-Nickel Complexes Through Control of Axial Chirality by Chiral Diamines," Org. Lett. 4(1):99-101 (2002).
Mikami et al., "Tropos or Atropos? That Is the Question!," Synlett 10:1561-78 (2002).
Miyashita et al., "Synthesis of 2,2'-Bis(Diphenylphosphino)-1,1'-Binaphthyl (BINAP), an Atropisomeric Chiral Bis (Triaryl)Phosphine, and Its Use in the Rhodium(I)-Catalyzed Asymmetric Hydrogenation of α-(Acylamino)Acrylic Acids," J. Am. Chem. Soc. 102:7932-34 (1980).
Nieto et al., "A Facile CD Protocol for Rapid Determination of Enantiomeric Excess and Concentration of Chiral Primary Amines," Chemistry 16(1):227-32 (2010).
Pubchem CID 20820440, "14-Chloro-13,15-dioxa-14-phosphapentacyclo[14.8.0.03,12.04,9.019,24]tetracosa-1(16),3(12),4,6,8,10,17,19,21,23-decaene," https://pubchem.ncbi.nlm.nih.gov/compound/20820440 (last accessed Nov. 9, 2019).
Suvitha et al., "NBO, Homo-Lumo, UV, NLO, NMR and Vibrational Analysis of Vertrole using FT-IR, FT-Raman, FT-NMR Spectra and HF-DFT Computational Methods," Spectrochim. Acta A Mol. Biomol. Spectrosc. 138:357-369 (2015).
Wolf & Bentley, "Chirality Sensing Using Stereodynamic Probes with Distinct Electronic Circular Dichroism Output," Chem. Soc. Rev. 42:5408-24 (2013).
Wu, et al., "Vibrational and Electronic Circular Dichroism Monitoring of Copper(II) Coordination with a Chiral Ligand," Chirality, 24:451-458 (2012).
Wu, et al., "Enhancement of Visual Chiral Sensing Via An Anion-Binding Approach: Novel Ionic Liquids as the Chiral Selectors," Analytica Chimica Acta, 962:97-103 (2017).
You et al., "An Exciton-Coupled Circular Dichroism Protocol for the Determination of Identity, Chirality, and Enantiomeric Excess of Chiral Secondary Alcohols," J. Am. Chem Soc. 134:7117-25 (2012).
Yu et al., "Simultaneous Determination of Both the Enantiomeric Composition and Concentration of a Chiral Substrate with One Fluorescent Sensor," J. Am. Chem.Soc. 134(50):20282-85 (2012).

(56) References Cited

OTHER PUBLICATIONS

Zardi et al., "Concentration-Independent Stereodynamic g-Probe for Chiroptical Enantiomeric Excess Determination," J. Am. Chem. Soc. 139(44):15616-15619 (2017).
Zhang & Wolf, "Sensing of the Concentration and Enantiomeric Excess of Chiral Compounds with Tropos Ligand Derived Metal Complexes," Chem. Commun. 49:7010-12 (2013).
PCT/US2014/29982, International Search Report and Written Opinion (Aug. 12, 2014).
PCT/US2014/028500, International Preliminary Report on Patentability (Sep. 15, 2015).
PCT/US2019/044189, International Search Report and Written Opinion (Oct. 1, 2019).
PCT/US2019/050628, International Search Report and Written Opinion (Nov. 27, 2019).
Joyce, et al., "A Simple Method for the Determination of Enantiomeric Excess and Identity of Chiral Carboxylic Acids," J. Am. Chem. Soc., 133(34):13746-13752 (2011).
Nieto, et al., "Rapid Enantiomeric Excess and Concentration Determination Using Simple Racemic Metal Complexes," Org. Lett., 10(22):5167-5170 (2008).
Folmer-Andersen, et al., "Colorimetric Enantiodiscrimination of alpha-Amino Acids in Protic Media," J. Am. Chem. Soc., 127(22):7986-7987 (2005).
PCT/US2019/050628, International Preliminary Report on Patentability (Mar. 25, 2021).
PCT/US2018/029109, International Search Report and Written Opinion (Aug. 1, 2018).
PCT/US2018/029109, International Preliminary Report on Patentability (Nov. 7, 2019).
Pubchem. CID No. 10008, https://pubchem.ncbi.nlm.nih.gov/compound/10008 (retrieved Jun. 8, 2018).

* cited by examiner

*anti*-25

26

36 (Leu)

37 (Pro)

38 (Phe)

12

17

76

32

32

8

8

76

8

37

38

39

43

44

45

A) Irreversible substrate binding with a coumarin Michael acceptor

B) Target compounds

CHIRALITY SENSING WITH MOLECULAR CLICK CHEMISTRY PROBES

This application is a national stage application under 35 U.S.C. § 371 of International Application No. PCT/US2019/044189, filed 30 Jul. 2019, which claims the priority benefit of U.S. Provisional Patent Application Ser. No. 62/712,150, filed 30 Jul. 2018, each of which is hereby incorporated by reference in its entirety.

This invention was made with government support under grant numbers CHE-1464547 and CHE-1764135 awarded by the National Science Foundation. The government has certain rights in the invention.

FIELD OF THE INVENTION

The present invention relates to an analytical method for the determination of the absolute configuration of an analyte in a sample, and/or the concentration of an analyte in a sample, and/or the enantiomeric composition of an analyte in a sample, based on chiroptical testing.

BACKGROUND OF THE INVENTION

Chirality plays an essential role across the chemical and pharmaceutical sciences, and the development of stereoselective methods for the synthesis and analysis of chiral compounds are frequently required tasks in academic and industrial laboratories. To accelerate the discovery process, it has become routine to perform hundreds of small-scale reactions in parallel using widely available high-throughput experimentation equipment (HTE) (McNally et al., "Discovery of an α-Amino C—H Arylation Reaction Using the Strategy of Accelerated Serendipity," *Science* 334:1114-1117 (2011); Santanilla et al., "Nanomolecular-Scale High-Throughput Chemistry for the Synthesis of Complex Molecules," *Science* 347:49-53 (2015)). With regard to asymmetric reaction development, many combinations of different chiral catalysts, solvents, additives and other parameters typically need to be evaluated. In the search for an optimized procedure, a chemist can easily alter a large set of reaction parameters and produce hundreds of chiral samples in a very short time using multi-well plate technology. In stark contrast with automated synthesis capabilities, the determination of the absolute configuration, yield and enantiomeric excess of asymmetric reactions with traditional chromatographic methods that are serial in nature and incompatible with HTE remains slow, and this has shifted increasing attention to contemporary screening techniques (Collins et al., "Contemporary Screening Approaches to Reaction Discovery and Development," *Nat. Chem.* 6:859-871 (2014)).

Optical methods are compatible with parallel data acquisition, miniaturization and multi-well plate formats and offer a new path to real high-throughput analysis of chiral samples (Leung et al., "Rapid Determination of Enantiomeric Excess: A Focus on Optical Approaches," *Chem. Soc. Rev.* 41:448-479 (2012); Wolf, C. & Bentley, K. W., "Chirality Sensing Using Stereodynamic Probes With Distinct Electronic Circular Dichroism Output," *Chem. Soc. Rev.* 42:5408-5424 (2013)). Few examples of asymmetric reaction analysis with sensors operating on the principles of dynamic covalent chemistry (Shabbir et al., "A General Protocol for Creating High-Throughput Screening Assays for Reaction Yield and Enantiomeric Excess Applied to Hydrobenzoin," *Proc. Natl. Acad. Sci. USA* 106:10487-10492 (2009); Nieto et al., "A Facile Circular Dichroism Protocol for Rapid Determination of Enantiomeric Excess and Concentration of Chiral Primary Amines," *Chem. Eur. J.* 16:227-232 (2010); Bentley et al., "Chirality Imprinting and Direct Asymmetric Reaction Screening Using a Stereodynamic Brønsted/Lewis Acid Receptor," *Nat. Commun.* 7:12539 (2016); Shcherbakova et al., "High-Throughput Assay for Enantiomeric Excess Determination in 1,2- and 1,3-Diols and Direct Asymmetric Reaction Screening," Chem. Eur. J. 23:10222-10229 (2017)), metal complex coordination (Bentley et al., "Miniature High-Throughput Chemosensing of Yield, ee, and Absolute Configuration From Crude Reaction Mixtures," *Science Advances* 2:e1501162 (2016)) and supramolecular chemistry (Biedermann, F. & Nau, W. M., "Noncovalent Chirality Sensing Ensembles for the Detection and Reaction Monitoring of Amino Acids, Peptides, Proteins, and Aromatic Drugs," *Angew. Chem. Int. Ed.* 53:5694-5699 (2014); Feagin et al., "High-Throughput Enantiopurity Analysis Using Enantiomeric DNA-Based Sensors," *J. Am. Chem. Soc.* 137:4198-4206 (2015); De los Santos, Z. A. & Wolf, C., "Chiroptical Asymmetric Reaction Screening via Multicomponent Self-Assembly," *J. Am. Chem. Soc.* 138:13517-13520 (2016)) to recognize a chiral target compound and to generate quantifiable UV, fluorescence and circular dichroism signals have been reported (Giuliano et al., "A Synergistic Combinatorial and Chiroptical Study of Peptide Catalysts for Asymmetric Baeyer-Villiger Oxidation," *Adv. Synth. Catal.* 357:2301-2309 (2015); Joyce et al., "Imine-Based Chiroptical Sensing for Analysis of Chiral Amines: From Method Design to Synthetic Application," *Chem. Sci.* 5:2855-2861 (2014); Jo et al., "Application of a High-Throughput Enantiomeric Excess Optical Assay Involving a Dynamic Covalent Assembly: Parallel Asymmetric Allylation and ee Sensing of Homoallylic Alcohols," *Chem. Sci.* 6:6747-6753 (2015)).

Circular dichroism spectroscopy is one of the most powerful techniques commonly used for elucidation of the three-dimensional structure, molecular recognition events, and stereodynamic processes of chiral compounds (Gawroński & Grajewski, *Org. Lett.* 5:3301-03 (2003); Allenmark, *Chirality* 15:409-22 (2003); Berova et al., *Chem. Soc. Rev.* 36:914-31 (2007)). The potential of chiroptical CD (circular dichroism) and CPL (circular polarized luminescence) assays with carefully designed probes that produce a circular dichroism signal upon recognition of a chiral substrate has received increasing attention in recent years, and bears considerable promise with regard to high-throughput ee screening (Nieto et al., *J. Am. Chem.* 130:9232-33 (2008); Leung et al., *Chem. Soc. Rev.* 41:448-79 (2012); Song et al., *Chem. Commun.* 49:5772-74 (2013) (chirality CPL sensing)).

In many cases, the CD output of a chemosensor allows determination of the absolute configuration and the enantiomeric composition of the chiral analyte (Wolf & Bentley, *Chem. Soc. Rev.* 42:5408-24 (2013)). But the analysis of the concentration and the enantiomeric composition of chiral substrates by a single optical chemosensor is a difficult task, and a practical method that is applicable to many chiral compounds and avoids time consuming derivatization and purification steps is very desirable (Nieto et al., *Org. Lett.* 10:5167-70 (2008); Nieto et al., *Chem. Eur. J.* 16:227-32 (2010); Yu et al., *J. Am. Chem. Soc.* 134:20282-85 (2012)).

Surprisingly, a molecular sensor design capable of comprehensive chirality sensing (CCS), i.e. determination of the absolute configuration, yield and ee, of crude asymmetric reaction mixtures via irreversible covalent product fixation has been largely neglected to date. Most recently, this strategy was used in the development of a cysteine-specific chiroptical assay that achieves CCS with micromolar sample concentrations in aqueous solutions (Thanzeel, F. Y. & Wolf, C., "Substrate-Specific Amino Acid Sensing Using a Molecular D/L-Cysteine Probe for Comprehensive Stereochemical Analysis in Aqueous Solution," *Angew. Chem. Int. Ed.* 56(25):7276-7281 (2017)). The inherent practicality and ruggedness of this approach encouraged the exploration of probe designs and sensing assays that overcome drawbacks of many currently used chiroptical methods such as limited substrate scope (amine sensors often utilize reversible Schiff base formation and are restricted to primary substrates), competing chiral recognition processes and equilibria that complicate the analysis and diminish CD readouts, and sensitivity to moisture and chemical interferences which limits both robustness and accuracy when complex mixtures and asymmetric reactions need to be examined. The introduction of a robust, readily available, easy to use, inexpensive molecular sensor having click chemistry features bears potential to change the way how asymmetric reaction development is pursued and may dramatically increase the speed of scientific discoveries in countless laboratories (Kolb et al., "Click Chemistry: Diverse Chemical Function From a Few Good Reactions," *Angel, v. Chem. Int. Ed.* 40:2004-2021 (2001)).

The present invention is directed to overcoming these and other deficiencies in the art.

SUMMARY OF THE INVENTION

The present invention relates to an analytical method that includes providing a sample potentially containing a chiral analyte that can exist in stereoisomeric forms, and providing a probe selected from the group consisting of coumarin-derived Michael acceptors, dinitrofluoroarenes and analogs thereof, arylsulfonyl chlorides and analogs thereof, arylchlorophosphines and analogs thereof, aryl halophosphites, and halodiazaphosphites. The sample is contacted with the probe under conditions to permit covalent binding of the probe to the analyte, if present in the sample; and, based on any binding that occurs, the absolute configuration of the analyte in the sample, and/or the concentration of the analyte in the sample, and/or the enantiomeric composition of the analyte in the sample is/are determined.

A second aspect of the present invention relates to a compound selected from the group consisting of

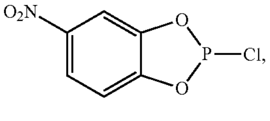

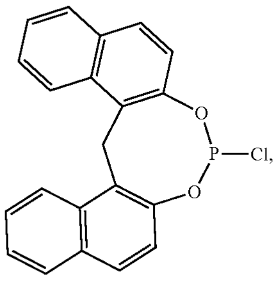

-continued

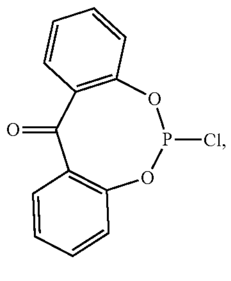

and

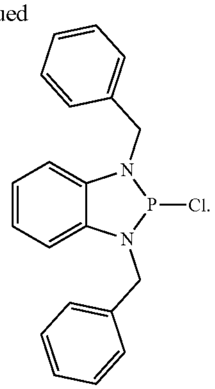

A rugged and operationally simple click chemistry sensing assay that is based on covalent bond formation of primary and secondary amines, amino alcohols, alcohols, hydroxy acids, and amino acids with readily available probes exhibiting a 4-halocoumarin, fluoroarene, arylsulfonyl chloride or phosphorus chloride moiety has been developed. Chirality chemosensing with 4-chloro-3-nitrocoumarin allows determination of the absolute configuration, concentration and ee of minute sample amounts and offers several attractive features, including a wide application spectrum, quantitative and fast substrate consumption at room temperature without by-product formation, excellent solvent compatibility, and tolerance of air and water. The general usefulness and practicality of this approach are demonstrated by comprehensive chirality sensing of nonracemic samples of 2-(2-naphthyl)ethylamine and by the direct analysis of small aliquots of crude reaction mixtures obtained by iridium catalyzed asymmetric hydrogenation of an imine to N-methyl 1-phenylethylamine. Among other benefits, this chemosensing strategy enables reaction scale miniaturization, adaption to high-throughput analysis equipment, i.e. multi-well plate CD/UV readers, and addresses time efficiency, cost, labor and chemical sustainability aspects which are increasingly important considerations in ongoing efforts to streamline asymmetric reaction development projects.

BRIEF DESCRIPTION OF THE DRAWINGS

FIG. 1A shows the CD spectra of 7 were obtained at 0.19 mM or 0.24 mM when MeOH was used as solvent. FIG. 1B is the X-ray structures of chiral amine derivatives of 3. FIG. 1C is the 1H NMR analysis of the reaction between probe 3 and (S)-8 in the presence of Et3N (all 5.0 mM) in 0.8 mL of CDCl3. 1) Probe 3; 2) (S)-1-phenylethylamine; 3) reaction mixture of (S)-1-phenylethylamine, Et3N and probe 3 after 5 minutes; 4) reaction after 10 minutes; 5) after 15 minutes; 6) isolated 3-nitro-4-((1-phenylethyl)amino)coumarin, 7, for comparison.

ratio of the reaction mixture of probe 3 and varying amounts of (S)-1-phenyl ethyl amine (10), plotted against the concentration of (S)-1-(2-naphthyl)ethylamine (10).

Figure 68:
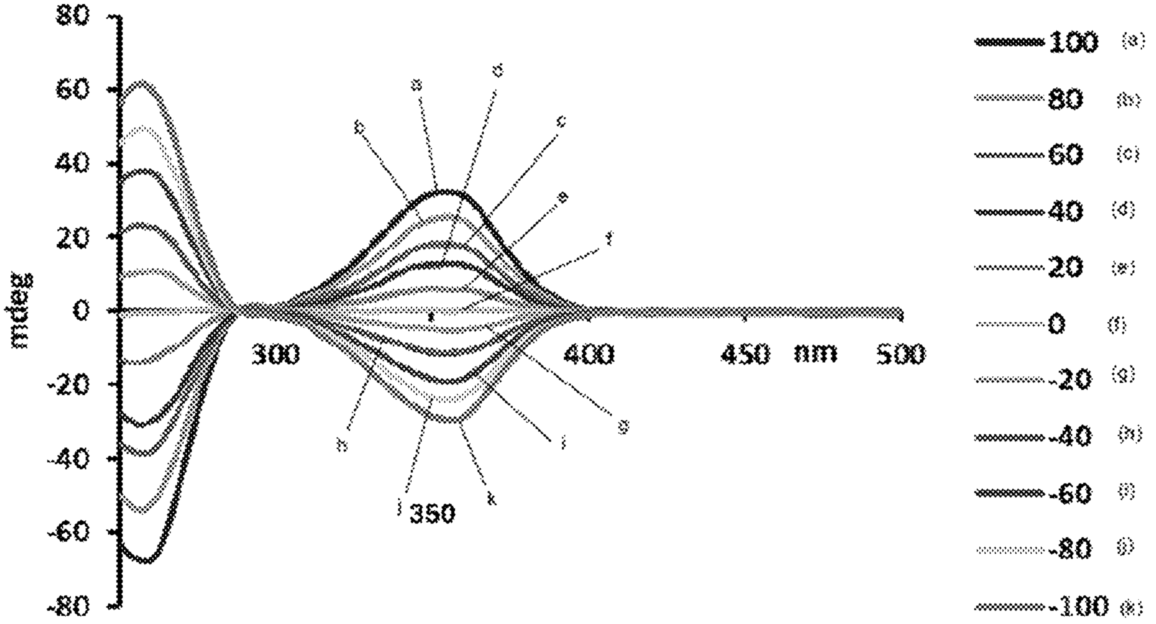

FIG. 68 shows the chiroptical response of probe 3 to scalemic samples of 1-(2-naphthyl)ethylamine (10).

Figure 69:
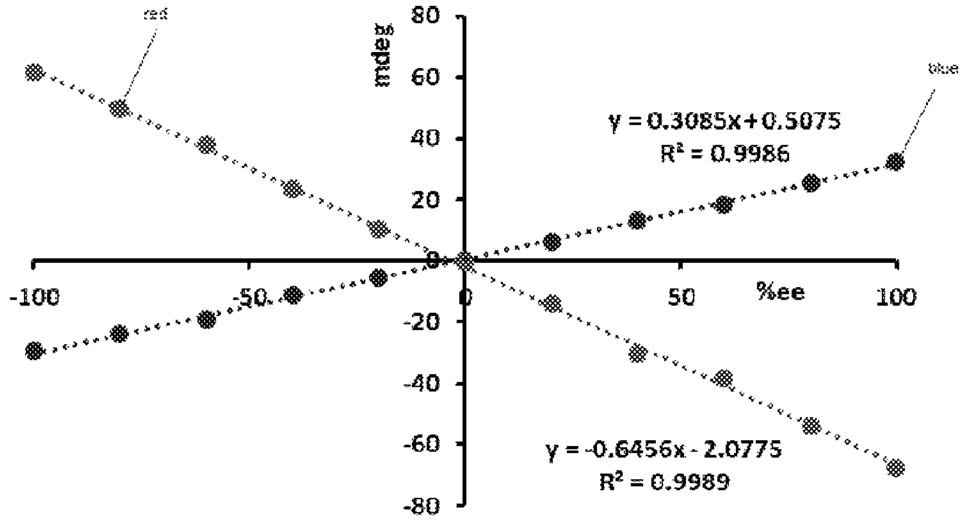

FIG. 69 is a plot of the CD amplitudes at 257 nm (red) and 355 nm (blue) of the reaction of probe 3 to scalemic samples of 1-(2-naphthyl)ethylamine (10) versus sample ee.

Figure 70:
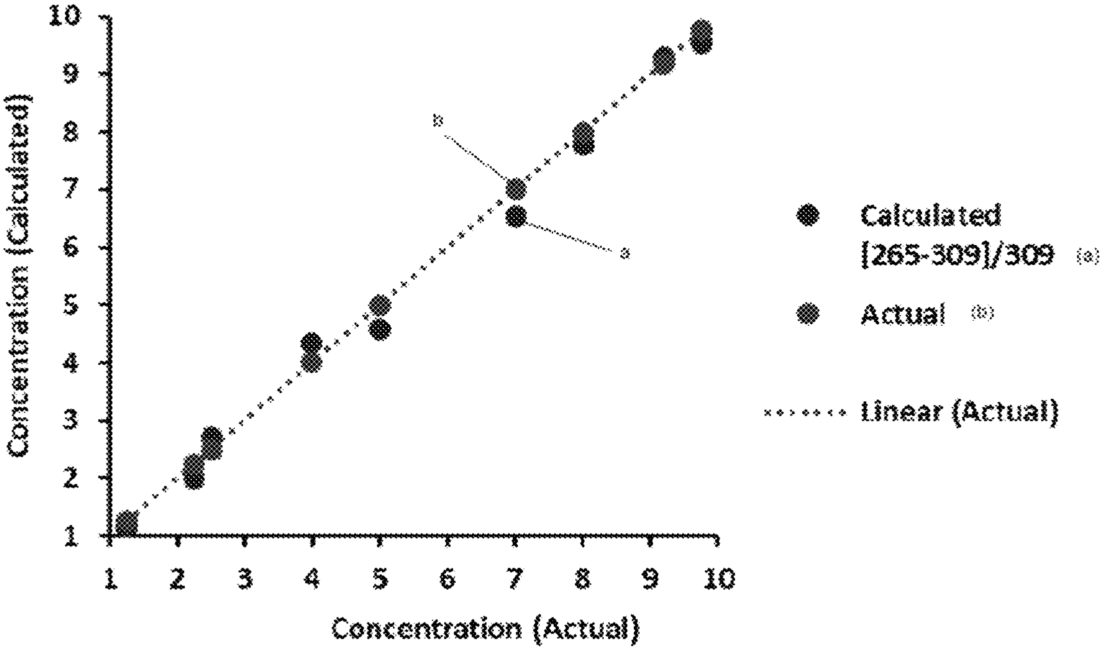

FIG. 70 is a plot of the calculated vs actual values of concentration samples of 1-(2-naphthyl)ethylamine (10).

Figure 71:
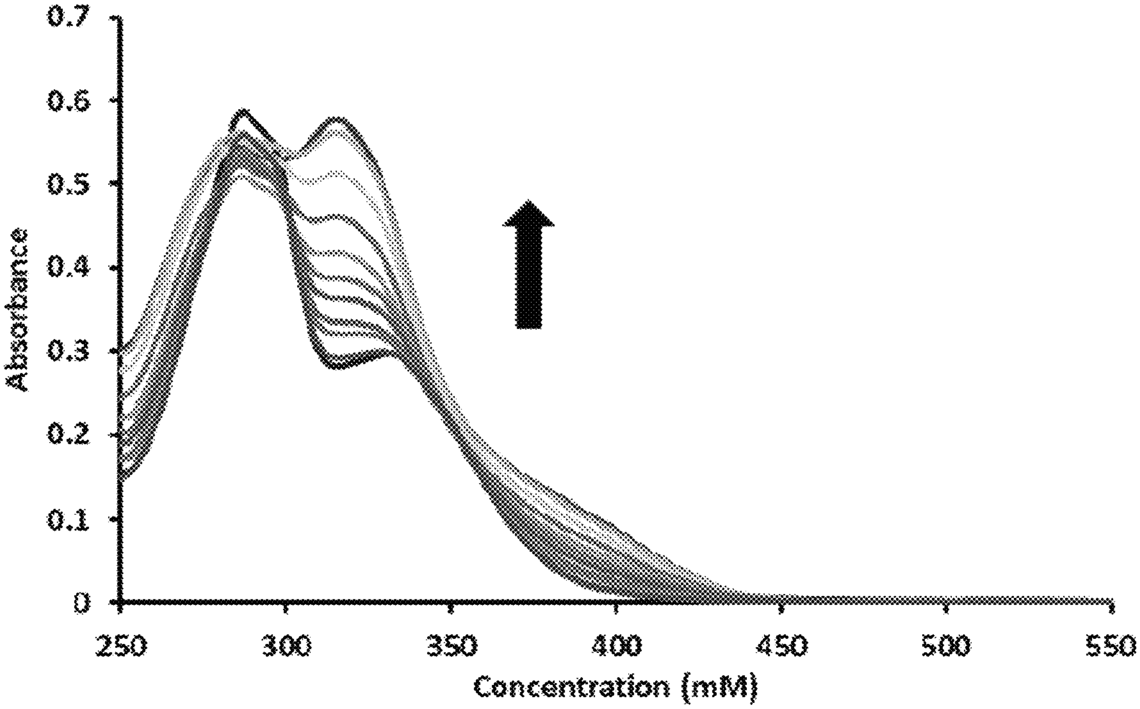

FIG. 71 is the UV spectra obtained from the reaction between probe 3 and varying amounts of (S)-N-methyl-1-phenylethylamine (17).

Figure 72:
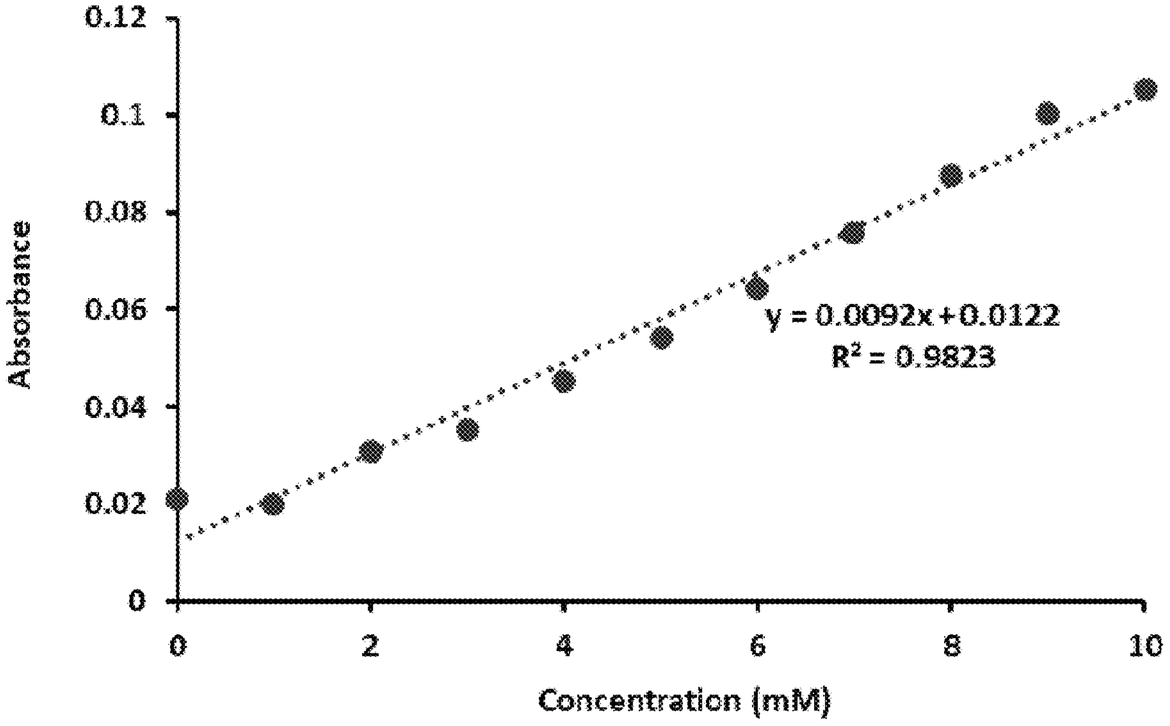

FIG. 72 shows the absorbance at 392 nm of the reaction mixture of probe 3 and varying amounts of (S)-N-methyl-1-phenylethylamine (17), plotted against the concentration of (S)-N-methyl-1-phenyl ethyl amine (17).

Figure 73:
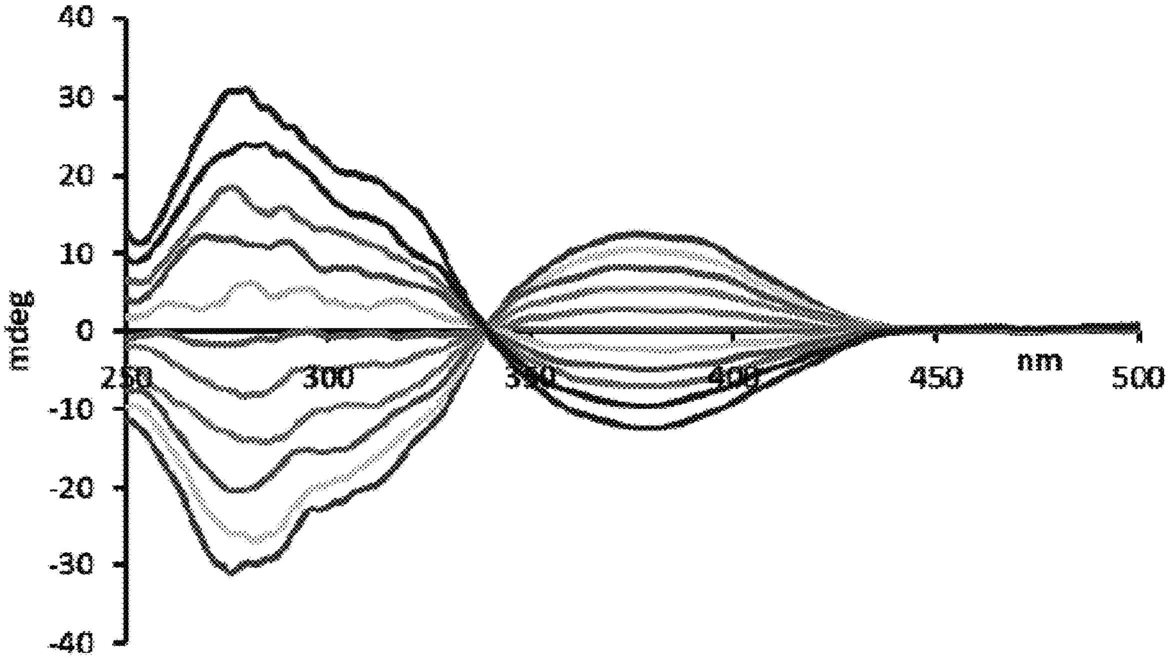

FIG. 73 shows the chiroptical response of probe 3 to scalemic samples of the reference (S)-N-methyl-1-phenyl ethyl amine (17).

Figure 74:
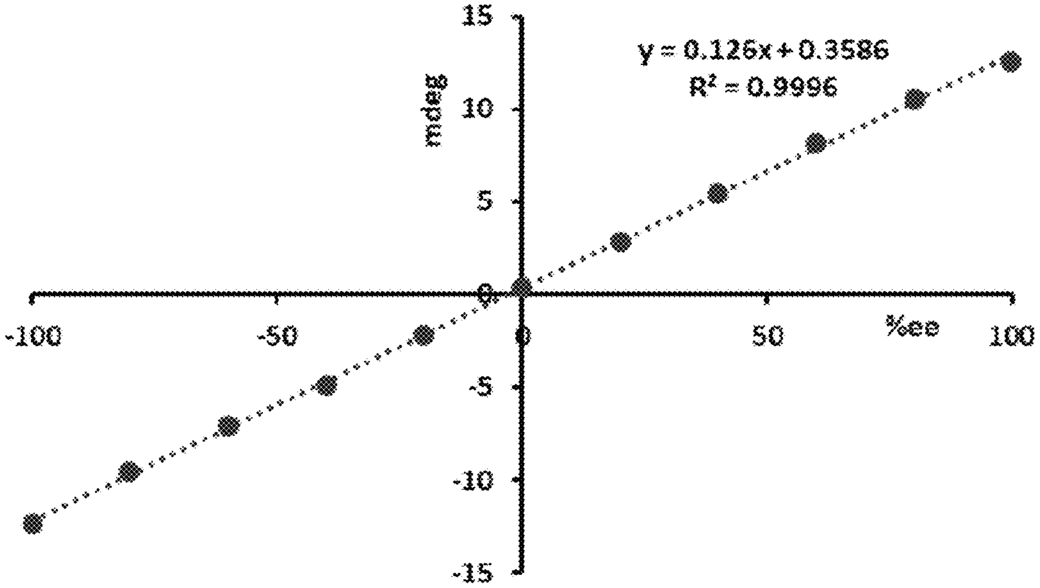

FIG. 74 is a plot of the CD amplitudes at 376 nm versus sample enantiomeric excess of the reaction of probe 3 to scalemic samples of the reference (S)-N-methyl-1-phenyl-ethylamine (17).

Figure 75:
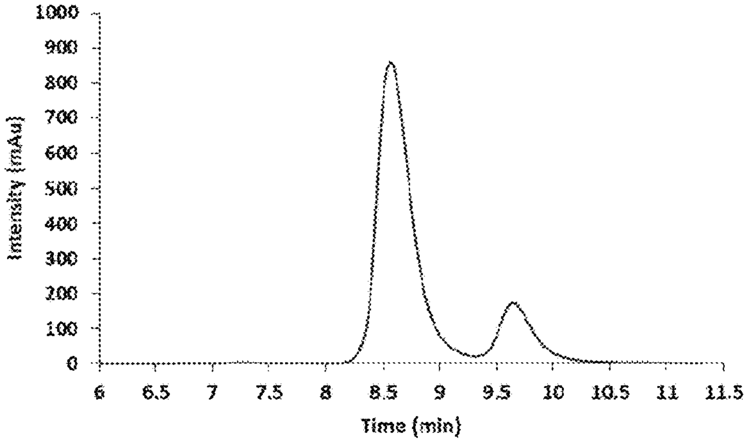

FIG. 75 is the HPLC trace of (S)-N-Boc-N-methyl-1-phenylethylamine. S,S-WhelkO using hexanes:IPA (99:1) as the mobile phase at 1.0 mL/min, $t_R$ (major)=8.6 min, $t_R$ (minor)=9.6 min.

Figure 76:
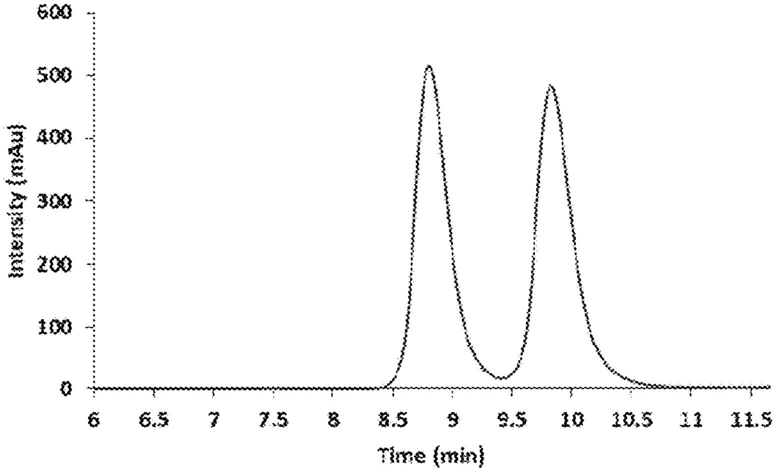

FIG. 76 is the HPLC trace of (±) N-Boc-N-methyl-1-phenylethylamine. S,S-WhelkO using hexanes:IPA (99:1) as the mobile phase at 1.0 mL/min, $t_R$ (major)=8.6 min, $t_R$ (minor)=9.6 min.

Figure 77:
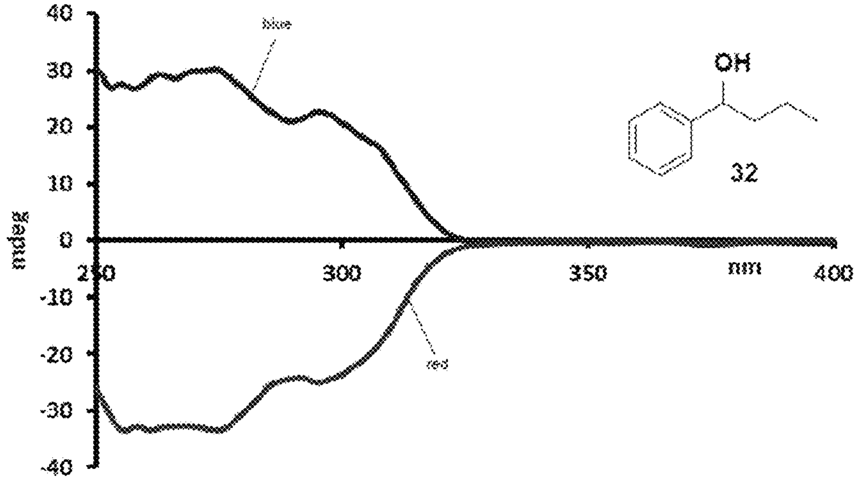

FIG. 77 is the CD spectra obtained from probe 63 with (S)-32 (red) and (R)-32 (blue). The CD measurements were taken at 0.25 mM in chloroform.

Figure 78:
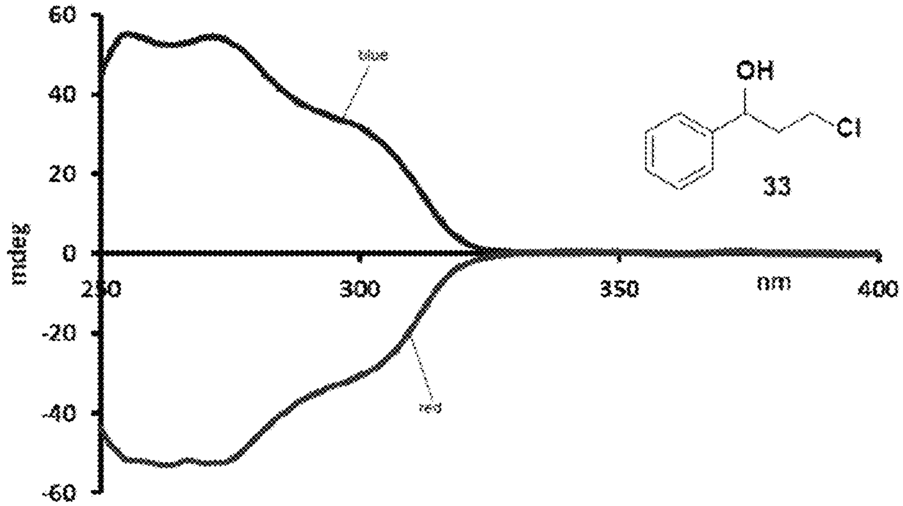

FIG. 78 is the CD spectra obtained from probe 63 with (S)-33 (red) and (R)-33 (blue). The CD measurements were taken at 0.22 mM in chloroform.

Figure 79:
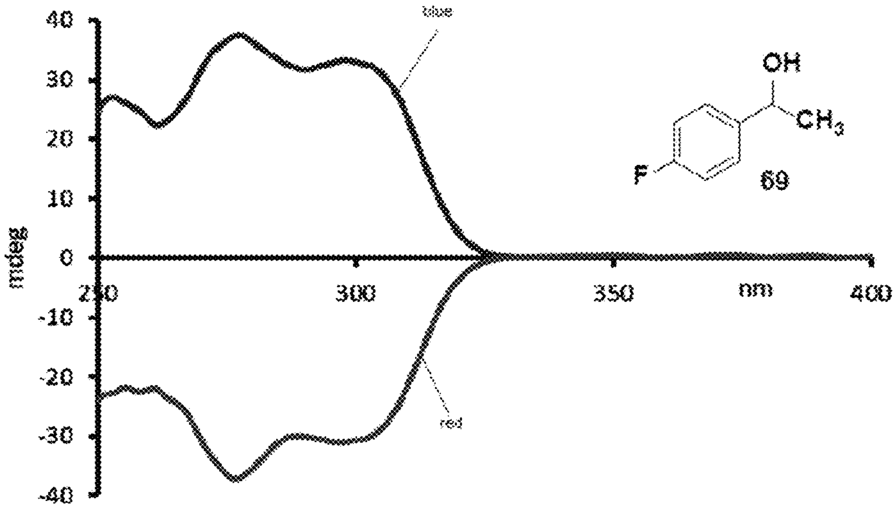

FIG. 79 is the CD spectra obtained from probe 63 with (S)-69 (red) and (R)-69 (blue). The CD measurements were taken at 0.22 mM in chloroform.

Figure 80:
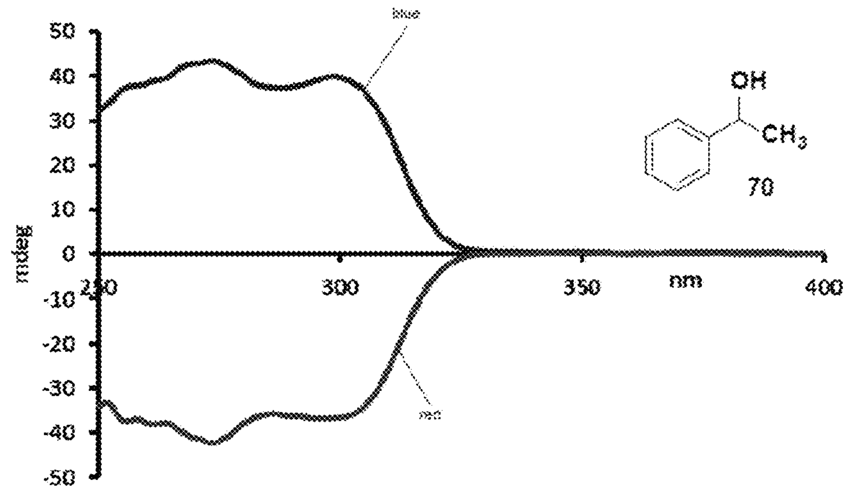

FIG. 80 is the CD spectra obtained from probe 63 with (S)-70 (red) and (R)-70 (blue). The CD measurements were taken at 0.22 mM in chloroform.

Figure 81:
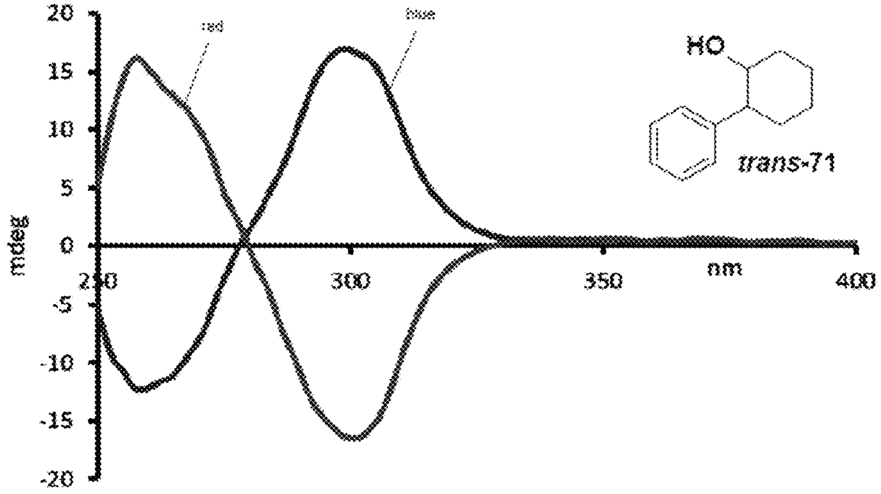

FIG. 81 is the CD spectra obtained from probe 63 with (1S,2R)-71 (red) and (1R,2S)-71 (blue). The CD measurements were taken at 0.22 mM in chloroform.

Figure 82:
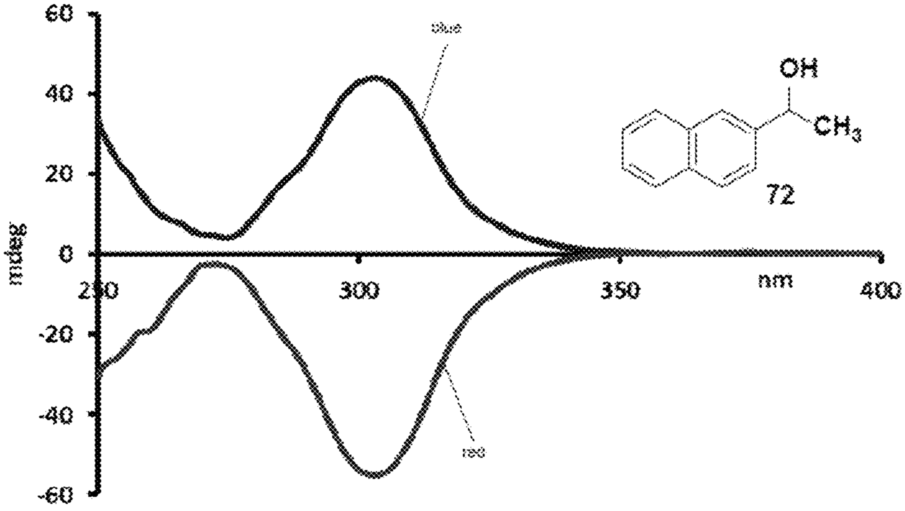

FIG. 82 is the CD spectra obtained from probe 63 with (S)-72 (red) and (R)-72 (blue). The CD measurements were taken at 0.17 mM in chloroform.

Figure 83:
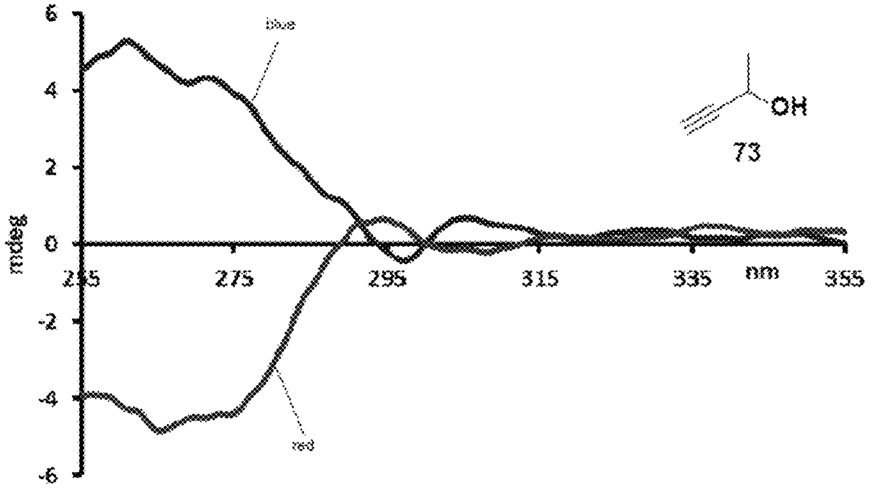

FIG. 83 is the CD spectra obtained from probe 63 with (S)-73 (red) and (R)-73 (blue). The CD measurements were taken at 0.22 mM in chloroform.

Figure 84:
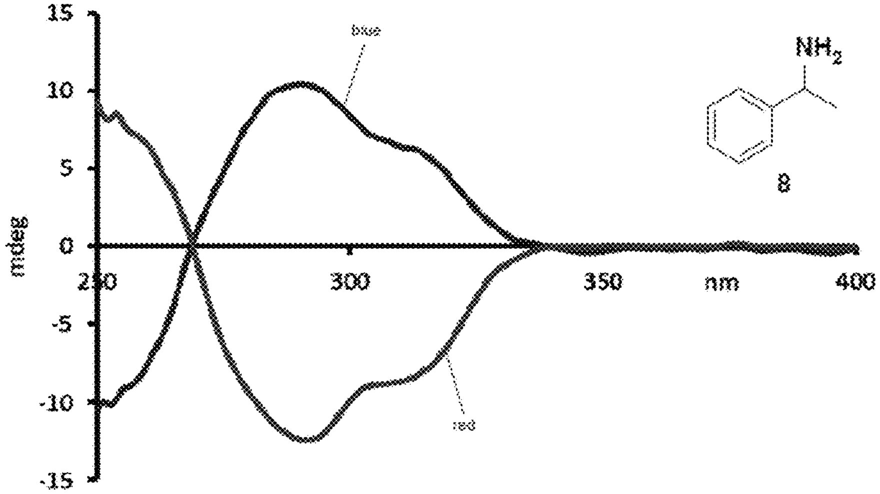

FIG. 84 is the CD spectra obtained from probe 63 with (S)-8 (red) and (R)-8 (blue). The CD measurements were taken at 0.25 mM in chloroform.

Figure 85:
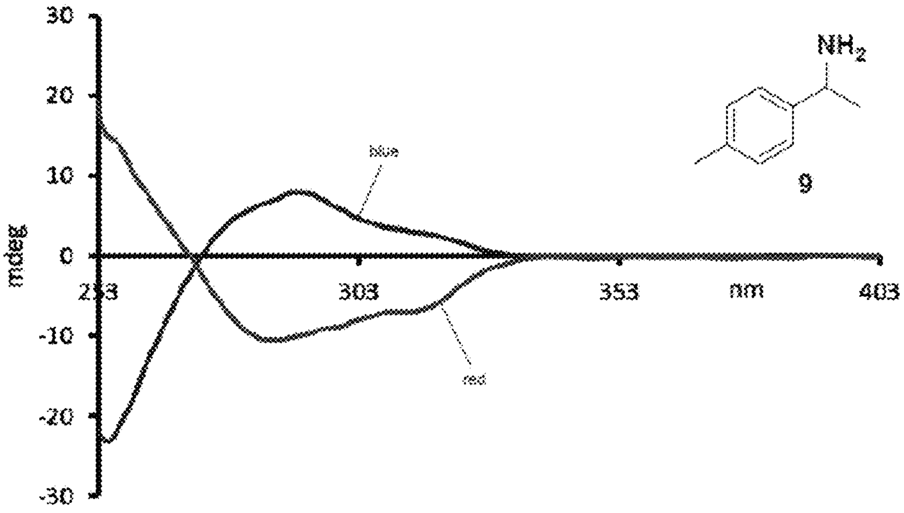

FIG. 85 is the CD spectra obtained from probe 63 with (S)-9 (red) and (R)-9 (blue). The CD measurements were taken at 0.25 mM in chloroform.

Figure 86:
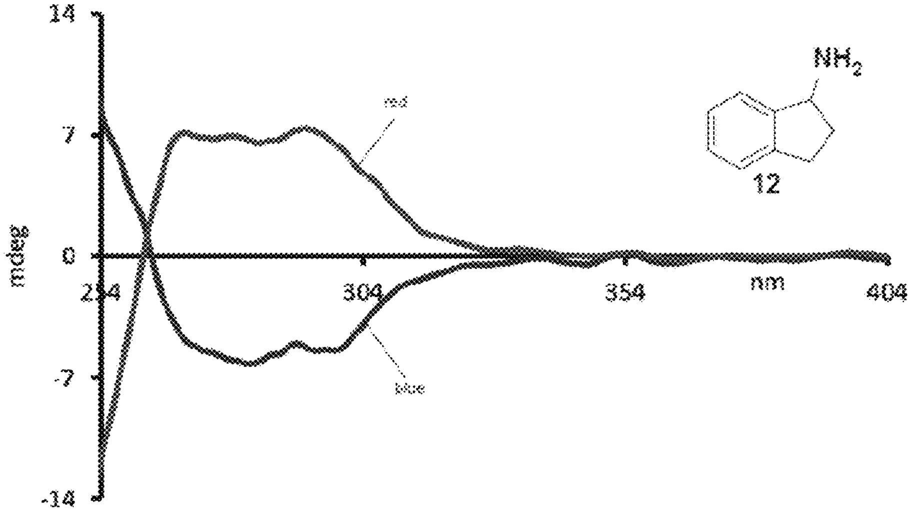

FIG. 86 is the CD spectra obtained from probe 63 with (S)-12 (red) and (R)-12 (blue). The CD measurements were taken at 0.25 mM in chloroform.

Figure 87:
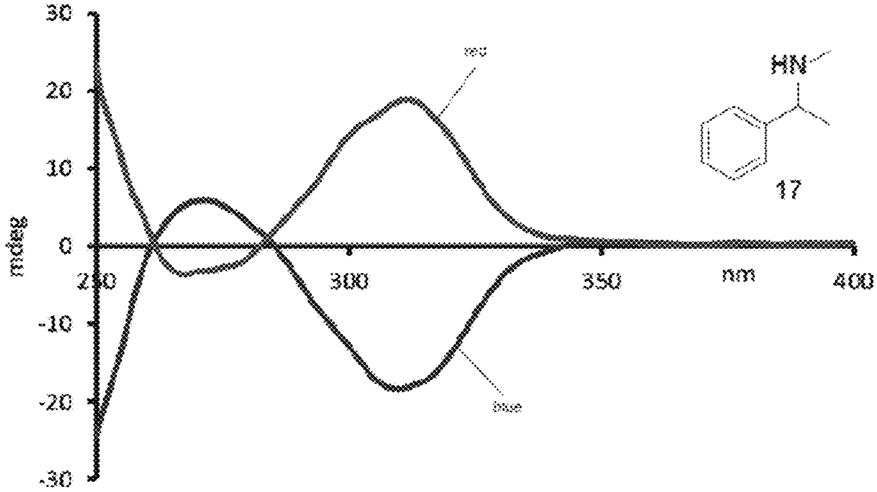

FIG. 87 is the CD spectra obtained from probe 63 with (S)-17 (red) and (R)-17 (blue). The CD measurements were taken at 0.25 mM in chloroform.

Figure 88:
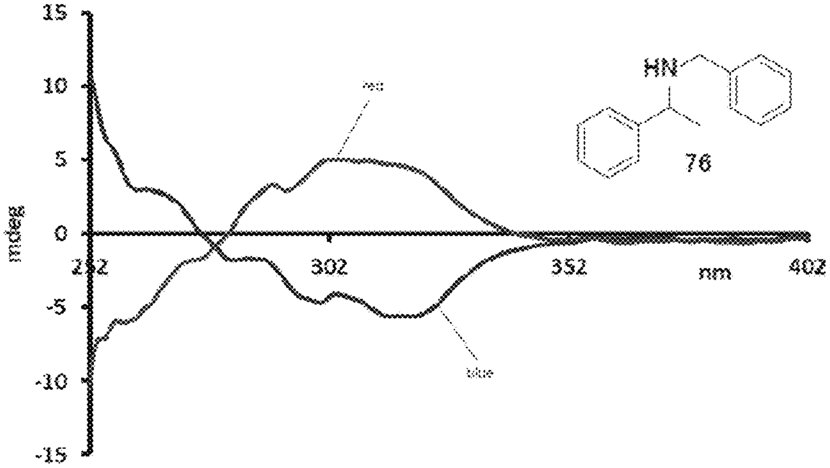

FIG. 88 is the CD spectra obtained from probe 63 with (S)-76 (red) and (R)-76 (blue). The CD measurements were taken at 0.25 mM in chloroform.

Figure 89:
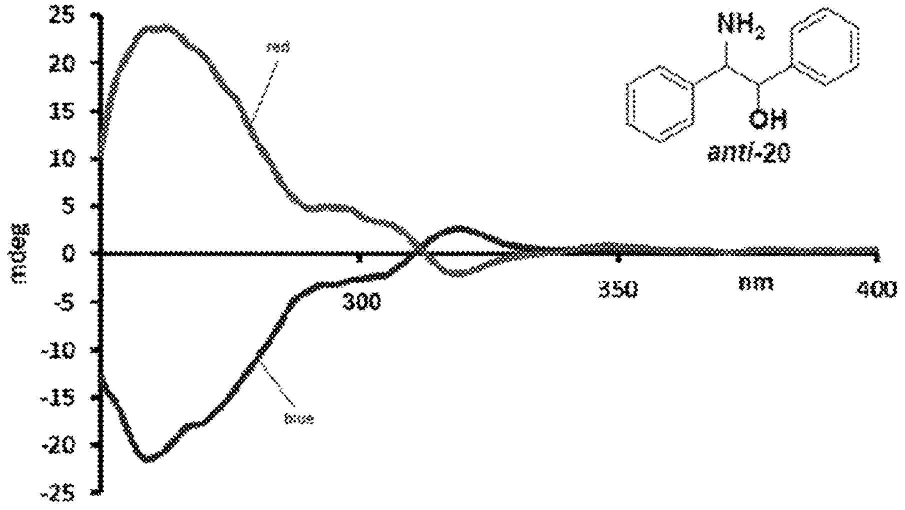

FIG. 89 is the CD spectra obtained from probe 63 with (1S,2R)-20 (red) and (1R,2S)-20 (blue). The CD measurements were taken at 0.13 mM in chloroform.

Figure 90:
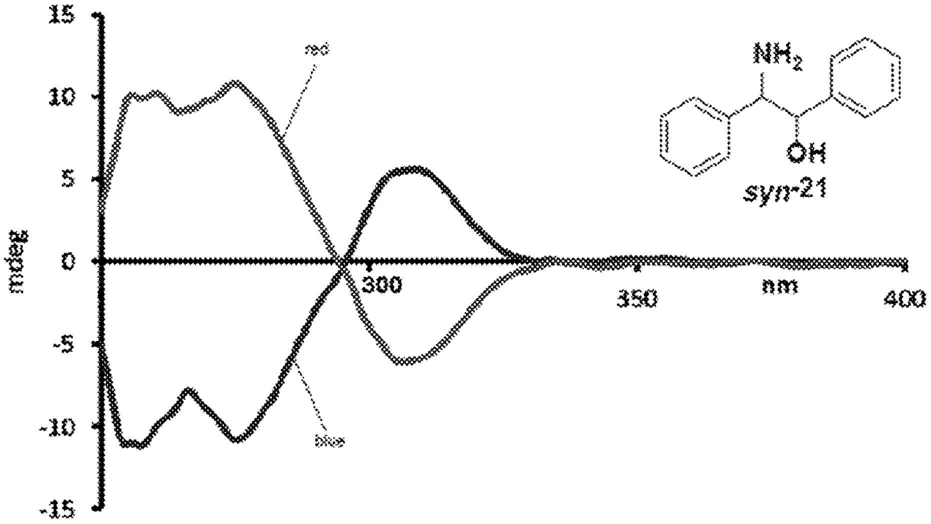

FIG. 90 is the CD spectra obtained from probe 63 with (1S,2R)-21 (red) and (1R,2S)-21 (blue). CD measurements were taken at 0.13 mM in chloroform.

Figure 91:
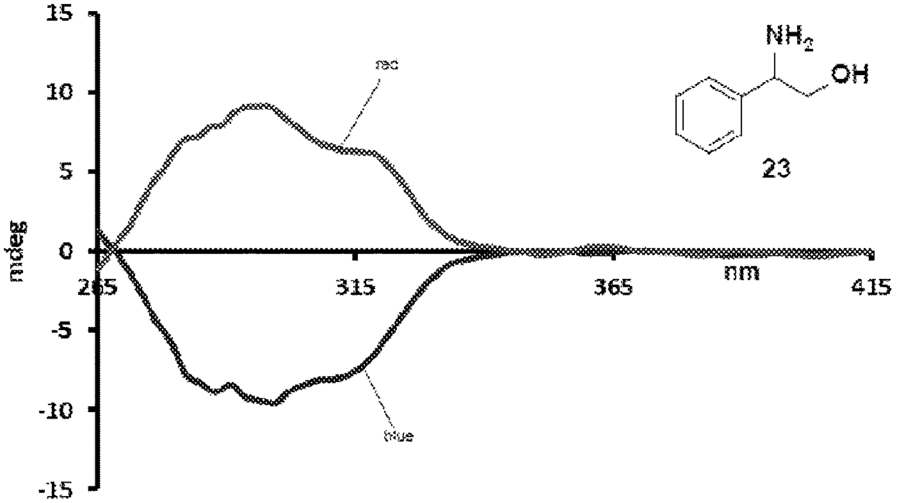

FIG. 91 is the CD spectra obtained from probe 63 with (S)-23 (red) and (R)-23 (blue). The CD measurements were taken at 0.13 mM in chloroform.

Figure 92:
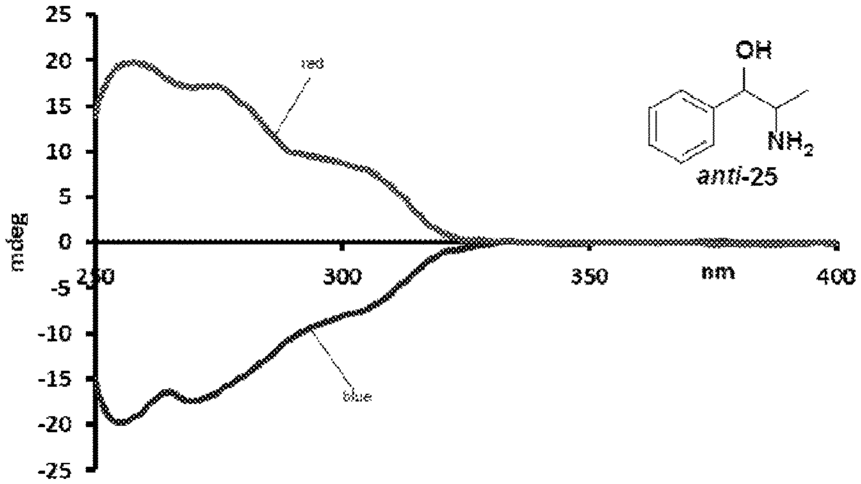

FIG. 92 is the CD spectra obtained from probe 63 with (1S,2R)-25 (red) and (1R,2S)-25 (blue). The CD measurements were taken at 0.13 mM in chloroform.

Figure 93:
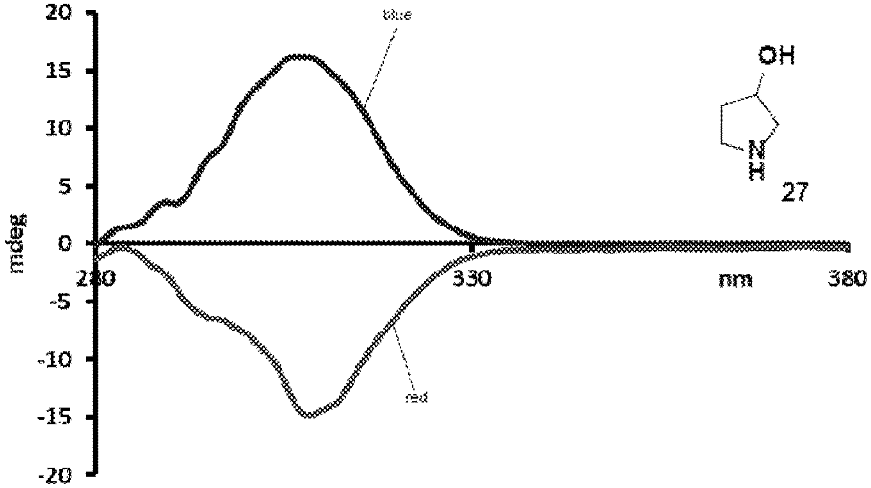

FIG. 93 is the CD spectra obtained from probe 63 with (S)-27 (red) and (R)-27 (blue). The CD measurements were taken at 0.13 mM in chloroform.

Figure 94:
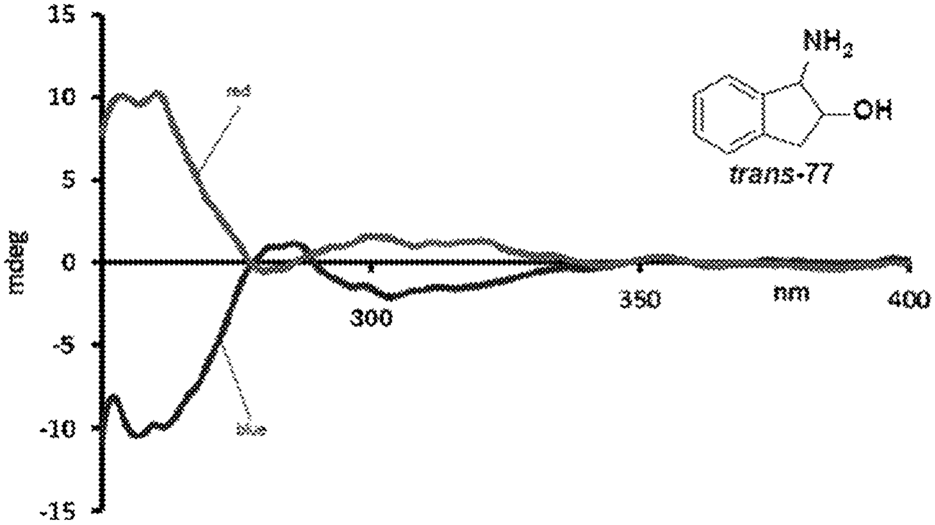

FIG. 94 is the CD spectra obtained from probe 63 with (1S,2S)-trans-77 (red) and (1R,2R)-trans-77 (blue). The CD measurements were taken at 0.13 mM in chloroform.

Figure 95:
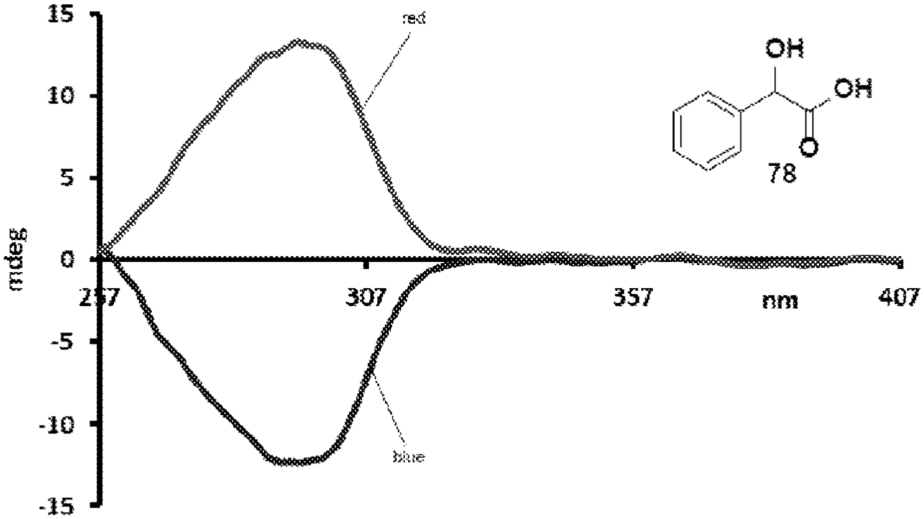

FIG. 95 is the CD spectra obtained from probe 63 with (S)-78 (red) and (R)-78 (blue). The CD measurements were taken at 0.13 mM in chloroform.

Figure 96:
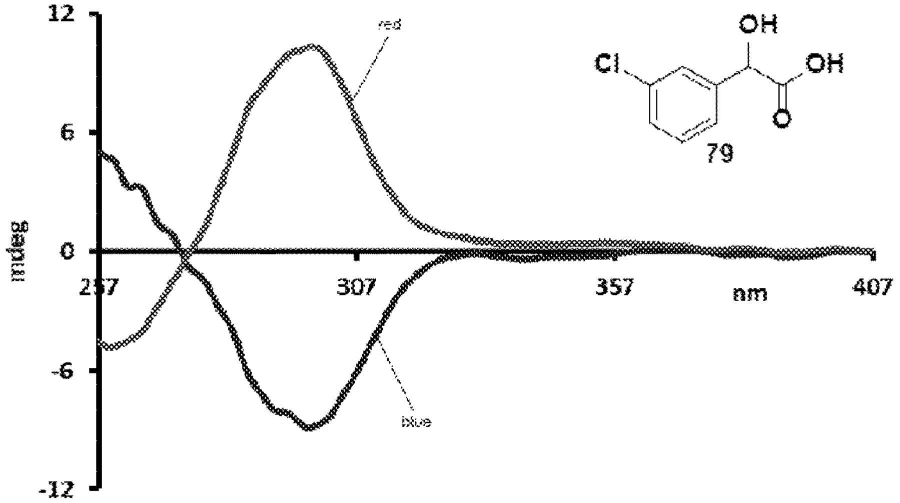

FIG. 96 is the CD spectra obtained from probe 63 with (S)-79 (red) and (R)-79 (blue). The CD measurements were taken at 0.13 mM in chloroform.

Figure 97:
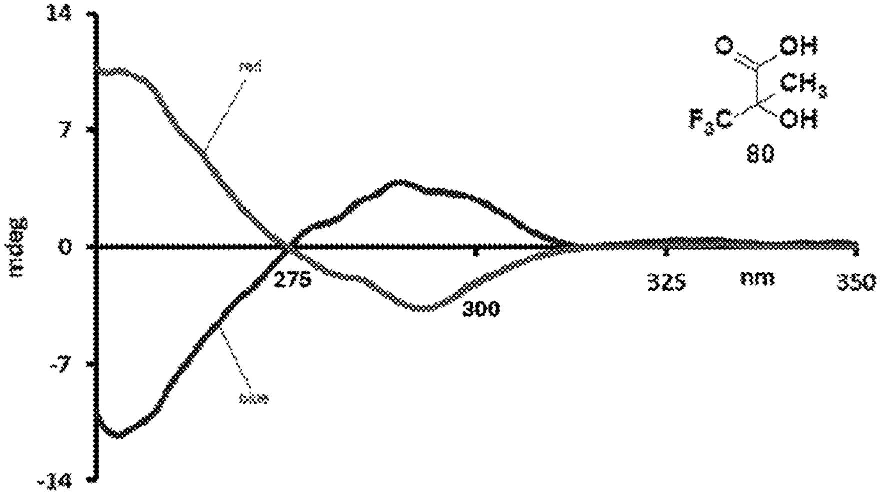

FIG. 97 is the CD spectra obtained from probe 63 with (S)-80 (red) and (R)-80 (blue). The CD measurements were taken at 0.13 mM in chloroform.

Figure 98:
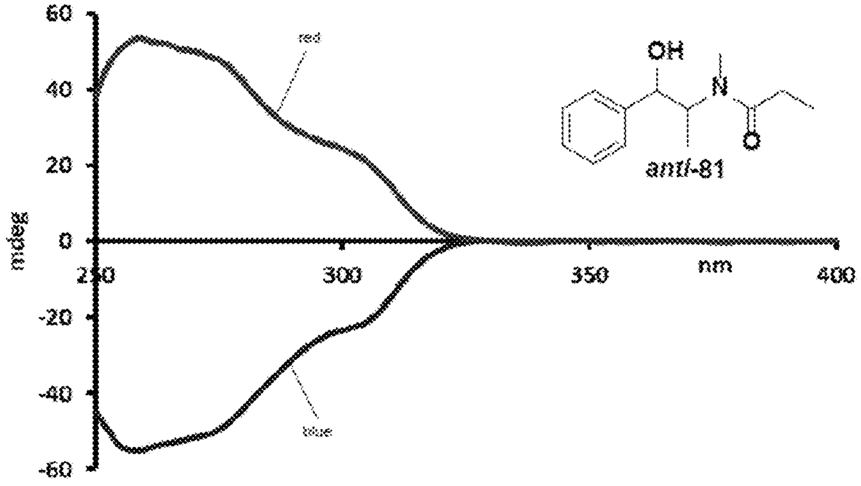

FIG. 98 is the CD spectra obtained from probe 63 with (1S,2S)-81 (red) and (1R,2R)-81 (blue). The CD measurements were taken at 0.25 mM in chloroform.

Figure 99:
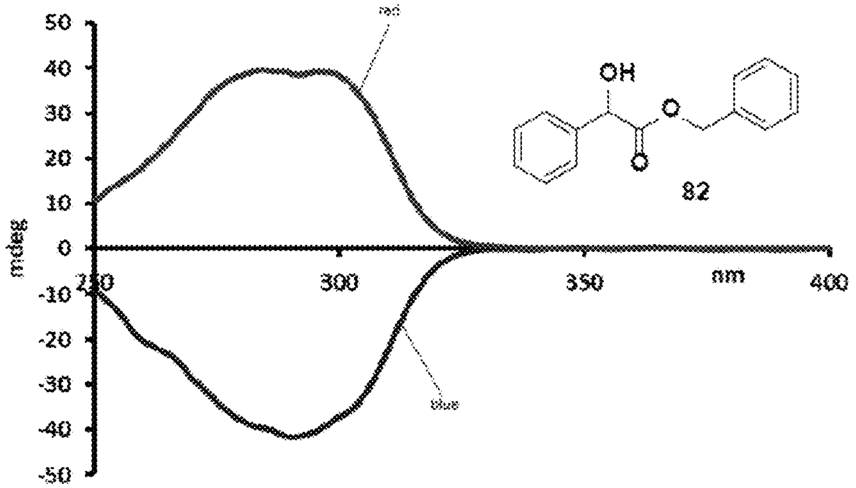

FIG. 99 is the CD spectra obtained from probe 63 with (S)-82 (red) and (R)-82 (blue). The CD measurements were taken at 0.25 mM in chloroform.

Figure 100:
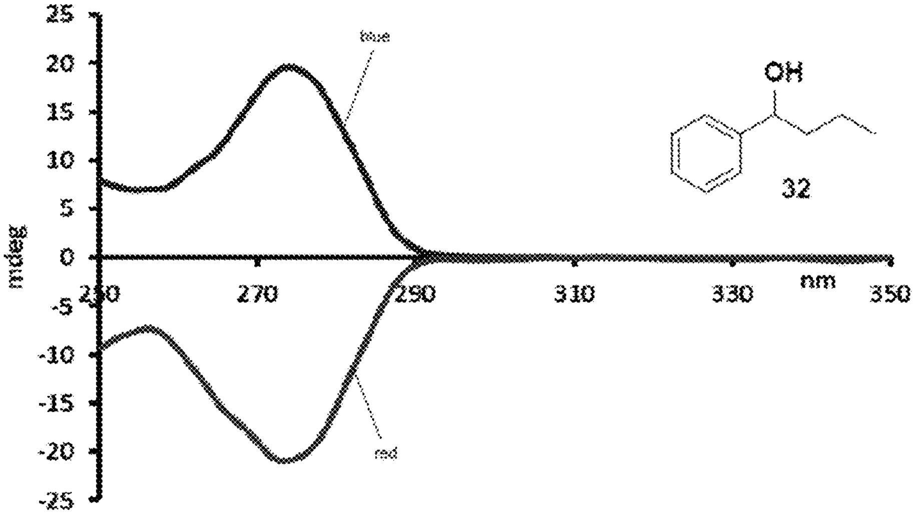

FIG. 100 is the CD spectra obtained from probe 56 with (S)-32 (red) and (R)-32 (blue). The CD measurements were taken at 0.61 mM in chloroform.

Figure 101:
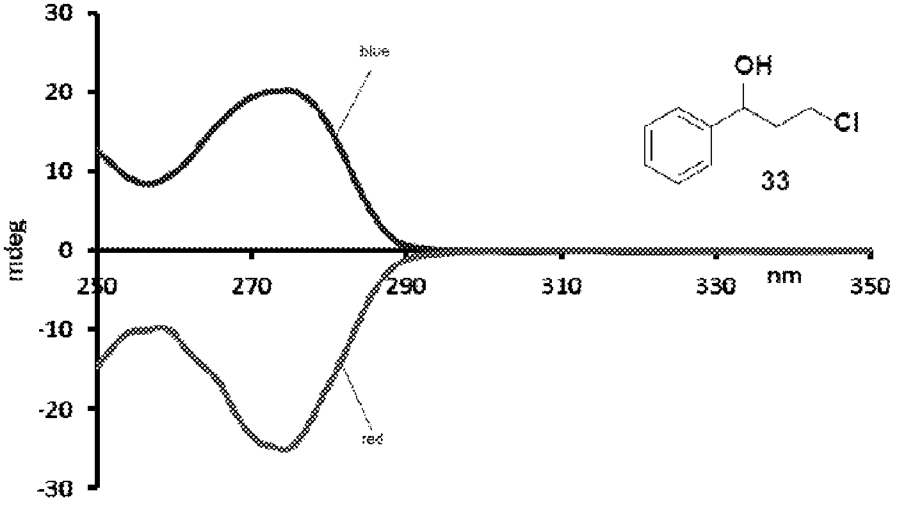

FIG. 101 is the CD spectra obtained from probe 56 with (S)-33 (red) and (R)-33 (blue). The CD measurements were taken at 0.75 mM in chloroform.

Figure 102:
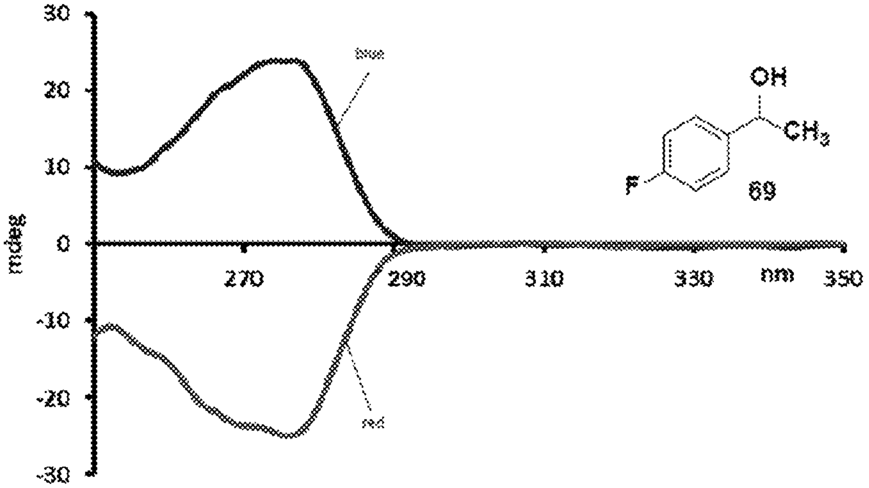

FIG. 102 is the CD spectra obtained from probe 56 with (S)-69 (red) and (R)-69 (blue). The CD measurements were taken at 0.75 mM in chloroform.

Figure 103:
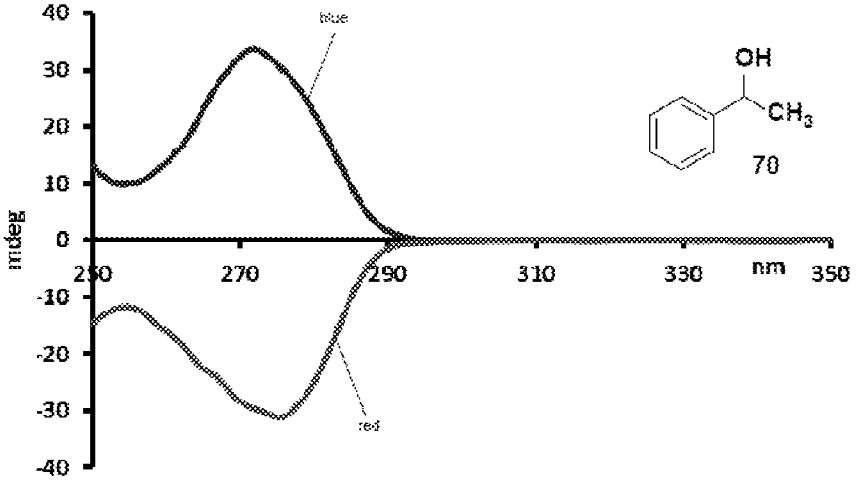

FIG. 103 is the CD spectra obtained from probe 56 with (S)-70 (red) and (R)-70 (blue). The CD measurements were taken at 0.75 mM in chloroform.

Figure 104:
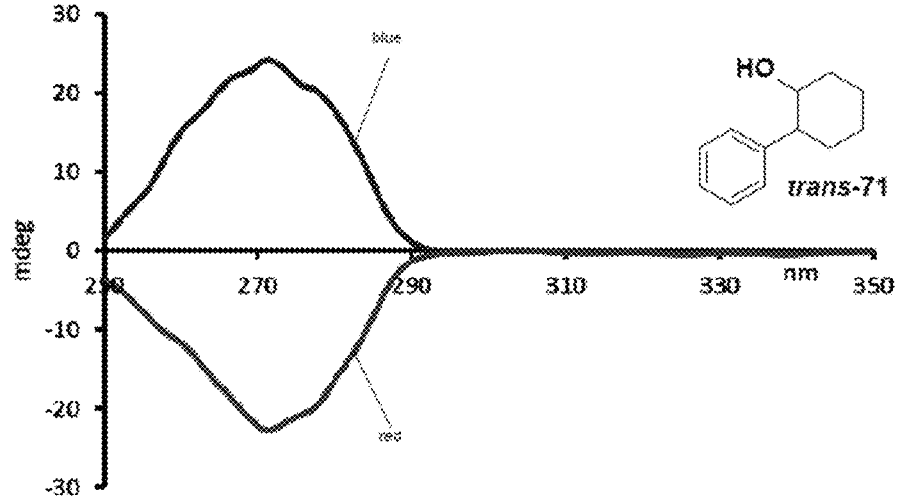

FIG. 104 is the CD spectra obtained from probe 56 with (1S,2R)-71 (red) and (1R,2S)-71 (blue). The CD measurements were taken at 0.61 mM in chloroform.

Figure 105:
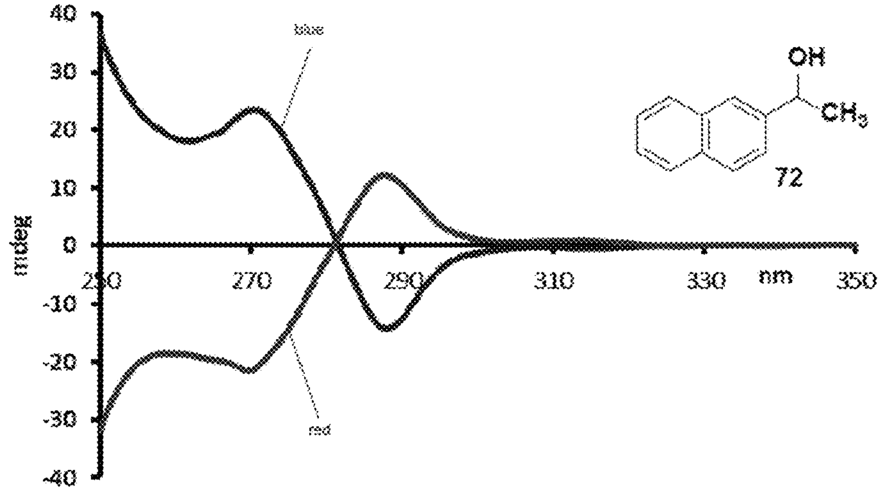

FIG. 105 is the CD spectra obtained from probe 56 with (S)-72 (red) and (R)-72 (blue). The CD measurements were taken at 0.25 mM in chloroform.

Figure 106:
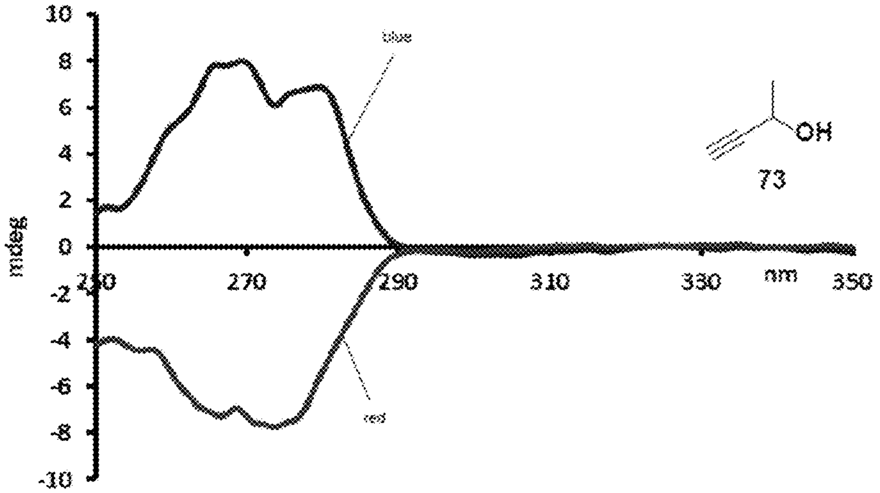

FIG. 106 is the CD spectra obtained from probe 56 with (S)-73 (red) and (R)-73 (blue). The CD measurements were taken at 0.81 mM in chloroform.

Figure 107:
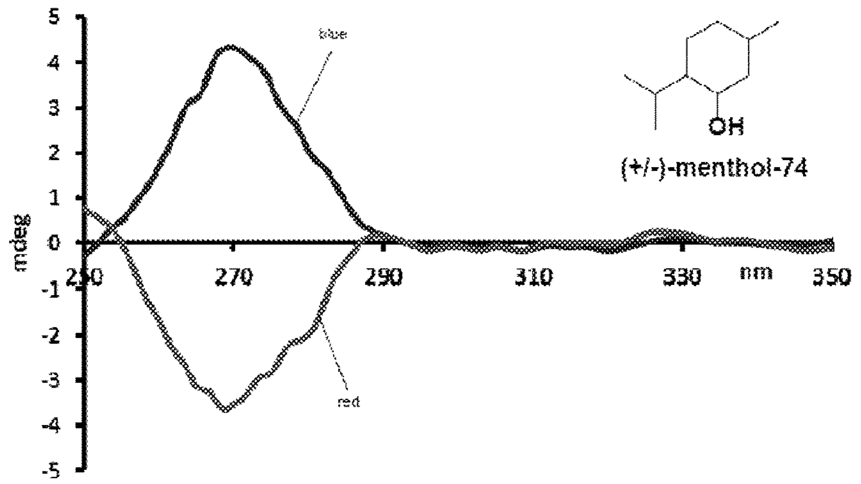

FIG. 107 is the CD spectra obtained from probe 56 with (1S,2R,5S)-74 (red) and (1R,2S,5R)-74 (blue). The CD measurements were taken at 0.90 mM in chloroform.

Figure 108:
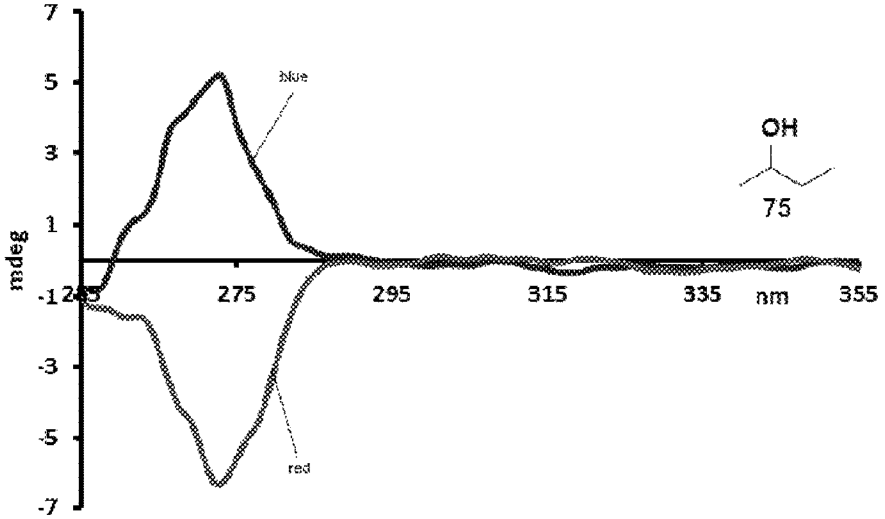

FIG. 108 is the CD spectra obtained from probe 56 with (S)-75 (red) and (R)-75 (blue). The CD measurements were taken at 0.61 mM in acetonitrile.

Figure 109:
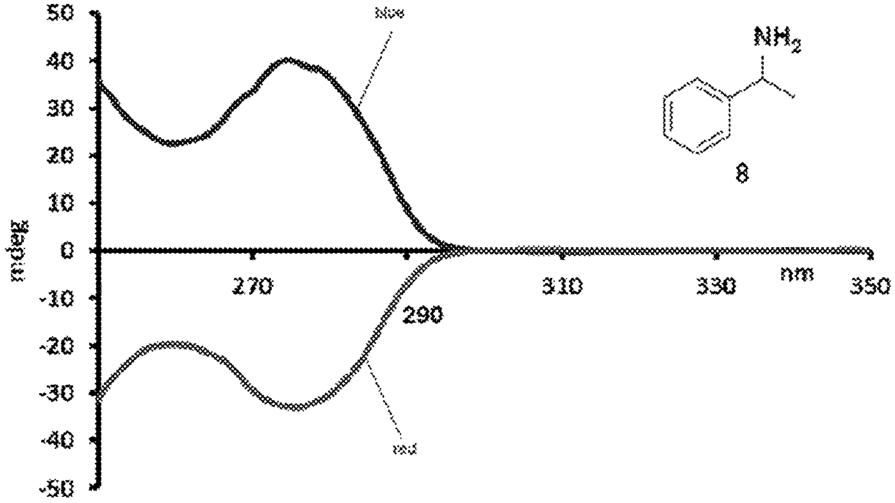

FIG. 109 is the CD spectra obtained from probe 56 with (S)-8 (red) and (R)-8 (blue). The CD measurements were taken at 0.34 mM in chloroform.

Figure 110:
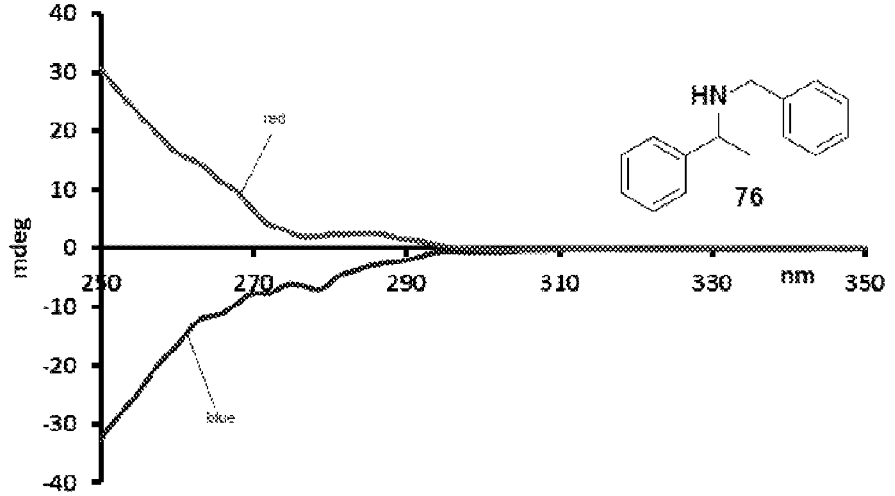

FIG. 110 is the CD spectra obtained from probe 56 with (S)-76 (red) and (R)-76 (blue). The CD measurements were taken at 0.61 mM in chloroform.

Figure 111:
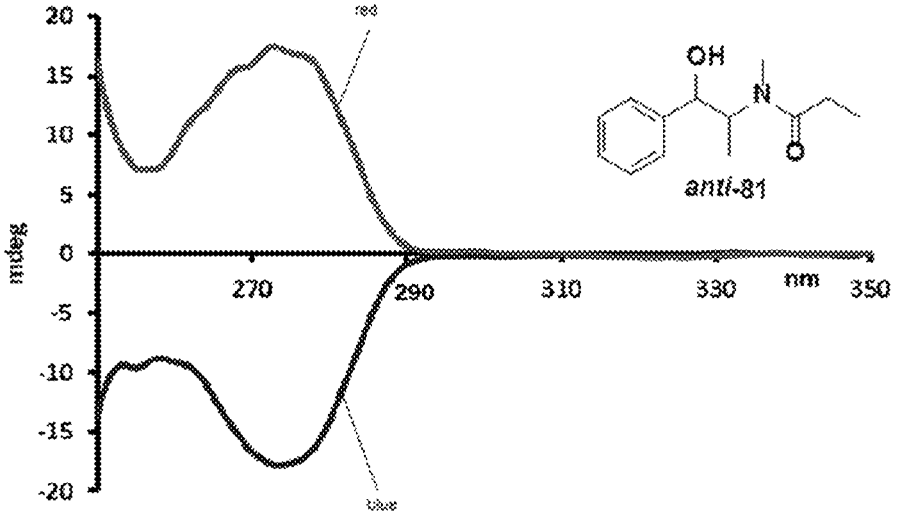

FIG. 111 is the CD spectra obtained from probe 56 with (1S,2S)-81 (red) and (1R,2R)-81 (blue). The CD measurements were taken at 0.40 mM in chloroform.

Figure 112:
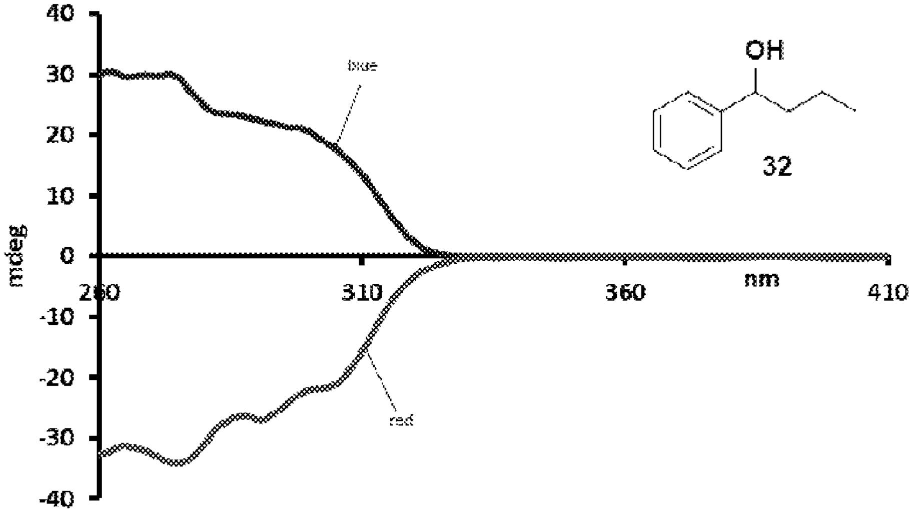

FIG. 112 is the CD spectra obtained from probe 57 with (S)-32 (red) and (R)-32 (blue). The CD measurements were taken at 0.25 mM in chloroform.

Figure 113:
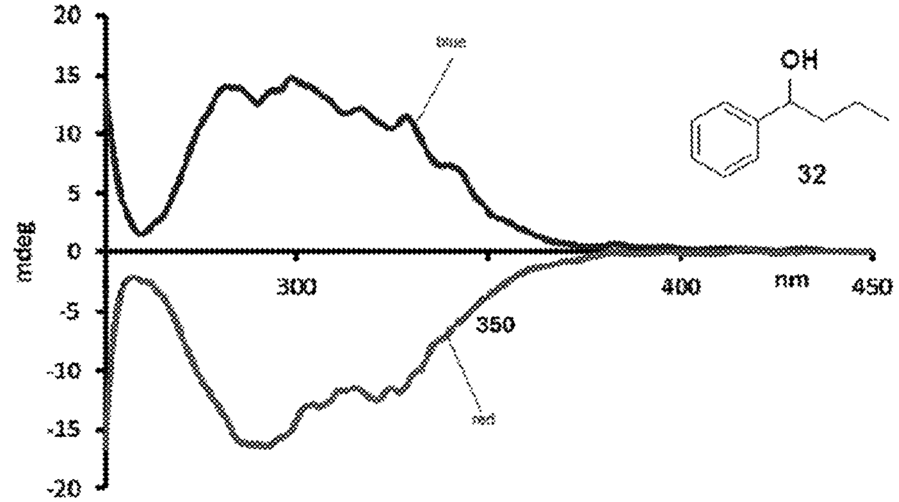

FIG. 113 is the CD spectra obtained from probe 58 with (S)-32 (red) and (R)-32 (blue). The CD measurements were taken at 0.37 mM in chloroform.

Figure 114:
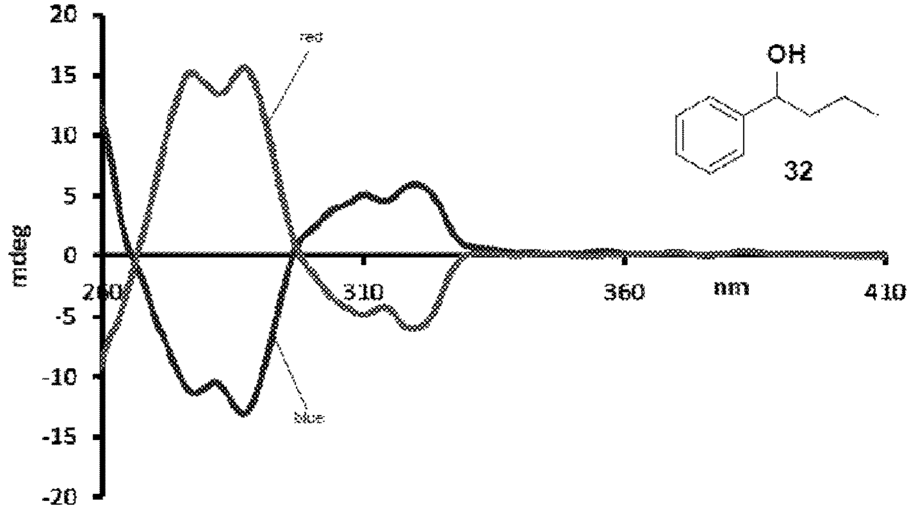

FIG. 114 is the CD spectra obtained from probe 59 with (S)-32 (red) and (R)-32 (blue). The CD measurements were taken at 0.25 mM in chloroform.

Figure 115:
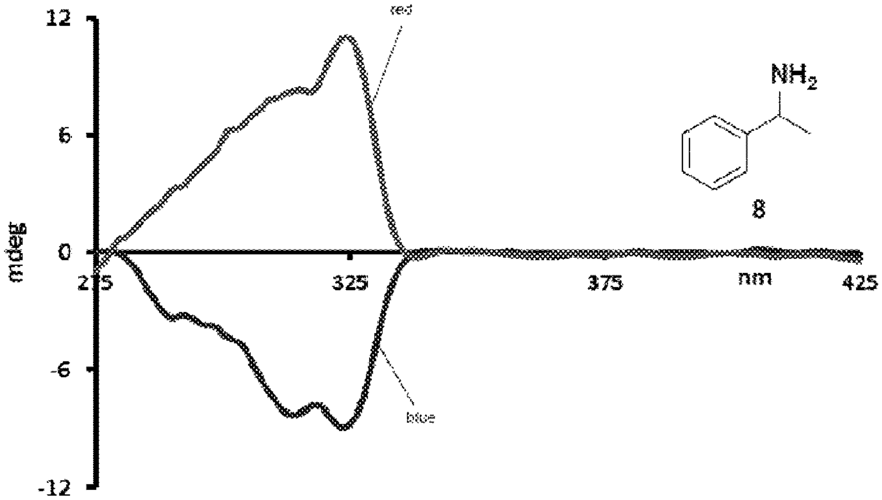

FIG. 115 is the CD spectra obtained from probe 60 with (S)-8 (red) and (R)-8 (blue). The CD measurements were taken at 0.125 mM in chloroform.

Figure 116:
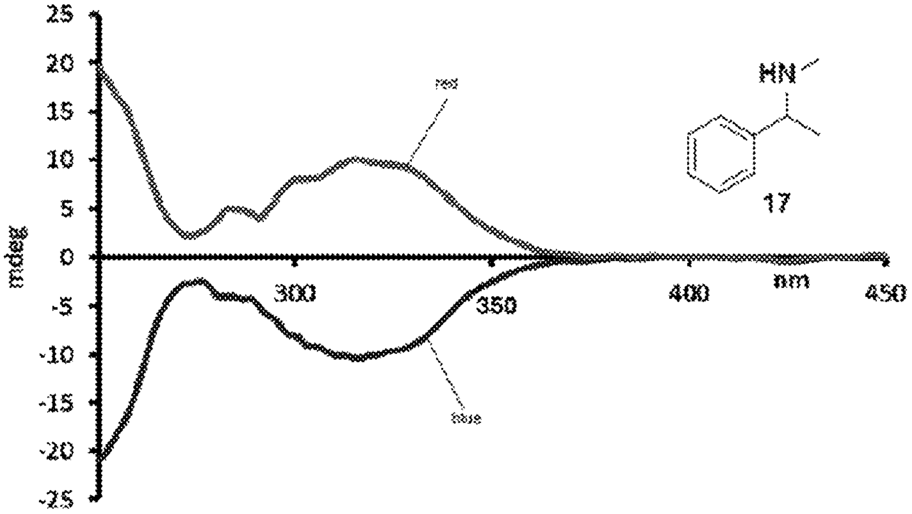

FIG. 116 is the CD spectra obtained from probe 60 with (S)-17 (red) and (R)-17 (blue). The CD measurements were taken at 0.125 mM in chloroform.

Figure 117:
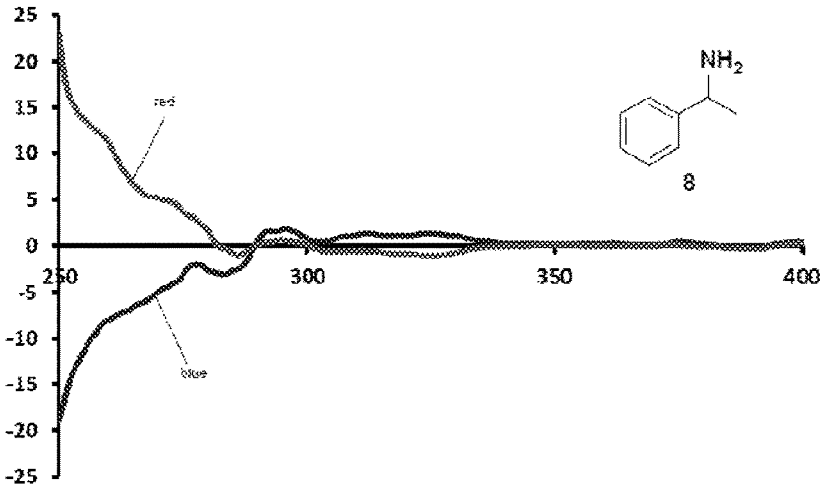

FIG. 117 is the CD spectra obtained from probe 61 with (S)-8 (red) and (R)-8 (blue). The CD measurements were taken at 0.15 mM in chloroform.

Figure 118:
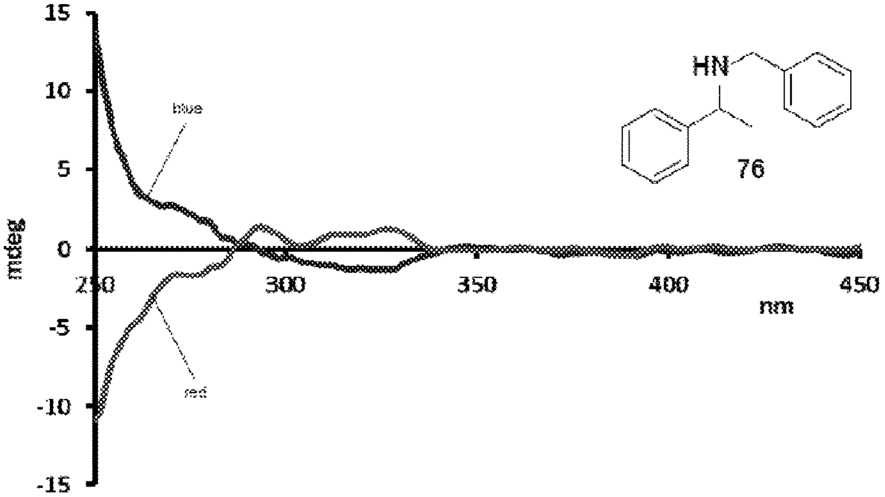

FIG. 118 is the CD spectra obtained from probe 61 with (S)-76 (red) and (R)-76 (blue). The CD measurements were taken at 0.15 mM in chloroform.

Figure 119:
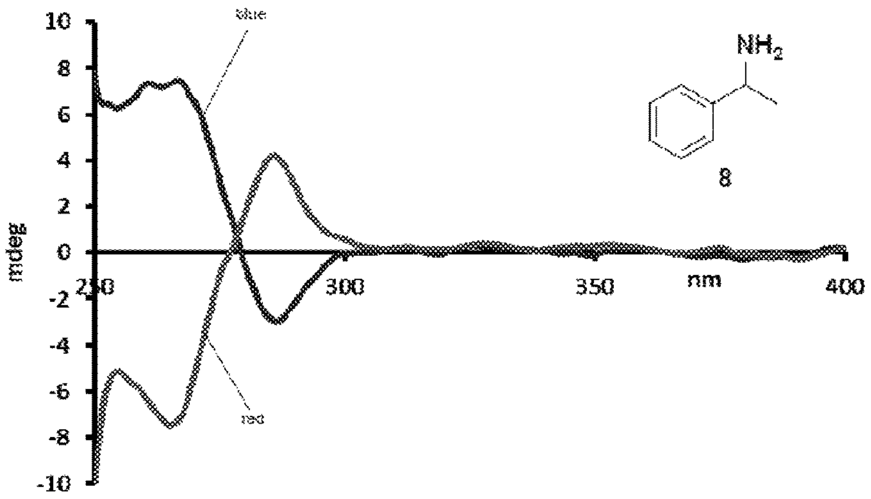

FIG. 119 is the CD spectra obtained from probe 62 with (S)-8 (red) and (R)-8 (blue). The CD measurements were taken at 0.40 mM in chloroform.

Figure 120:
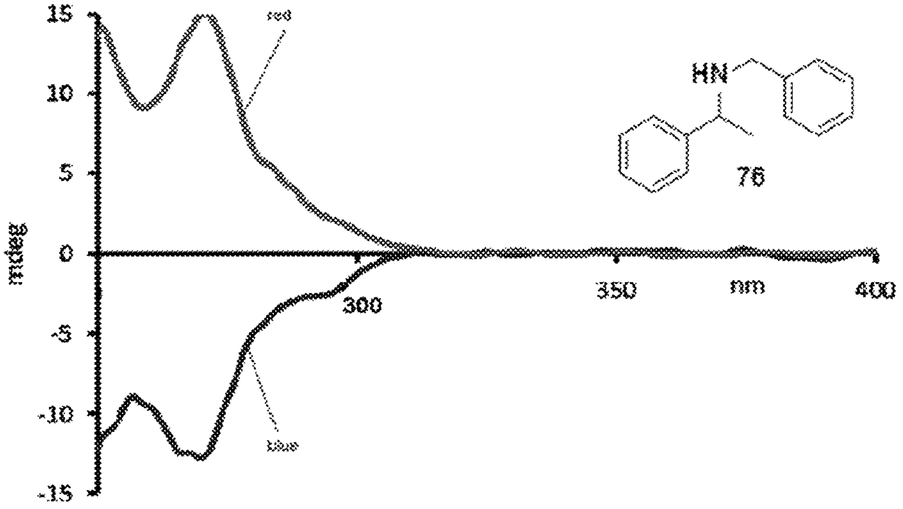

FIG. 120 is the CD spectra obtained from probe 62 with (S)-76 (red) and (R)-76 (blue). The CD measurements were taken at 0.40 mM in chloroform.

Figure 121:
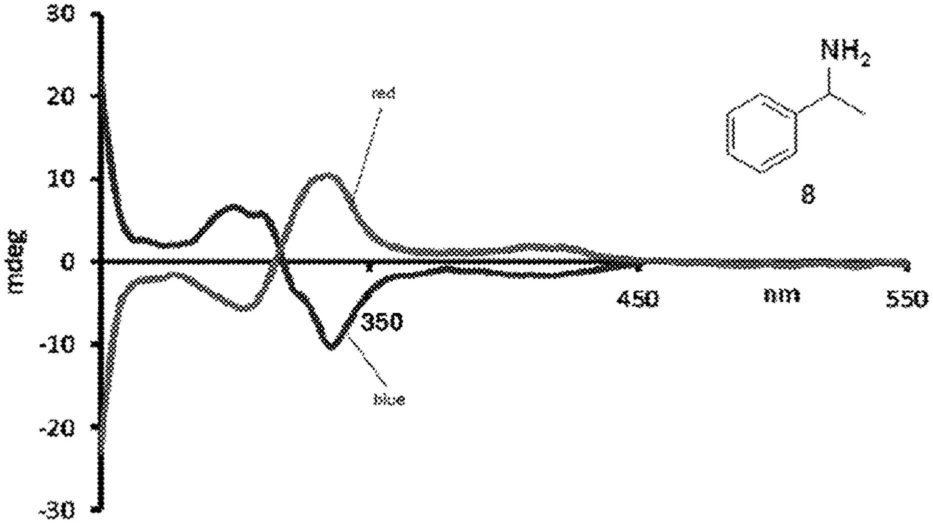

FIG. 121 is the CD spectra obtained from probe 64 with (S)-8 (red) and (R)-8 (blue). The CD measurements were taken at 0.15 mM in acetonitrile.

Figure 122:
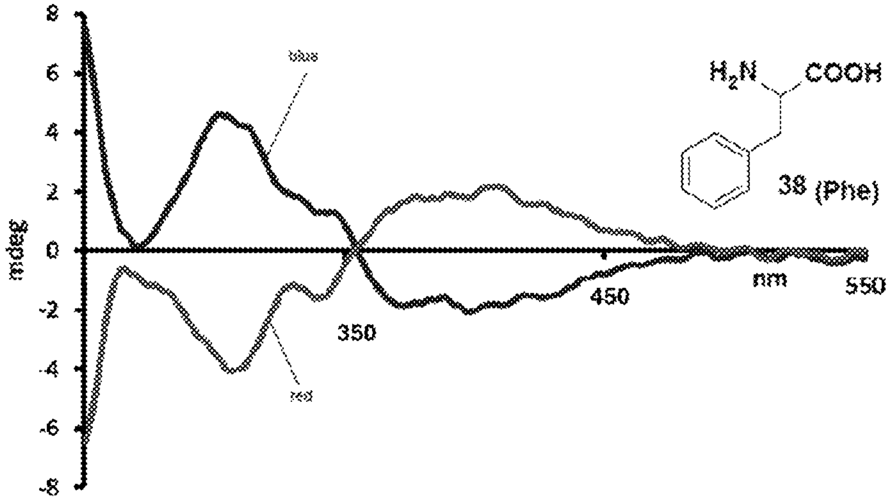

FIG. 122 is the CD spectra obtained from probe 64 with (S)-38 (red) and (R)-38 (blue). The CD measurements were taken at 0.15 mM in acetonitrile.

Figure 123:
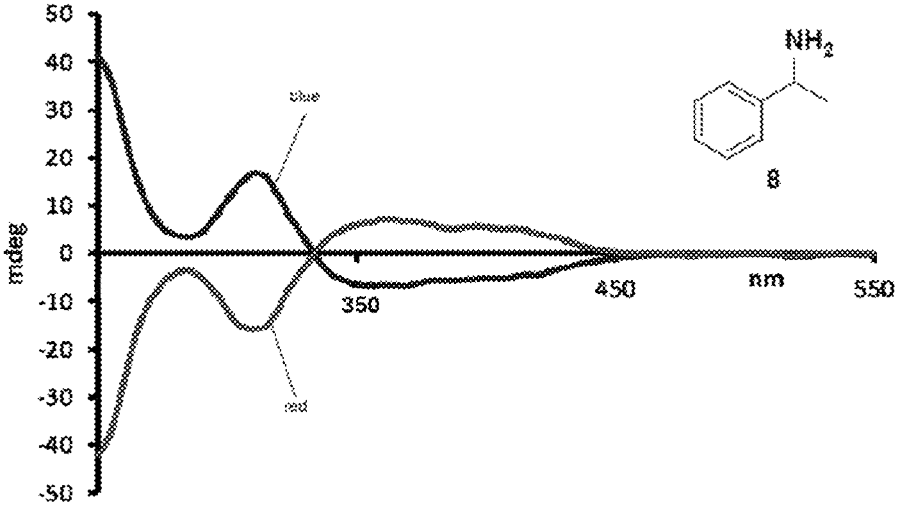

FIG. 123 is the CD spectra obtained from probe 65 with (S)-8 (red) and (R)-8 (blue). The CD measurements were taken at 0.05 mM in acetonitrile.

Figure 124:
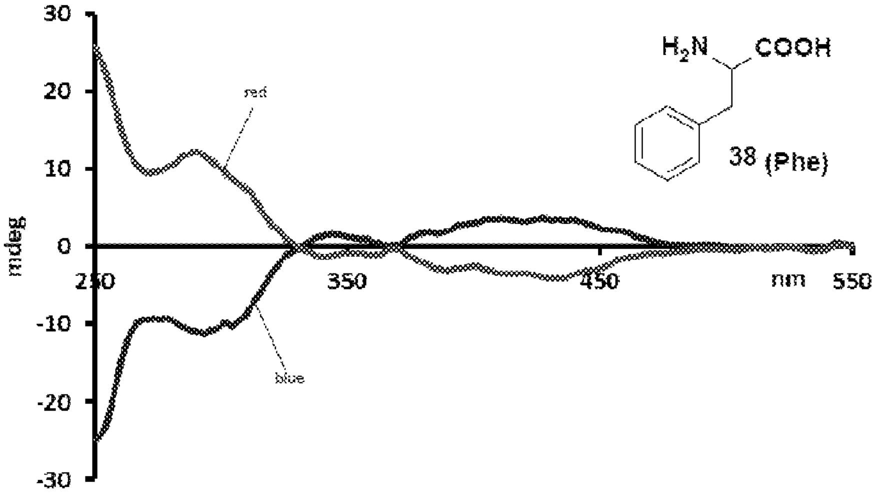

FIG. 124 is the CD spectra obtained from probe 65 with (S)-38 (red) and (R)-38 (blue). The CD measurements were taken at 0.29 mM in acetonitrile.

Figure 125:
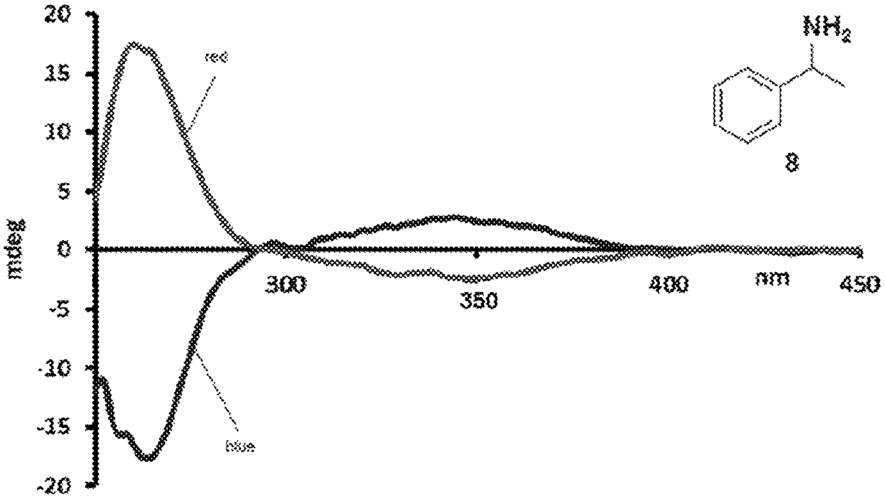

FIG. 125 is the CD spectra obtained from probe 66 with (S)-8 (red) and (R)-8 (blue). The CD measurements were taken at 0.20 mM in acetonitrile.

Figure 126:
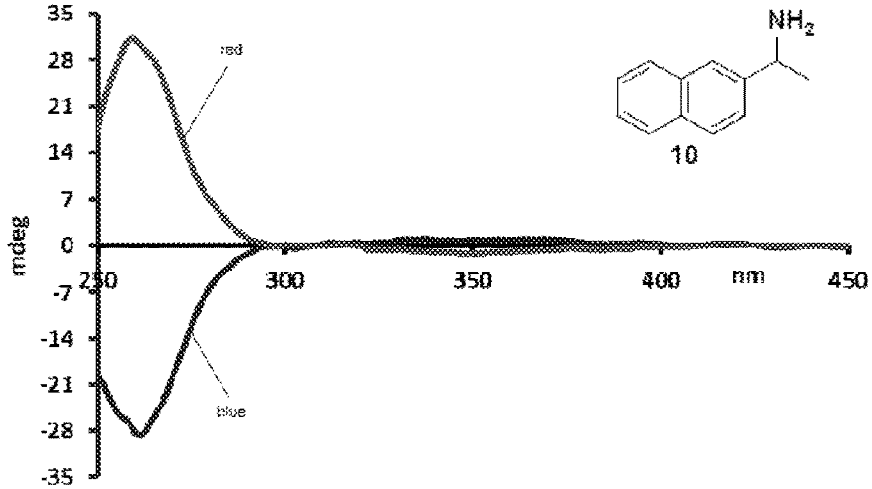

FIG. 126 is the CD spectra obtained from probe 66 with (S)-10 (red) and (R)-10 (blue). The CD measurements were taken at 0.15 mM in acetonitrile.

Figure 127:
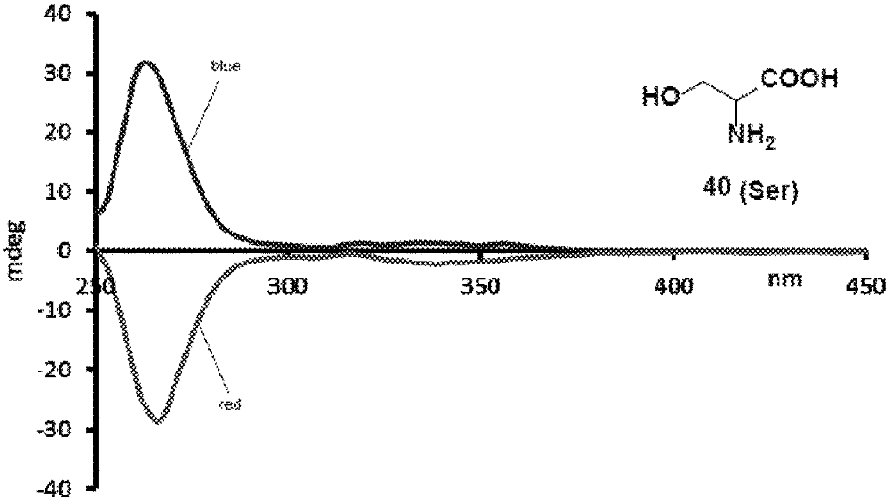

FIG. 127 is the CD spectra obtained from probe 66 with (S)-40 (red) and (R)-40 (blue). The CD measurements were taken at 0.17 mM in acetonitrile.

Figure 128:
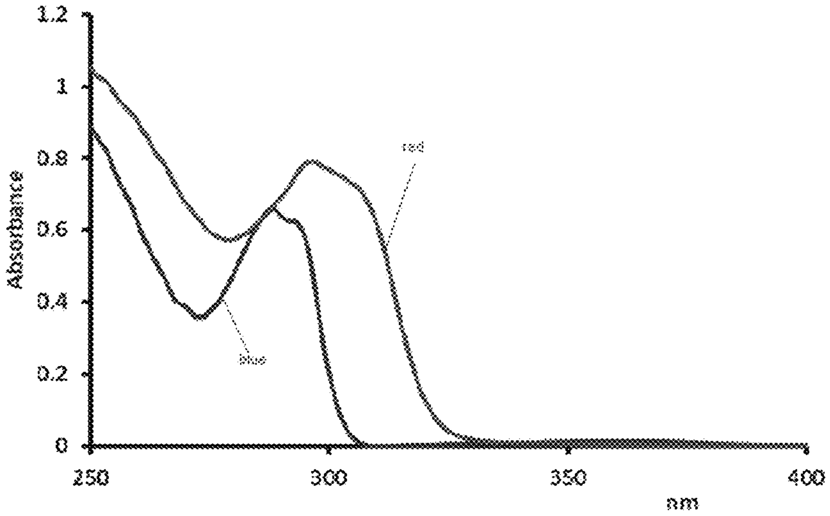

FIG. 128 is the UV spectrum of the probe 63 (blue) and the reaction between probe 63 and 32 (red).

Figure 129:
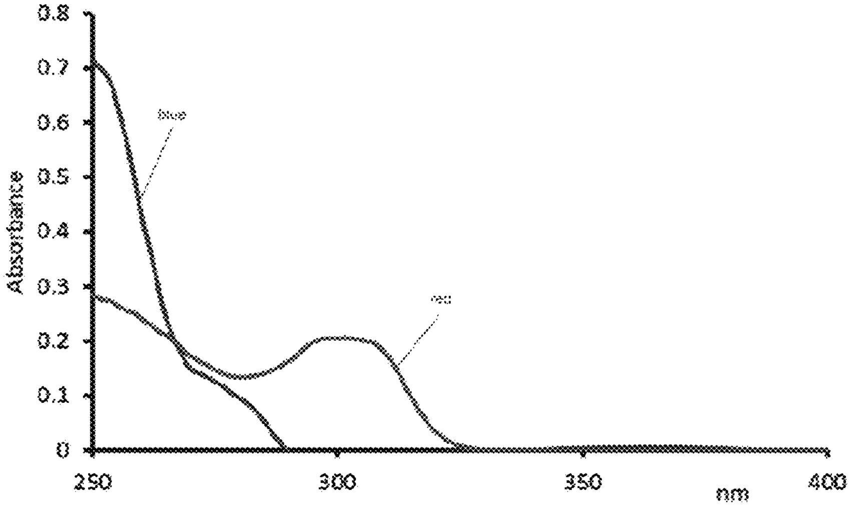

FIG. 129 is the UV spectrum of the probe 57 (blue) and the reaction between probe 57 and 32 (red).

Figure 130:
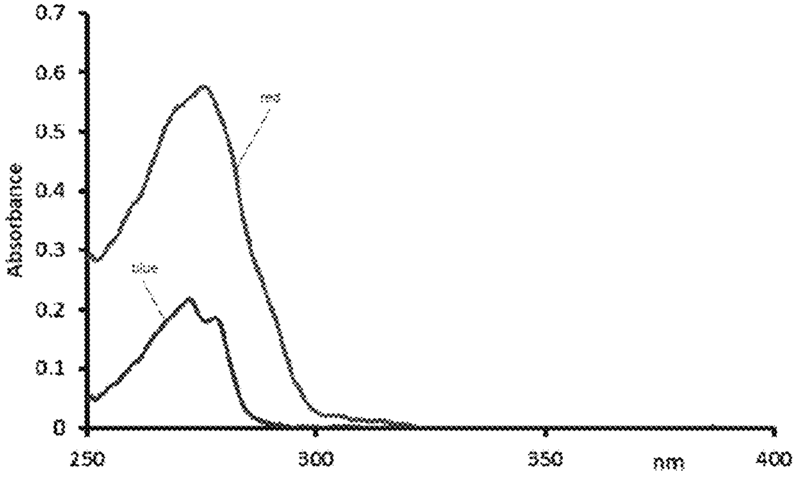

FIG. 130 is the UV spectrum of the probe 56 (blue) and the reaction between probe 56 and 72 (red).

Figure 131:
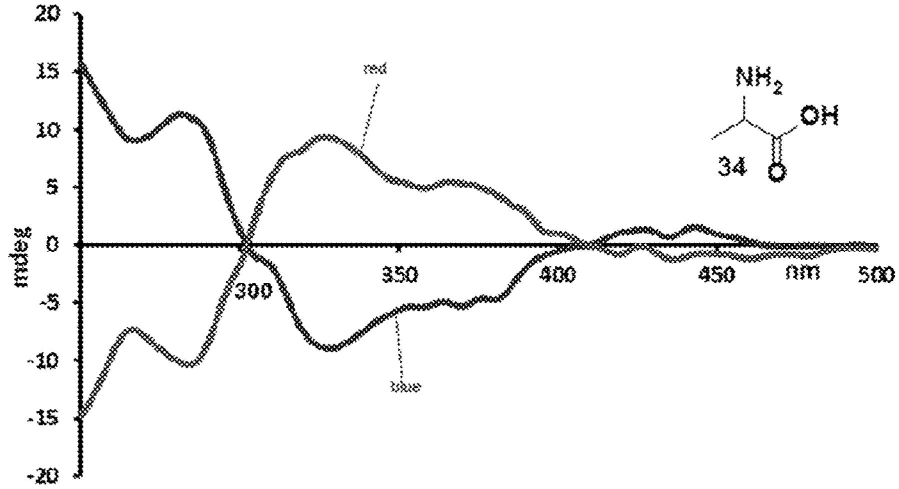

FIG. 131 is the CD spectra obtained from probe 65 with (R)-34 (red) and (S)-34 (blue).

Figure 132:
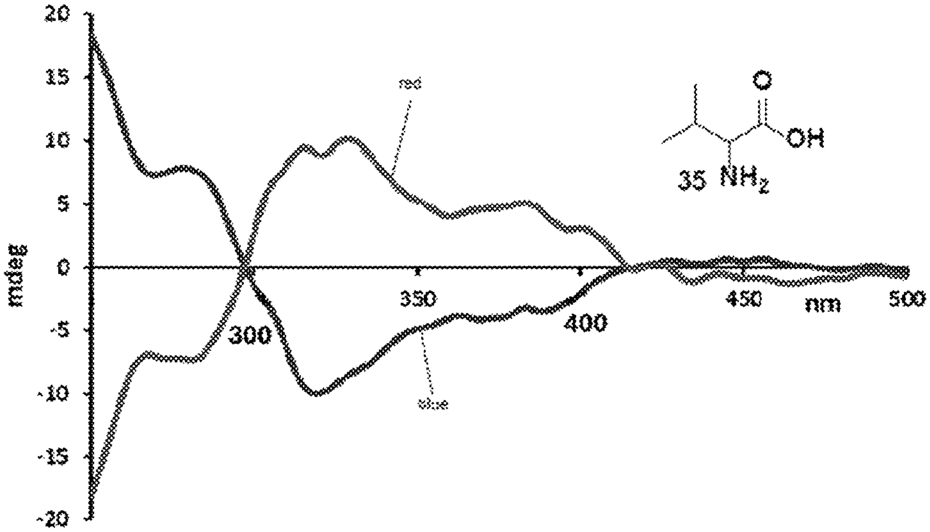

FIG. 132 is the CD spectra obtained from probe 65 with (R)-35 (red) and (S)-35 (blue).

Figure 133:
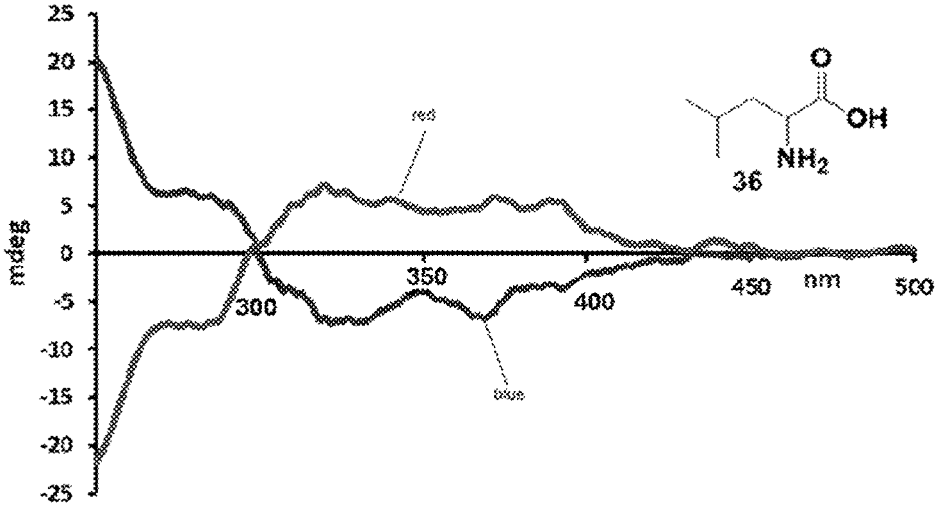

FIG. 133 is the CD spectra obtained from probe 65 with (R)-36 (red) and (S)-36 (blue).

Figure 134:
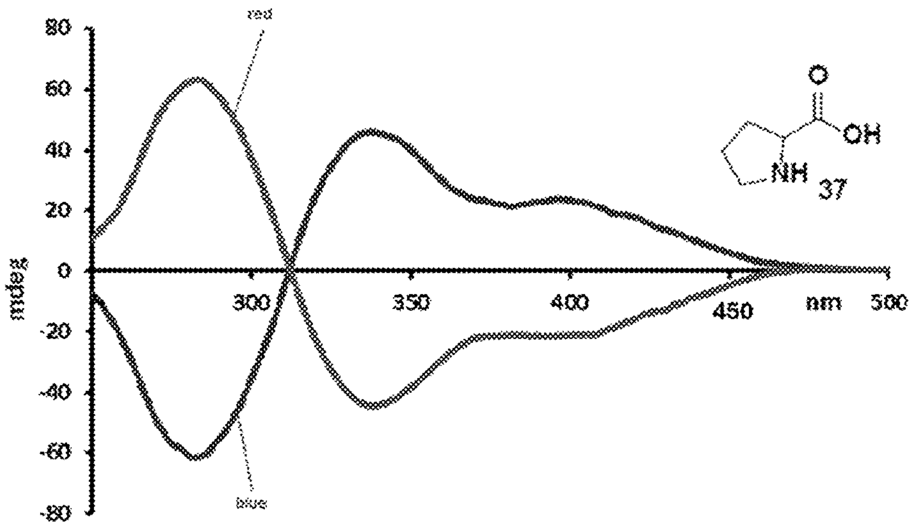

FIG. 134 is the CD spectra obtained from probe 65 with (S)-37 (red) and (R)-37 (blue).

Figure 135:
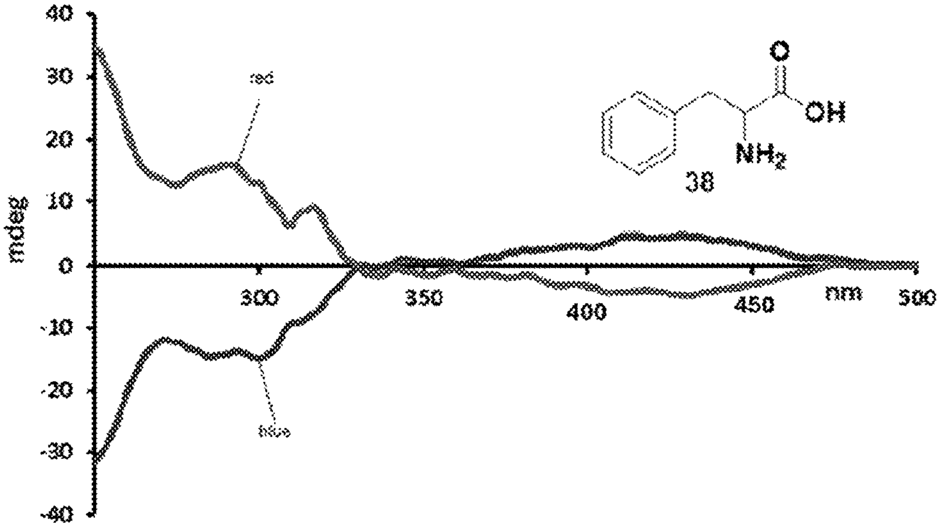

FIG. 135 is the CD spectra obtained from probe 65 with (S)-38 (red) and (R)-38 (blue).

Figure 136:
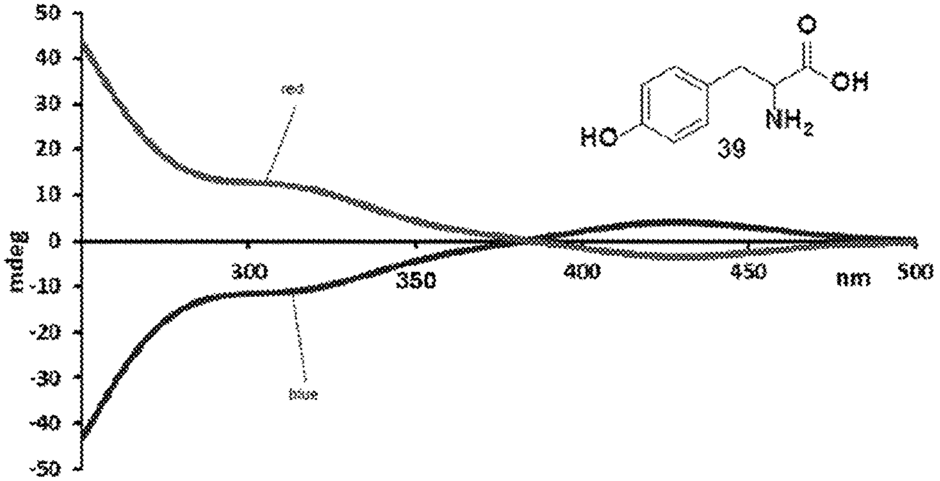

FIG. 136 is the CD spectra obtained from probe 65 with (S)-39 (red) and (R)-39 (blue).

Figure 137:
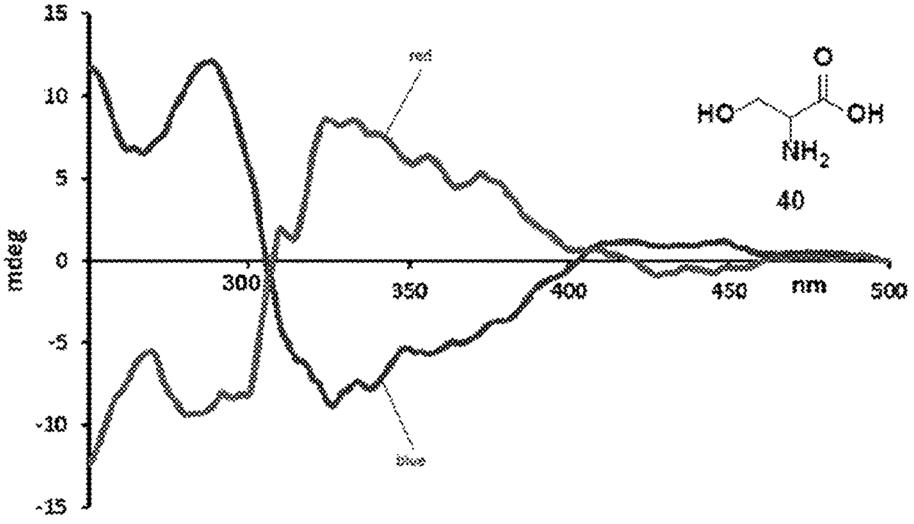

FIG. 137 is the CD spectra obtained from probe 65 with (R)-40 (red) and (S)-40 (blue).

Figure 138:
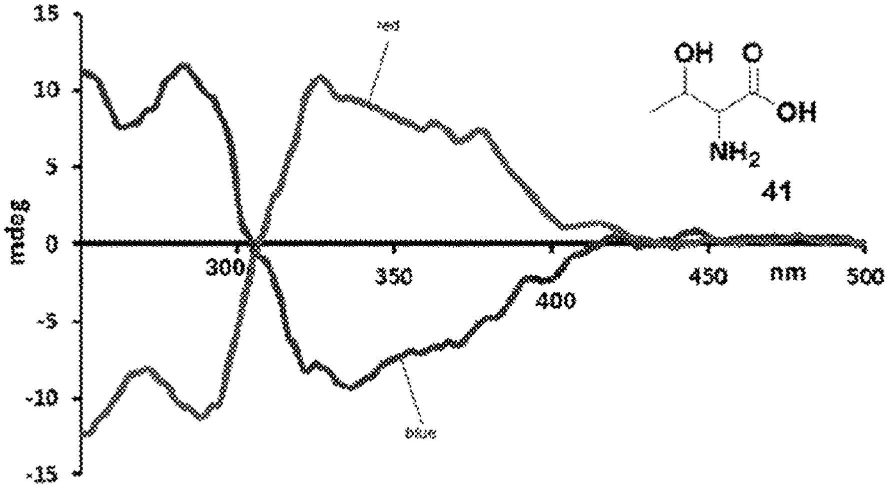

FIG. 138 is the CD spectra obtained from probe 65 with (S)-41 (red) and (R)-41 (blue).

Figure 139:
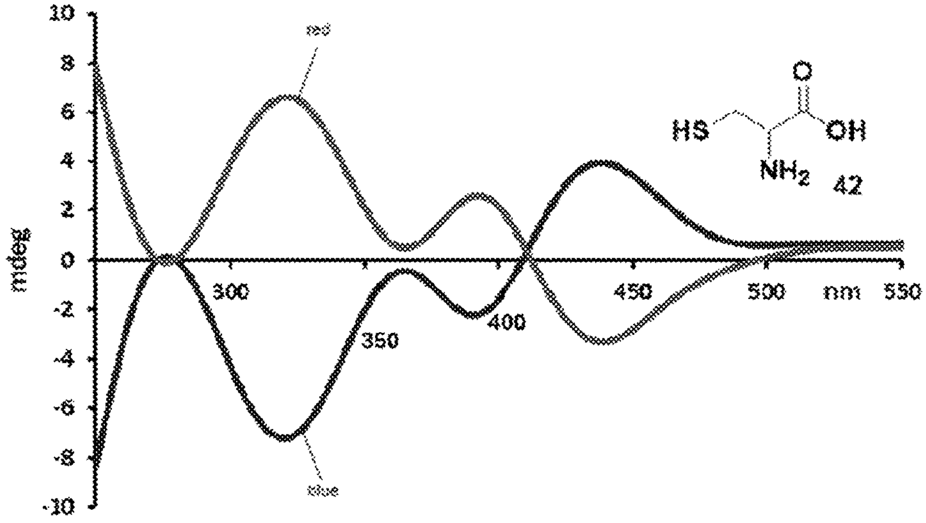

FIG. 139 is the CD spectra obtained from probe 65 with (R)-42 (red) and (S)-42 (blue).

Figure 140:
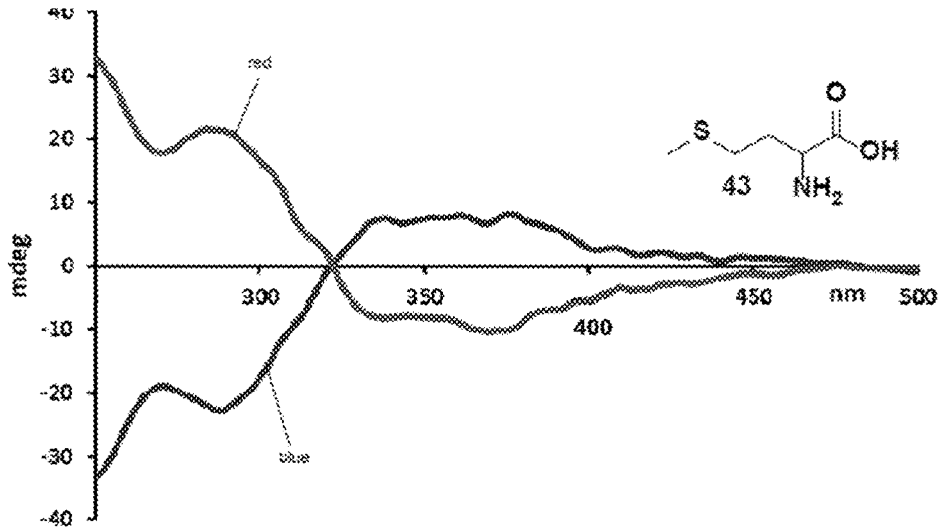

FIG. 140 is the CD spectra obtained from probe 65 with (S)-43 (red) and (R)-43 (blue).

Figure 141:
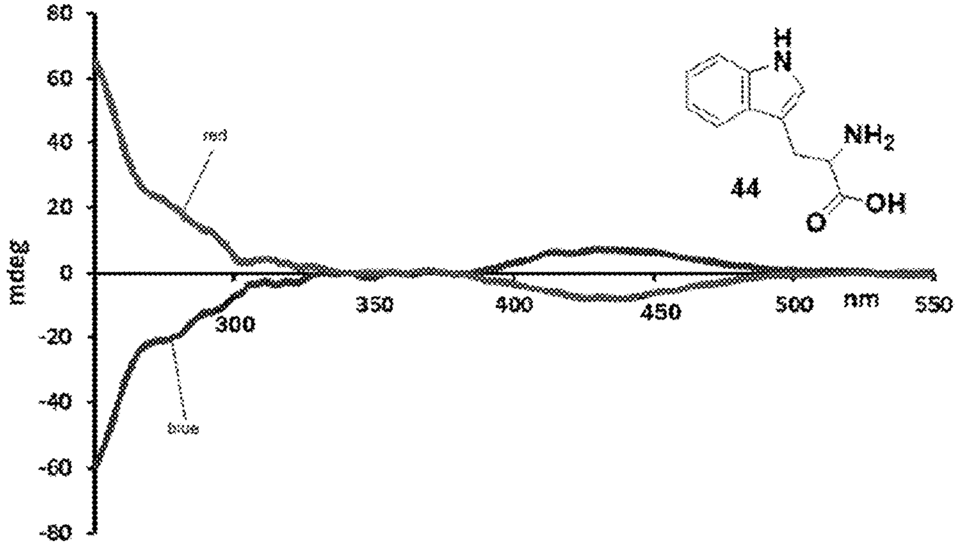

FIG. 141 is the CD spectra obtained from probe 65 with (S)-44 (red) and (R)-44 (blue).

Figure 142:
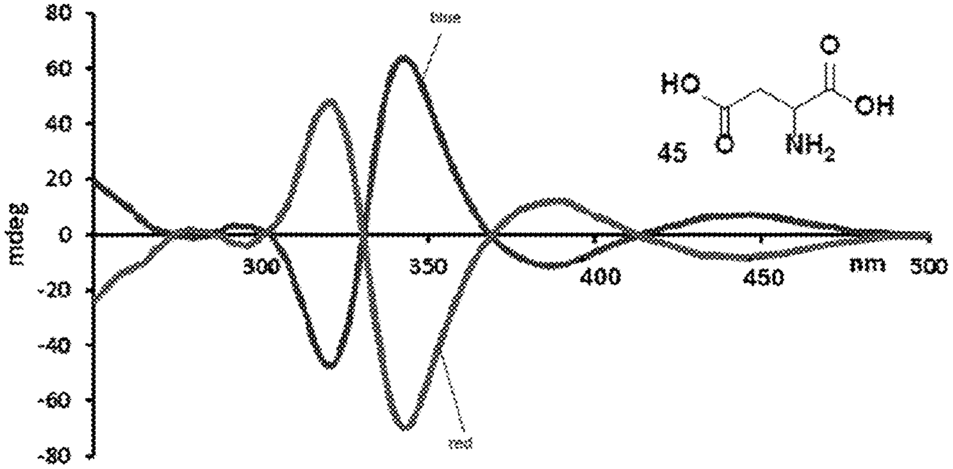

FIG. 142 is the CD spectra obtained from probe 65 with (R)-45 (red) and (S)-45 (blue).

Figure 143:
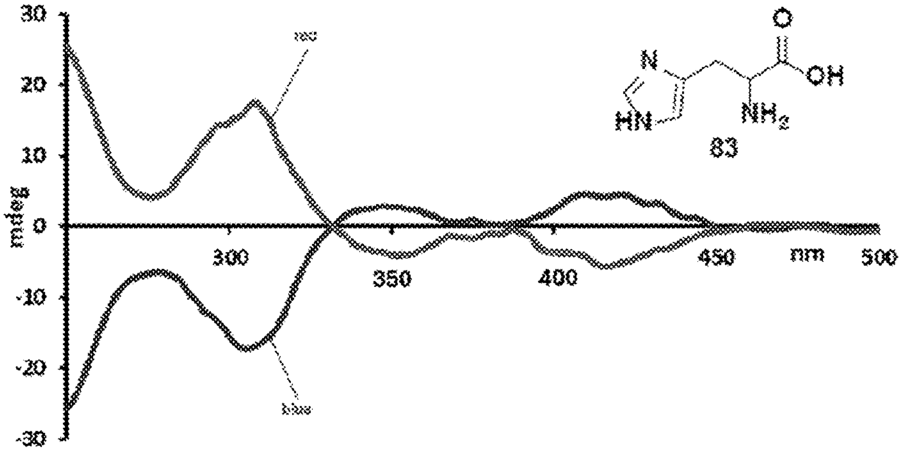

FIG. 143 is the CD spectra obtained from probe 65 with (S)-83 (red) and (R)-83 (blue).

Figure 144:
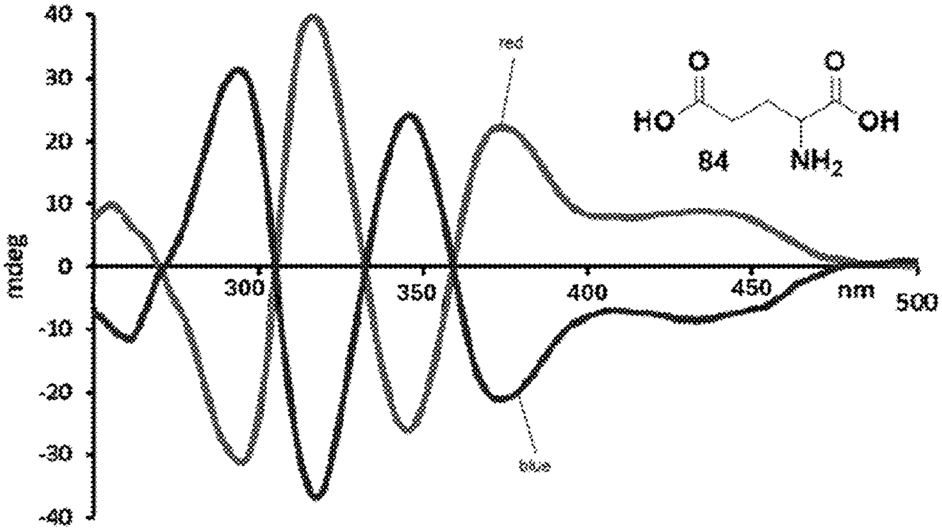

FIG. 144 is the CD spectra obtained from probe 65 with (S)-84 (red) and (R)-84 (blue).

Figure 145:
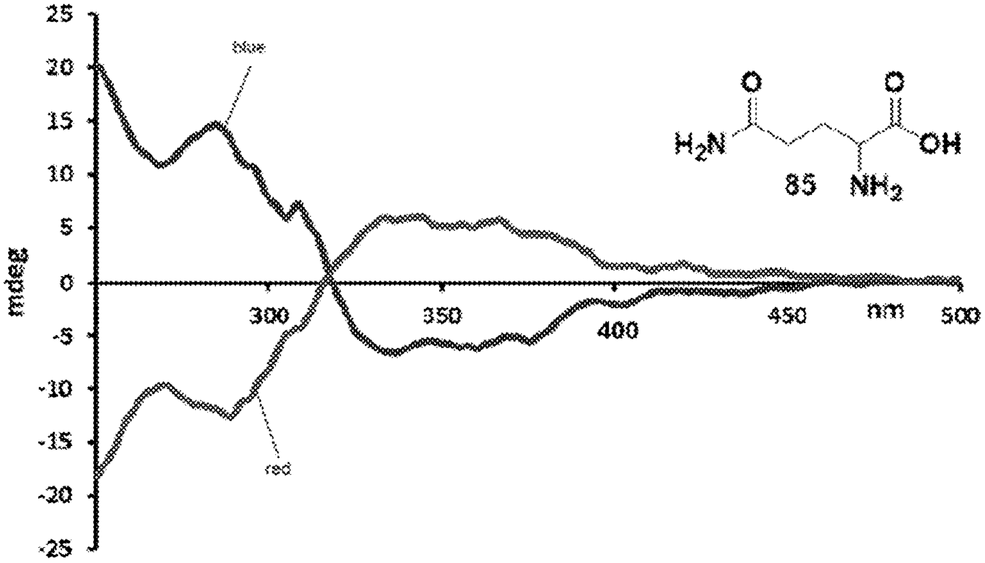

FIG. 145 is the CD spectra obtained from probe 65 with (R)-85 (red) and (S)-85 (blue).

Figure 146:
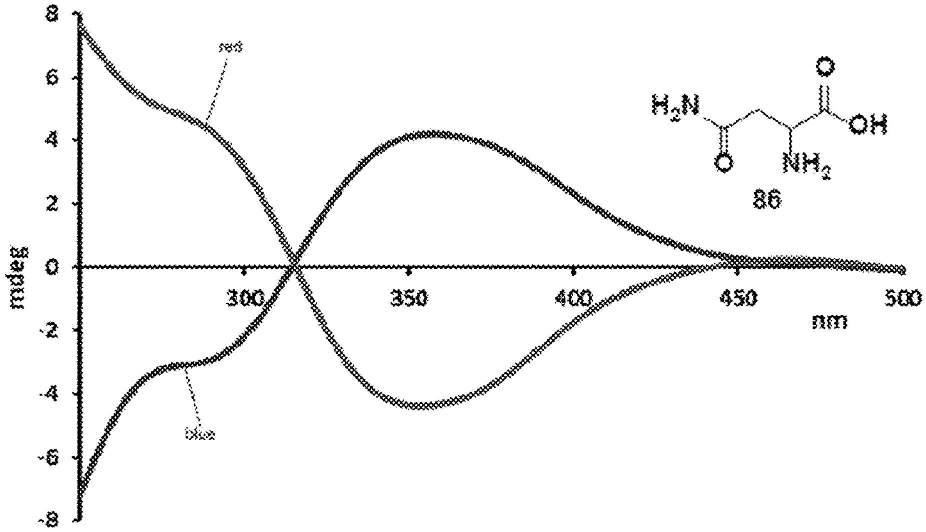

FIG. 146 is the CD spectra obtained from probe 65 with (S)-86 (red) and (R)-86 (blue).

Figure 147:
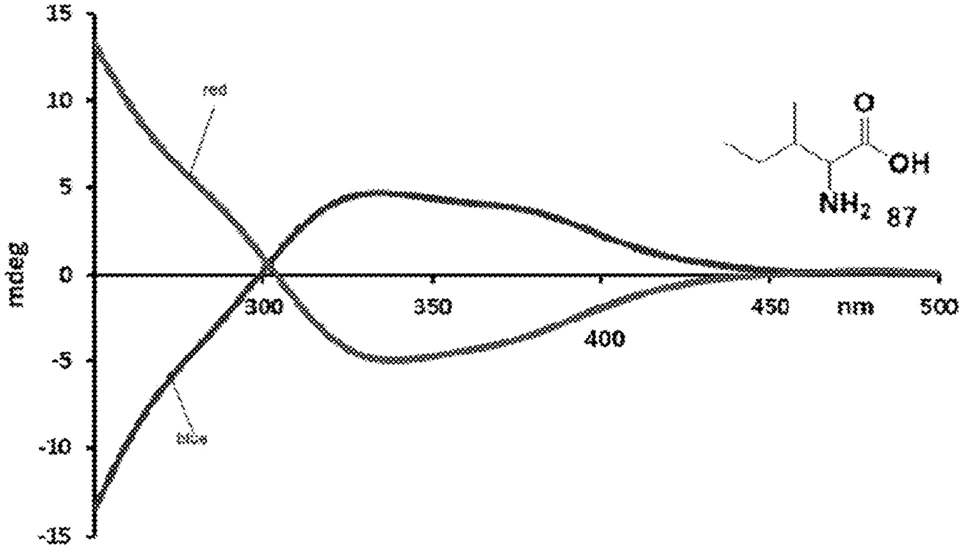

FIG. 147 is the CD spectra obtained from probe 65 with (S)-87 (red) and (R)-87 (blue).

Figure 148:
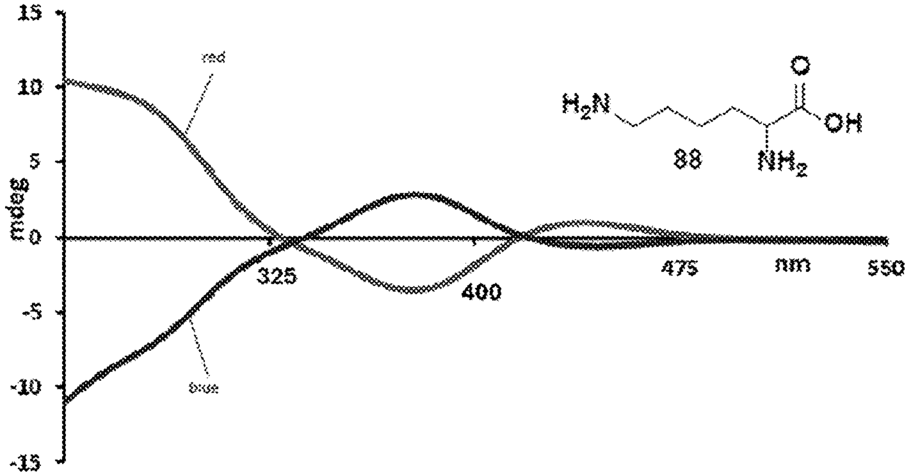

FIG. 148 is the CD spectra obtained from probe 65 with (R)-88 (red) and (S)-88 (blue).

Figure 149:
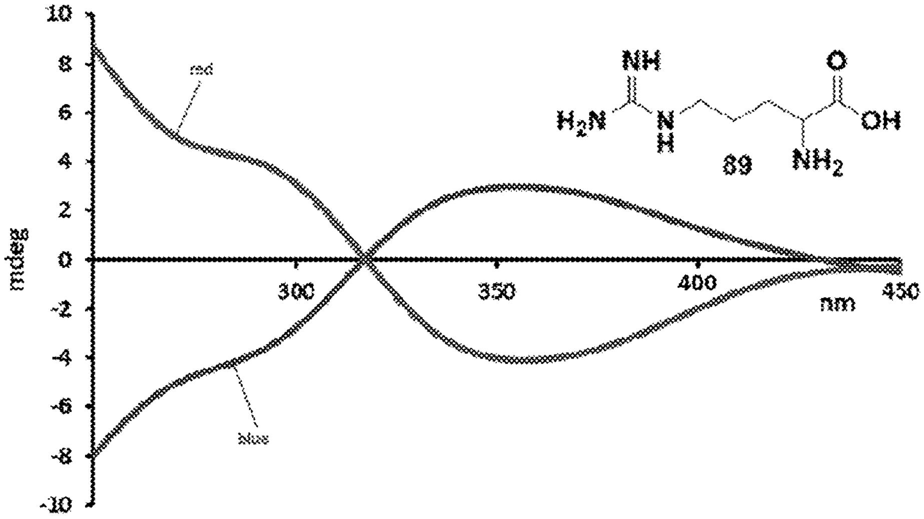

FIG. 149 is the CD spectra obtained from probe 65 with (S)-89 (red) and (R)-89 (blue).

Figure 150:
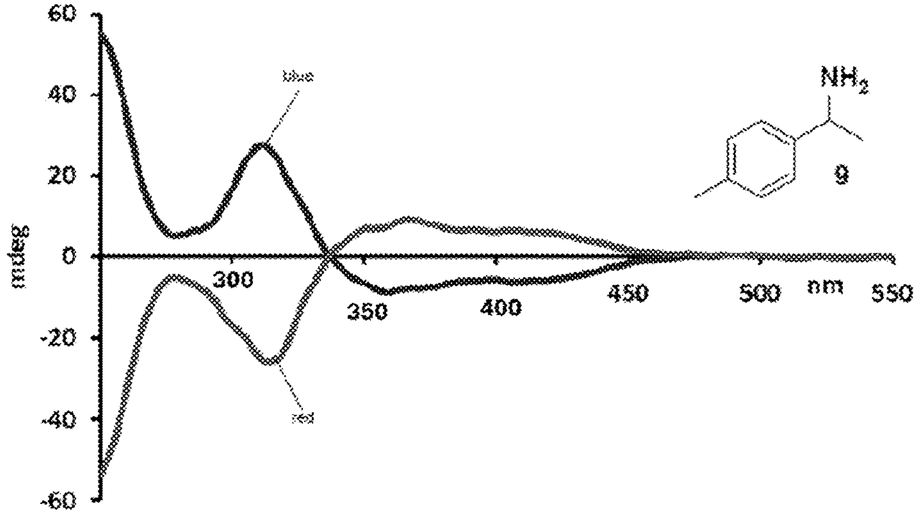

FIG. 150 is the CD spectra obtained from probe 65 with (S)-9 (red) and (R)-9 (blue). The CD measurements were taken at 0.09 mM in chloroform.

Figure 151:
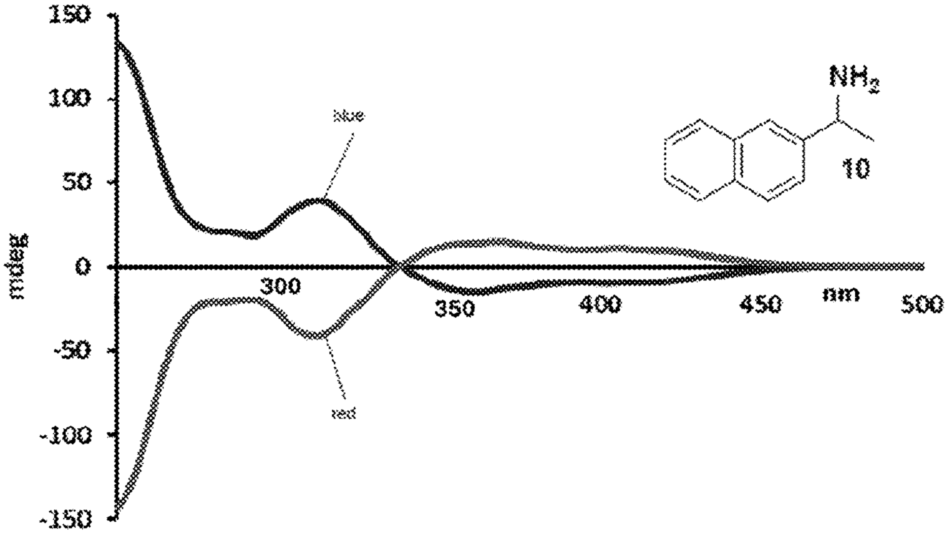

FIG. 151 is the CD spectra obtained from probe 65 with (S)-10 (red) and (R)-10 (blue). The CD measurements were taken at 0.09 mM in chloroform.

Figure 152:
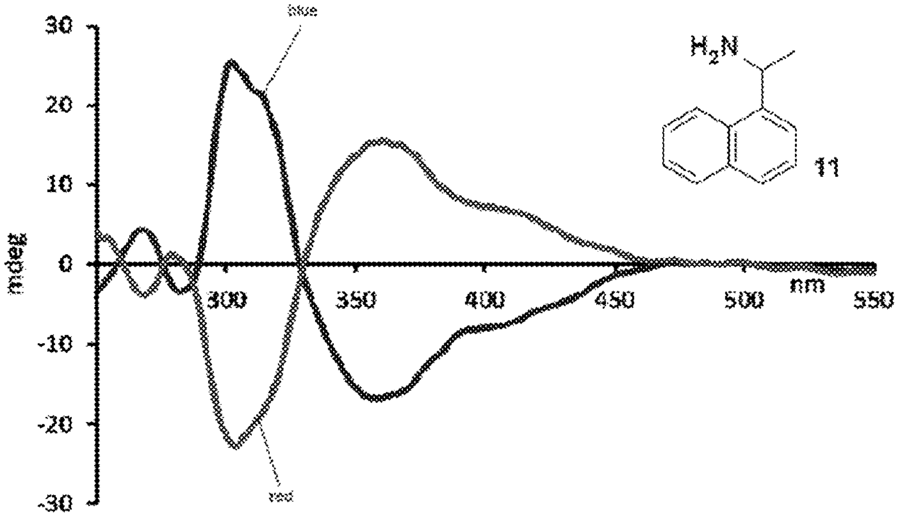

FIG. 152 is the CD spectra obtained from probe 65 with (S)-11 (red) and (R)-11 (blue). The CD measurements were taken at 0.09 mM in chloroform.

Figure 153:
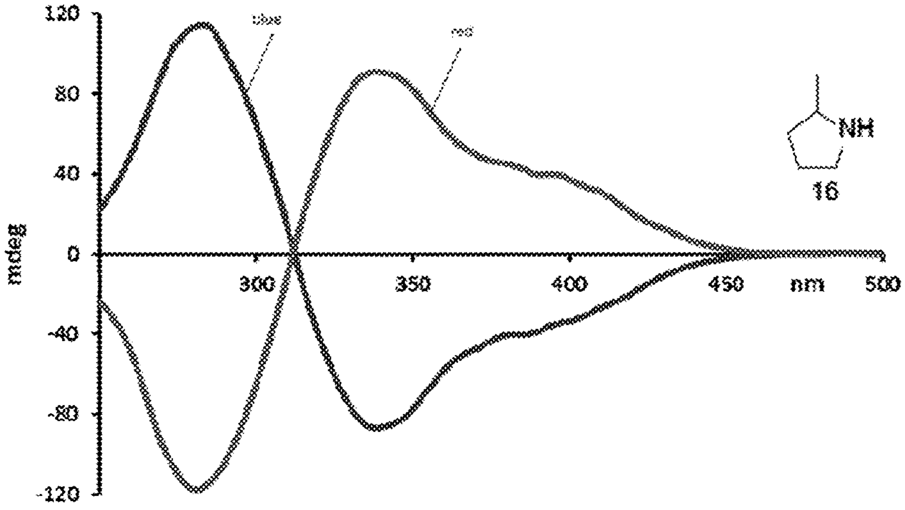

FIG. 153 is the CD spectra obtained from probe 65 with (S)-16 (red) and (R)-16 (blue). The CD measurements were taken at in 0.079 mM chloroform.

Figure 154:
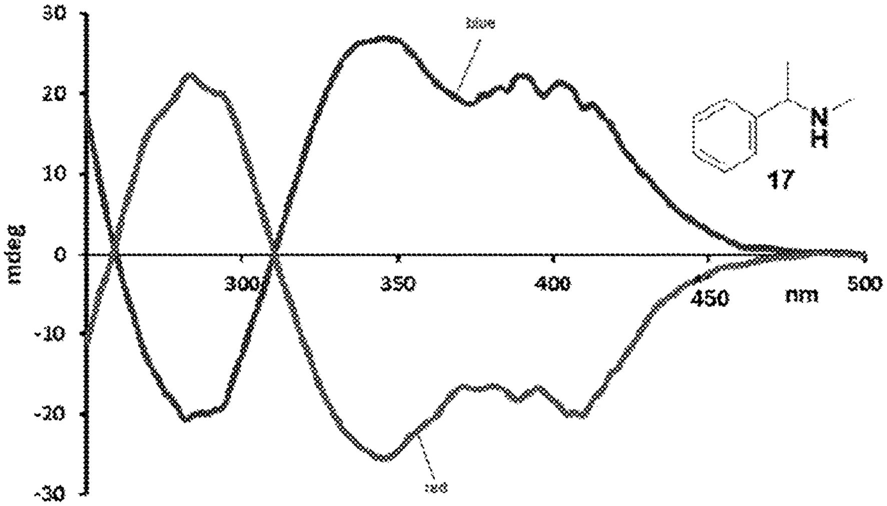

FIG. 154 is the CD spectra obtained from probe 65 with (S)-17 (red) and (R)-17 (blue). The CD measurements were taken at 0.060 mM in chloroform.

Figure 155:
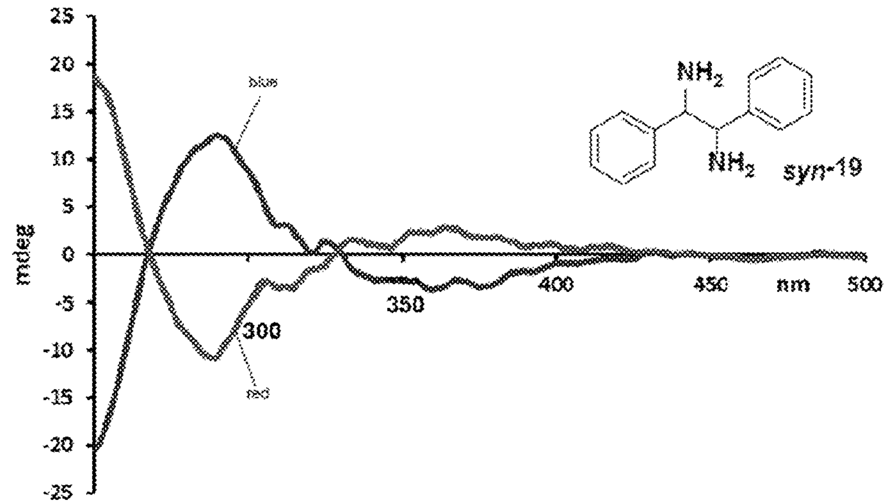

FIG. 155 is the CD spectra obtained from probe 65 (2 equivalents) with (1S,2S)-19 (red) and (1R,2R)-19 (blue). The CD measurements were taken after at 0.05 mM in chloroform.

Figure 156:
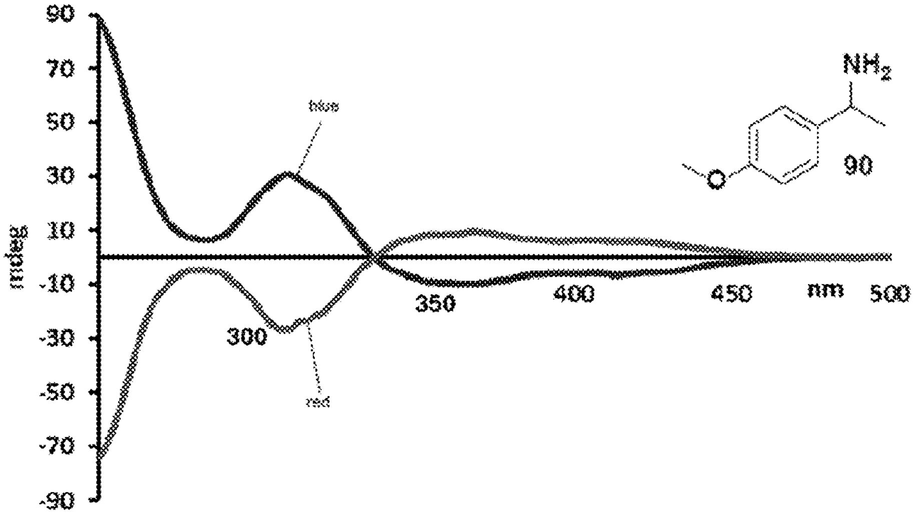

FIG. 156 is the CD spectra obtained from probe 65 with (S)-90 (red) and (R)-90 (blue). The CD measurements were taken at 0.09 mM in chloroform.

Figure 157:
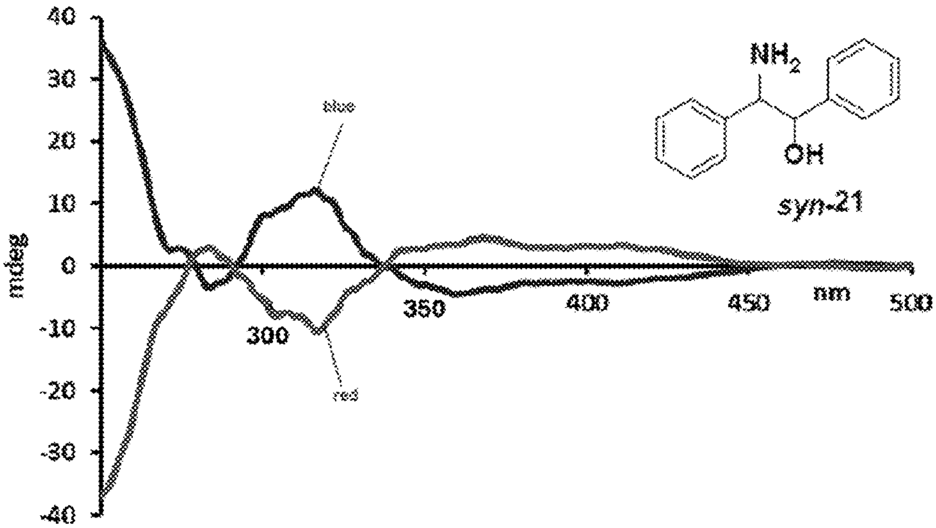
Figure 158:
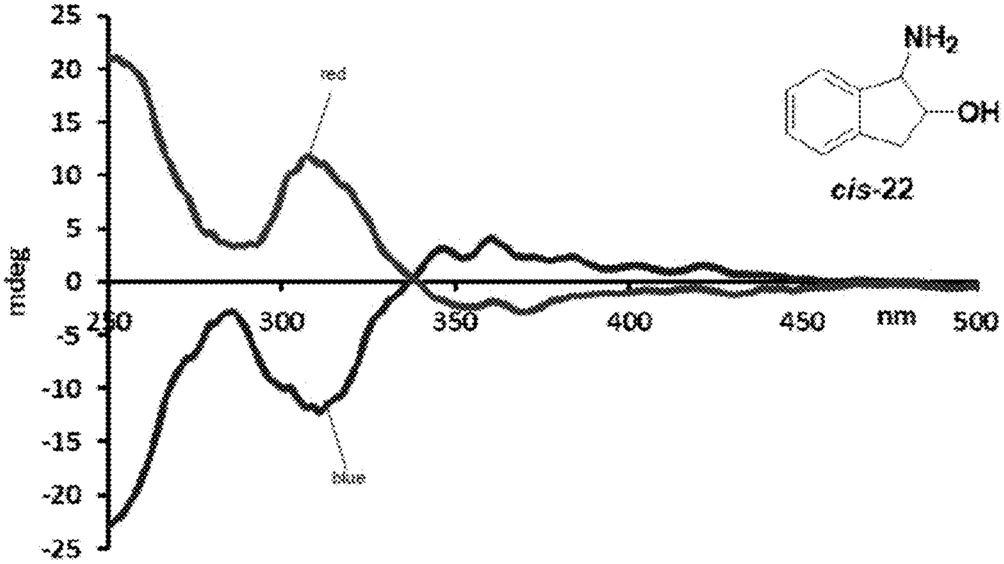

FIG. 157 is the CD spectra obtained from probe 65 with (1S,2R)-21 (red) and (1R,2S)-21 (blue). CD measurements were taken at 0.12 mM in chloroform FIG. 158 is the CD spectra obtained from probe 65 with (1S,2R)-22 (red) and (1R,2S)-22 (blue). The CD measurements were taken at 0.12 mM in chloroform.

Figure 159:
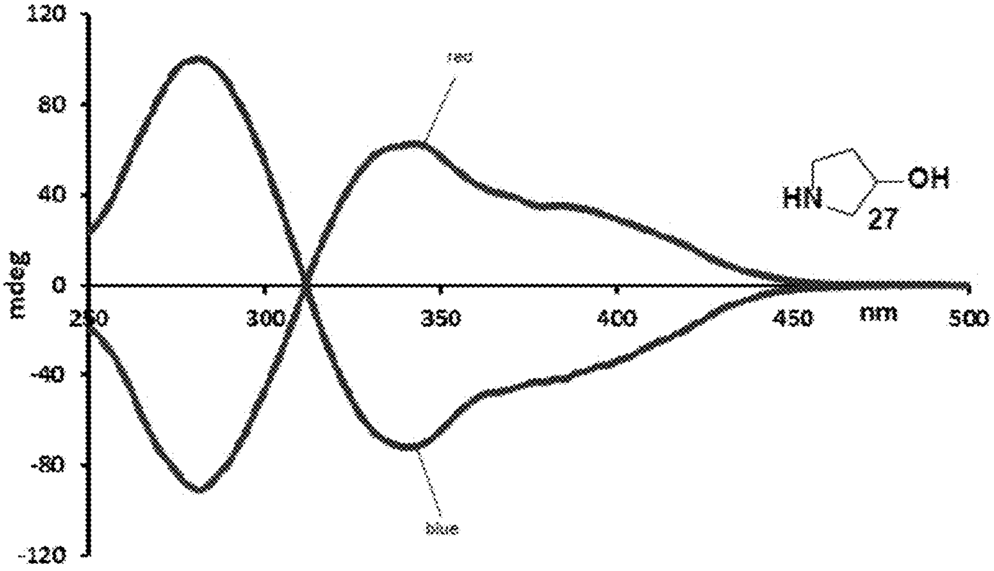

FIG. 159 is the CD spectra obtained from probe 65 with (S)-27 (red) and (R)-27 (blue). The CD measurements were taken at 0.079 mM in chloroform.

Figure 160:
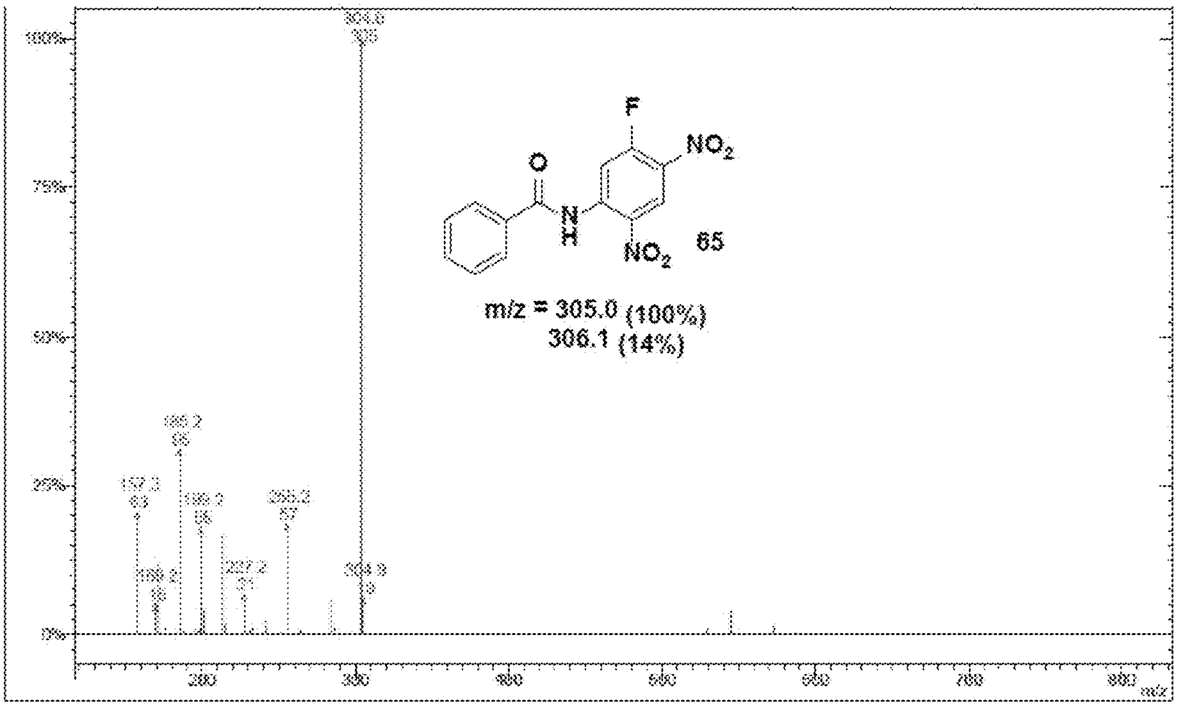

FIG. 160 is the electrospray ionization mass spectrometry (ESI-MS) spectrum of the probe 65 (negative mode).

Figure 161:
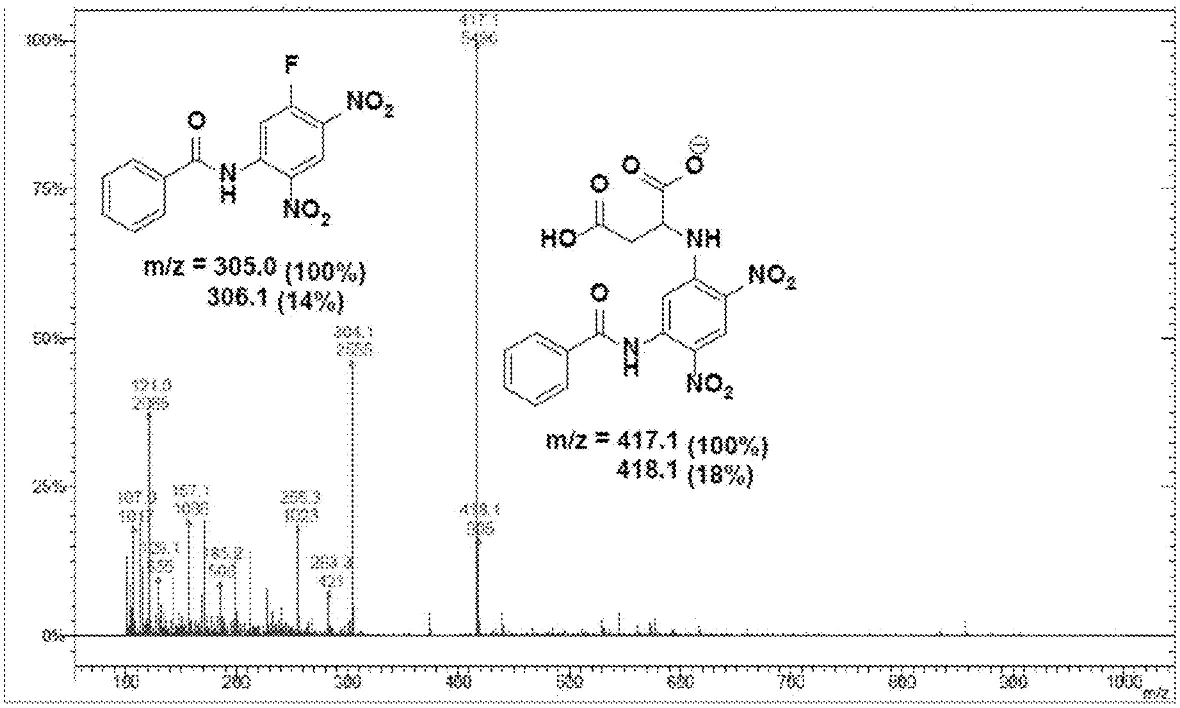

FIG. 161 is the ESI-MS spectrum of the reaction between (R)-aspartic acid (45) (4 mM) and probe 65 (4.8 mM) (negative mode).

Figure 162:
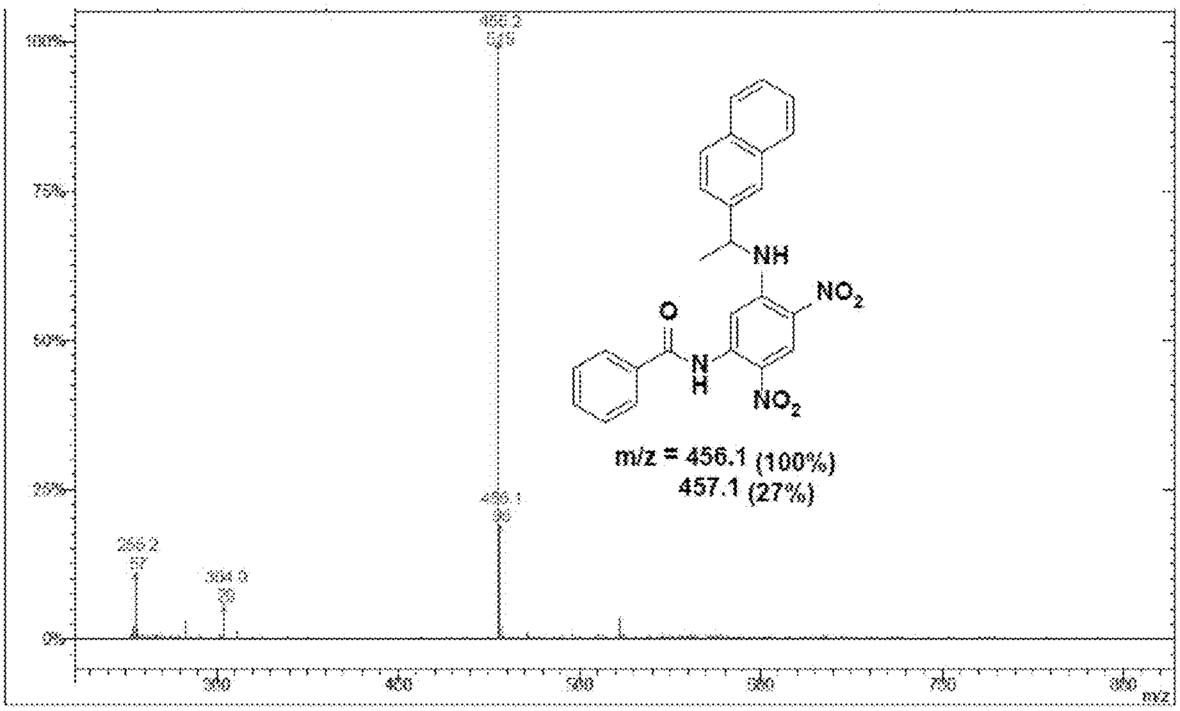

FIG. 162 is the ESI-MS spectrum of the isolated product between (R)-1-(2-naphthylethylamine) (10) and probe 65 (negative mode).

Figure 163:
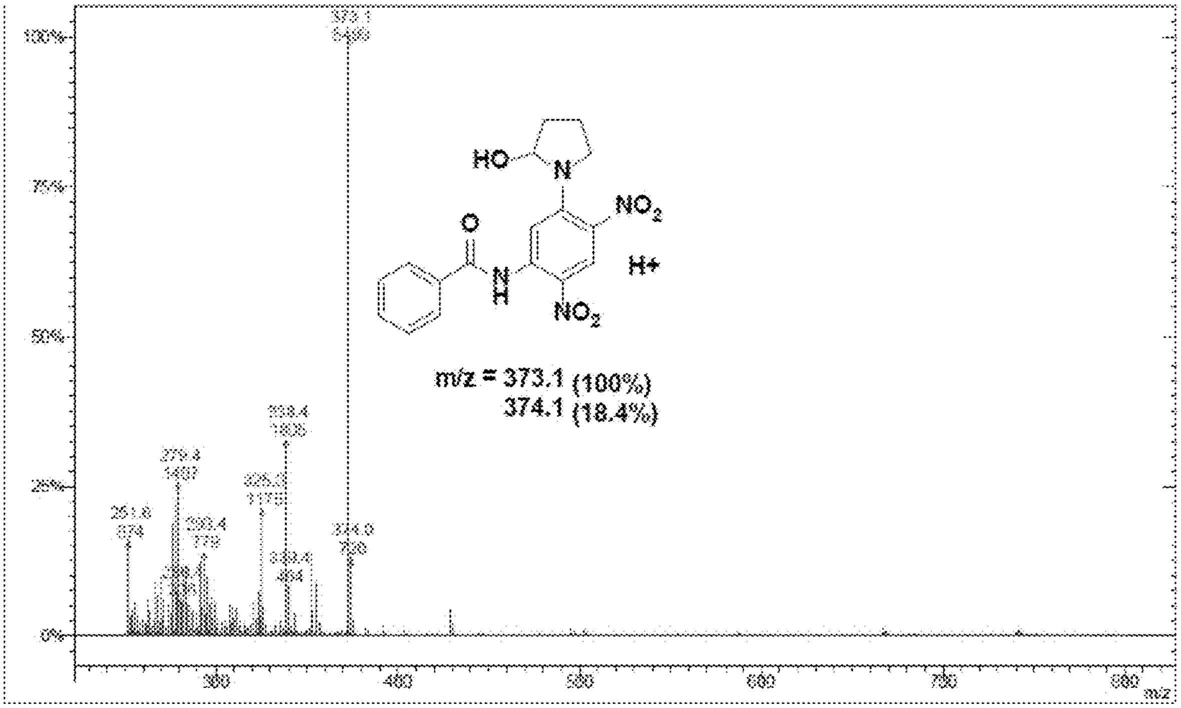

FIG. 163 is the ESI-MS spectrum of the isolated product between (R)-2-pyrrolidinol (27) and probe 65 (positive mode).

Figure 164:
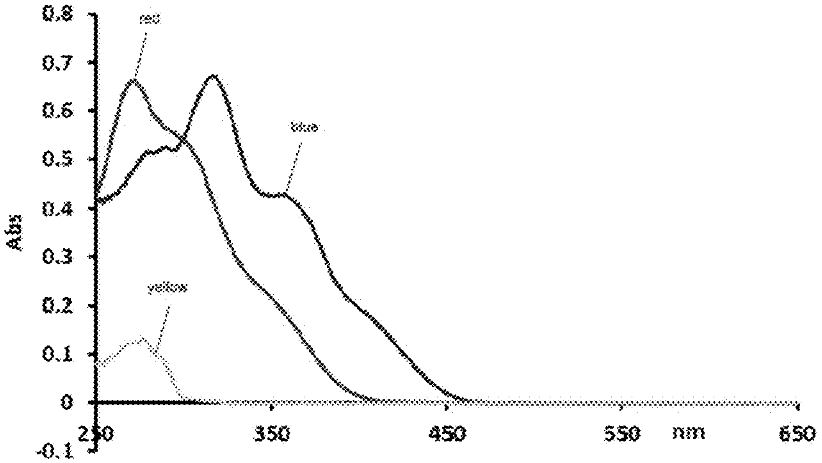

FIG. 164 shows the UV change of the reaction between probe 65 and (R)-1-(2-naphthyl)ethylamine (10). Reaction mixture (blue), probe 65 (red) and (R)-1-(2-naphthyl)ethylamine (10) (yellow). All UV measurements were taken at 0.02 mM in chloroform.

Figure 165:
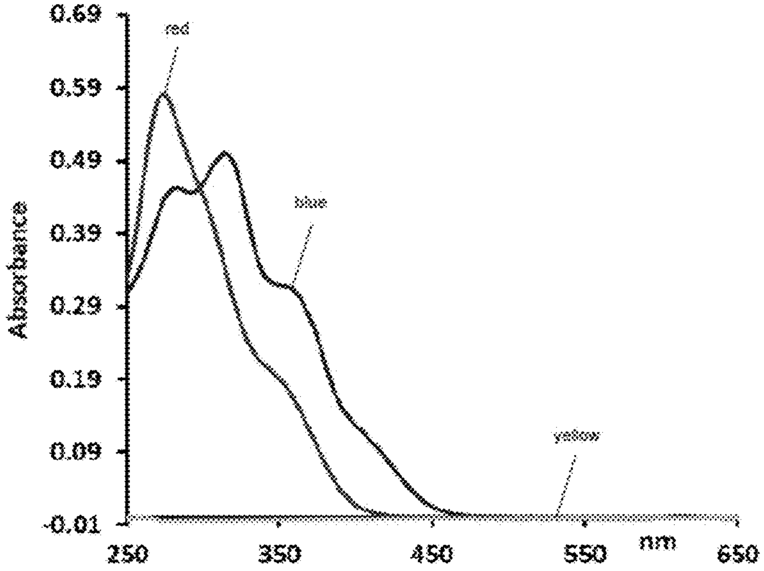

FIG. 165 shows the UV change of the reaction between probe 65 and (S)-1-phenylethylamine (8). Sensing mixture (blue), probe 65 (red) and (S)-1-phenylethylamine (8) (yellow). All UV measurements were taken at 0.02 mM in chloroform.

Figure 166:
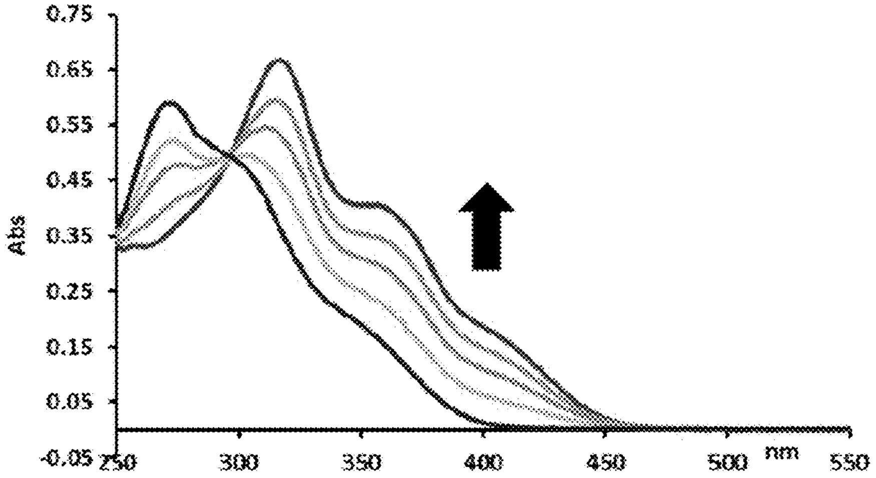

FIG. 166 is the UV spectra obtained from the reaction between probe 65 and varying amounts of (R)-1-phenylethylamine (8).

Figure 167:
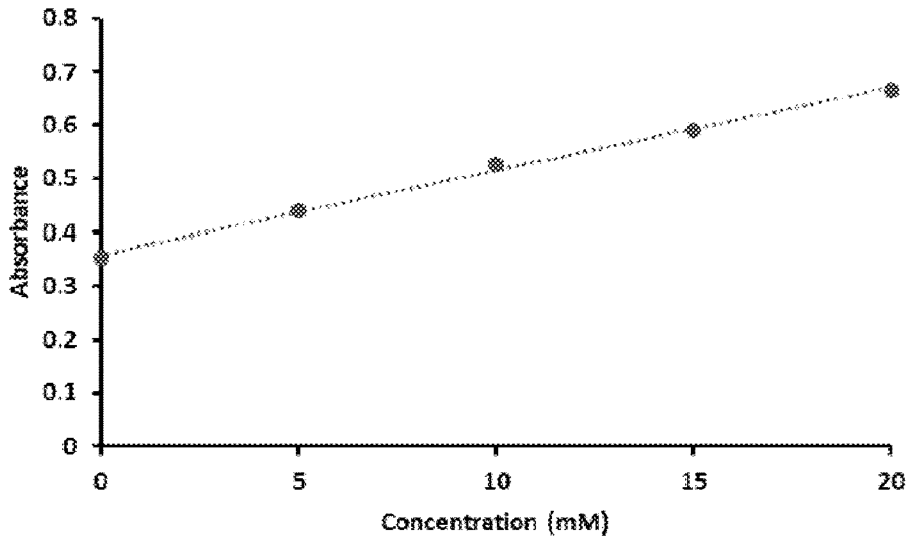

FIG. 167 shows the absorbance at 318 nm of the reaction mixture of probe 65 and varying amounts of (R)-1-phenylethylamine (8), plotted against the concentration of (R)-1-phenylethylamine (8).

Figure 168:
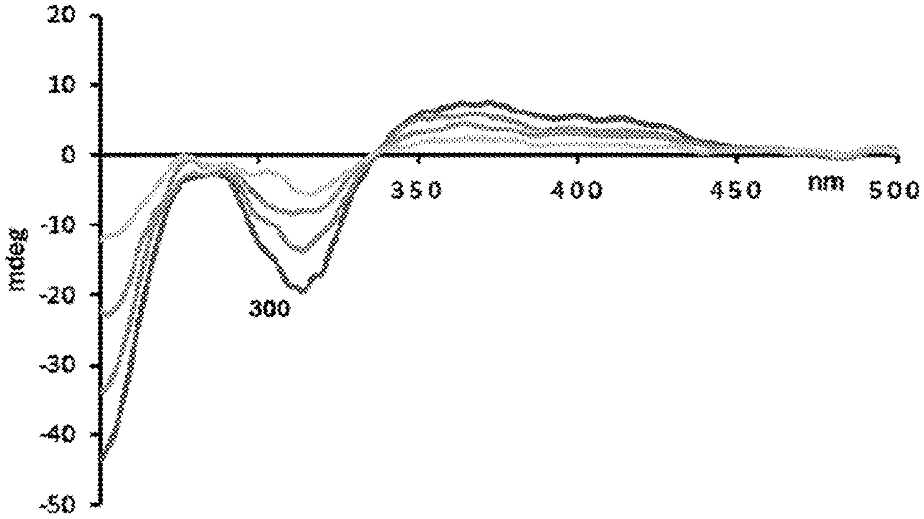

FIG. 168 is the CD spectra obtained from the reaction between probe 65 and varying amounts of (R)-1-phenylethylamine (8).

Figure 169:
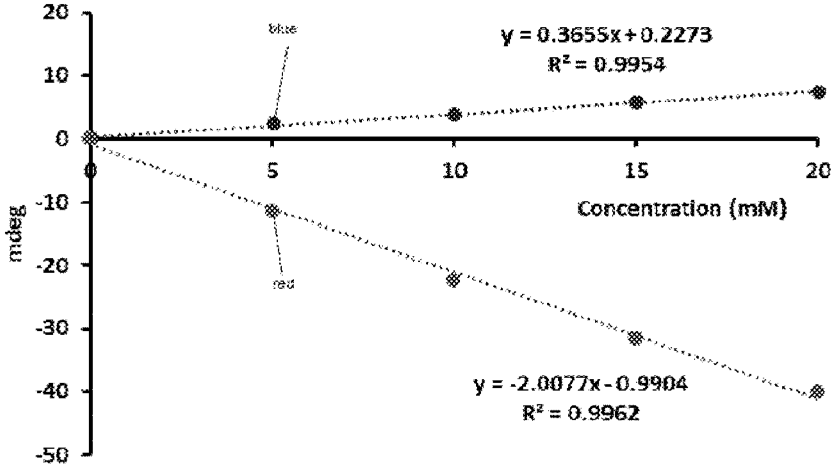

FIG. 169 is the CD amplitude at 371 nm (blue) and 254 nm (red) of the reaction mixture of probe 65 and varying amounts of (R)-1-phenylethylamine (8), plotted against the concentration of (R)-1-phenylethylamine (8).

Figure 170:
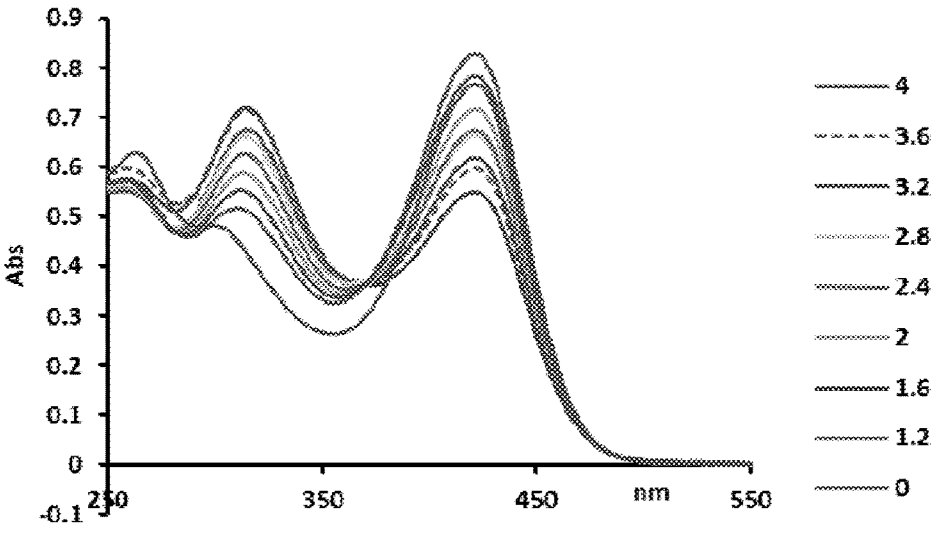

FIG. 170 is the UV spectra obtained from the reaction between probe 65 and varying amounts of (R)-aspartic acid (45).

Figure 171:
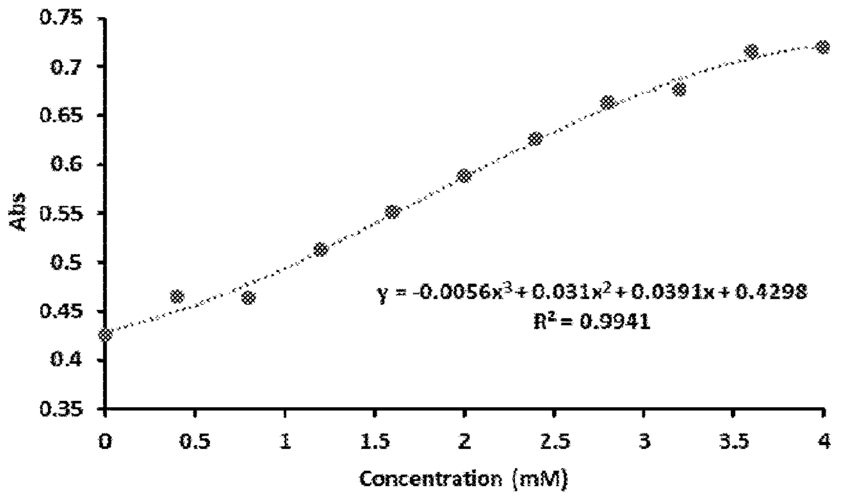

FIG. 171 shows the absorbance at 315 nm of the reaction mixture of probe 65 and varying amounts of (R)-aspartic acid (45), plotted against the concentration of (R)-aspartic acid (45).

Figure 172:
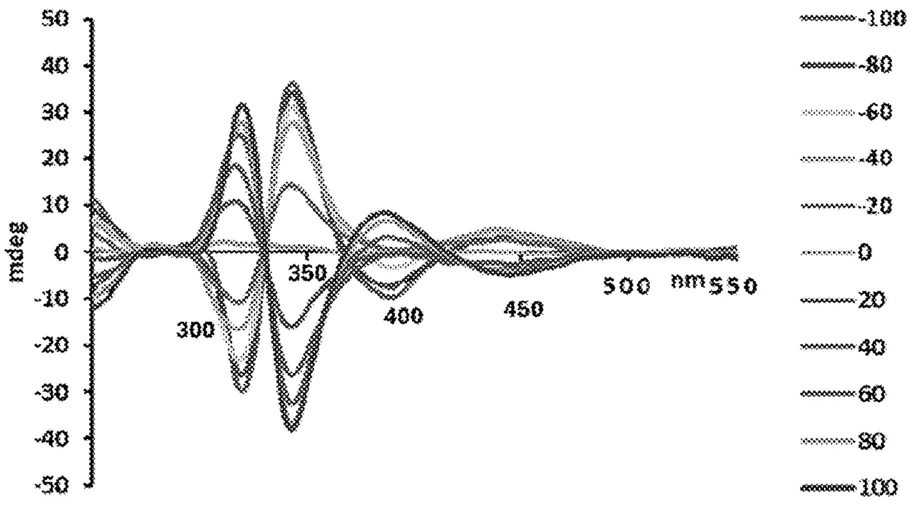

FIG. 172 shows the chiroptical response of probe 65 to scalemic samples of aspartic acid (45).

Figure 173:
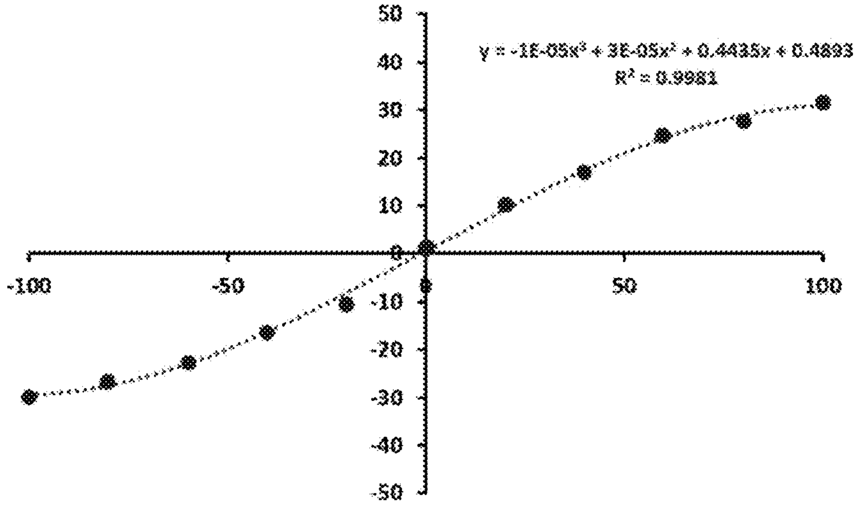

FIG. 173 is the plot of the CD amplitudes at 320 nm of the chiroptical response of probe 65 to scalemic samples of aspartic acid (45) versus sample ee.

Figure 174:
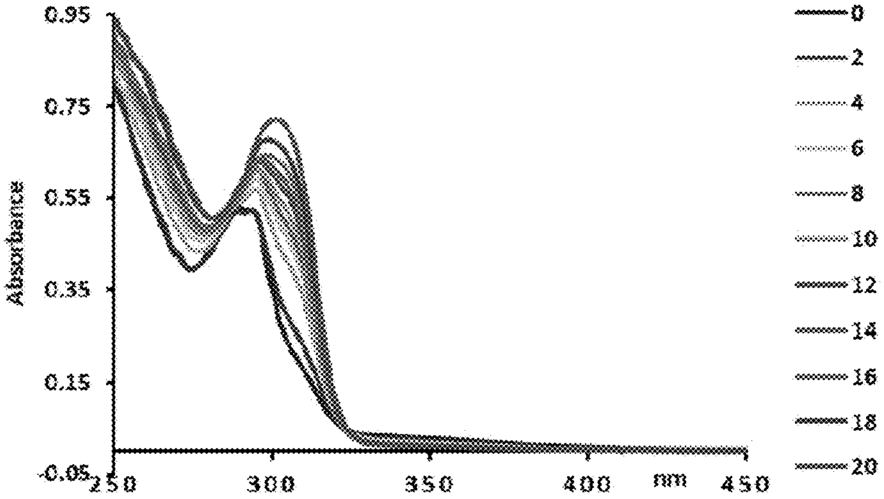

FIG. 174 is the UV spectra obtained from the reaction between probe 63 and varying amounts of (R)-1-phenylethanol (70).

Figure 175:
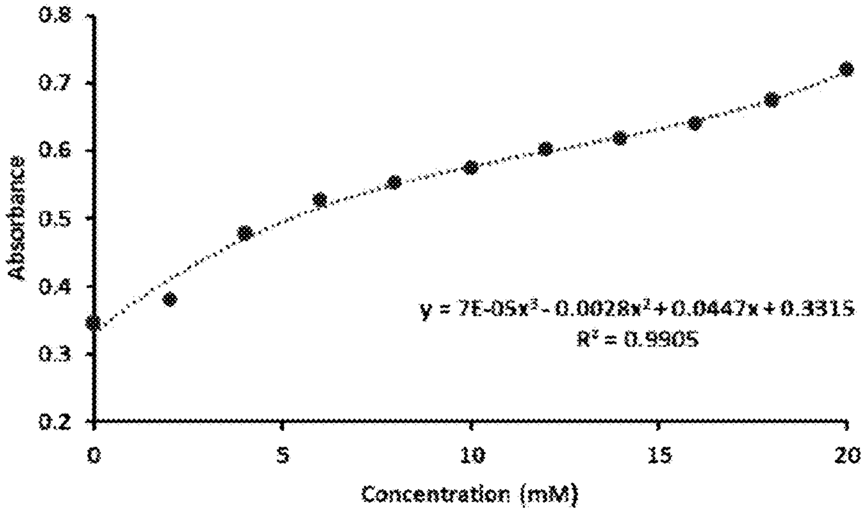

FIG. 175 shows the absorbance at 300.0 nm of the reaction of probe 63 and varying amounts of (R)-1-phenylethanol (70), plotted against the concentration of (R)-1-phenylethanol (70).

Figure 176:
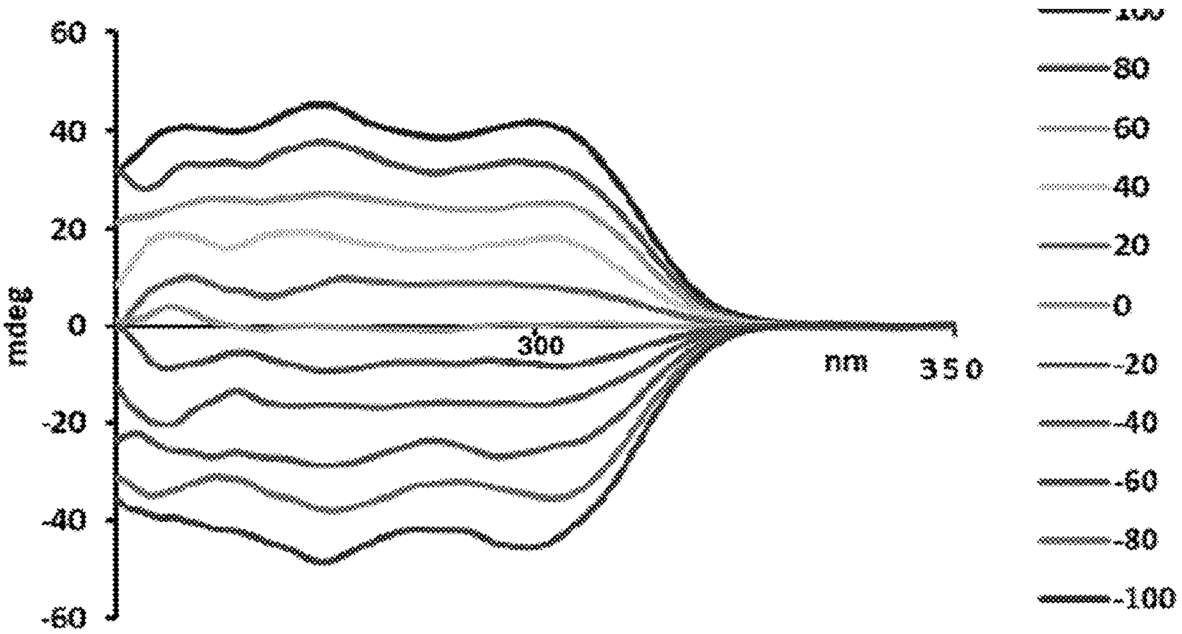

FIG. 176 shows the chiroptical response of probe 63 to scalemic samples of 1 phenylethanol (70).

Figure 177:
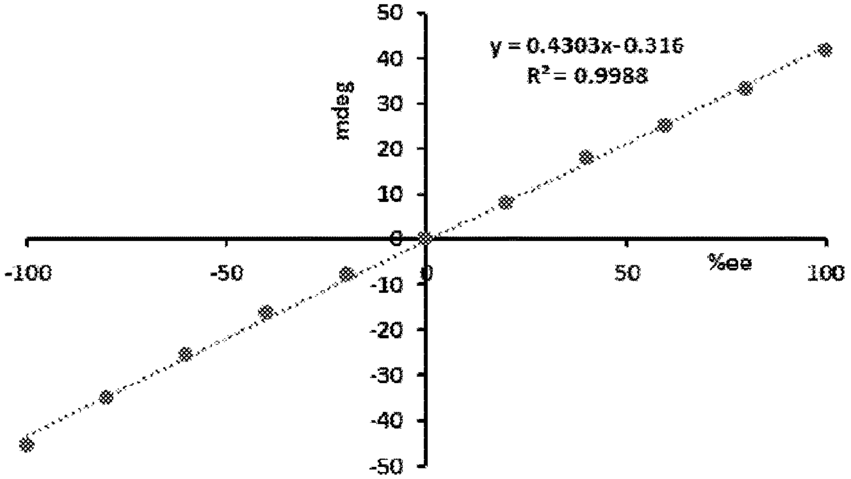

FIG. 177 shows the plot of the CD amplitudes at 300 nm of the chiroptical response of probe 63 to scalemic samples of 1-phenylethanol (70), versus sample % ee.

Figure 178A:
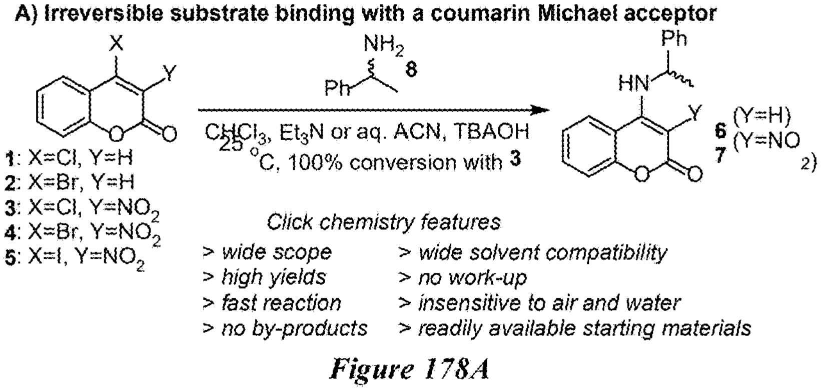
Figure 178B:
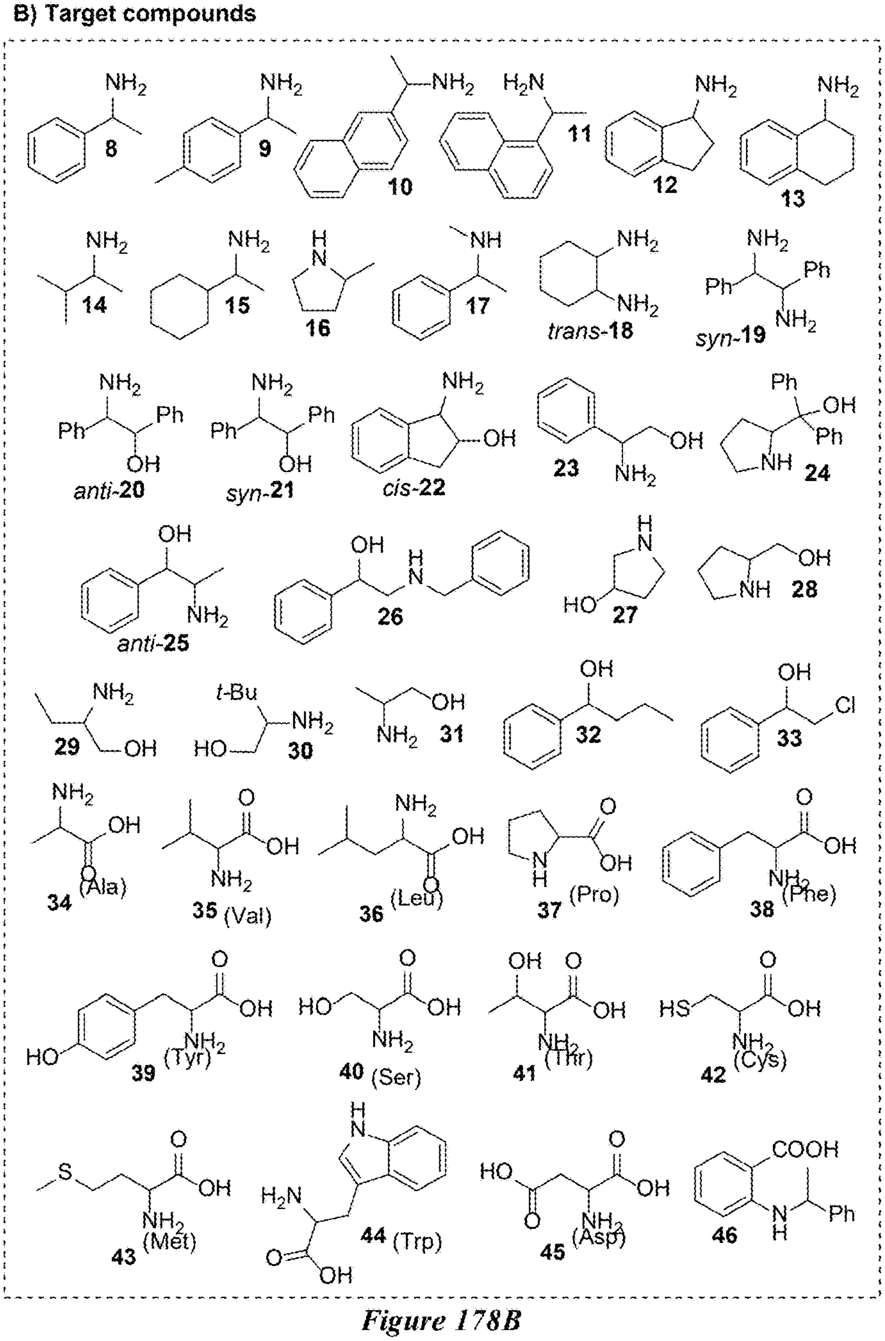
Figure 178C:
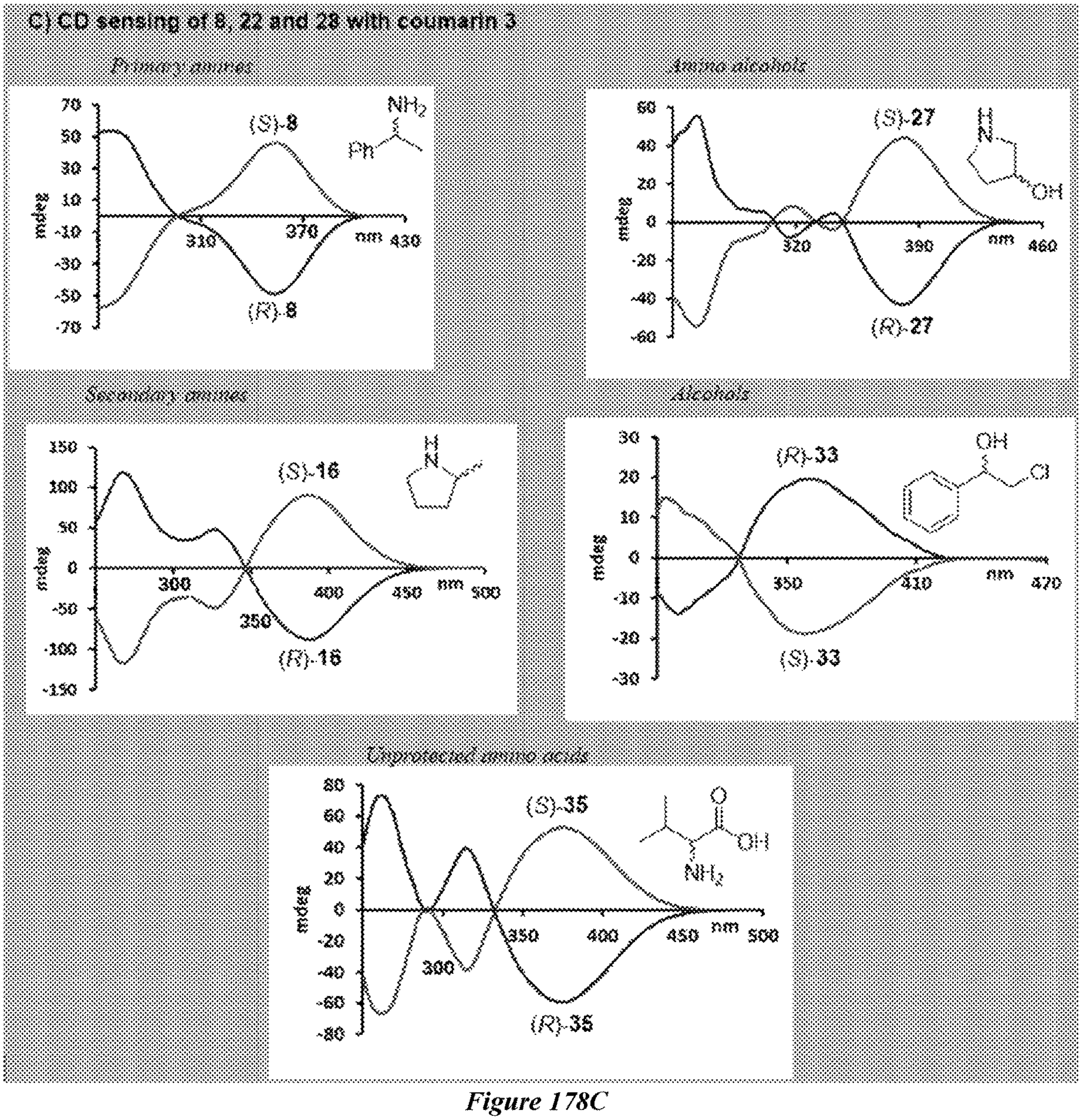

FIGS. 178A-178C show chiroptical click chemistry sensing (FIG. 178A), target scope (FIG. 178B), and selected examples of the distinct CD signals (FIG. 178C) obtained at high wavelengths using 3 as probe.

Figure 179:
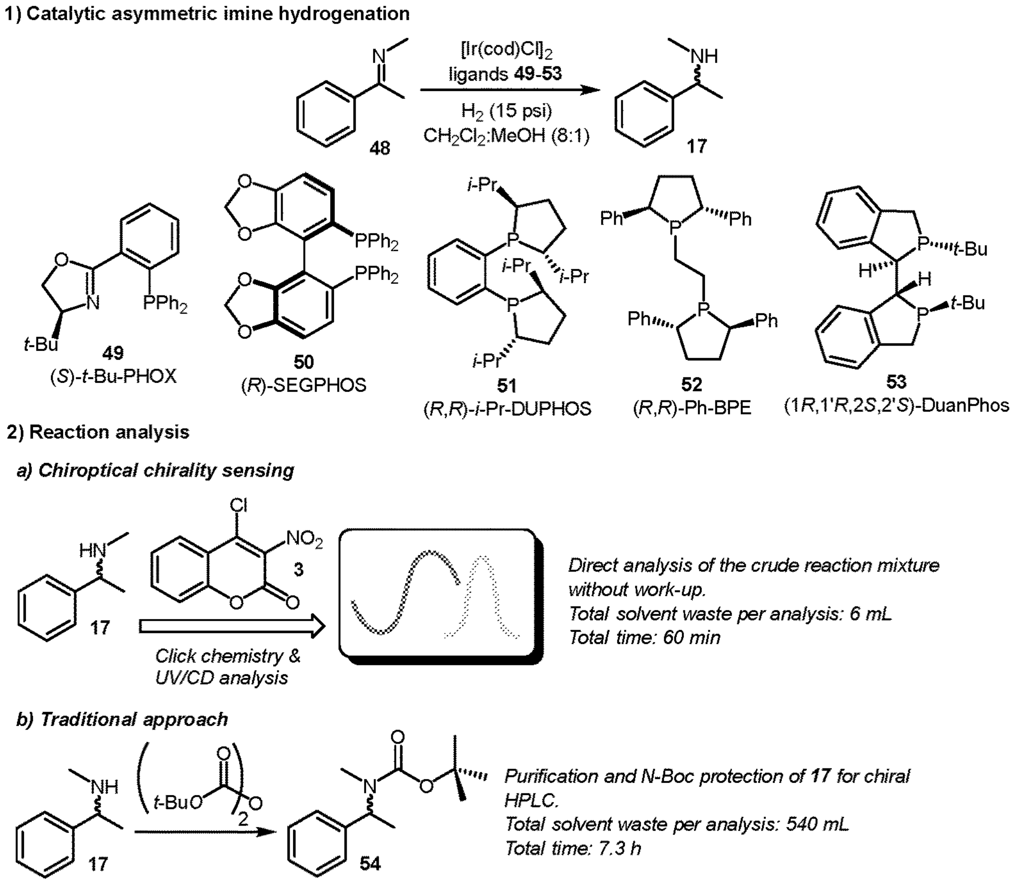

FIG. 179 shows the preparation of samples of amines in varying concentrations and ee's via asymmetric imine hydrogenation (top) and the chiroptical chirality sensing of the amines (bottom). The results of the UV/CD sensing are provided in Table 1.

Figure 180:
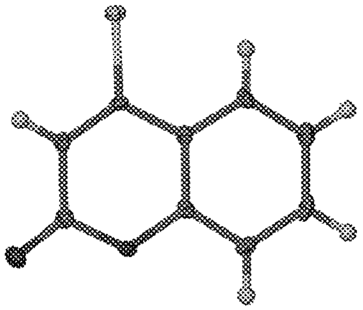

FIG. 180 shows the three-dimensional molecular structure for 4-chlorocoumarin (1).

Figure 181:
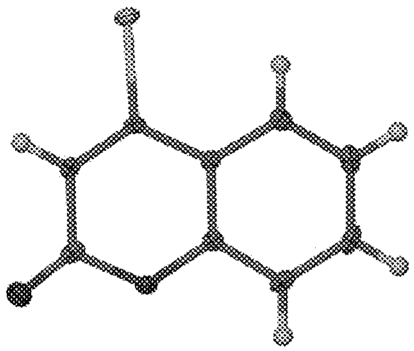

FIG. 181 shows the three-dimensional molecular structure for 4-bromocoumarin (2).

Figure 182:
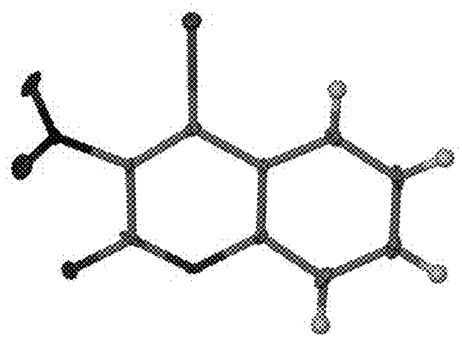

FIG. 182 shows the three-dimensional molecular structure for 4-iodo-3-nitrocoumarin (5).

Figure 183:
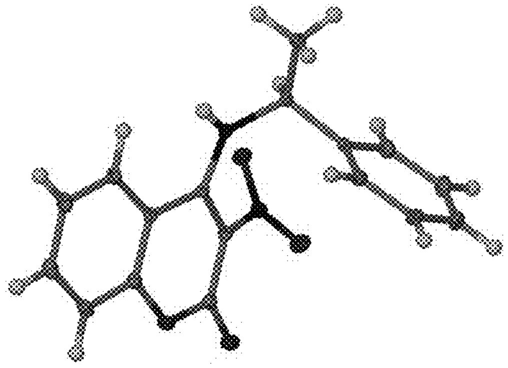

FIG. 183 shows the three-dimensional molecular structure for(S)-3-Nitro-4-((1-phenylethyl)amino) coumarin (7).

Figure 184:
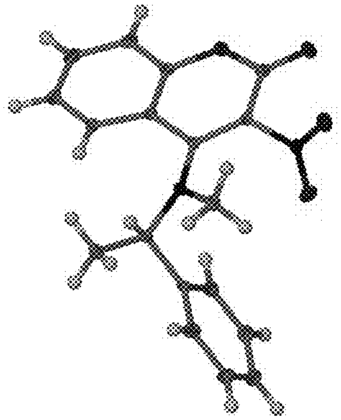

FIG. 184 shows the three-dimensional molecular structure for (R)-3-Nitro-4-(N,α-dimethylbenzyl)amino) coumarin.

DETAILED DESCRIPTION OF THE INVENTION

One aspect of the present invention relates to an analytical method that includes: providing a sample potentially containing a chiral analyte that can exist in stereoisomeric forms; providing a probe selected from the group consisting of coumarin-derived Michael acceptors, dinitrofluoroarenes and analogs thereof, arylsulfonyl chlorides and analogs thereof, arylchlorophosphines and analogs thereof, aryl halophosphites, and halodiazaphosphites; contacting the sample with the probe under conditions to permit covalent binding of the probe to the analyte, if present in the sample; and determining, based on any binding that occurs, the absolute configuration of the analyte in the sample, and/or the concentration of the analyte in the sample, and/or the enantiomeric composition of the analyte in the sample.

In at least one embodiment the probe is a coumarin-derived Michael acceptor of Formula I:

I

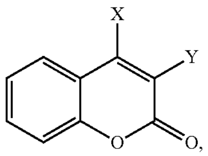

wherein:

Y is hydrogen or an electron withdrawing group selected from the group consisting of —$CF_3$, —C(O)$R_a$, —$SO_2R_a$, —CN, and —$NO_2$; wherein each $R_a$ is independently selected from the group consisting of —H, -alkyl, —O-alkyl, —N-alkyl, -alkenyl, -alkynyl, -aryl, —O-aryl, —N-aryl, -heteroaryl, —O-heteroaryl, —N-heteroaryl, -cycloalkyl, —O-cycloalkyl, —N—cycloalkyl, -heterocycloalkyl, —O-heterocycloalkyl, and —N-heterocycloalkyl; and X is a leaving group selected from halogen, —$OR_b$, —OC(O)$R_b$, —OS(O)$_2R_b$, —S(O)$_2$—O—$R_b$, —$N_2^+$, —$N^+(R_b)_3$, —$S^+(R_b)_2$, and —$P^+(R_b)_3$; wherein each $R_b$ is independently selected from the group consisting of -alkyl, —O-alkyl, —N-alkyl, -alkenyl, -alkynyl, -perfluoroalkyl, -perfluoroalkenyl, -perfluoroalkynyl, -aryl, -perfluoroaryl, —O-aryl, —N-aryl, —O— perfluoroaryl, —N-perfluoroaryl, -heteroaryl, —O-heteroaryl, —N-heteroaryl, -cycloalkyl, —O-cycloalkyl, —N-cycloalkyl, -heterocycloalkyl, —O-heterocycloalkyl, and —N— heterocycloalkyl.

In at least one embodiment, X in Formula I is a halogen or —OS(O)$_2R_b$.

Exemplary coumarin-derived Michael acceptor probes that may be used in the present method include, but are not limited to,

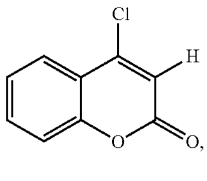

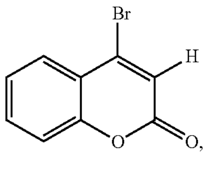

-continued

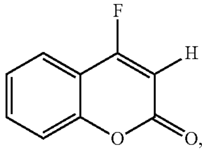

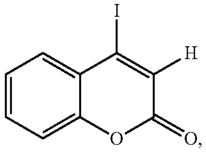

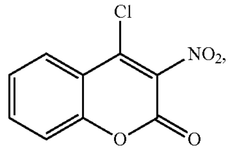

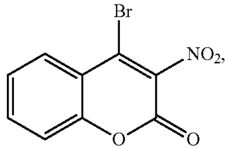

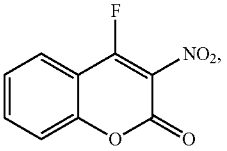

and

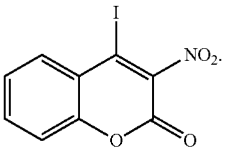

In at least one embodiment the probe is a dinitrofluoroarene or analog thereof of Formula II:

II

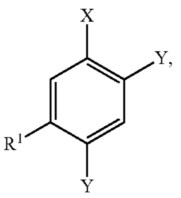

wherein:

each Y is independently selected from the group consisting of —$NO_2$, —CN, —C(O)$R_a$, and —$SO_2R_a$, wherein each $R_a$ is independently selected from the group consisting of —H, -alkyl, —O-alkyl, —N-alkyl, -alkenyl, -alkynyl, -perfluoroalkyl, -aryl, -perfluoroaryl, —O-aryl, —N-aryl, -heteroaryl, —O-heteroaryl, —N-heteroaryl, -cycloalkyl, —O-cycloalkyl, —N-cycloalkyl, -heterocycloalkyl, —O-heterocycloalkyl, and —N-heterocycloalkyl;

X is a leaving group selected from halogen, —$OR_b$, —OC(O)$R_b$, —OS(O)$_2R_b$, —S(O)$_2$—O—$R_b$, —$N_2$+, —$N^+(R_b)_3$, —$S^+(R_b)_2$, and —$P^+(R_b)_3$; wherein each $R_b$ is independently selected from the group consisting of -alkyl, —O-alkyl, —N-alkyl, -alkenyl, -alkynyl, -perfluoroalkyl, -perfluoroalkenyl, -perfluoroalkynyl, -aryl, -perfluoroaryl, —O-aryl, —N-aryl, -heteroaryl, —O-heteroaryl, —N-heteroaryl, -cycloalkyl, —O-cycloalkyl, —N-cycloalkyl, -heterocycloalkyl, —O-heterocycloalkyl, and —N-heterocycloalkyl; and $R^1$ is selected from the group consisting of —$NH_2$, —NHC(O)$CH_2$Ar, —NHC(O)Ar, -hydrogen, -alkyl, —O-alkyl, —N-alkyl, -alkenyl, -alkynyl, -aryl, —O-aryl, —N-aryl, -heteroaryl, —O— heteroaryl, —N-heteroaryl, -cycloalkyl, —O-cycloalkyl, —N-cycloalkyl, -heterocycloalkyl, —O-heterocycloalkyl, —N-heterocycloalkyl, —CN, —C(O)$R_c$, —$CO_2R_c$, —$SO_2R_c$, —C(O)NH$R_c$, —S-alkyl, —S-aryl, and —S-heteroaryl;

wherein:

each $R_c$ is independently —Ar, -alkyl, or —$CH_2$Ar; and each Ar is independently an aryl, heteroaryl, cycloalkyl, heterocycloalkyl, perfluoroalkyl, or perfluoroaryl.

An analog of a dinitrofluoroarene is a dinitrofluoroarene in which the fluorine atom has been replaced with a different leaving group.

Exemplary dinitroflourarene probes that may be used in the present method include, but are not limited to,

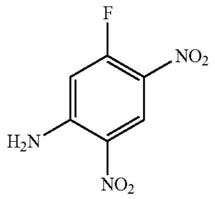

and

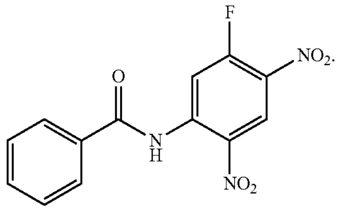

In at least one embodiment the probe is an arylsulfonyl chloride or analog thereof of Formula III: 0

III

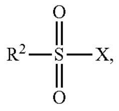

wherein:

X is selected from the group consisting of -halogen, —O-aryl, —O-heteroaryl, —O-cycloalkyl, —O— heterocycloalkyl, —O-alkyl, —O-perfluoroalkyl, —O-perfluoroaryl, —N-aryl, —N-heteroaryl, —N-cycloalkyl, —N-heterocycloalkyl, —N-alkyl, —N-perfluoroalkyl, —N-perfluoroaryl, —N(Ar)$SO_2$Ar, —$NHSO_2$Ar, and —NHAr; and $R^2$ is an aryl or heteroaryl, wherein the aryl or heteroaryl is optionally substituted with one or more groups selected from -alkyl, —O-alkyl, —N-alkyl, -alkenyl, -alkynyl, —O-aryl, —O— heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each $R_c$ is independently Ar, alkyl, or $CH_2$Ar;

wherein each Ar is independently an aryl or heteroaryl.

An analog of an arylsulfonyl chloride is an arylsulfonyl chloride in which the chlorine atom has been replaced with another halogen or with —O-aryl, —O-perfluoroaryl, —O— heteroaryl, —O-cycloalkyl, —O-heterocycloalkyl, —O-alkyl, or —O-perfluoroalkyl.

Exemplary arylsulfonyl chloride probes that may be used in the present method include, but are not limited to,

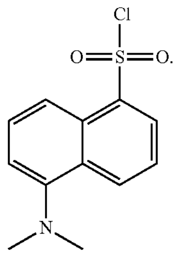 [SMILES: CN(C)c1cccc2c(S(=O)(=O)Cl)cccc12]

In at least one embodiment the probe is an arylchlorophosphine or analog thereof of Formula IV:

IV

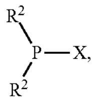

wherein:

X is selected from the group consisting of -halogen, —O-aryl, —O-heteroaryl, —O-cycloalkyl, —O— heterocycloalkyl, —O-alkyl, —O-perfluoroalkyl, and —O-perfluoroaryl; and each $R^2$ is independently an aryl or heteroaryl, wherein the aryl or heteroaryl is optionally substituted with one or more groups selected from -alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each R, is independently Ar, alkyl, or $CH_2$Ar and Ar is an aryl or heteroaryl.

An analog of an arylchlorophosphine is an arylchlorophosphine in which the chlorine atom has been replaced with another halogen or with —O-aryl, —O-perfluoroaryl, —O— heteroaryl, —O-cycloalkyl, —O-heterocycloalkyl, —O-alkyl, or —O-perfluoroalkyl.

Exemplary aryl arylchlorophosphine probes that may be used in the present method include, but are not limited to,

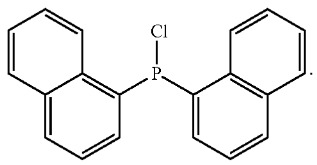 [SMILES: ClP(c1cccc2ccccc12)c1cccc2ccccc12]

In at least one embodiment the probe is an aryl halophosphite of Formula V:

V

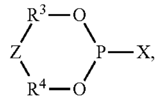

wherein:

X is a halogen; and (i) $R^3$ and $R^4$ are each independently an aryl or heteroaryl, wherein the aryl or heteroaryl is optionally substituted with one or more groups selected from -alkyl, —O-alkyl, —N-alkyl, -alkenyl, -alkynyl, —O-aryl, —O-perfluoroaryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each $R_c$ is independently Ar, alkyl, or $CH_2$Ar and Ar is an aryl or heteroaryl; and Z is selected from the group consisting of a bond, —C(O)—, —O—, —$NR_d$—, —S—, and —$CH_2$—, wherein $R_d$ is H, alkyl, aryl, or heteroaryl; or (ii) $R^3$ and $R^4$, together with the carbon atoms to which they are attached, form a monocyclic or bicyclic ring system selected from the group consisting of cycloalkyl, heterocycloalkyl, aryl, and heteroaryl, wherein the ring system is optionally substituted with one or more groups selected from -alkyl, —O-alkyl, —N-alkyl, -alkenyl, -alkynyl, —O-aryl, —O— heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each $R_c$ is independently Ar, alkyl, or $CH_2$Ar and Ar is an aryl or heteroaryl; and Z is absent.

Exemplary aryl chlorophosphite probes that may be used in the present method include, but are not limited to,

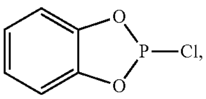
,
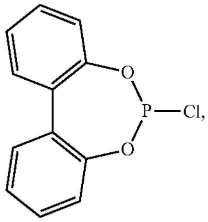
,
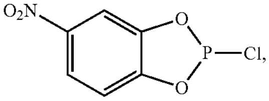
,
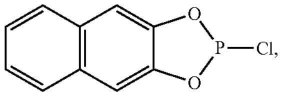
,
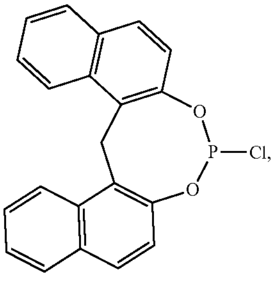
, and
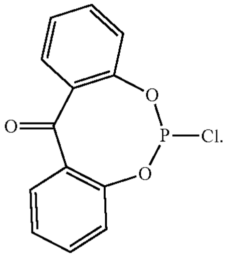
.

In at least one embodiment the probe is a halodiazaphosphite of Formula VI:

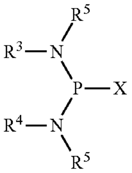

VI wherein:

X is a halogen;

$R^3$ and $R^4$ are each independently -aryl or -heteroaryl, wherein the aryl or heteroaryl is optionally substituted with one or more groups selected from -alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O) $R_c$ $NO_2$, —CN, -halogen, and —$SO_2R_c$, wherein each $R_c$ is independently Ar, alkyl, or $CH_2$Ar and Ar is an aryl or heteroaryl; or $R^3$ and $R^4$, together with the carbon atoms to which they are attached, form a monocyclic or bicyclic ring system selected from the group consisting of cycloalkyl, heterocycloalkyl, aryl, and heteroaryl, wherein the ring system is optionally substituted with one or more groups selected from -alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each $R_c$ is independently Ar, alkyl, or $CH_2$Ar and Ar is an aryl or heteroaryl; and each $R^5$ is independently selected from -alkyl, -aryl, —$CH_2$-aryl, —$CH_2$-heteroaryl, -cycloalkyl, -heterocycloalkyl, and -heteroaryl, wherein the alkyl, aryl, $CH_2$-aryl, $CH_2$-heteroaryl, cycloalkyl, heterocycloalkyl, or heteroaryl is optionally substituted with one or more groups selected from -alkyl, —O-alkyl, —N-alkyl, -alkenyl, -alkynyl, —O-aryl, —O— heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each $R_c$ is independently Ar, alkyl, or $CH_2$Ar and Ar is an aryl or heteroaryl.

Exemplary chlorodiazaphosphite probes that may be used in the present method include, but are not limited to,

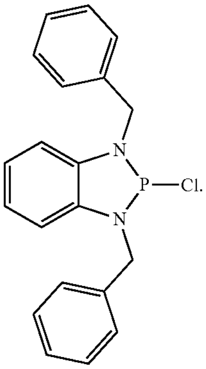 [SMILES: ClP1N(Cc2ccccc2)c2ccccc2N1Cc1ccccc1]
.

As used herein, the term "alkyl" refers to a straight or branched, saturated aliphatic radical containing one to about twenty (e.g., 1, 2, 3, 4, 5, 6, 7, 8, 9, 10, 11, 12, 13, 14, 15, 16, 17, 18, 19, 20, 1-2, 1-3, 1-4, 1-5, 1-6, 1-7, 1-8, 1-9, 1-10, 1-11, 1-12, 1-13, 1-14, 1 15, 1-16, 1-17, 1-18, 1-19, 1-20, 2-3, 2-4, 2-5, 2-6, 2-7, 2-8, 2-9, 2-10, 2-11, 2-12, 2-13, 2 14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4 14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6 17, 6-18, 6-19, 6-20, 7-8, 7-9, 7-10, 7-11, 7-12, 7-13, 7-14, 7-15, 7-16, 7-17, 7-18, 7-19, 7 20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms and, unless otherwise indicated, may be optionally substituted. In at least one embodiment, the alkyl is a $C_1$-$C_{10}$ alkyl. In at least one embodiment, the alkyl is a $C_1$-$C_6$ alkyl. Suitable examples include, without limitation, methyl, ethyl, propyl, isopropyl, butyl, sec-butyl, isobutyl, tert-butyl, 3-pentyl, and the like.

As used herein, the term "alkenyl" refers to a straight or branched aliphatic unsaturated hydrocarbon of formula $C_nH_{2n}$ having from two to about twenty (e.g., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms in the chain and, unless otherwise indicated, may be optionally substituted. Exemplary alkenyls include, without limitation, ethylenyl, propylenyl, n-butylenyl, and i-butylenyl.

As used herein, the term "alkynyl" refers to a straight or branched aliphatic unsaturated hydrocarbon of formula $C_nH_{2n-2}$ having from two to about twenty (e.g., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 15, 6-16, 6-17, 6-18, 18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms in the chain and, unless otherwise indicated, may be optionally substituted. Exemplary alkynyls include acetylenyl, propynyl, butynyl, 2-butynyl, 3-methylbutynyl, and pentynyl.

As used herein, the term "cycloalkyl" refers to a non-aromatic saturated or unsaturated monocyclic or polycyclic (e.g., bicyclyic, tricyclic, tetracyclic) ring system which may contain 3 to 24 (3, 4, 5, 6, 7, 8, 9, 10, 11, 12, 13, 14, 15, 16, 17, 18, 19, 20, 21, 22, 23, 24, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 7-8, 7-9, 7-10, 7-11, 7-12, 7-13, 7-14, 7-15, 7-16, 7-17, 7-18, 7-19, 7-20, 7-21, 7-22, 7-23, 7-24, 8-9, 8-10, 8-11, 8-12, 8-13, 8-14, 8-15, 8-16, 8-17, 8-18, 8-19, 8-20, 8-21, 8-22, 8-23, 8-24, 9-10, 9-9-12, 9-13, 9-14, 9-15, 9-16, 9-17, 9-18, 9-19, 9-20, 9-21, 9-22, 9-23, 9-24, 10-11, 10-10-13, 10-14, 10-15, 10-16, 10-17, 10-18, 10-19, 10-20, 10-21, 10-22, 10-23, 10-24, 11-12, 11-13, 11-14, 11-15, 11-16, 11-17, 11-18, 11-19, 11-20, 11-21, 11-22, 11-23, 11-24, 12-13, 12-14, 12-15, 12-16, 12-17, 12-18, 12-19, 12-20, 12-21, 12-22, 12-23, 12-24, 13-14, 13-15, 13-16, 13-17, 13-18, 13-19, 13-20, 13-21, 13-22, 13-23, 13-24, 14-15, 14-16, 14-17, 14-18, 14-19, 14-20, 14-21, 14-22, 14-23, 14-24, 15-16, 15-17, 15-18, 15-19, 15-20, 15-21, 15-22, 15-23, 15-24, 16-17, 16-18, 16-19, 16-20, 16-21, 16-22, 16-23, 16-24, 17-18, 17-19, 17-20, 17-21, 17-22, 17-23, 17-24, 18-19, 18-20, 18-21, 18-22, 18-23, 18-24, 19-20, 19-21, 19-22, 19-23, 19-24, 20-21, 20-22, 20-23, 20-24, 21-22, 22-23, 22-24, 23-24) carbon atoms, which may include at least one double bond and, unless otherwise indicated, the ring system may be optionally substituted. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, and syn-bicyclopropane.

As used herein, the term "heterocycloalkyl" refers to a cycloalkyl group as defined above having at least one O, S, and/or N interrupting the carbocyclic ring structure. Examples of heterocycloalkyls include, without limitation, piperidine, piperazine, morpholine, thiomorpholine, pyrrolidine, tetrahydrofuran, pyran, tetrahydropyran, and oxetane. Unless otherwise indicated, the heterocycloalkyl ring system may be optionally substituted.

As used herein, the term "aryl" refers to an aromatic monocyclic or polycyclic (e.g., bicyclyic, tricyclic, tetracyclic) ring system from 6 to 24 (6, 7, 8, 9, 10, 11, 12, 13, 14, 15, 17, 18, 19, 20, 21, 22, 23, 24, 6-7, 6-8, 6-9, 6-10, 6-11, 6-12, 6-13, 6-14, 6-15, 6-16, 6-6-18, 6-19, 6-20, 6-21, 6-22, 6-23, 6-24, 7-8, 7-9, 7-10, 7-11, 7-12, 7-13, 7-14, 7-15, 7-16, 7-17, 7-18, 7-19, 7-20, 7-21, 7-22, 7-23, 7-24, 8-9, 8-10, 8-11, 8-12, 8-13, 8-14, 8-15, 8-16, 8-17, 8-18, 8-19, 8-20, 8-21, 8-22, 8-23, 8-24, 9-10, 9-11, 9-12, 9-13, 9-14, 9-15, 9-16, 9-17, 9-18, 9-19, 9-20, 9-21, 9-22, 9-23, 9-24, 10-11, 10-12, 10-13, 10-14, 10-15, 10-16, 10-17, 10-18, 10-19, 10-20, 10-21, 10-22, 10-23, 10-24, 11-12, 11-13, 11-14, 11-15, 11-11-17, 11-18, 11-19, 11-20, 11-21, 11-22, 11-23, 11-24, 12-13, 12-14, 12-15, 12-16, 12-12-18, 12-19, 12-20, 12-21, 12-22, 12-23, 12-24, 13-14, 13-15, 13-16, 13-17, 13-18, 13-13-20, 13-21, 13-22, 13-23, 13-24, 14-15, 14-16, 14-17, 14-18, 14-19, 14-20, 14-21, 14-22, 14-23, 14-24, 15-16, 15-17, 15-18, 15-19, 15-20, 15-21, 15-22, 15-23, 15-24, 16-17, 16-16-19, 16-20, 16-21, 16-22, 16-23, 16-24, 17-18, 17-19, 17-20, 17-21, 17-22, 17-23, 17-24, 18-19, 18-20, 18-21, 18-22, 18-23, 18-24, 19-20, 19-21, 19-22, 19-23, 19-24, 20-21, 20-22, 20-23, 20-24, 21-22, 22-23, 22-24, 23-24) carbon atoms and, unless otherwise indicated, the ring system may be optionally substituted. Aryl groups of the present technology include, but are not limited to, groups such as phenyl, naphthyl, azulenyl, phenanthrenyl, anthracenyl, fluorenyl, pyrenyl, triphenylenyl, chrysenyl, naphthacenyl, biphenyl, triphenyl, and tetraphenyl. In at least one embodiment, an aryl within the context of the present technology is a 6 or 10 membered ring. In at least one embodiment, each aryl is phenyl or naphthyl.

As used herein, the term "heteroaryl" refers to an aryl group as defined above having at least one O, S, and/or N interrupting the carbocyclic ring structure. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in Comprehensive Heterocyclic Chemistry: The Structure, Reactions, Synthesis and Use of Heterocyclic Compounds (Katritzky et al. eds., 1984), which is hereby incorporated by reference in its entirety. Unless otherwise indicated, the heteroaryl ring system may be optionally substituted.

As used herein, the terms "perfluoroalkyl", "perfluoroalkenyl", "perfluoroalkynyl", and "perfluoroaryl" refer to an alkyl, alkenyl, alkynyl, or aryl group as defined above in which the hydrogen atoms on at least one of the carbon atoms have all been replaced with fluorine atoms.

The term "monocyclic" as used herein indicates a molecular structure having one ring.

The term "polycyclic" as used herein indicates a molecular structure having two or more rings, including, but not limited to, fused, bridged, spiro, or covalently bound rings. In at least one embodiment, the polycyclic ring system is a bicyclic, tricyclic, or tetracyclic ring system. In at least one embodiment, the polycyclic ring system is fused. In at least one embodiment, the polycyclic ring system is a bicyclic ring system such as naphthyl or biphenyl.

As used herein, the term "optionally substituted" indicates that a group may have a substituent at each substitutable atom of the group (including more than one substituent on a single atom), provided that the designated atom's normal valency is not exceeded and the identity of each substituent is independent of the others. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" is meant a compound that is sufficiently robust to survive isolation to a useful degree of purity from a reaction mixture, and formulation into an efficacious agent.

As used herein, the term "halogen" includes fluorine, bromine, chlorine, and iodine.

Suitable leaving groups are substituents that are present on the compound that can be displaced. Suitable leaving groups are apparent to a skilled artisan.

The analytical methods described herein may be used to evaluate a wide range of chiral analytes. The analyte is one that can exist in stereoisomeric forms. This includes enantiomers, diastereomers, and a combination thereof.

In at least one embodiment of the analytical method of the present invention, the analyte has low nucleophilicity. Analytes with low nucleophilicity include, for example, alcohols.

In at least one embodiment of the analytical method of the present invention, the analyte is selected from the group consisting of primary amines, secondary amines, amino alcohols, alcohols, carboxylic acids, hydroxy acids, amino acids, thiols, amides, and combinations thereof.

The amino acid analyte can be any natural or non-natural chiral amino acid, including alpha amino acids, beta amino acids, gamma amino acids, L-amino acids, and D-amino acids. In some embodiments, the amino acid comprises a functionalized side chain. In some embodiments, the analyte is an unprotected amino acid.

In the analytical methods described herein, the enantiomeric composition of the analyte can be determined by correlating the chiroptical signal of the probe-analyte complexes that form to the enantiomeric composition of the analyte. The chiroptical signal of the complexes can be measured using standard techniques, which will be apparent to the skilled artisan. Such techniques include circular dichroism spectroscopy (e.g., Stereochemistry of Organic Compounds 1003-07 (E. L. Eliel & S. H. Wilen eds., 1994); Dynamic Stereochemistry of Chiral Compounds 140-43 (Christian Wolf ed., 2008), each of which is hereby incorporated by reference in its entirety), optical rotatory dispersion (e.g., Stereochemistry of Organic Compounds 999-1003 (E. L. Eliel & S. H. Wilen eds., 1994), which is hereby incorporated by reference in its entirety), and polarimetry (e.g., Stereochemistry of Organic Compounds 217-21, 1071-80 (E. L. Eliel & S. H. Wilen eds., 1994); Dynamic Stereochemistry of Chiral Compounds 140-43 (Christian Wolf ed., 2008), each of which is hereby incorporated by reference in its entirety). By way of example, stereomerically pure samples of each isomer of an analyte of interest can be mixed with the particular probe to generate standard samples, and their optical spectra obtained. The chiroptical signal of the probe-analyte complexes in the test sample can be measured by generating an optical spectrum of the test sample. The enantiomeric composition of the analyte originally present in the sample can then be determined by comparing the optical spectrum of the test sample to that of the standard sample(s).

In the analytical methods described herein, the concentration of the analyte can be determined by correlating a non-chiroptical spectroscopic signal of the probe-analyte complexes that form to the concentration of the analyte. The non-chiroptical spectroscopic signal can be measured using standard techniques, which will be apparent to the skilled artisan. Such techniques include, but are not limited to, UV spectroscopy (Principles of Instrumental Analysis 342-47 (Douglas A. Skoog et al. eds., $5^{th}$ ed. 1998), which is hereby incorporated by reference in its entirety), fluorescence spectroscopy, and other spectroscopic techniques. By way of example, serial titrations of the analyte of interest can be mixed with the particular probe to generate standard samples and their spectra (e.g., UV, fluorescence) obtained. The spectroscopic signal (e.g., UV, fluorescence) of the probe-analyte complexes can be measured by generating a spectrum (e.g., UV, fluorescence) of the test sample. The total concentration of the analyte originally present in the sample can then be determined by comparing the spectrum of the test sample to the titration curve of the standard samples. As will be apparent to the skilled artisan, if the stereoisomeric excess of the analyte is also determined, the concentration of individual isomers originally present in the test sample can be determined by comparing the stereoisomeric excess to the total analyte concentration.

In the analytical methods described herein, the absolute configuration of the analyte can be assigned from the chiroptical signal of the probe-analyte complexes that form. This assignment can be based on the sense of chirality induction with a reference or by analogy. The chiroptical signal of the complexes can be measured using standard techniques, which will be apparent to the skilled artisan. Such techniques include circular dichroism spectroscopy (e.g., Stereochemistry of Organic Compounds 1003-07 (E. L. Eliel & S. H. Wilen eds., 1994); Dynamic Stereochemistry of Chiral Compounds 140-43 (Christian Wolf ed., 2008), each of which is hereby incorporated by reference in its entirety), optical rotatory dispersion (e.g., Stereochemistry of Organic Compounds 999-1003 (E. L. Eliel & S. H. Wilen eds., 1994), which is hereby incorporated by reference in its entirety), and polarimetry (e.g., Stereochemistry of Organic Compounds 217-21, 1071-80 (E. L. Eliel & S. H. Wilen eds., 1994); Dynamic Stereochemistry of Chiral Compounds 140-43 (Christian Wolf ed., 2008), each of which is hereby incorporated by reference in its entirety). By way of example, stereoisomerically pure samples of each isomer of an analyte of interest can be mixed with the particular probe to generate standard samples, and their optical spectra obtained. The chiroptical signal of the probe-analyte complexes in the test sample can be measured by generating an optical spectrum of the test sample. The absolute configuration of the analyte originally present in the sample can then be determined by comparing the optical spectrum of the test sample to that of the standard sample(s).

The analytical methods of the present invention provide, among other things, rapid and convenient tools for determining the enantiomeric composition, and/or concentration, and/or absolute configuration of chiral analytes. These analytical methods may be particularly useful, for example, for evaluating high-throughput reactions whose desired product is chiral. For example, the present methods can be used to determine the enantiomeric composition of the desired product, thus indicating the stereoselectivity of the reaction. Similarly, the present methods can be used to determine the concentration of the total product and/or the desired isomer, thus indicating the overall or individual yield of the reaction.

In one embodiment of all aspects of the analytical method of the present invention, the contacting of the probe and analyte is carried out in a solvent selected from aqueous solvents, protic solvents, aprotic solvents, and any combination thereof. Exemplary solvents useful in the analytical method include, but are not limited to chloroform, dichloromethane, acetonitrile, toluene, tetrahydrofuran, methanol, ethanol, isopropanol, water, dimethyl sulfoxide (DMSO), dimethylformamide (DMF), hexane, hexane isomers, ether, dichloroethane, acetone, ethyl acetate, butanone, and mixtures of any combination thereof. Additionally, the contacting can be carried out in air, and/or in an aqueous environment.

In at least one embodiment of any analytical method herein, contacting is carried out for about 1 to about 300 minutes (e.g., carried out for a duration range having an upper limit of about 5, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, or about 300 minutes, and a lower limit of about 1, about 5, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, or about 290 minutes, or any combination thereof). In all embodiments, contacting is carried out for a time that is sufficient for the probe to bind to any analyte present in the sample. As will be apparent to the skilled chemist, the speed at which binding takes place will depend on various factors, including the particular probe selected and the analyte, whether a catalyst is present, and the temperature.

As will be apparent to the skilled chemist, the analytical methods may be carried out at room temperature, at high temperatures (e.g., about 50° C. to about 100° C., e.g., a temperature range with an upper limit of about 55° C., about 60° C., about 65° C., about 70° C., about 75° C., about 80° C., about 85° C., about 90° C., about 95° C., or about 100° C., and a lower limit of about 50° C., about 55° C., about 60° C., about 65° C., about 70° C., about 75° C., about 80° C., about 85° C., about 90° C., or about 95° C., or any combination thereof), or at low temperatures (e.g., below about 25° C., e.g., below about 25° C., below about 20° C., below about 15° C., below about 10° C., below about 5° C., below about 0° C., below about −5° C., below about −10° C., below about −15° C., below about −20° C., below about −25° C., below about −30° C., below about −35° C., below about −40° C., below about −45° C., below about −50° C., below about −55° C., below about −60° C., below about −65° C., below about −70° C., or below about −75° C., preferably no lower than about −78° C.; e.g., a temperature range with an upper limit of about 25° C., about 20° C., about 15° C., about 10° C., about 5° C., about 0° C., about −5° C., about −10° C., about −15° C., about −20° C., about −25° C., about −30° C., about −35° C., about −40° C., about −45° C., about −50° C., about −55° C., about −60° C., about −65° C., about −70° C., or about −75° C., and a lower limit of about 20° C., about 15° C., about 10° C., about 5° C., about 0° C., about −5° C., about −10° C., about −15° C., about −20° C., about −25° C., about −30° C., about −35° C., about −40° C., about −45° C., about −50° C., about −55° C., about −60° C., about −65° C., about −70° C., about −75° C., or about −78° C., or any combination thereof). Furthermore, the analytical methods may be carried out under ambient conditions (e.g., 23±3° C. and 38±5% relative humidity).

For example, the temperature could be increased to speed up the binding reaction. Some analyte-probe combinations may have side reactions at certain temperatures; the temperature could be decreased to prevent such side reactions.

The analytical methods of the present invention can also optionally be carried out in the presence of a base. The analytical methods described herein may generate an acid. Adding an equivalent of base could be helpful, e.g., to avoid side reactions. The base could be organic or inorganic. Exemplary bases include, but are not limited to: alkoxides such as sodium tert-butoxide; alkali metal amides such as sodium amide, lithium diisopropylamide, and alkali metal bis(trialkylsilyl)amide, e.g., such as lithium bis(trimethylsilyl)amide (LiHMDS) or sodium bis(trimethylsilyl)amide (NaHMDS); tertiary amines (e.g. triethylamine, trimethylamine, 4-(dimethylamino)pyridine (DMAP), 1,5-diazabicycl[4.3.0]non-5-ene (DBN), 1,5-diazabicyclo[5.4.0]undec-5-ene (DBU); alkali or alkaline earth carbonate, bicarbonate or hydroxide (e.g. sodium, magnesium, calcium, barium, potassium carbonate, phosphate, hydroxide and bicarbonate); and ammonium hydroxides, e.g. tetrabutylammonium hydroxide (TBAOH).

Another aspect of the present invention relates to a compound selected from the group consisting of

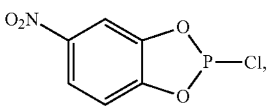

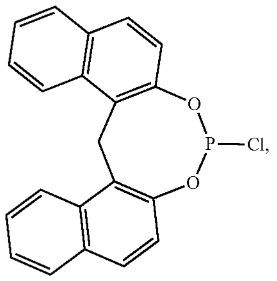

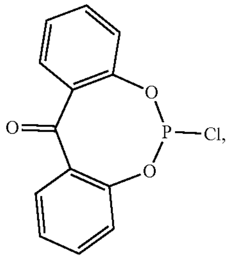

and

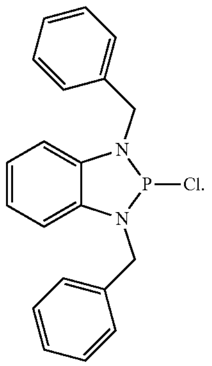

Preferences and options for a given aspect, feature, embodiment, or parameter of the technology described herein should, unless the context indicates otherwise, be regarded as having been disclosed in combination with any and all preferences and options for all other aspects, features, embodiments, and parameters of the technology.

The present technology may be further illustrated by reference to the following examples.

EXAMPLES

The following examples are provided to illustrate embodiments of the present technology but are by no means intended to limit its scope.

Example 1—Chirality Sensing with Molecular Click Chemistry: Discussion of Examples 2-13

As described more fully below, the search for a suitable chromophoric probe that can quickly and quantitatively capture a variety of chiral target compounds through irreversible covalent bond formation at room temperature led to the preparation and investigation of the coumarin-derived Michael acceptors 1-5 (Scheme 1). Initial screening with chiral amines revealed that these 4-halocoumarins undergo smooth Michael addition and subsequent halide elimination toward 6 and 7, respectively. Further analysis of the chiroptical properties showed that the covalent attachment of 1-phenylethylamine, 8, which was one of the initially tested amines, to the coumarin scaffold results in a strong CD signal and a distinct UV change at high wavelengths at micromolar concentrations. Importantly, the Michael addition/elimination substrate binding strategy does not generate a new chirality center. In contrast to other sensor designs, this feature avoids complications arising from the formation of diastereomeric mixtures which simplifies the chirality sensing protocol described herein. Comparison of the reactivity and chiroptical responses of the five probes revealed superior properties of 4-chloro-3-nitrocoumarin, 3. When this sensor is employed, the reaction proceeds quantitatively at room temperature without by-product formation in various solvents ranging from chloroform to aqueous acetonitrile. The presence of the nitro group is important for two reasons: it significantly accelerates the covalent substrate fixation and it increases the corresponding Cotton effect.

The scope of this sensor turned out to be very large, significantly exceeding the general utility of NMR chiral solvating agents and derivatizing reagents. Encouraged by the practicality of the sensing assay and the large Cotton effects observed upon binding of 8, it was decided to apply coumarin 3 to a variety of amines, amino alcohols, alcohols and amino acids, including aspartic acid, threonine, cysteine and others with functionalized sidechains. Distinct chiroptical responses were obtained in all cases. Representative CD spectra are shown in Scheme 1. The binding of the S-enantiomers of the amines, amino alcohols and amino acids 8, 16, 27 and 35 yields a positive Cotton effect above 300 nm whereas the R-substrates induce the opposite CD response. The reverse relationship between the absolute configuration and the sign of the induced Cotton effects was observed using the alcohol 33 as the sensing target. It is noteworthy that among the 39 sensing targets are several with a secondary amino group, i.e. 16, 17, 24, 27, 28, 37 and 46, that cannot be sensed via the commonly used Schiff base formation approach (Ghosn, M. W. & Wolf, C., "Chiral Amplification With a Stereodynamic Triaryl Probe: Assignment of the Absolute Configuration and Enantiomeric Excess of Amino Alcohols," *J. Am. Chem. Soc.* 131:16360-16361 (2009); Nieto et al., "A Facile Circular Dichroism Protocol for Rapid Determination of Enantiomeric Excess and Concentration of Chiral Primary Amines," *Chem. Eur. J.* 16:227-232 (2010); Iwaniuk, D. P. & Wolf, C., "A Stereodynamic Probe Providing a Chiroptical Response to Substrate-Controlled Induction of an Axially Chiral Arylacetylene Framework," *J. Am. Chem. Soc.* 133:2414-2417 (2011); Dragna et al., "In Situ Assembly of Octahedral Fe(II) Complexes for the Enantiomeric Excess Determination of Chiral Amines Using Circular Dichroism Spectroscopy," *J. Am. Chem. Soc.* 134:4398-4407 (2012); Bentley, K. W. & Wolf, C., "Stereodynamic Chemosensor With Selective Circular Dichroism and Fluorescence Readout for In Situ Determination of Absolute Configuration, Enantiomeric Excess, and Concentration of Chiral Compounds," *J. Am. Chem. Soc.* 135:12200-12203 (2013); Huang et al., "Zn(II) Promoted Dramatic Enhancement in the Enantioselective Fluorescent Recognition of Functional Chiral Amines by a Chiral Aldehyde," *Chem. Sci.* 5:3457-3462 (2014); Wen et al., "Rational Design of a Fluorescent Sensor to Simultaneously Determine Both the Enantiomeric Composition and the Concentration of Chiral Functional Amines," *J. Am. Chem. Soc.* 137:4517-4524 (2015); Pilicer et al., "Biomimetic Chirality Sensing With Pyridoxal-5'-phosphate," *J. Am. Chem. Soc.* 139(5):1758-1761 (2017); Zardi et al., "Concentration-Independent Stereodynamic g-Probe for Chiroptical Enantiomeric Excess Determination," *J. Am. Chem. Soc.* 139:15616-15619 (2017); Ni et al., "Dynamic Covalent Chemistry Within Biphenyl Scaffolds: Reversible Covalent Bonding, Control of Selectivity, and Chirality Sensing With One Single System," *Angew. Chem. Int. Ed.* 57:1300-1305 (2018), which are hereby incorporated by reference in their entirety). The successful sensing of 32, 33 and 46 exhibiting low nucleophilicity further underscores the wide utility of the coumarin probes of the present invention.

Figure 1:
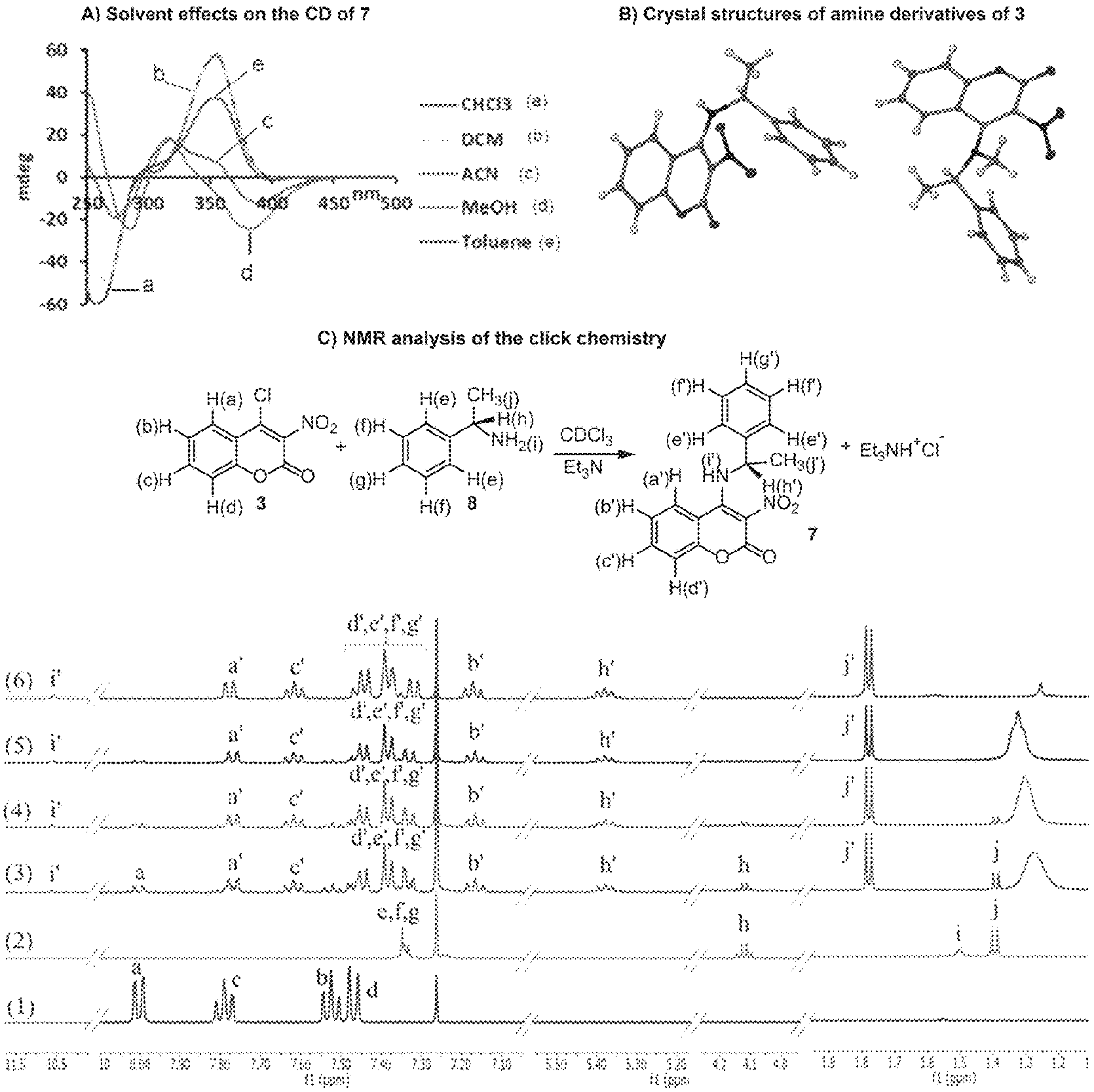
FIGS. 1A-C relate to the analysis of the sensing chemistry.

Comparison of the chiroptical signals observed with the 4-halocoumarins 1 and 2 versus the nitro analogues 3-5 upon binding of 8 shows a strong contribution of the nitro dipole in the sensor scaffold to the CD intensity of the Michael addition/elimination product. The nitro group contribution results in a stronger and remarkably red-shifted CD signal which is advantageous for direct asymmetric reaction analysis because it eliminates interference from CD-active catalysts with the chiroptical measurements, vide infra. Although intramolecular hydrogen bonding (—NH—$O_2N$—) is likely to occur with 7 in aprotic solvents it is not a prerequisite for this sensor to function. Strong albeit quite different CD effects were obtained using chloroform, dichloromethane, toluene acetonitrile and methanol, which is expected to disturb the hydrogen bonding motif, as solvent (FIG. 1A). In fact, intramolecular hydrogen bonding interactions are absent in the crystal structure of the primary amine addition product 7 (see FIG. 1B) and very strong CD effects upon binding of substrates with secondary amino groups were observed, for example 16, which affords a product devoid of an NH donor site (Scheme 1; see FIG. 1). These features of the probe do not only result in a large application scope. The inherently wide solvent compatibility is also very attractive from an operational perspective because it simplifies adaption to asymmetric reaction conditions, for example when alcoholic co-solvents are used in catalytic enantioselective imine hydrogenations as described herein. The sensing reaction and the corresponding CD effects were further investigated by UV, CD and NMR spectroscopy. The products of the reactions of 3 with 8, 17 and cis-22, respectively, were separately prepared. The CDs of these isolated compounds match those generated in the sensing assays. The reaction between 1-phenylethylamine and probe 3 in the presence of $Et_3N$ was closely monitored by $^1H$ NMR spectroscopy (FIG. 1C). The spectra collected after 5, 10 and 15 minutes show the clean transformation of 3 and 8 into 7 which is complete after approximately 15 minutes at room temperature. For example, the signals at 1.39 ppm ($H_j$) and 4.12 ppm ($H_h$) of 8 undergo a downfield shift to 1.78 ppm and 5.38 ppm, respectively, as 7 is formed. Accordingly, the doublet at 8.00 ppm ($H_a$) of probe 3 shows an upfield shift to 7.78 ppm in the reaction mixture.

Altogether, the sensing chemistry with 3 features the major elements of click chemistry (Kolb et al., "Click Chemistry: Diverse Chemical Function From a Few Good Reactions," *Angew. Chem. Int. Ed.* 40:2004-2021 (2001), which is hereby incorporated by reference in its entirety): it is fast, wide in scope, displays smooth substrate transformation with very high yield at room temperature, is compatible with a wide range of environmentally benign solvents such as methanol and acetonitrile, avoids formation of by-products, eliminates chromatographic or any type of work-up, is insensitive to air and moisture, and utilizes readily available starting materials, i.e. the coumarin probe 3. These preferable reaction characteristics in combination with the strong, red-shifted chiroptical readouts were anticipated to generate unique sensing opportunities.

The term "click chemistry" comprises and identifies various groups of chemical reactions characterized by particular properties such as rapidity, regioselectivity and high yield and having a high thermodynamic driving force, generally greater than or equal to 20 kcal/mol. Click chemistry techniques are described, for example, in the following references: Kolb, H. C. and Sharpless, K. B., *Drug Discovery Today* 8:1128-1137 (2003); Rostovtsev, et al., *Angew. Chem. Int. Ed.* 41: 2596-2599 (2002); Tome et al., *J. Org. Chem.* 67: 3057-3064 (2002); Wang, et al., *J. Am. Chem. Soc.* 125:3192-3193 (2003); Lee, et al., *J. Am. Chem. Soc.* 125:9588-9589 (2003); Lewis et al., *Angew. Chem. Int. Ed.* 41:1053-1057 (2002); Manetsch ae al., *J. Am. Chem. Soc.* 126:12809-12818 (2004); and Mocharla, et al., *Angew. Chem. Int. Ed.,* 44:116-120 (2005), which are hereby incorporated by reference in their entirety.

Figure 2:
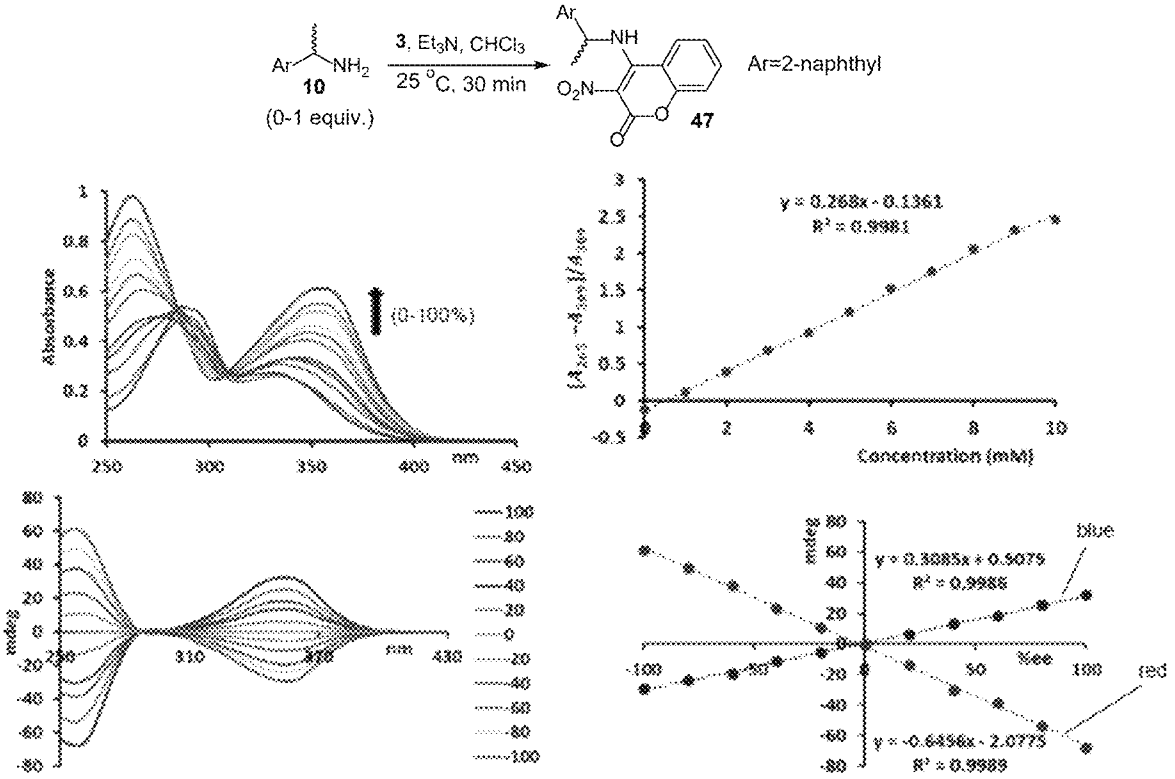
FIG. 2 shows the chiroptical sensing of 10. Top: UV response of 3 to varying amounts of 10. Bottom: CD response of 3 to nonracemic samples of 10 and linear correlation between the induced CD signals at 257 (red) and 355 (blue) nm and the sample ee.

A closer look at the sensing of 1-(2-naphthyl)ethylamine, 10, revealed that the irreversible substrate binding concurs with a drastic UV increase at 265 and 355 nm while the absorption at 309 nm remains unchanged (FIG. 2). This unique feature allows ratiometric sensing of the amine concentration. Circular dichroism experiments were then conducted and it was discovered that the induced CD maxima at 257 and 355 nm increase linearly with the substrate ee. The absolute configuration of 10 or another target compound can be assigned based on the sign of the induced CD signals and quantitative information about the substrate amount (concentration) and its enantiomeric composition is directly accessible from the UV changes and the CD amplitudes, respectively. This is particularly attractive because modern CD instruments generate UV and CD spectra simultaneously.

The robustness of the fast and quantitative Michael addition/elimination chemistry with a wide variety of chiral compounds in combination with the distinct chiroptical readouts of the coumarin sensor 3 greatly facilitates asymmetric reaction screening. First it was decided to verify that the UV/CD responses of the coumarin probe allow reliable assignment of the absolute configuration together with accurate determination of the ee and concentration of micromolar samples of 10. Nine samples containing the amine in varying concentration and ee were prepared and subjected to the CCS assay (Table 1). In all cases, the absolute configuration of the major enantiomer was correctly identified and the concentrations and ee's were determined with good accuracy. For example, the sensing analysis of the sample containing (S)-10 in 33.3% ee at 2.50 μM determined that the S-enantiomer was present in 36.0% ee at 2.70 μM (entry 5, Table 1).

TABLE 1

UV/CD sensing of samples of 10 with varying concentrations and ee's using 3.

| | Sample Composition | | | Ratiometric Sensing | | | | |
|---|---|---|---|---|---|---|---|---|
| Entry | Abs. Config. | Conc. (μM) | % Ee | Abs. Config. | Conc. (μM) | % Ee (257 nm) | % Ee (355 nm) | % Ee (averaged) |
| 1 | *R* | 4.00 | 25.0 | *R* | 4.34 | 23.4 | 24.7 | 24.0 |
| 2 | *R* | 2.25 | 55.5 | *R* | 2.01 | 56.0 | 56.9 | 56.5 |
| 3 | *S* | 5.00 | 50.0 | *S* | 4.59 | 54.7 | 54.1 | 54.4 |
| 4 | *R* | 9.20 | 8.0 | *R* | 9.29 | 11.9 | 11.1 | 11.5 |
| 5 | *S* | 2.50 | 33.3 | *S* | 2.70 | 36.6 | 35.5 | 36.0 |
| 6 | *R* | 7.00 | 42.8 | *R* | 6.55 | 47.1 | 46.6 | 46.8 |
| 7 | *S* | 8.00 | 37.5 | *S* | 7.78 | 43.5 | 41.7 | 42.6 |
| 8 | *S* | 9.75 | 79.0 | *S* | 9.54 | 81.3 | 84.7 | 83.0 |
| 9 | *S* | 1.25 | 60.0 | *S* | 1.14 | 56.5 | 52.5 | 54.5 |

Finally, the chirality sensing method with chlorocoumarin 3 was applied to asymmetric reaction analysis (Table 2). Iridium catalyzed hydrogenation of the N-methyl imine 48 to the secondary amine 17 was chosen for this purpose (Verdaguer et al., "Amine Additives Greatly Expand the Scope of Asymmetric Hydrosilylation of Imines," *Angew. Chem. Int. Ed.* 37:1103-1107 (1998); Klahn et al., "Menthyl-Substituted Group 4 Metallocene Dihalides," *Organometallics* 27:5846-5851 (2005); Schnider et al., "Enantioselective Hydrogenation of Imines with Chiral Phosphanodihydrooxazole Iridium Catalysts," *Chem. Eur. J.* 3:887-892

(1997); Lindqvist et al., "Chiral Molecular Tweezers: Synthesis and Reactivity in Asymmetric Hydrogenation," *J. Am. Chem. Soc.* 137:4038-4041 (2015); Wakchaure et al., "Disulfonimide-Catalyzed Asymmetric Reduction of N-Alkyl Imines," *Angew. Chem. Int. Ed.* 54:11852-11856 (2015), which are hereby incorporated by reference in their entirety). Several ligands 49-53 and catalyst loadings were varied to determine the value of chiroptical sensing and to compare it with traditional NMR/chiral HPLC analysis. The inherent ruggedness of the click chemistry sensing approach of the present invention together with the wide solvent compatibility allowed us to simply take 200 μL aliquots from the methanolic reaction mixtures for click sensing and direct UV/CD analysis. Based on a conservative estimate the analysis time per sample was 60 minutes and 6 mL of solvent waste for diluting the samples were generated. The vast majority of the analysis time is required for the reaction of the amine product with the probe. If necessary this can be accelerated at higher temperatures, however, one can easily conduct hundreds of these experiments in parallel using multi-well plate technology. In such a high-throughput screening (HTS) scenario, the analysis of hundreds of reaction mixtures would still take approximately one hour. A chiral HPLC method was developed with Boc-protected 17 to verify the results from the sensing assay. The traditional NMR and chiral HPLC analysis of the enantioselective imine hydrogenation required more than 7 hours and 540 mL of solvent waste were accumulated, which can be mostly attributed to the formation and purification of the Boc-protected derivative 54. Overall, the results obtained by both methods are in good agreement. For example, the reaction with 5 mol % of the Phox ligand derived Ir catalyst gave (S)-17 in 55.8% ee and quantitative yield according to NMR and HPLC analysis which compares well to the 59.8% ee and 96.0% yield determined by sensing (entry 1). The error margins of the chiroptical sensing are fairly small and acceptable, in particular if one would apply the sensing assay to HTS of hundreds of samples. The minimization of time and chemical waste compared to traditional methods underscores the efficiency, practicality, cost and environmental sustainability advantages of chiroptical sensing with the coumarin 3.

TABLE 2

Analysis of the asymmetric hydrogenation of N-methyl-1-phenylethan-1-imine.

| | Reaction conditions | | | Traditional analysis[a] | | | Chiroptical sensing[b] | | |
|---|---|---|---|---|---|---|---|---|---|
| Entry | Ligand | Cat. load. (mol %) | Time (h) | Abs. Config. | % ee | Conv. | Abs. Config. | % ee | Conv. |
| 1 | 49 | 5.00 | 18 | S | 55.8 | 99.9 | S | 59.8 | 96.0 |
| 2 | 50 | 5.00 | 18 | R | 16.3 | 99.9 | R | 14.3 | 99.9 |
| 3 | 51 | 5.00 | 18 | R | 31.0 | 99.9 | R | 32.2 | 99.1 |
| 4 | 52 | 5.00 | 18 | R | 31.4 | 99.9 | R | 25.8 | 98.0 |
| 5 | 53 | 5.00 | 18 | S | 16.3 | 92.0 | S | 14.2 | 96.3 |
| 6 | 49 | 2.50 | 1 | S | 46.2 | 51.1 | S | 47.8 | 53.9 |
| 7 | 49 | 3.25 | 1 | S | 57.3 | 63.3 | S | 54.5 | 68.4 |

[a]The enantiomeric excess and conversion were determined by chiral HPLC and $^1H$ NMR.
[b]The enantiomeric excess and conversion were determined by CD and UV sensing at 376 nm and 392 nm, respectively.
Cat. load. = catalyst loading, Conv. = conversion.

Figure 3:
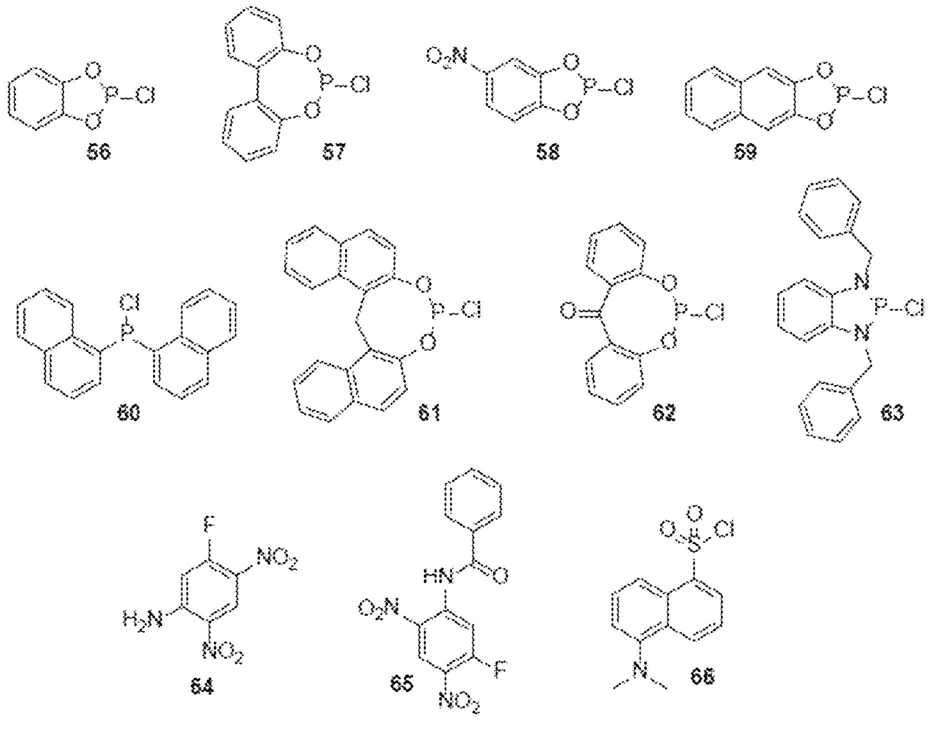
FIG. 3 shows the structures of the chiroptical sensors 56-66.

In analogy to the coumarin sensors, the sensors 56-66, carrying a fluoroarene, arylsulfonyl chloride or phosphorus chloride moiety, were investigated (FIG. 3). Sensors 56, 60, 64 and 66 were commercially available and the others were prepared in the laboratory. It was found that these sensors also undergo smooth covalent bond formation with a variety of amines, amino alcohols, alcohols, hydroxy acids, and amino acids. This results in characteristic chiroptical CD and UV responses suitable for determination of the absolute configuration and quantitative chirality sensing of the concentration and ee of a broad variety of chiral compounds as described with the coumarins. The chirality sensing with sensors 1-5 and 56-66 is exemplified for many classes of compounds here and is expected to also work with others, for example thiols and compounds carrying combinations of these functional groups.

Example 2—General Materials and Methods

All reagents and solvents were commercially available and used without further purification. Reactions were carried out under inert and anhydrous conditions. Flash chromatography was performed on silica gel, particle size 40-63 μm. $^1H$ NMR and $^{13}C$ NMR spectra were obtained at 400 MHz and 100 MHz, respectively, using deuterated acetonitrile and chloroform as solvents. Chemical shifts were reported in ppm relative to TMS or to the solvent peak.

Example 3—Synthesis and Characterization of Probes and Selected Sensing Products

4-Chlorocoumarin (1)

Scheme 2: Synthesis of 4-chlorocoumarin (1)

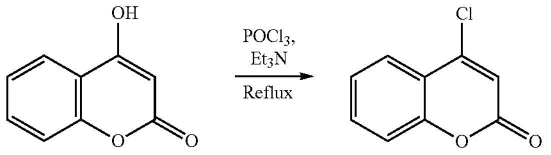

To a mixture of 4-hydroxycoumarin (250.0 mg, 1.54 mmol) and $POCl_3$ (5.0 mL), $Et_3N$ (322.4 μL, 2.31 mmol) was added slowly over a period of 5-10 minutes and then the mixture was heated under reflux for 12 hours. After the reaction was completed, the mixture was quenched by pouring it slowly onto ice-cold water. The crude product was extracted with dichloromethane. The combined organic layers were washed with water, brine and dried over $MgSO_4$ and concentrated in vacuo. Purification by flash column chromatography on silica gel (4% ethyl acetate in hexanes) afforded 201.7 mg (1.12 mmol, 73%) of a white solid. $^1H$ NMR (400 MHz, $CDCl_3$): δ=7.87 (m, 1H), 7.62 (ddd, J=8.7, 7.3, 1.5 Hz, 1H), 7.42-7.34 (m, 2H), 6.61 (s, 1H). $^{13}C$ NMR (100 MHz, $CDCl_3$): δ=160.0, 153.0, 149.6, 133.3, 125.5, 124.8, 118.0, 117.0, 115.5. Anal. Calcd. for $C_9H_5ClO_2$: C, 59.86; H, 2.79. Found: C, 59.62; H, 2.91.

4-Bromocoumarin (2)

Scheme 3: Synthesis of 4-iodocoumarin (2)

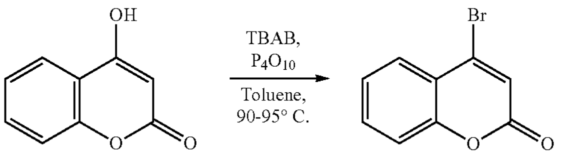

A mixture of 4-hydroxycoumarin (250.0 mg, 1.54 mmol), TBAB (575.9 mg, 1.78 mmol) and $P_4O_{10}$ (524.6 mg, 3.69 mmol) in toluene was stirred at 90-95° C. and the reaction was monitored by GC-MS. After 2 hours, the mixture was allowed to cool to room temperature and washed with water, sat. $NaHCO_3$ and extracted with dichloromethane. The combined organic layers were dried over $MgSO_4$ and concentrated in vacuo. Purification by flash column chromatography on silica gel (4% ethyl acetate in hexanes) afforded 204.2 mg (0.91 mmol, 59%) of a white solid. $^1$H NMR (400 MHz, $CDCl_3$): δ=7.84 (dd, J=8.0, 1.5 Hz, 1H), 7.60 (ddd, J=8.7, 7.4, 1.5 Hz, 1H), 7.41-7.29 (m, 2H), 6.86 (s, 1H). $^{13}$C NMR (100 MHz, $CDCl_3$): δ=158.6, 152.5, 141.4, 133.2, 128.0, 124.9, 119.6, 118.9, 117.0. Anal. Calcd. for $C_9H_5BrO_2$: C, 48.04; H, 2.24. Found: C, 48.00; H, 2.25.

4-Bromo-3-nitrocoumarin (4)

Scheme 4: Synthesis of 4-Bromo-3-nitrocoumarin (4)

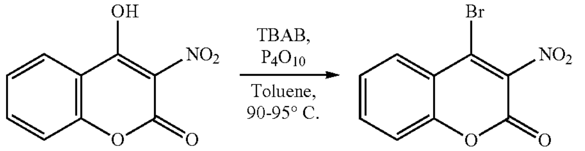

A mixture of 4-hydroxy-3-nitrocoumarin (250.0 mg, 1.21 mmol), tetra-n-butylammonium bromide (451.3 mg, 1.40 mmol) and $P_4O_{10}$ (340.7 mg, 2.89 mmol) in toluene was stirred at 90-95° C. The solution was allowed to cool to room temperature, washed with water and sat. $NaHCO_3$ and extracted with dichloromethane. The combined organic layers were dried over $MgSO_4$ and concentrated in vacuo. Purification by flash column chromatography on silica gel (10% ethyl acetate in hexanes) afforded 194.4 mg (0.72 mmol, 60%) of a brown solid. $^1$H NMR (400 MHz, $CDCl_3$): δ=7.98 (dd, J=8.1, 1.6 Hz, 1H), 7.76 (ddd, J=8.6, 7.3, 1.5 Hz, 1H), 7.51 (ddd, J=8.3, 7.4, 1.2 Hz, 1H), 7.44 (dd, J=8.4, 1.1 Hz, 1H). $^{13}$C NMR (100 MHz, $CDCl_3$): δ=151.6, 151.3, 135.3, 133.7, 129.8, 126.4, 117.4, 117.2. Anal. Calcd. for $C_9H_4BrNO_4$: C, 40.03; H, 1.49; N, 5.19. Found: C, 40.02; H, 1.71; N, 5.22.

4-Iodo-3-nitrocoumarin (5)

Scheme 5: Synthesis of 4-Iodo-3-nitrocoumarin (5)

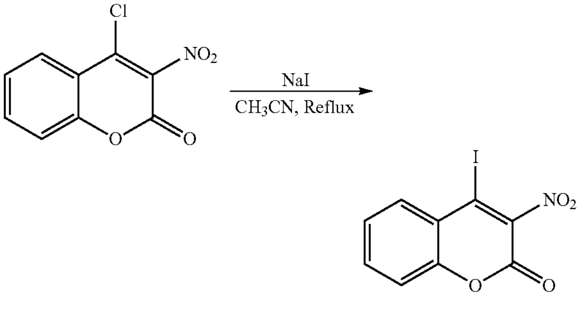

A mixture of 4-chloro-3-nitrocoumarin (3) (100.0 mg, 0.21 mmol) and NaI (263.7 mg, 1.76 mmol) was heated under reflux in acetonitrile. The reaction was monitored by GC-MS and full conversion was observed after 18 hours. After cooling to room temperature, the reaction mixture was washed with water, $NaHCO_3$ and extracted with dichloromethane. The combined organic layers were dried over $MgSO_4$ and concentrated in vacuo to give 140.8 mg (0.44 mmol, 99%) of a yellow solid. $^1$H NMR (400 MHz, $CDCl_3$): δ=7.84 (dd, J=8.2, 1.4 Hz, 1H), 7.72 (ddd, J=8.0, 7.6, 1.4 Hz, 1H), 7.47 (ddd, J=7.8, 7.6, 1.0 Hz, 1H), 7.38 (dd, J=8.4, 0.8 Hz, 1H). $^{13}$C NMR (100 MHz, $CDCl_3$): δ=150.7, 150.6, 135.0, 134.6, 126.6, 119.4, 117.4, 113.8. Anal. Calcd. for $C_9H_4INO_4$: C, 34.10; H, 1.27; N, 4.42. Found: C, 34.11; H, 1.39; N, 4.33.

(S)-3-Nitro-4-((1-phenylethyl)amino)coumarin (7)

Scheme 6: Reaction between 4-chloro-3-nitrocoumarin (3) and (S)-1-phenylethylamine (8)

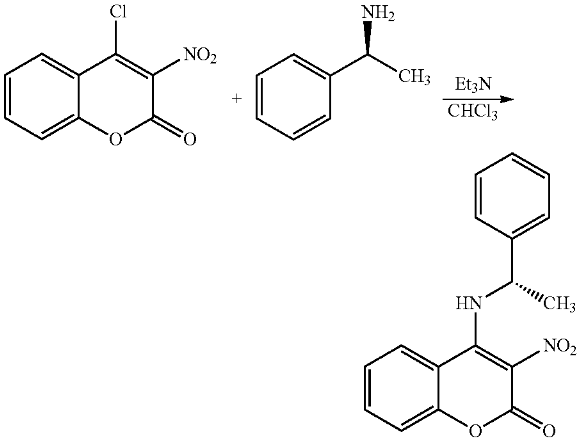

A mixture of 4-chloro-3-nitrocoumarin (3) (100.0 mg, 0.44 mmol), (S)-1 phenylethylamine (8) (57.2 μL, 53.7 mg) and $Et_3N$ (61.7 μL, 0.44 mmol) was stirred in chloroform (3.0 mL). After the reaction was completed, the reaction mixture was concentrated in vacuo. Purification by flash chromatography (14% ethyl acetate in hexanes) afforded 122.7 mg (90%, 0.40 mmol) of a yellow solid. $^1$H NMR (400 MHz, $CDCl_3$): δ=10.58 (s, 1H), 7.78 (dd, J=8.3, 1.4 Hz, 1H), 7.62 (ddd, J=8.6, 7.3, 1.4 Hz, 1H), 7.50-7.42 (m, 2H), 7.41-7.35 (m, 3H), 7.32 (m, 1H), 7.17 (ddd, J=8.4, 7.2, 1.3 Hz, 1H), 5.38 (m, 1H), 1.78 (d, J=6.6 Hz, 3H). $^{13}$C NMR (100 MHz, $CDCl_3$): δ=154.4, 153.6, 152.7, 141.5, 135.2, 129.6, 128.5, 127.2, 125.3, 124.2, 118.3, 115.9, 112.8, 57.9, 26.3. Anal. Calcd. for $C_{17}H_{14}N_2O_4$: C, 65.80; H, 4.55; N, 9.03. Found: C, 65.87; H, 4.78; N, 8.81.

4-(((1S,2R)-2-Hydroxy-2,3-dihydro-1H-inden-1-yl)amino)-3-nitrocoumarin

Scheme 7: Reaction between 4-chloro-3-nitrocoumarin (3) and (1S,2R)-cis-1-amino-2-indanol (22)

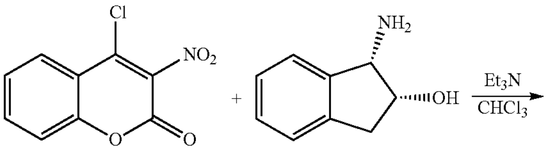

-continued

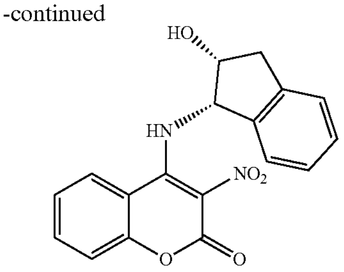

A mixture of 4-chloro-3-nitrocoumarin (3) (100.0 mg, 0.44 mmol), (1S,2R)-cis-1-amino-2-indanol (22) (66.1 mg, 0.44 mmol) and $Et_3N$ (61.7 μL, 0.44 mmol) was stirred in chloroform (3.0 mL). After the reaction was completed, the mixture was concentrated in vacuo. Purification by flash chromatography (50% ethyl acetate in hexanes) afforded 133.1 mg (89%, 0.39 mmol) of a brown solid. $^1H$ NMR (400 MHz, $(CD_3)_2SO$): δ=8.28 (d, J=8.3 Hz, 1H), 7.78 (m, 1H), 7.46 (m, 1H), 7.44-7.38 (m, 2H), 7.37-7.24 (m, 3H), 5.83 (s, 1H), 5.44 (b s, 1H), 4.58 (q, J=4.4 Hz, 1H), 3.18 (dd, J=16.4, 4.7 Hz, 1H), 2.92 (d, J=16.4 Hz, 1H). $^{13}C$ NMR (100 MHz, $(CD_3)_2SO$): δ=154.8, 152.1, 141.8, 139.9, 135.2, 128.8, 127.2, 126.5, 125.8, 125.2, 124.9, 118.1, 116.0, 113.9, 73.4, 63.8, 55.3. Anal. Calcd. for $C_{18}H_{14}N_2O_5$: C, 63.90; H, 4.17; N, 8.28. Found: C, 63.62; H, 4.25; N, 8.11.

(R)-3-Nitro-4-(N,α-dimethylbenzyl)amino)coumarin

Scheme 8: Reaction between 4-chloro-3-nitrocoumarin (3) and (R)-N-methyl-1-phenylethylamine (17)

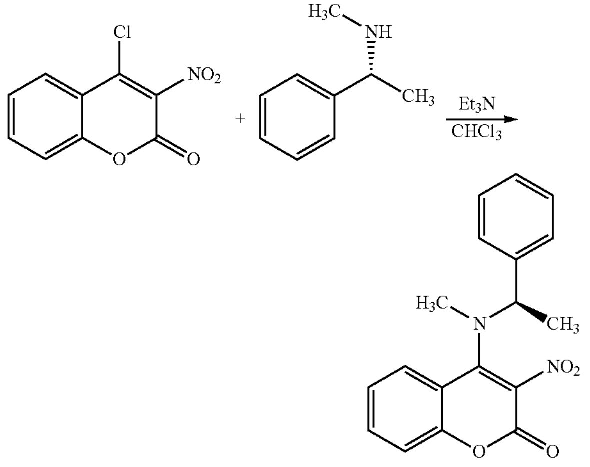

A mixture of 4-chloro-3-nitrocoumarin (3) (45.0 mg, 0.20 mmol), (R)-N-methyl-1-phenylethylamine (17) (29.2 μL, 0.24 mmol) and $Et_3N$ (33.5 μL, 0.24 mmol) was stirred in chloroform (1.0 mL). After the reaction was completed, the reaction mixture was concentrated in vacuo. Purification by flash chromatography (30% ethyl acetate in hexanes) afforded 62 mg (96%, 0.19 mmol) of a yellow solid. $^1H$ NMR (400 MHz, $CDCl_3$): δ=7.83 (dd, J=8.2, 1.5 Hz, 1H), 7.60 (ddd, J=8.6, 7.2, 1.5 Hz, 1H), 7.49-7.42 (m, 2H), 7.42-7.35 (m, 4H), 7.25-7.19 (m, 1H), 5.32 (q, J=6.9 Hz, 1H), 2.82 (s, 3H), 1.77 (d, J=6.8 Hz, 3H). $^{13}C$ NMR (100 MHz, $CDCl_3$): δ=155.7, 152.9, 152.5, 138.5, 133.4, 129.0, 128.4, 128.2, 126.9, 126.2, 124.6, 118.3, 116.6, 62.3, 33.2, 17.9. Anal. Calcd. for $C_{18}H_{16}N_2O_4$: C, 66.66; H, 4.97; N, 8.64. Found: C, 66.65; H, 5.17; N, 8.60.

Example 4—Coumarin Probe Development and Optimization Studies

General Information

Initially, reactions were performed with 5.0 mM (S)-1-phenylethylamine (8) concentrations as described herein to identify a probe with superior chiroptical properties. The CD spectra of the diluted solutions (0.24 mM) were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm and a scan rate of 400 nm/s.

CD Analysis with Different Derivatives of Coumarin

Figure 4:
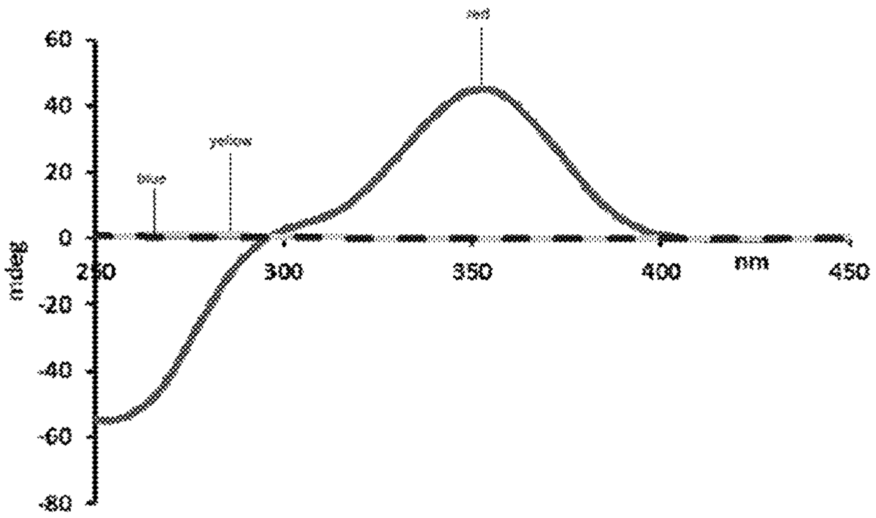
FIG. 4 is the CD spectra obtained using 4-chloro-3-nitrocoumarin (3, red), 4-chlorocoumarin (1, blue) and 4-bromocoumarin (2, yellow) with (S)-1-phenylethylamine (8) at room temperature.

A solution of 4-chloro-3-nitrocoumarin (3) (5.0 mM), (S)-1-phenylethylamine (8) (5.0 mM) and $Et_3N$ (5.0 mM) in 2.0 mL of chloroform was stirred for 1 hour. To 100 μL of this solution chloroform (2.0 mL) was added and the mixture was subjected to CD analysis (0.24 mM). Control experiments with (S)-1-phenylethylamine (8) in the absence of the probe did not show any CD signal at the wavelengths of interest (FIG. 4). The analysis was repeated with 4-chloro-coumarin (1) and 4-bromocoumarin (2). No reaction occurred under the conditions described above. A mixture of 4-chlorocoumarin (1) (9.2 mg, 0.05 mmol), (S)-1-phenyl-ethylamine (8) (6.5 μL, 0.05 mmol) and $Et_3N$ (7.0 μL, 0.05 mmol) was heated to 60-70° C. in $CHCl_3$ in a closed vessel for 3 hours. No reaction occurred based on $^1H$ NMR and TLC analysis.

(S)-1-Phenylethylamine (8) Addition to 4-chlorocoumarin (1)

Scheme 9: Reaction between 4-chlorocoumarin (1) and (S)-1-phenylethylamine (8)

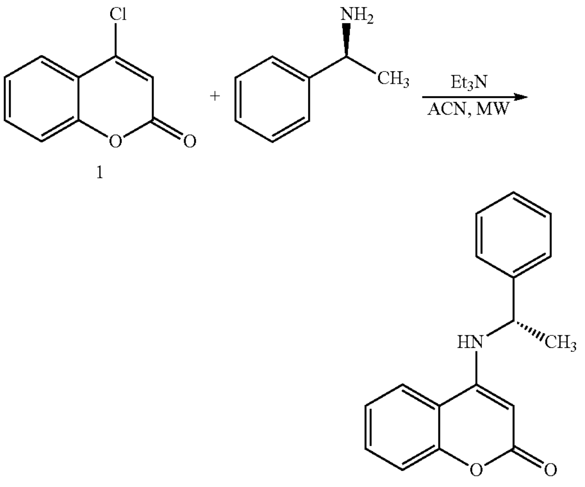

1

Figure 5:
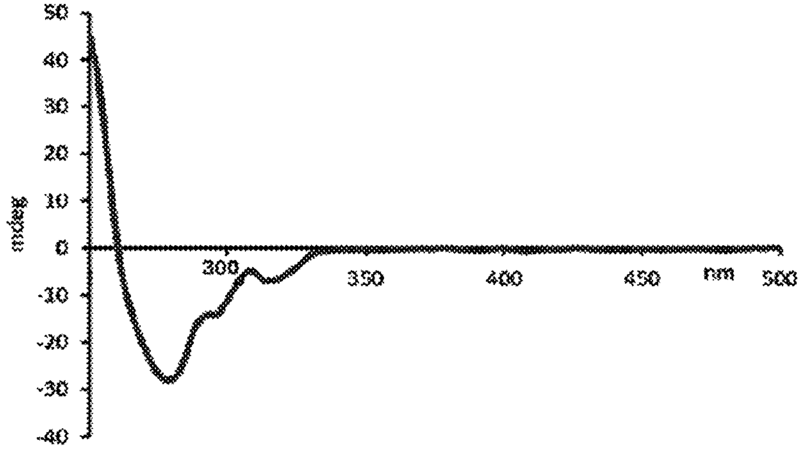
FIG. 5 is the CD spectrum of (S)-4-((1-phenylethyl) amino)coumarin (6) in chloroform taken at 0.24 mM.

A mixture of 4-chlorocoumarin (1) (9.8 mg, 0.05 mmol), (S)-1-phenylethylamine (8) (6.9 μL, 0.05 mmol) and $Et_3N$ (7.5 μL, 0.05 mmol) was heated in acetonitrile to 120° C. in a microwave reactor (150 W). After 1 hour, the reaction mixture was concentrated in vacuo. Purification by flash chromatography (0%-5% MeOH in dichloromethane) afforded 7 mg (49%, 0.03 mmol) of a white solid. $^1H$ NMR (400 MHz, $CDCl_3$): δ=7.59-7.50 (m, 2H), 7.40-7.27 (m, 7H), 5.37 (d, J=5.6 Hz, 1H), 5.21 (s, 1H), 4.67 (m, 1H), 1.66 (d, J=6.8 Hz, 3H). The CD of (S)-4-((1-phenylethyl)amino) coumarin (6) in chloroform taken at 0.24 mM is shown in FIG. 5.

Amine Sensing Using 4-chloro-3-nitrocoumarin (3)

Figure 6:
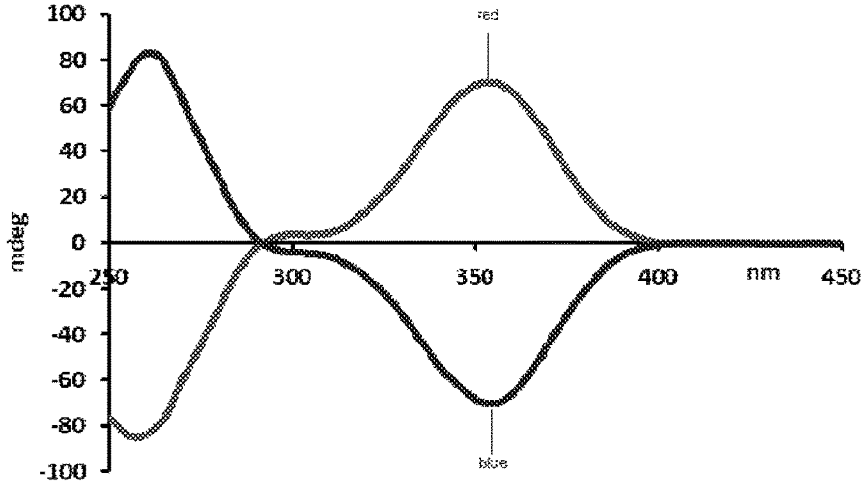
FIG. 6 is the CD spectra obtained using 4-chloro-3-nitrocoumarin (3) with (S)-1-phenylethylamine (8) (red) and (R)-1-phenylethylamine (8) (blue).

A solution of 4-chloro-3-nitrocoumarin (3) (5.0 mM), (S)-1-phenylethylamine (8) (5.0 mM) and $Et_3N$ (5.0 mM) in 2.0 mL of chloroform was stirred for 1 hour. To 100 μL of this solution, chloroform (2.0 mL) was added and the mixture was subjected to CD analysis (0.24 mM) (FIG. 6). Control experiments with (S)-1-phenylethylamine (8) in the absence of the probe did not show any CD signal at the wavelengths of interest.

Amine Sensing Using 4-bromo-3-nitrocoumarin (4)

Figure 7:
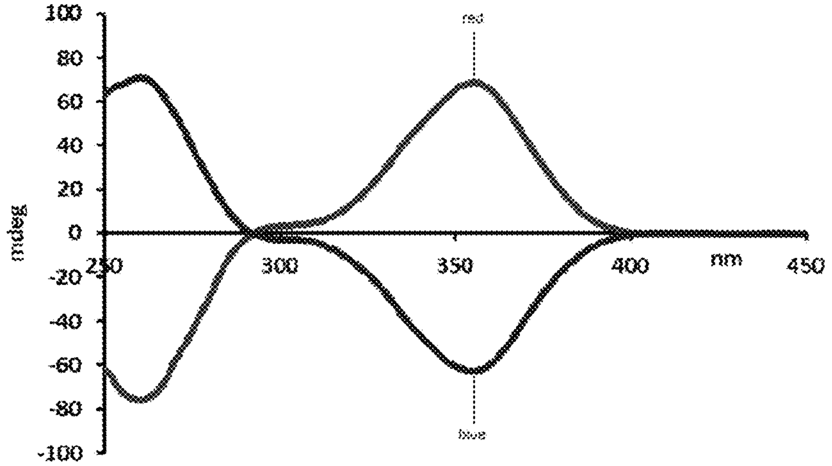
FIG. 7 is the CD spectra obtained using 4-bromo-3-nitrocoumarin (4) with (S)-1-phenylethylamine (8) (red) and (R)-1-phenylethylamine (8) (blue).

A solution of 4-bromo-3-nitrocoumarin (4) (5.0 mM), (S)-1-phenylethylamine (8) (5.0 mM) and $Et_3N$ (5.0 mM) in 2.0 mL of chloroform was stirred for 1 hour. To 100 μL of this solution, chloroform (2.0 mL) was added and the mixture was subjected to CD analysis (0.24 mM) (FIG. 7). Control experiments with (S)-1-phenylethylamine (8) in the absence of the probe did not show any CD signal at the wavelengths of interest.

Amine Sensing Using 4-iodo-3-nitrocoumarin (5)

Figure 8:
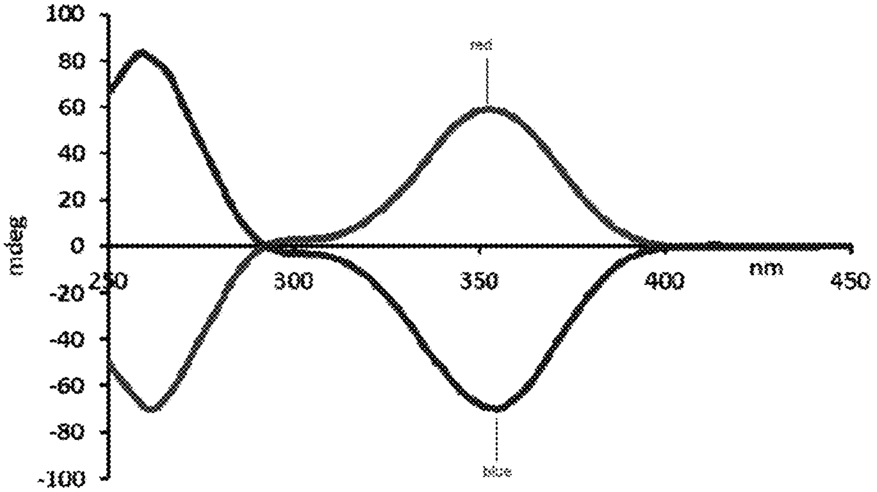
FIG. 8 is the CD spectra obtained using 4-iodo-3-nitrocoumarin (5) with (S)-1-phenylethylamine (8) (red) and (R)-1-phenylethylamine (8) (blue).
Figure 9:
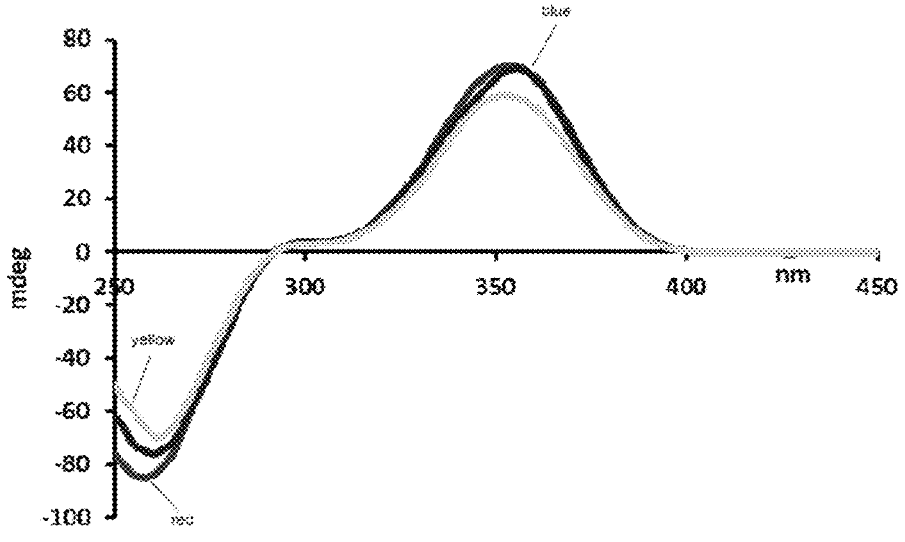
FIG. 9 is a comparison of the CD spectra obtained with (S)-1-phenylethylamine (8) and probes 3 (red), 4 (blue) and 5 (yellow).

A solution of 4-iodo-3-nitrocoumarin (5) (5.0 mM), (S)-1-phenylethylamine (8) (5.0 mM) and $Et_3N$ (5.0 mM) in 2.0 mL of chloroform was stirred for 1 hour. To 100 μL of this solution, chloroform (2.0 mL) was added and the mixture was subjected to CD analysis (0.24 mM) (FIG. 8). Control experiments with (S)-1-phenylethylamine (8) in the absence of the probe did not show any CD signal at the wavelengths of interest. FIG. 9 shows a comparison of the CD spectra obtained with (S)-1-phenylethylamine (8) and probe 3 (red), 4 (blue) and 5 (yellow).

Solvent and Base Optimization Using 4-chloro-3-nitrocoumarin (3)

Figure 10:
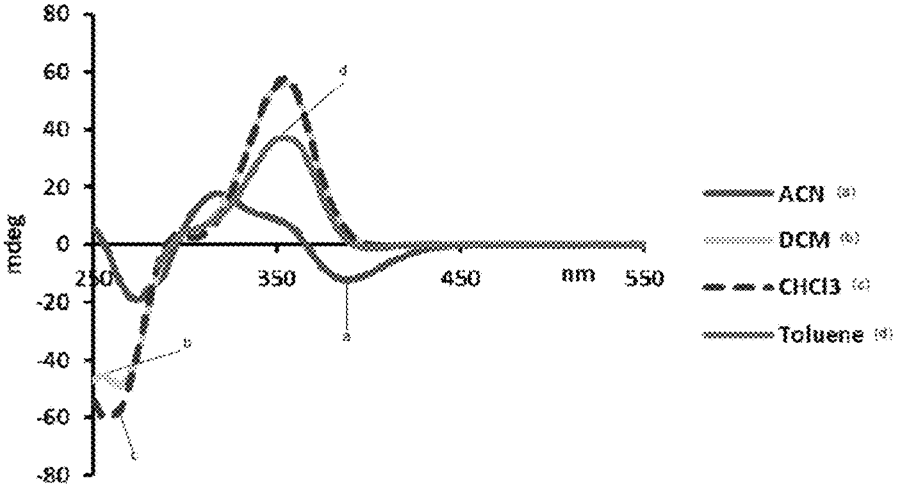
FIG. 10 is a CD comparison of the sensing of (S)-phenylethylamine (8) with probe 3 in different solvents with $Et_3N$.
Figure 11:
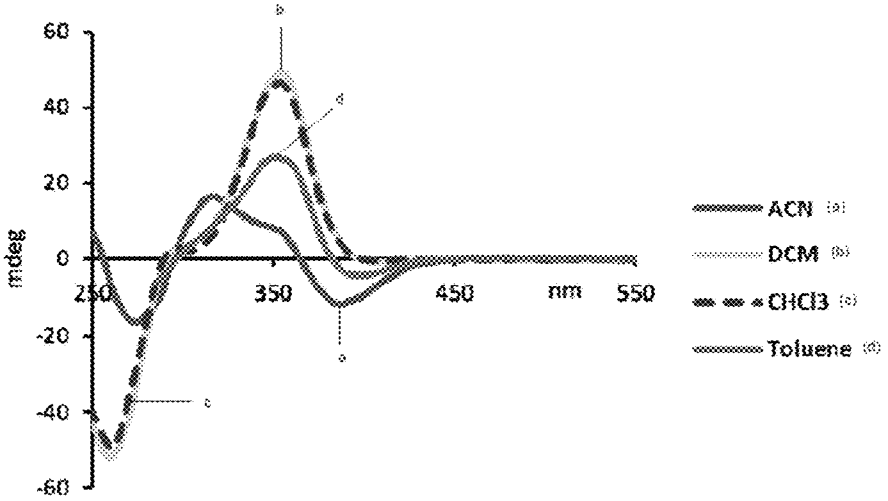
FIG. 11 is a CD comparison of the sensing of (S)-phenylethylamine (8) with probe 3 in different solvents with TBAOH.
Figure 12:
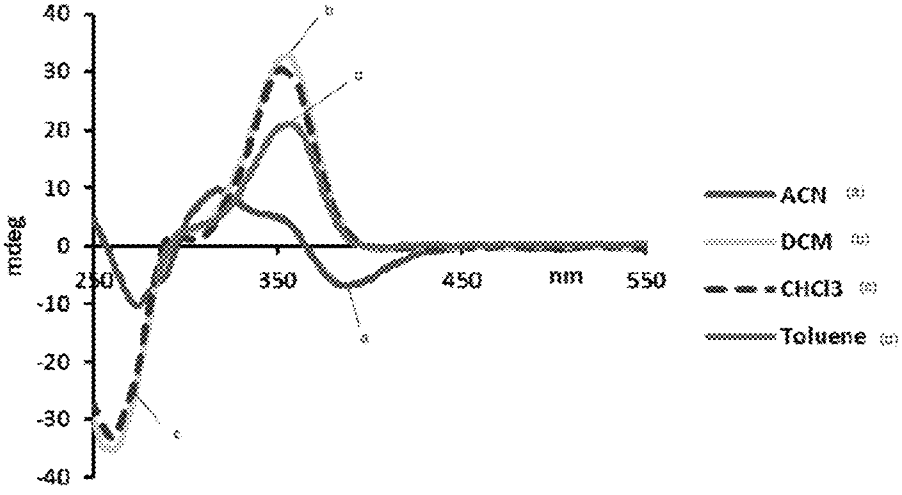
FIG. 12 is a CD comparison of the sensing of (S)-phenylethylamine (8) with probe 3 in different solvents in the absence of base.

A solution of probe 3 (5.0 mM), (S)-phenylethylamine (8) (5.0 mM) and $Et_3N$ (5.0 mM) in 2.0 mL of chloroform was stirred for 1 hour. To 80 μL of this solution, chloroform (2.0 mL) was added and the mixture was subjected to CD analysis (0.19 mM). The above experiment was repeated with dichloromethane, acetonitrile and toluene as solvents with TBAOH and in the absence of base (FIGS. 10-12).

Example 5—Mechanistic Studies

General Information

The CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.1 s, a data interval of 1.00 nm and a scan rate of 600 nm/min.

Figure 13:
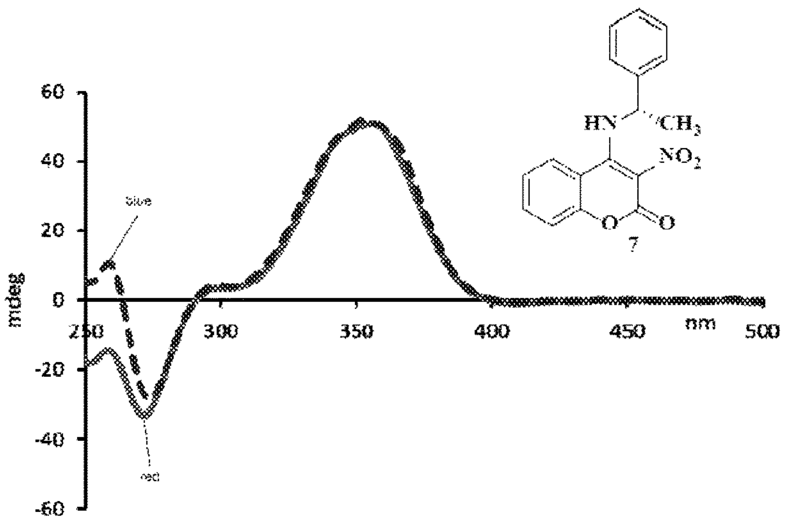
FIG. 13 is a comparison of the CD spectra of the isolated product (S)-3-Nitro-4-((1-phenylethyl)amino)coumarin (7) (red) with the reaction mixture of probe 3 and (S)-phenylethylamine (8) (blue).

Identification of the Sensing Product (S)-3-Nitro-4-((1-phenylethyl)amino)coumarin (7) was synthesized from probe 3 and (S)-phenylethylamine (8) as described above. Comparison of the CD spectrum of the isolated product with the CD spectrum obtained from the reaction mixture showed that they were identical (FIG. 13). CD measurements were taken at 0.24 mM concentrations.

Figure 14:
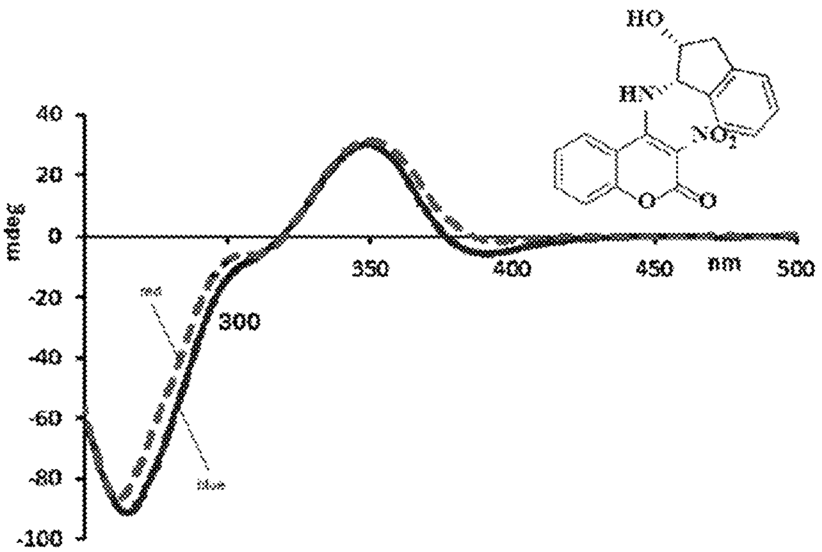
FIG. 14 is a comparison of the isolated product 4-(((1S,2R)-2-Hydroxy-2,3-dihydro-1H-inden-1-yl)amino)-3-nitrocoumarin (red) with the reaction mixture of probe 3 and (1S,2R)-cis-1-amino-2-indanol (22) (blue).

4-(((1S,2R)-2-Hydroxy-2,3-dihydro-1H-inden-1-yl) amino)-3-nitrocoumarin was synthesized from probe 3 and (1S,2R)-cis-1-amino-2-indanol (22) as described above. Comparison of the CD spectrum of the isolated product with the CD spectrum obtained from the reaction mixture, showed that they were identical (FIG. 14). CD measurements were taken at 0.24 mM concentrations.

Figure 15:
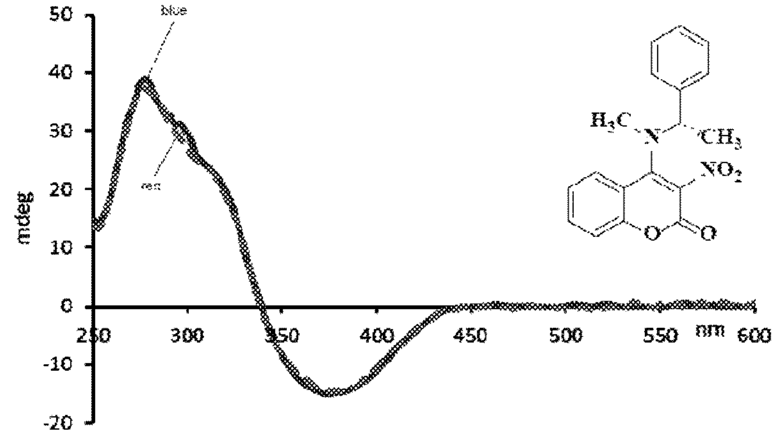
FIG. 15 is a comparison of the isolated product (R)-3-Nitro-4-(N,α-dimethylbenzyl)amino)coumarin (red) with the reaction mixture of probe 3 and (R)-N-methyl-1-phenylethylamine (17) (blue).

(R)-3-Nitro-4-(N,α-dimethylbenzyl)amino)coumarin was synthesized from probe 3 and (R)-N-methyl-1-phenylethylamine (17) as described above. Comparison of the CD spectrum of the isolated product with the CD spectrum obtained from the reaction mixture showed that they were identical (FIG. 15). CD measurements were taken at 0.10 mM concentrations.

Reaction Analysis

Figure 16:
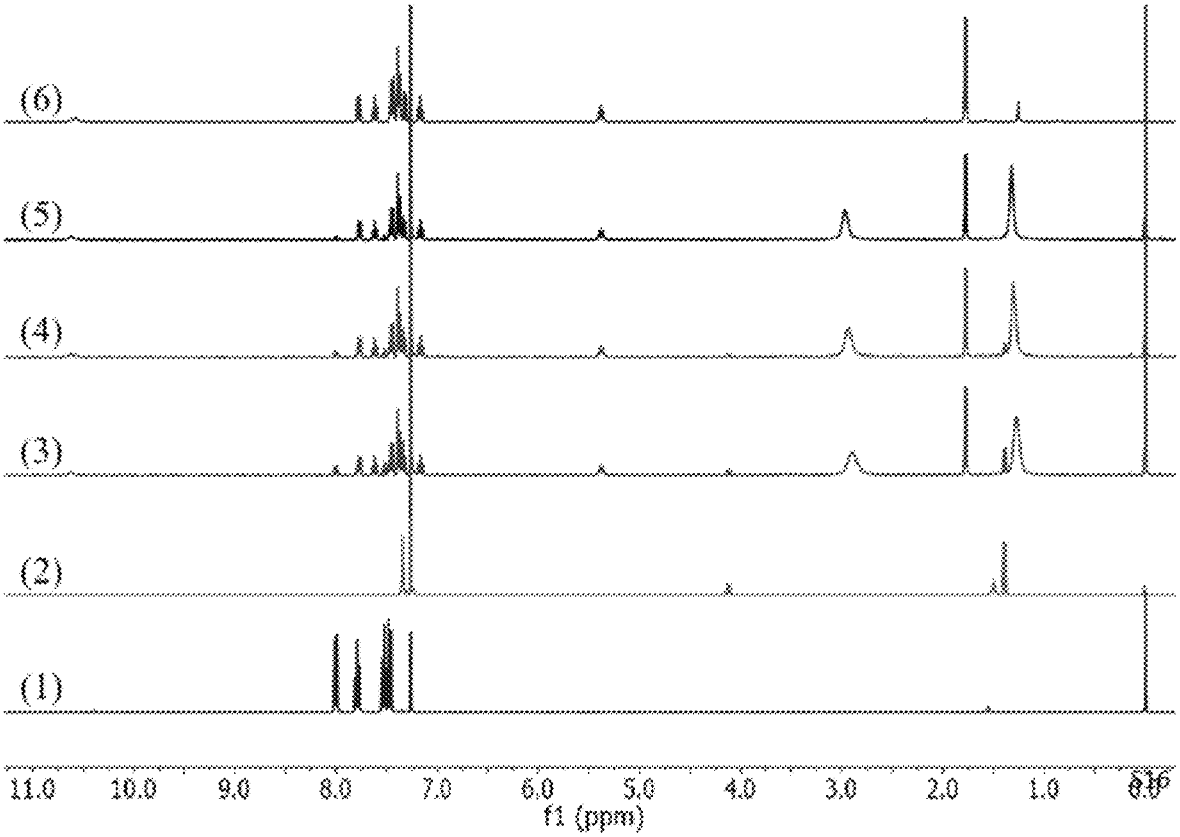
FIG. 16 is the $^1$H NMR spectra of the reaction between probe 3 and (S)-1-phenylethylamine (8). 1) Probe 3; 2) (S)-1-phenylethylamine; 3) reaction mixture of (S)-1-phenylethylamine, Et3N and probe 3 after 5 minutes; 4) reaction after 10 minutes; 5) after 15 minutes; 6) isolated 3-nitro-4-((1-phenylethyl)amino)coumarin, 7, for comparison. (See FIG. 17.)
Figure 17:
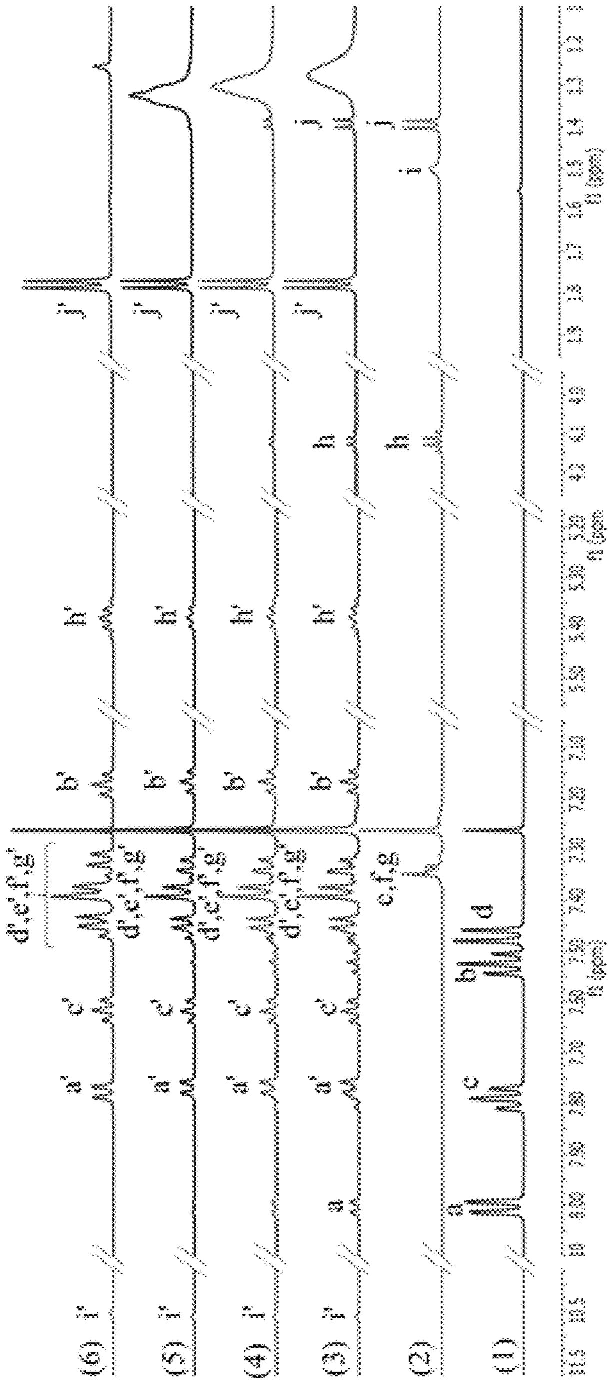
FIG. 17 is the $^1$H NMR analysis of the reaction between probe 3 and (S)-1-phenylethylamine (8). 1) Probe 3; 2) (S)-1-phenylethylamine; 3) reaction mixture of (S)-1-phenylethylamine, Et3N and probe 3 after 5 minutes; 4) reaction after 10 minutes; 5) after 15 minutes; 6) isolated 3-nitro-4-((1-phenylethyl)amino)coumarin, 7, for comparison. (See FIG. 1.)

The reaction between (S)-phenylethylamine (8) (5.0 mM) and probe 3 (5.0 mM) in the presence of $Et_3N$ (5.0 mM) in 0.80 mL of $CDCl_3$ was monitored by $^1H$ NMR (FIGS. 16-17). The reaction was complete within 15 minutes under these conditions.

Scheme 10: Reaction between 4-chloro-3-nitrocoumarin (3) and (S)-1-phenylethylamine (8) for NMR analysis

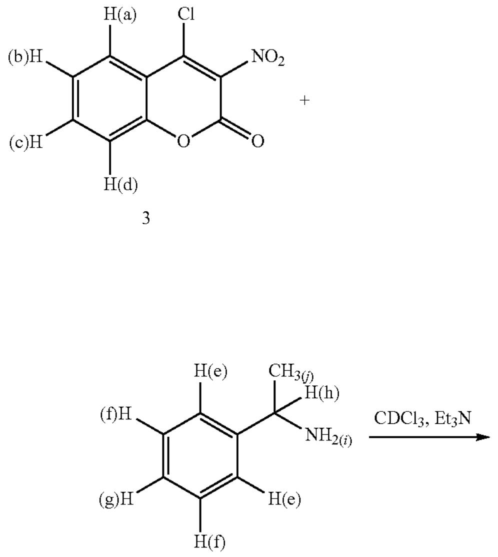

3

-continued

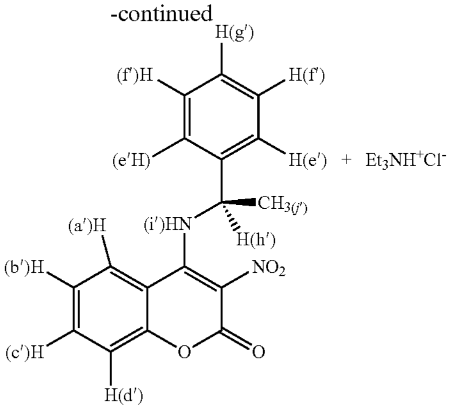

7

The signal at 1.39 ppm ($H_j$) of (S)-1-phenylethylamine (8) (spectrum 2, FIG. 17) decreases in intensity with time and shows a downfield shift ($H_{j'}$, 1.78 ppm) in the reaction mixture (see spectra 3, 4, and 5, FIG. 17). The signal at 4.12 ppm ($H_h$) of (S)-1-phenylethylamine (8) (spectrum 2, FIG. 17) decreases in intensity with time and shows a downfield shift ($H_{h'}$, 5.38 ppm) in the reaction mixture (see spectra 3, 4, and 5, FIG. 17). The signal at 8.00 ppm ($H_a$) of probe 3 (spectrum 1) decreases in intensity with time and shows an upfield shift ($H_{a'}$, 7.78 ppm) in the reaction mixture (see spectra 3, 4, and 5, FIG. 17). The assignment of $H_{i'}$, was based on the fact that it disappeared upon addition of $CD_3OD$.

Reaction Time

Figure 18:
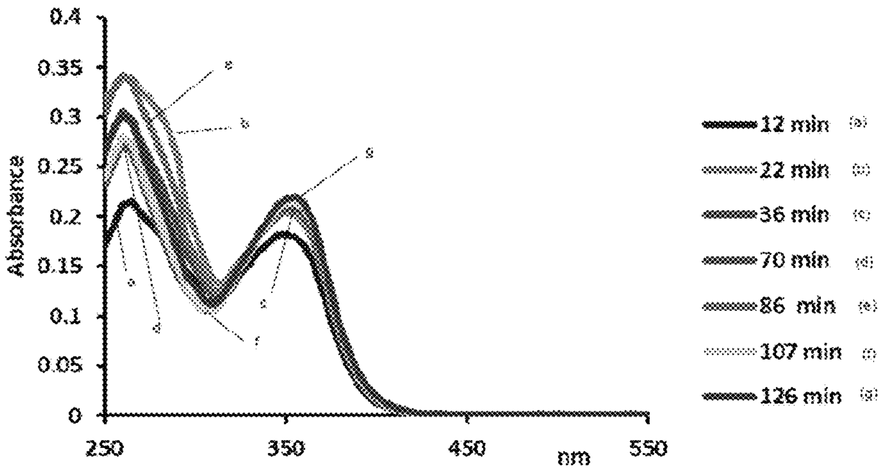
FIG. 18 is the UV analysis of the reaction between (S)-1-phenylethylamine (8) and probe 3.
Figure 19:
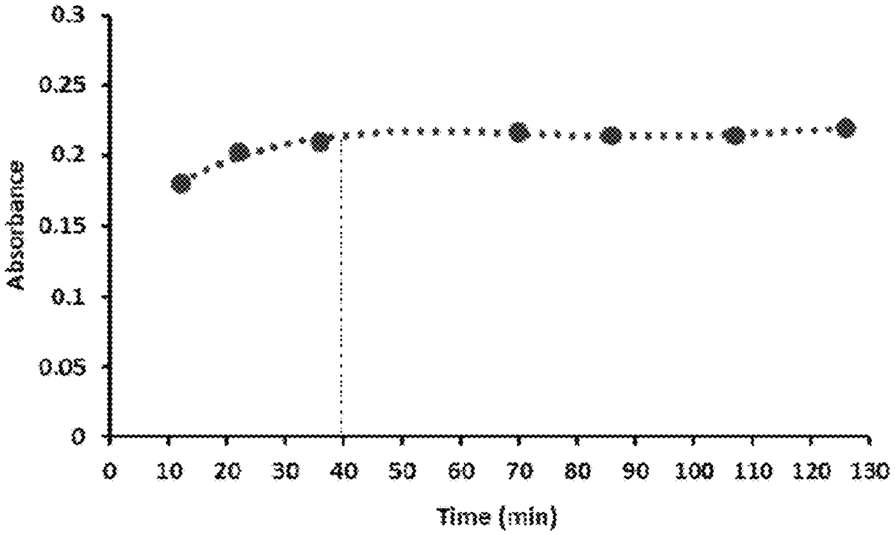
FIG. 19 is a plot of the absorbance (355 nm) vs. time for reaction between (S)-1-phenylethylamine (8) and probe 3.

The capture of (S)-1-phenylethylamine (8) (1.25 mM) by probe 3 (1.25 mM) in the presence of $Et_3N$ (1.25 mM) in 6.0 mL of chloroform was monitored using UV-Vis spectroscopy. Measurements were taken at 18 μM concentration, after dilution of 30 μL reaction mixture aliquots with 2.0 mL of chloroform. The reaction was complete in 40 minutes under these conditions (FIGS. 18-19).

Figure 20:
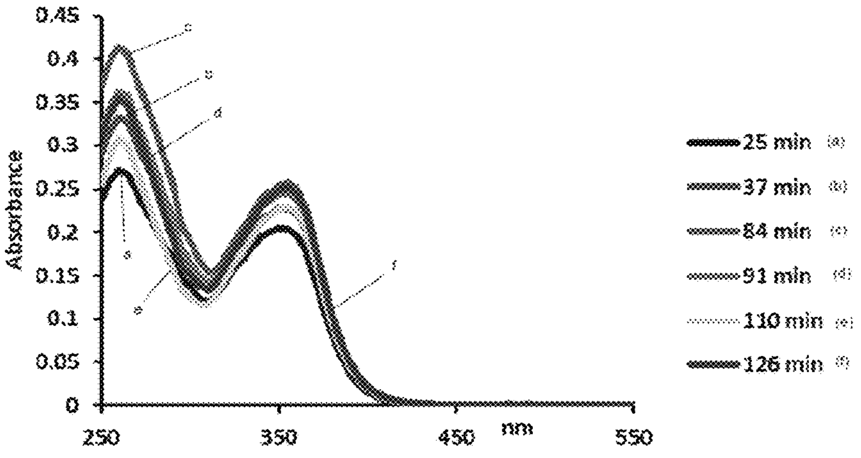
FIG. 20 is the UV analysis of the reaction between (S)-1-phenylethylamine (8) and probe 4.
Figure 21:
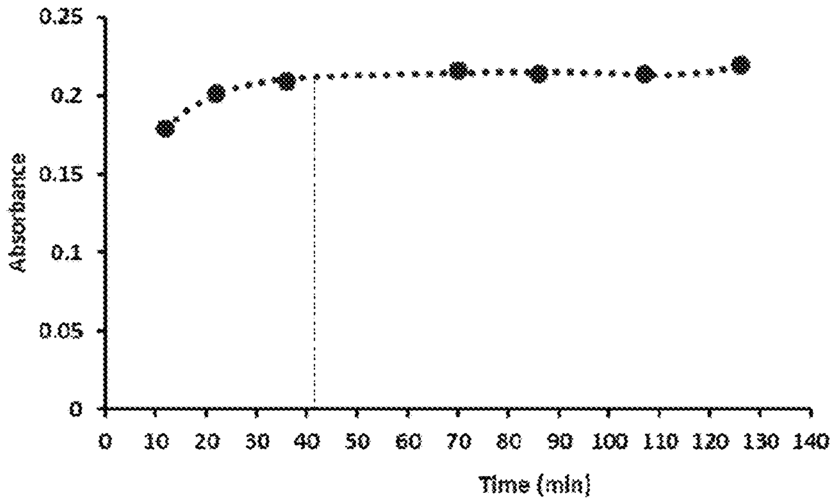
FIG. 21 is a plot of absorbance (355 nm) vs. time for the reaction between (S)-1-phenylethylamine (8) and probe 4.

The capture of (S)-1-phenylethylamine (8) (1.25 mM) by probe 4 (1.25 mM) in the presence of $Et_3N$ (1.25 mM) in 6.0 mL of chloroform was monitored using UV-Vis spectroscopy. Measurements were taken at 18 μM concentration, after dilution of 30 μL reaction mixture aliquots with 2.0 mL of chloroform. The reaction was complete after 40 minutes under these conditions (FIGS. 20-21).

Figure 22:
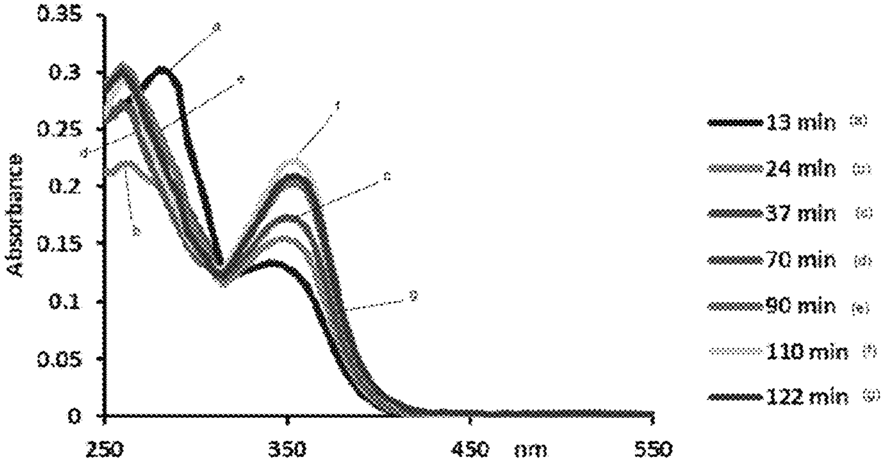
FIG. 22 is the UV analysis of the reaction between (S)-1-phenylethylamine (8) and probe 5.
Figure 23:
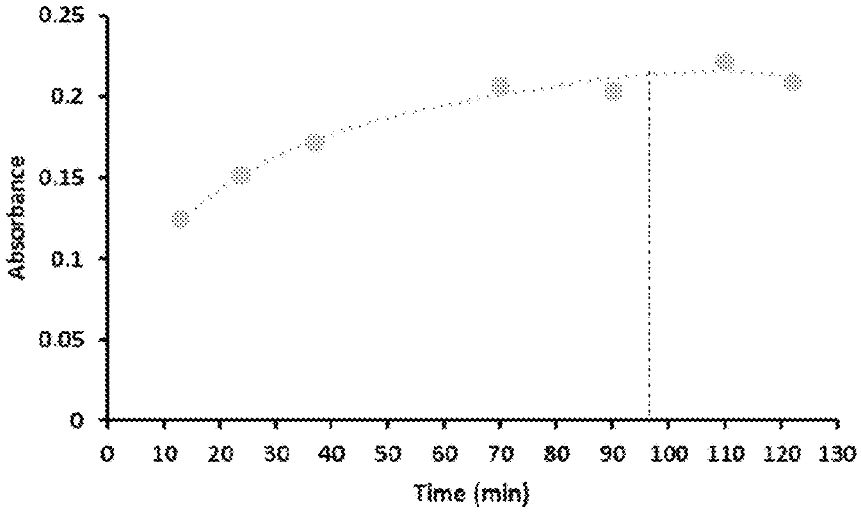
FIG. 23 is a plot of the absorbance (355 nm) vs. time for the reaction between (S)-1-phenylethylamine (8) and probe 5.

The capture of (S)-1-phenylethylamine (8) (1.25 mM) by probe 5 (1.25 mM) in the presence of $Et_3N$ (1.25 mM) in 6.0 mL of chloroform was monitored using UV-Vis spectroscopy. Measurements were taken at 18 μM concentration, after dilution of 30 μL reaction mixture aliquots with 2.0 mL of chloroform. The reaction was complete in less than 100 minutes under these conditions (FIGS. 22-23).

Sensing in Protic Solvents

Figure 24:
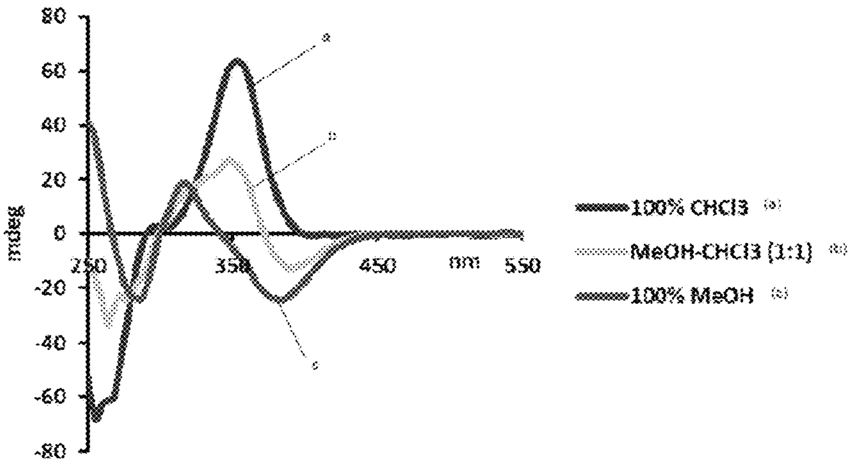
FIG. 24 is the CD sensing in protic solvents of probe 3 and (S)-phenylethylamine (8).
Figure 25:
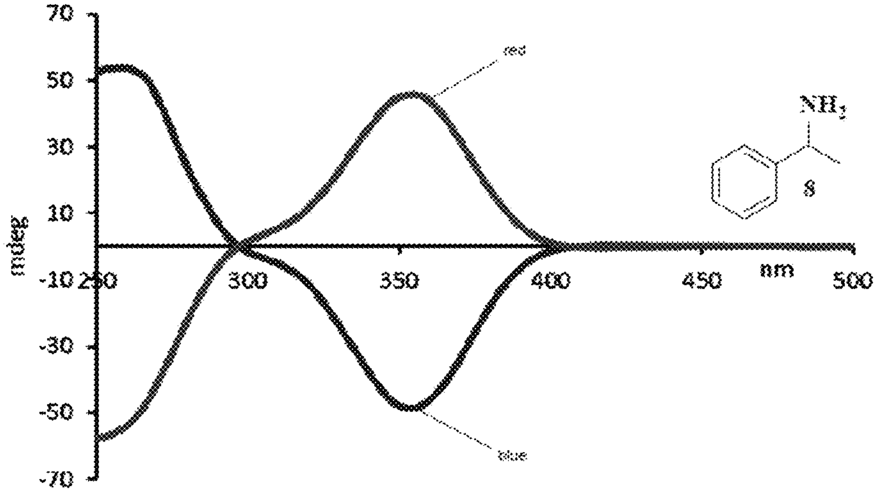
FIG. 25 is the CD spectra obtained from probe 3 with (S)-8 (red) and (R)-8 (blue). The CD measurements were taken at 0.24 mM in chloroform.
Figure 26:
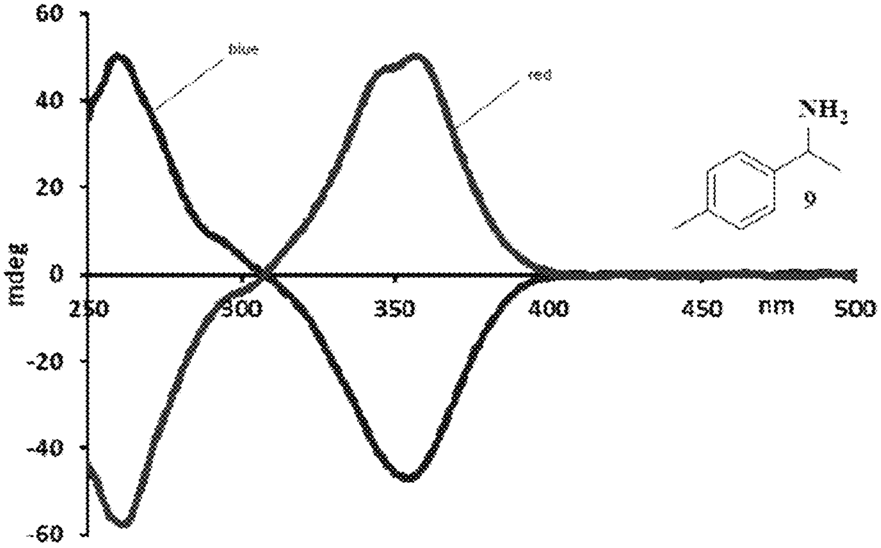
FIG. 26 is the CD spectra obtained from probe 3 with (S)-9 (red) and (R)-9 (blue). The CD measurements were taken at 0.24 mM in chloroform.
Figure 27:
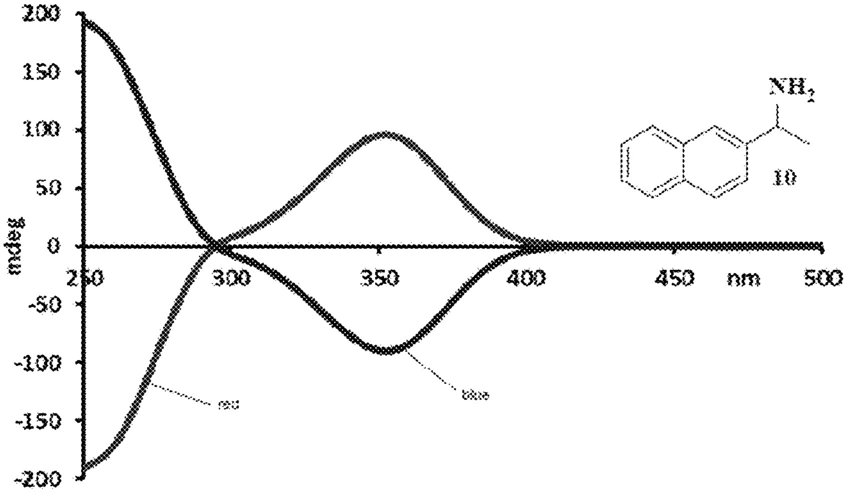
FIG. 27 is the CD spectra obtained from probe 3 with (S)-10 (red) and (R)-10 (blue). The CD measurements were taken at 0.24 mM in chloroform.
Figure 28:
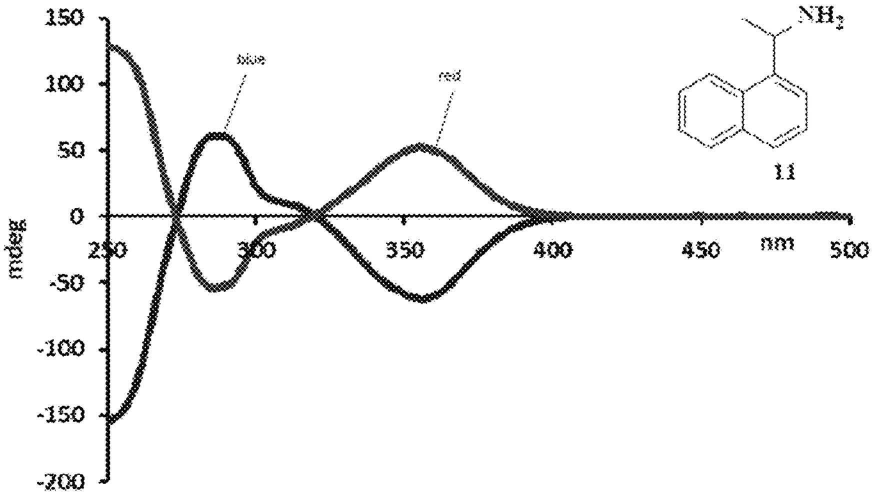
FIG. 28 is the CD spectra obtained from probe 3 with (S)-11 (red) and (R)-11 (blue). The CD measurements were taken at 0.19 mM in chloroform.
Figure 29:
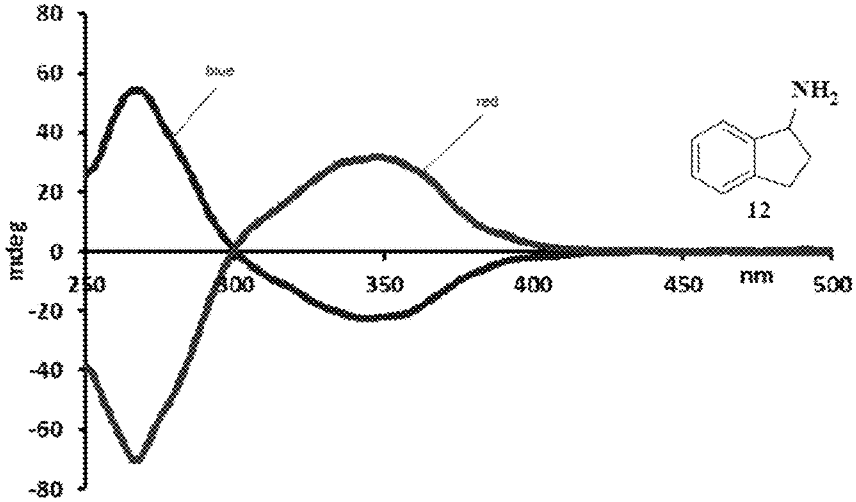
FIG. 29 is the CD spectra obtained from probe 3 with (S)-12 (red) and (R)-12 (blue). The CD measurements were taken at 0.35 mM in chloroform.
Figure 30:
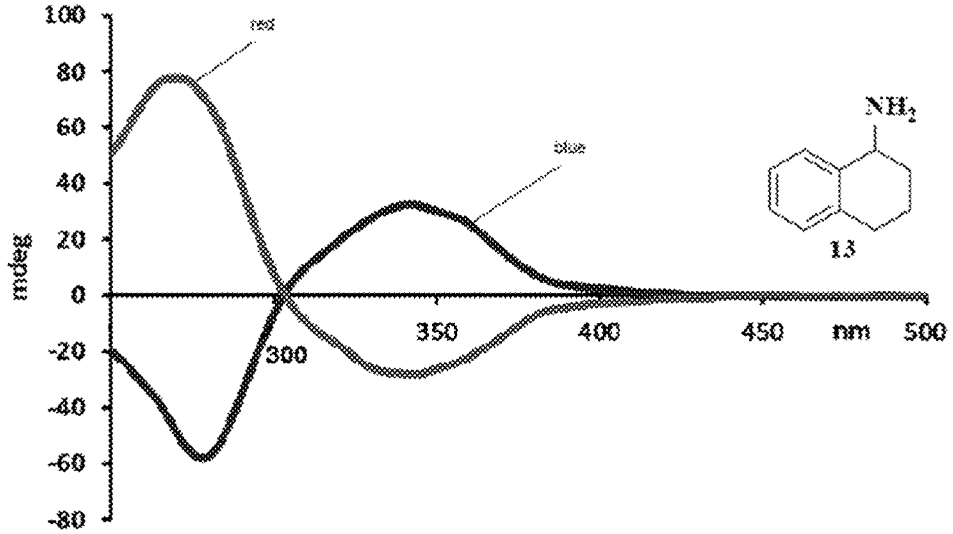
FIG. 30 is the CD spectra obtained from probe 3 with (S)-13 (red) and (R)-13 (blue). The CD measurements were taken at 0.16 mM in chloroform.
Figure 31:
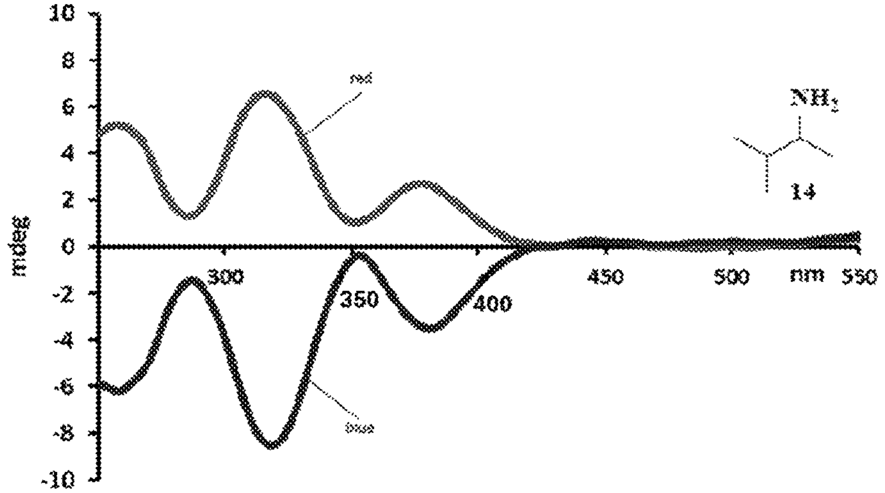
FIG. 31 is the CD spectra obtained from probe 3 with (S)-14 (red) and (R)-14 (blue). The CD measurements were taken at 0.24 mM in chloroform.
Figure 32:
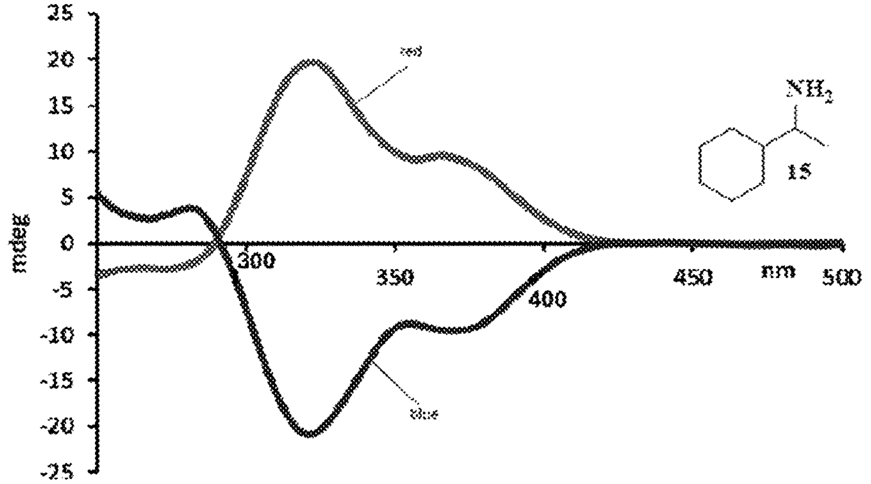
FIG. 32 is the CD spectra obtained from probe 3 with 0)-15 (red) and (R)-15 (blue). The CD measurements were taken at 0.24 mM in chloroform.
Figure 33:
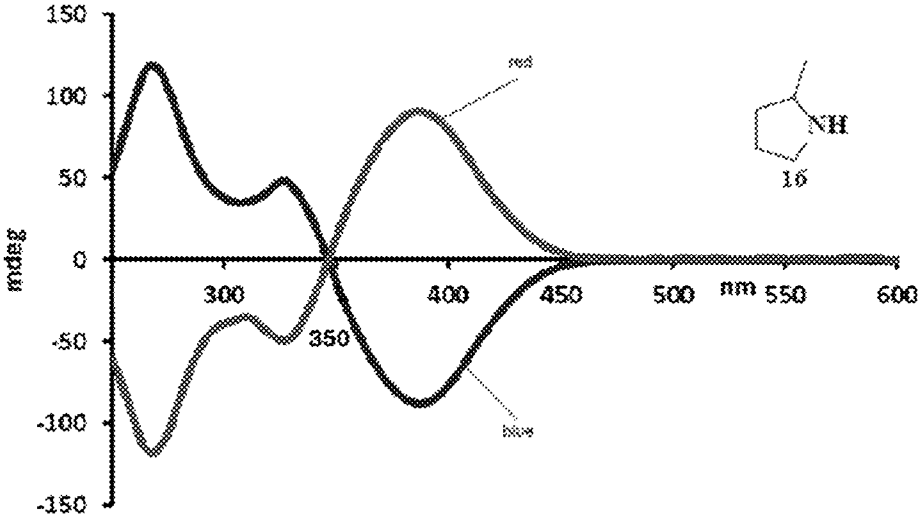
FIG. 33 is the CD spectra obtained from probe 3 with (S)-16 (red) and (R)-16 (blue). The CD measurements were taken at 0.24 mM in chloroform.
Figure 34:
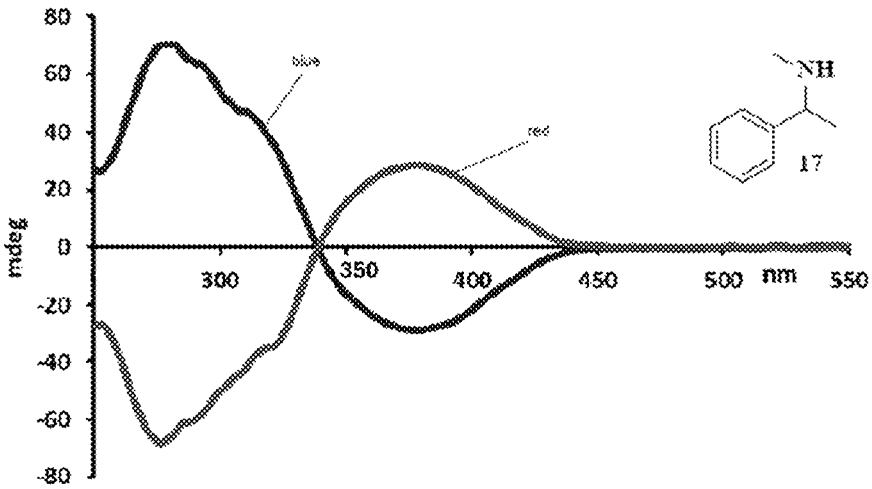
FIG. 34 is the CD spectra obtained from probe 3 with (S)-17 (red) and (R)-17 (blue). The CD measurements were taken at 0.24 mM in chloroform.
Figure 35:
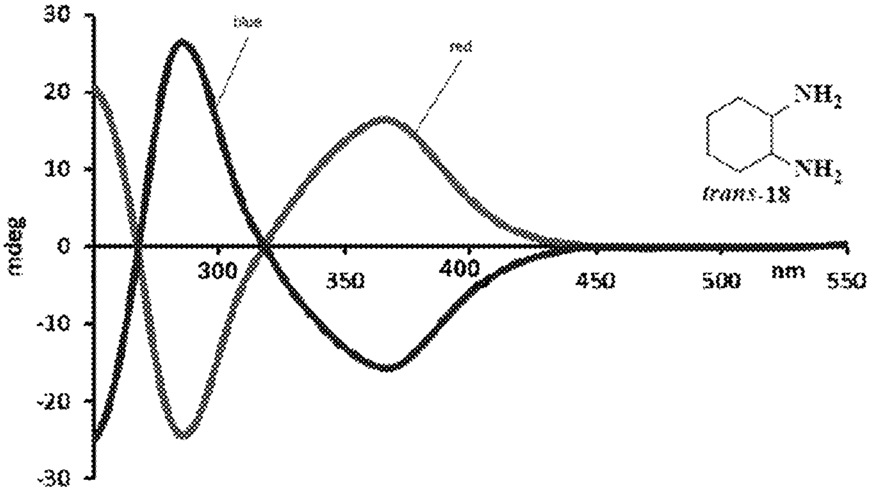
FIG. 35 is the CD spectra obtained from 1 equivalent of probe 3 with (S)-trans-18 (red) and (R)-trans-18 (blue). The CD measurements were taken at 0.24 mM in chloroform.
Figure 36:
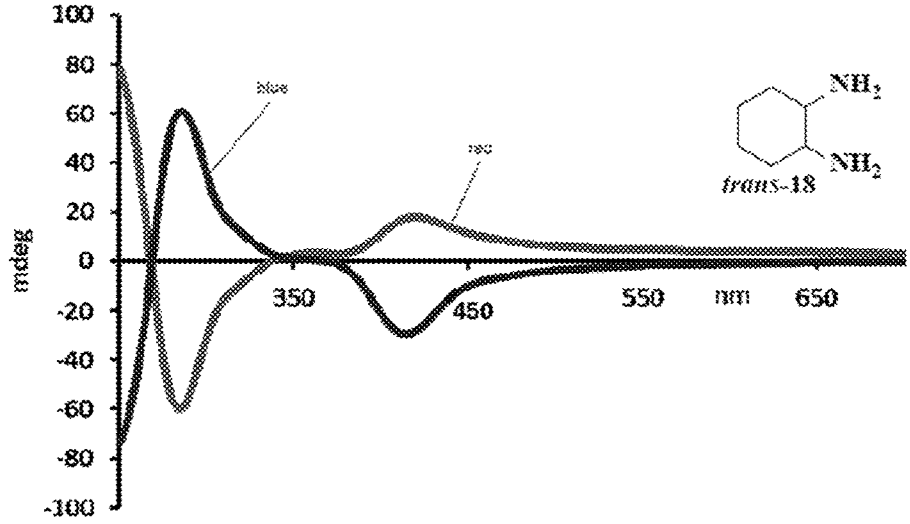
FIG. 36 is the CD spectra obtained from 2 equivalents of probe 3 with (S)-trans-18 (red) and (R)-trans-18 (blue). The CD measurements were taken at 0.24 mM in chloroform.
Figure 37:
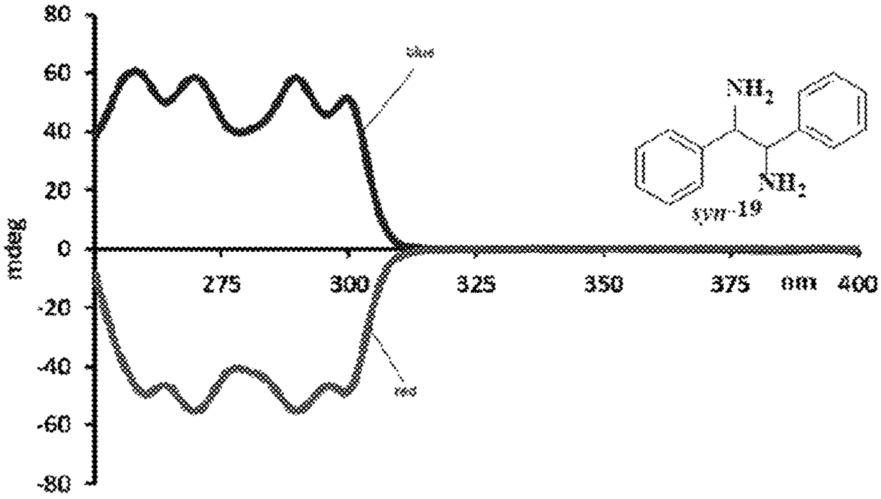
FIG. 37 is the CD spectra obtained from probe 3 with (S,S)-syn-19 (red) and (R,R)-syn-19 (blue). The CD measurements were taken at 0.23 mM in chloroform.
Figure 38:
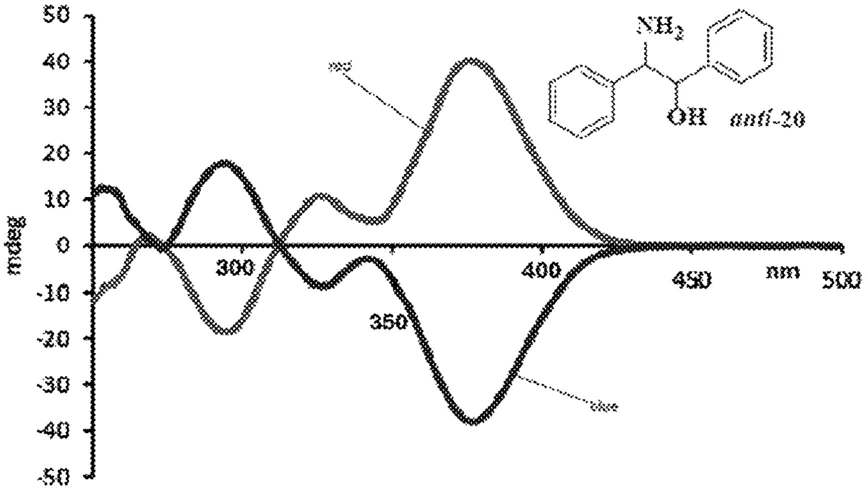
FIG. 38 is the CD spectra obtained from probe 3 with (1S,2S)-anti-20 (red) and (1R,2R)-anti-20 (blue). The CD measurements were taken at 0.19 mM in chloroform.
Figure 39:
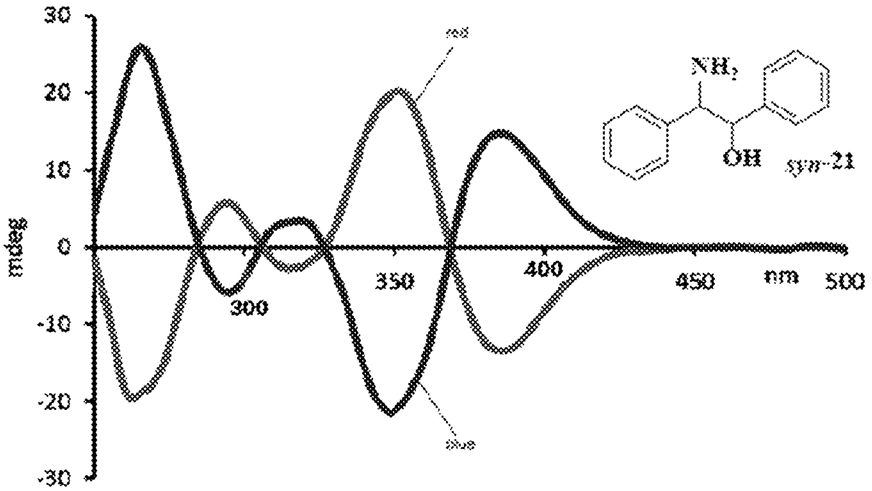
FIG. 39 is the CD spectra obtained from probe 3 with (1S,2R)-syn-21 (red) and (1R,2S)-syn-21 (blue). The CD measurements were taken at 0.17 mM in chloroform.
Figure 40:
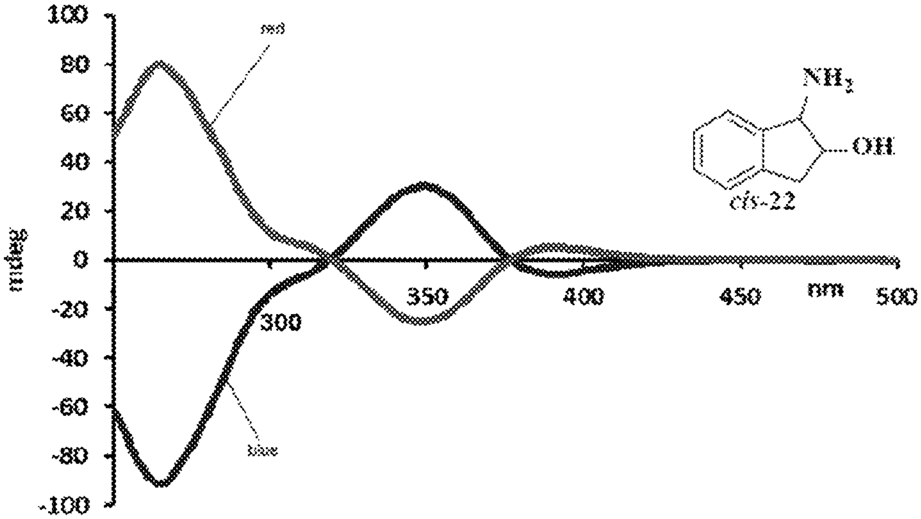
FIG. 40 is the CD spectra obtained from probe 3 with (1S,2R)-cis-22 (red) and (1R,2S)-cis-22 (blue). The CD measurements were taken at 0.24 mM in chloroform.
Figure 41:
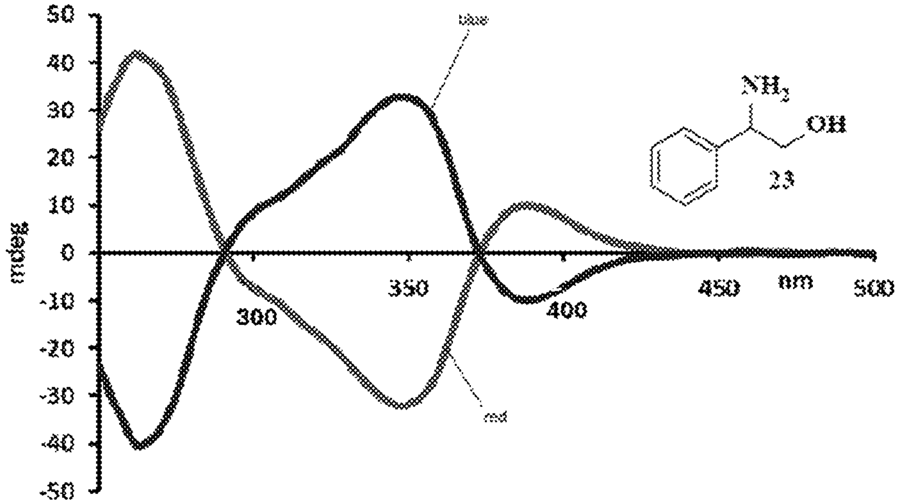
FIG. 41 is the CD spectra obtained from probe 3 with 0)-23 (red) and (R)-23 (blue). The CD measurements were taken at 0.17 mM in chloroform.
Figure 42:
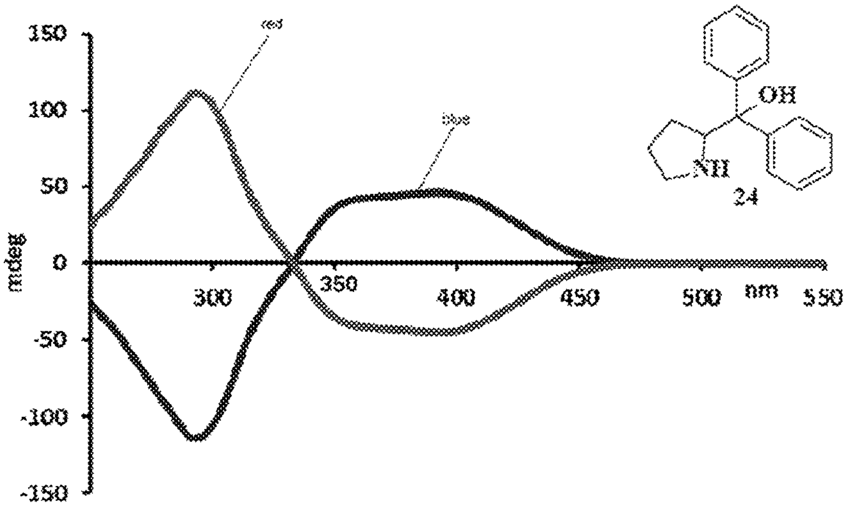
FIG. 42 is the CD spectra obtained from probe 3 with 0)-24 (red) and (R)-24 (blue). The CD measurements were taken at 0.26 mM in chloroform.
Figure 43:
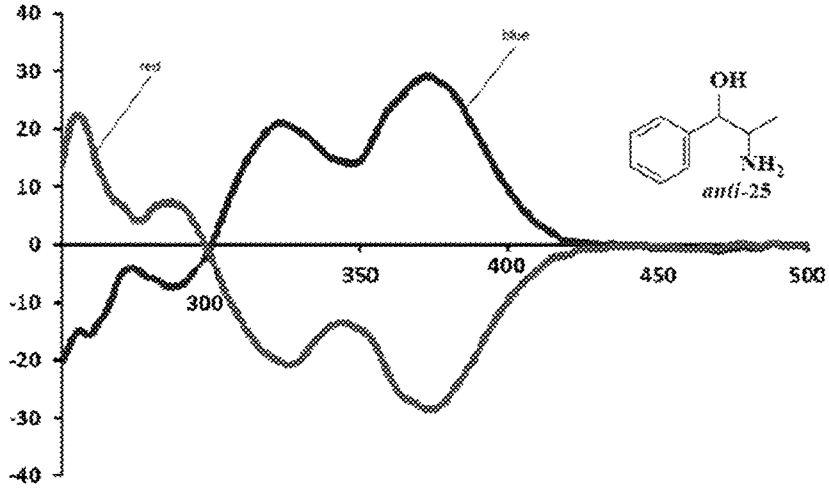
FIG. 43 is the CD spectra obtained from probe 3 with (1S,2R)-anti-25 (red) and (1R,2S)-anti-25 (blue). The CD measurements were taken at 0.24 mM in chloroform.
Figure 44:
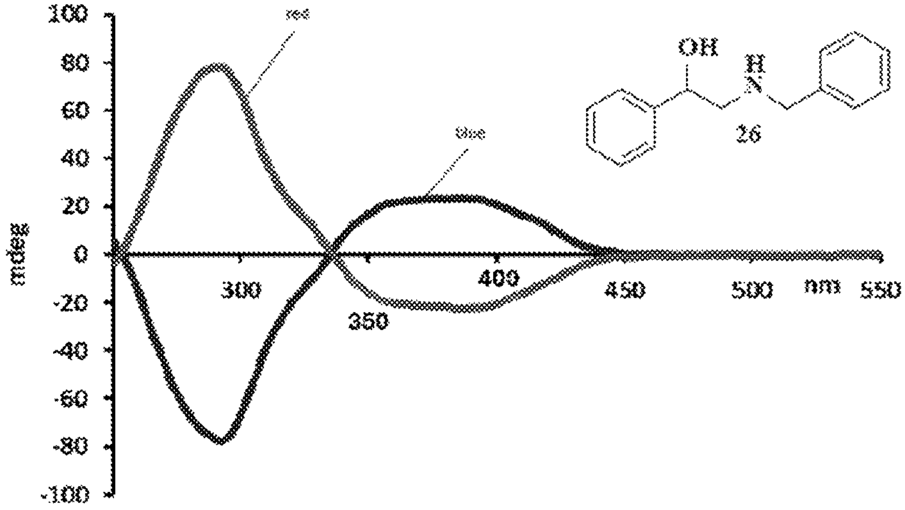
FIG. 44 is the CD spectra obtained from probe 3 with (S)-26 (red) and (R)-26 (blue). The CD measurements were taken at 0.17 mM in chloroform.
Figure 45:
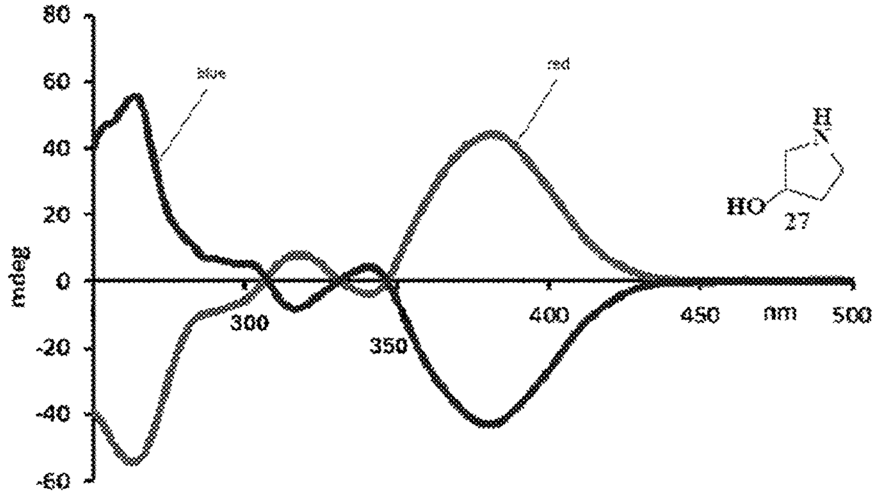
FIG. 45 is the CD spectra obtained from probe 3 with (S)-27 (red) and (R)-27 (blue). The CD measurements were taken at 0.24 mM in chloroform.
Figure 46:
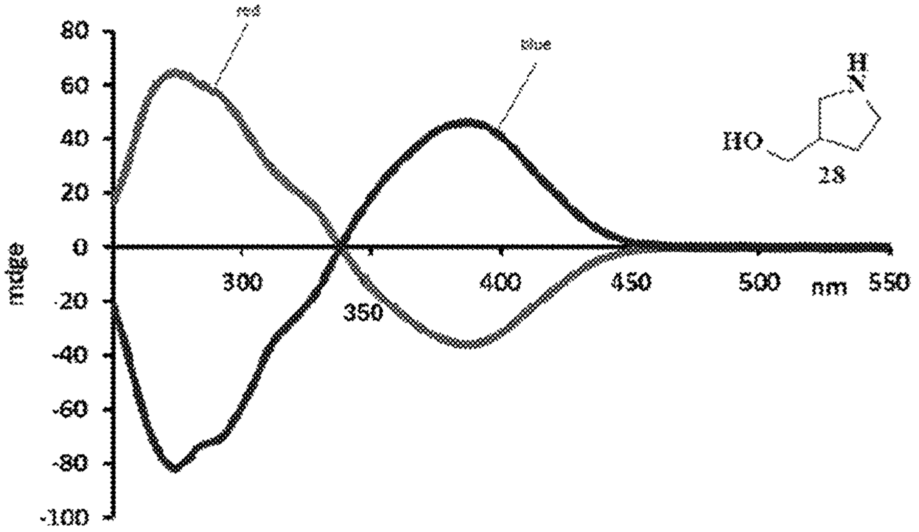
FIG. 46 is the CD spectra obtained from probe 3 with (S)-28 (red) and (R)-28 (blue). The CD measurements were taken at 0.24 mM in chloroform.
Figure 47:
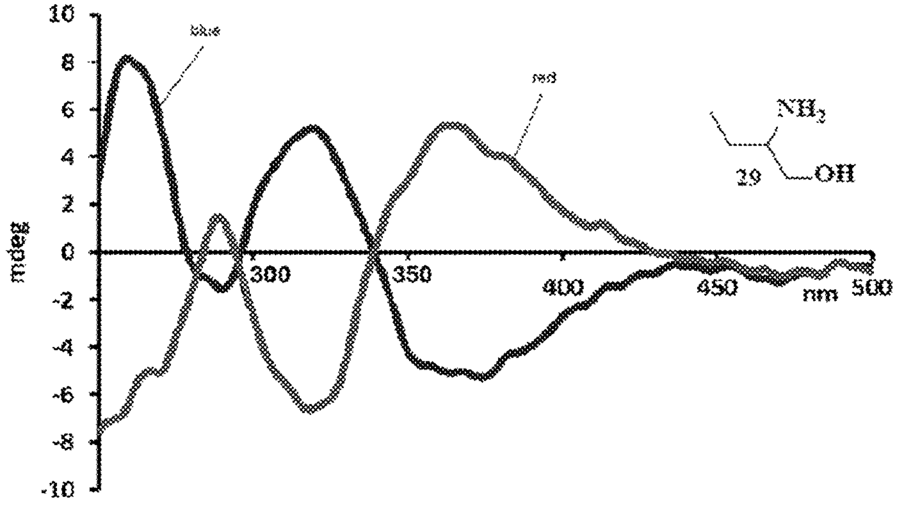
FIG. 47 is the CD spectra obtained from probe 3 with (1S,2R)-29 (red) and (1R,2S)-29 (blue). The CD measurements were taken at 0.24 mM in chloroform.
Figure 48:
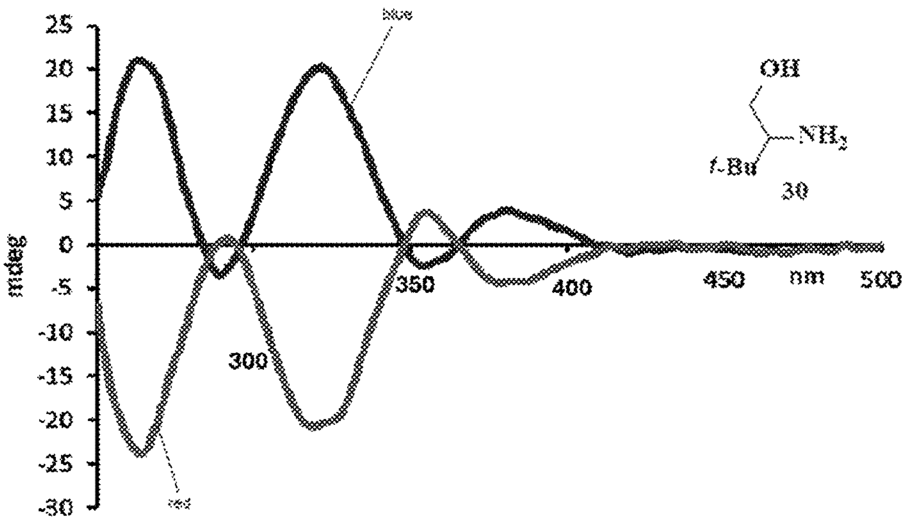
FIG. 48 is the CD spectra obtained from probe 3 with (S)-30 (red) and (R)-30 (blue). The CD measurements were taken at 0.24 mM in chloroform.
Figure 49:
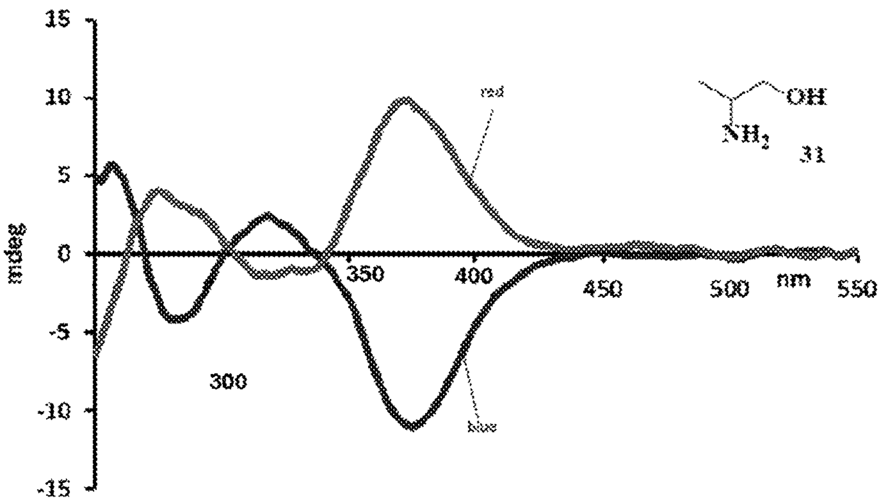
FIG. 49 is the CD spectra obtained from probe 3 with (S)-31 (red) and (R)-31 (blue). The CD measurements were taken at 0.24 mM in chloroform.

A solution of probe 3 (5.0 mM), (S)-phenylethylamine (8) (5.0 mM) and $Et_3N$ (5.0 mM) in 2.0 mL of chloroform was stirred for 1 hour. To 100 μL of this solution, solvent (2.0 mL) was added and the mixture was subjected to CD analysis (0.24 mM). CD spectra were collected in chloroform, methanol and chloroform-methanol (1:1) mixture (FIG. 24).

Example 6—Coumarin Sensing Scope

General Information

To test the utility of probe 3 as chirality chemosensor, CD spectra of the sensing experiments with chiral amines 8-19, chiral amino alcohols 20-31, chiral alcohols 32-33, and chiral amino acids 34-46 were obtained. The CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation.

Amines

A solution of probe 3 (5.0 mM), chiral amines (8-19) (5.0 mM) and $Et_3N$ (5.0 mM) in 2.0 mL of chloroform was stirred for 1 hour and subjected to CD (FIGS. 25-37) and UV analysis.

8

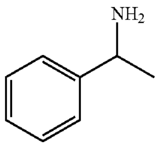

9

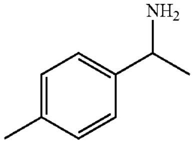

10

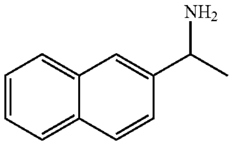

11

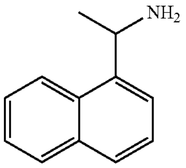

12

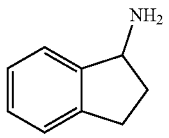

13

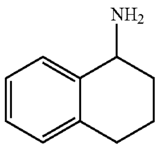

14

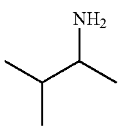

Figure 50:
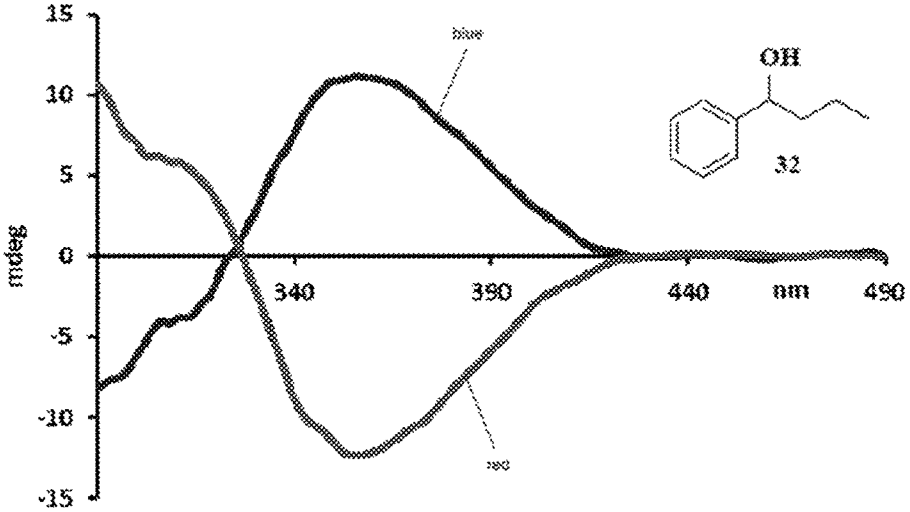
FIG. 50 is the CD spectra obtained from probe 3 with (S)-32 (red) and (R)-32 (blue). The CD measurements were taken at 0.34 mM in THF.
Figure 51:
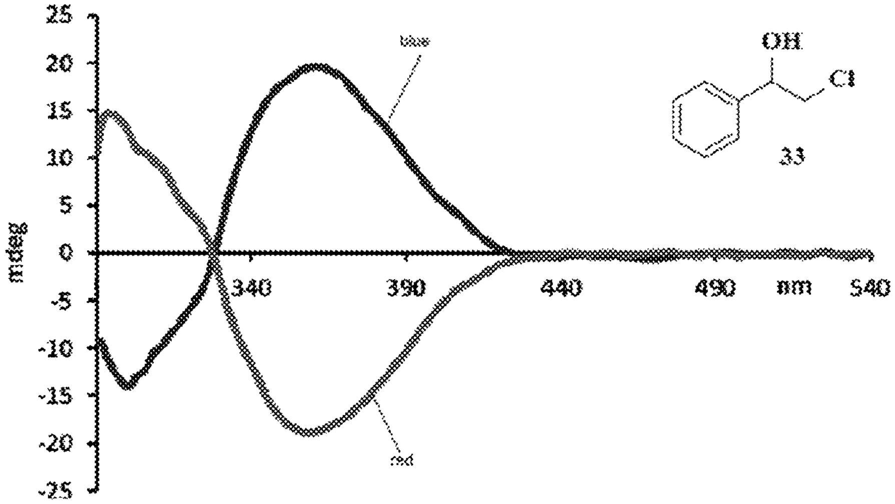
FIG. 51 is the CD spectra obtained from probe 3 with (S)-33 (red) and (R)-33 (blue). The CD measurements were taken at 0.24 mM in THF.
Figure 52:
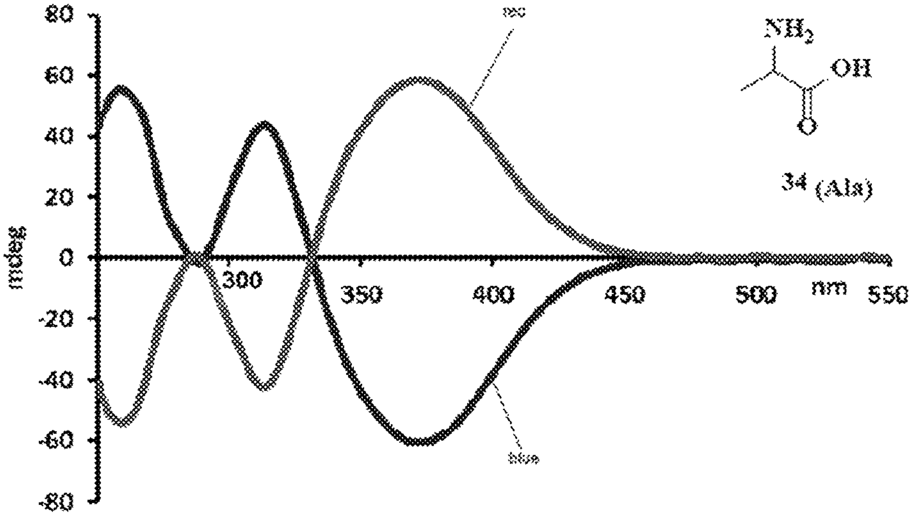
FIG. 52 is the CD spectra obtained from probe 3 with (S)-34 (red) and (R)-34 (blue). The CD measurements were taken at 0.28 mM in acetonitrile.
Figure 53:
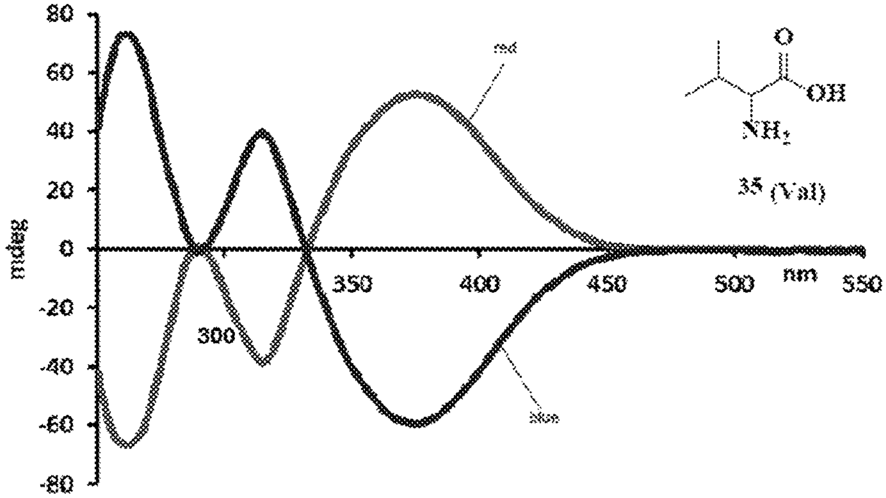
FIG. 53 is the CD spectra obtained from probe 3 with (S)-35 (red) and (R)-35 (blue). The CD measurements were taken at 0.24 mM in acetonitrile.
Figure 54:
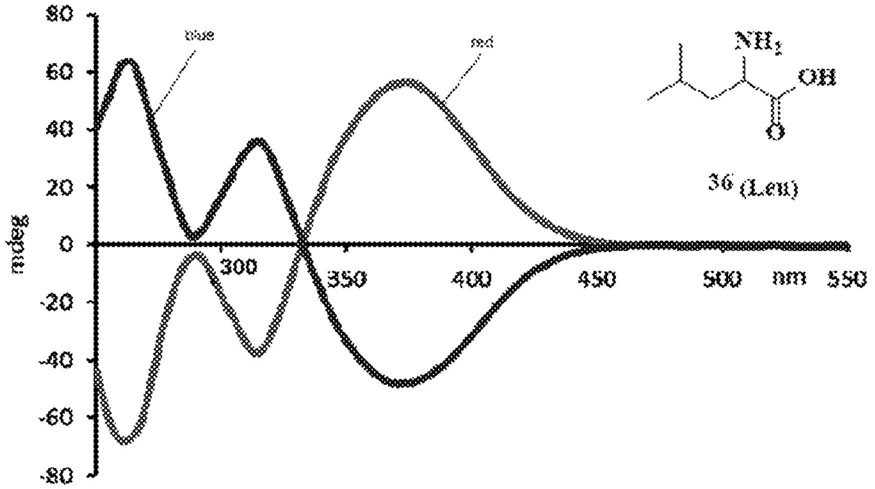
FIG. 54 is the CD spectra obtained from probe 3 with (S)-36 (red) and (R)-36 (blue). The CD measurements were taken at 0.24 mM in acetonitrile.
Figure 55:
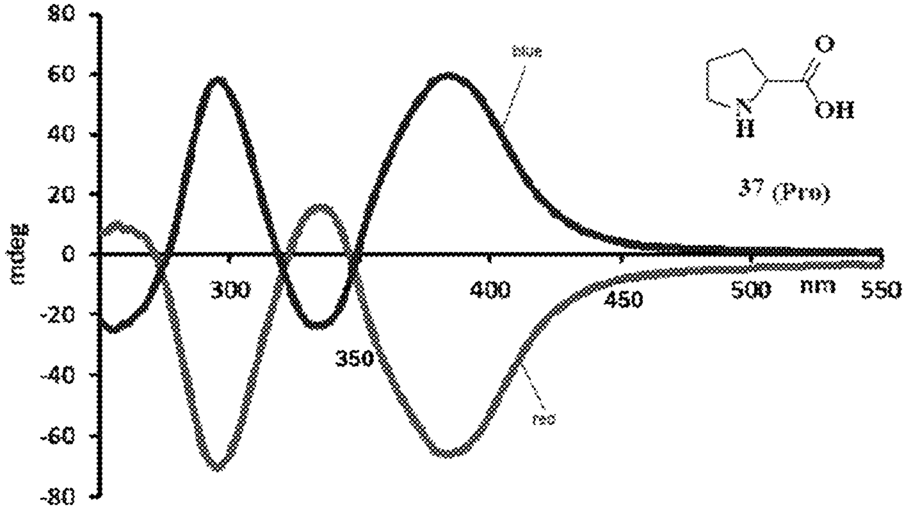
FIG. 55 is the CD spectra obtained from probe 3 with (S)-37 (red) and (R)-37 (blue). The CD measurements were taken at 0.35 mM in acetonitrile.
Figure 56:
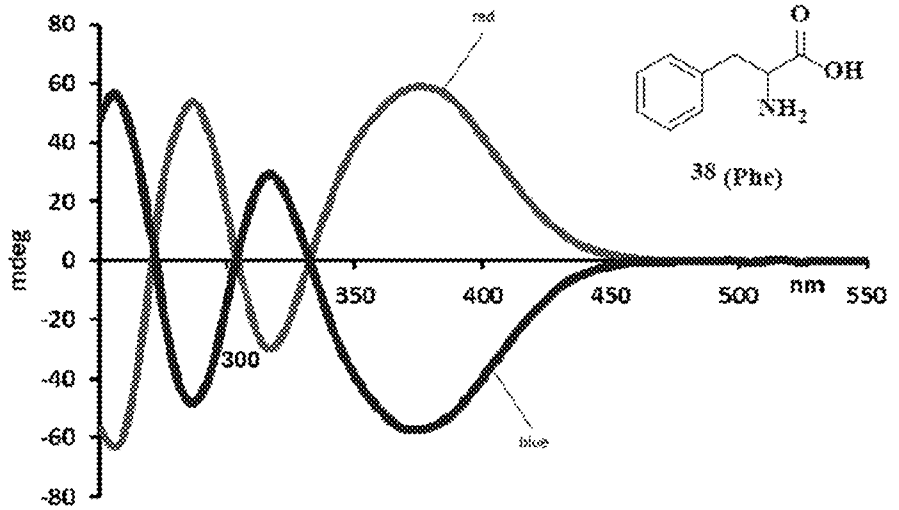
FIG. 56 is the CD spectra obtained from probe 3 with (S)-38 (red) and (R)-38 (blue). The CD measurements were taken at 0.28 mM in acetonitrile.
Figure 57:
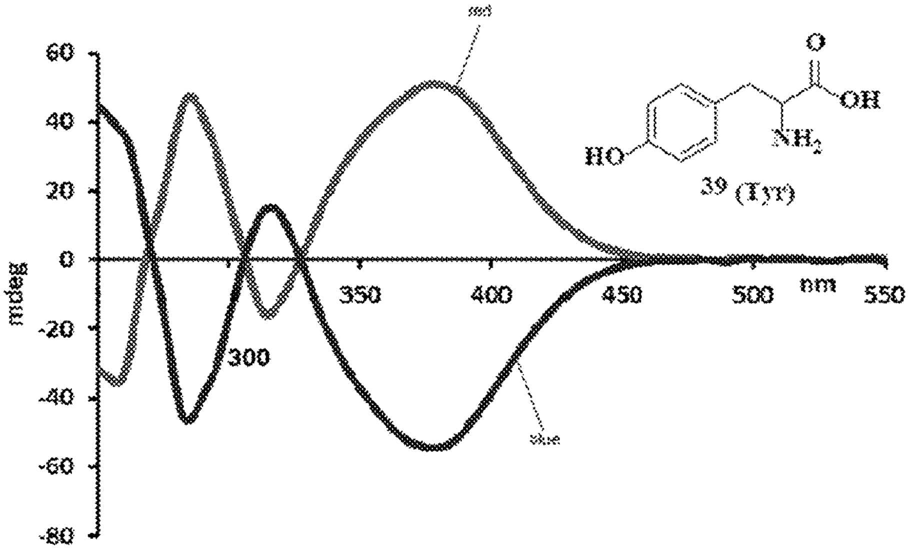
FIG. 57 is the CD spectra obtained from probe 3 with (S)-39 (red) and (R)-39 (blue). The CD measurements were taken at 0.28 mM in acetonitrile.
Figure 58:
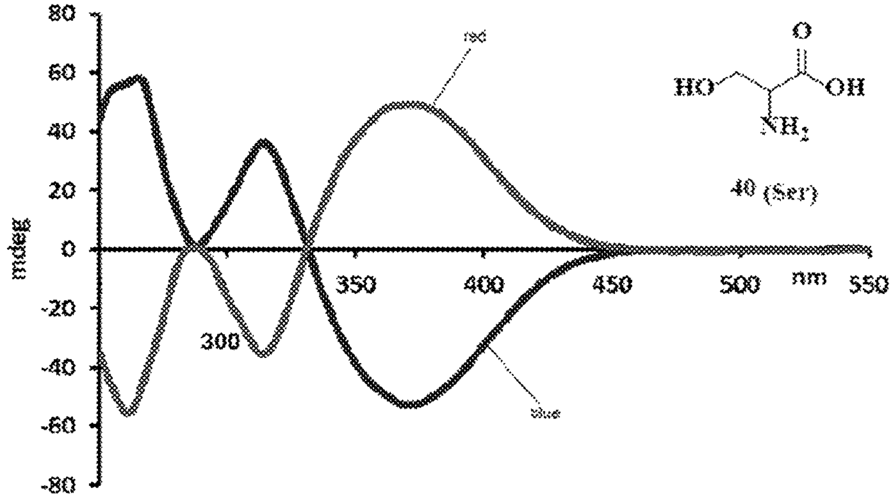
FIG. 58 is the CD spectra obtained from probe 3 with (S)-40 (red) and (R)-40 (blue). The CD measurements were taken at 0.28 mM in acetonitrile.
Figure 59:
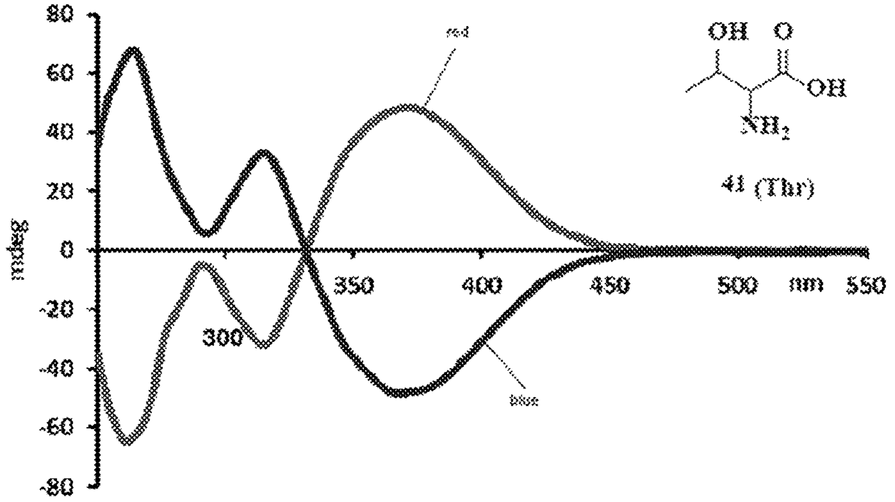
FIG. 59 is the CD spectra obtained from probe 3 with (S)-41 (red) and (R)-41 (blue). The CD measurements were taken at 0.24 mM in acetonitrile.
Figure 60:
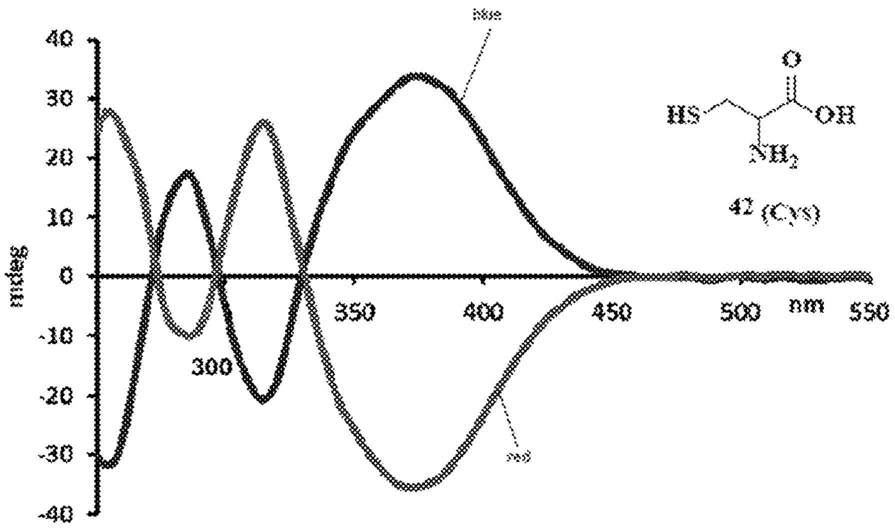
FIG. 60 is the CD spectra obtained from 1 equivalent of probe 3 (with (S)-42 (red) and (R)-42 (blue). The CD measurements were taken at 0.28 mM in acetonitrile.
Figure 61:
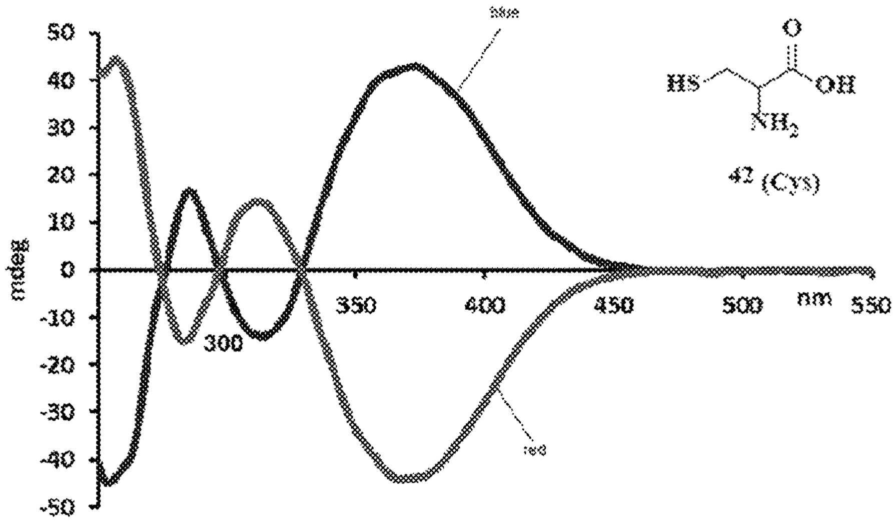
FIG. 61 is the CD spectra obtained from 2 equivalents of probe 3 (with (S)-42 (red) and (R)-42 (blue). The CD measurements were taken at 0.19 mM in acetonitrile.
Figure 62:
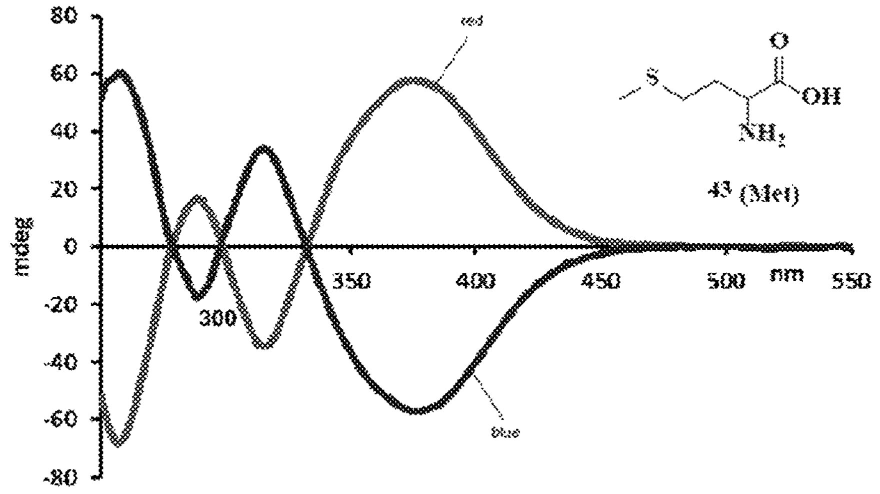
FIG. 62 is the CD spectra obtained from probe 3 with (S)-43 (red) and (R)-43 (blue). The CD measurements were taken at 0.24 mM in acetonitrile.
Figure 63:
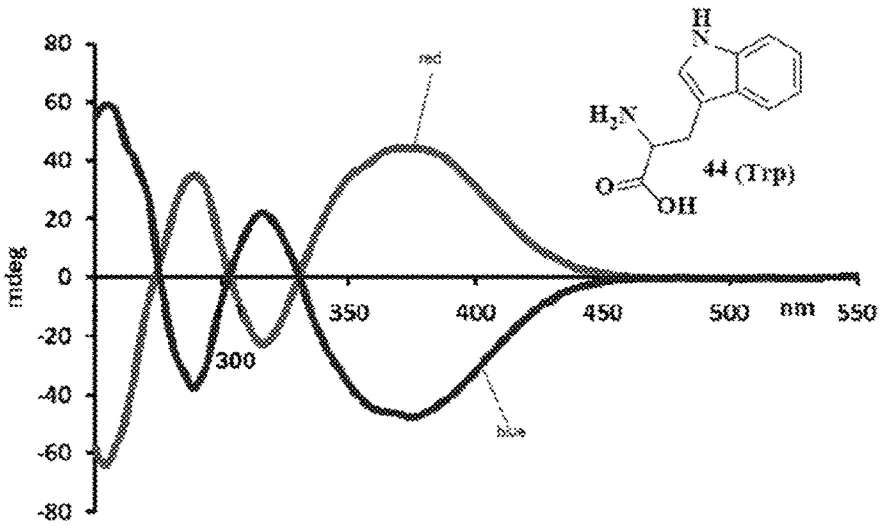
FIG. 63 is the CD spectra obtained from probe 3 with (S)-44 (red) and (R)-44 (blue). The CD measurements were taken at 0.28 mM in acetonitrile.
Figure 64:
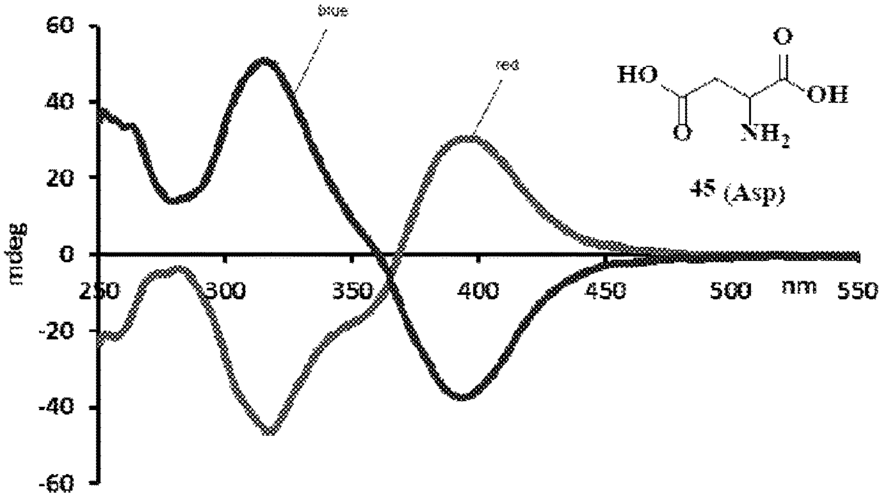
FIG. 64 is the CD spectra obtained from probe 3 with 0)-45 (red) and (R)-45 (blue). The CD measurements were taken at 0.39 mM in acetonitrile.
Figure 65:
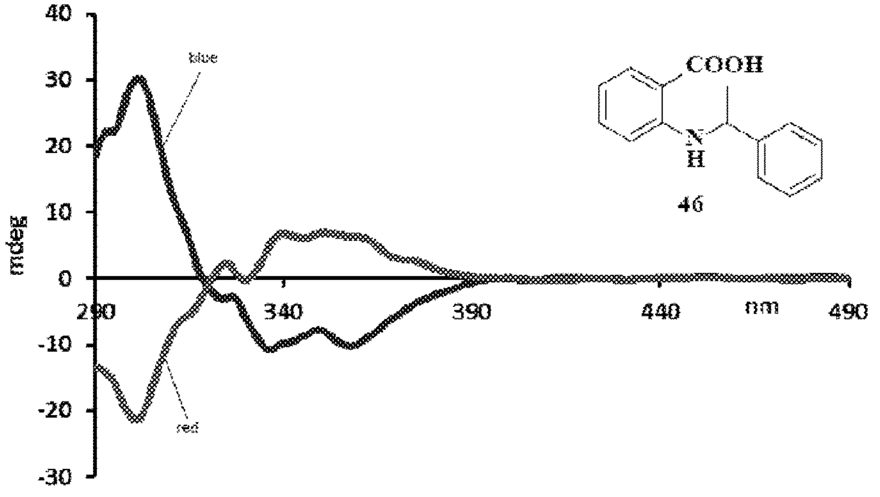
FIG. 65 is the CD spectra obtained from probe 3 with 0)-46 (red) and (R)-46 (blue). The CD measurements were taken at 0.35 mM in chloroform.

-continued
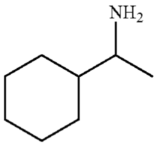
15
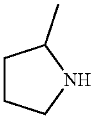
16
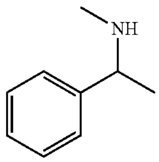
17
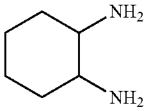
trans-18
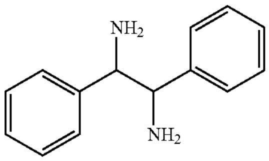
syn-19
Amino Alcohols
A solution of probe 3 (5.0 mM), chiral amino alcohols (20-31) (5.0 mM) and $Et_3N$ (5.0 mM) in 2.0 mL of chloroform was stirred for 1 hour and subjected to CD (FIGS. 38-49) and UV analysis.
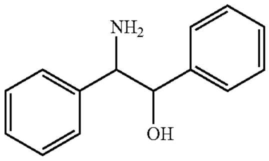
anti-20
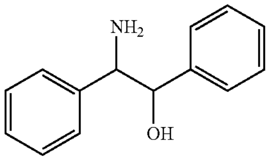
syn-21
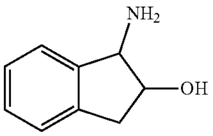
cis-22
-continued
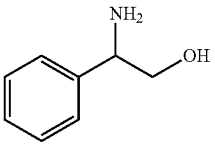
23
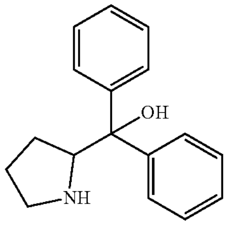
24
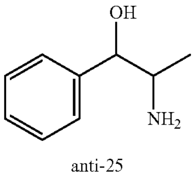
anti-25
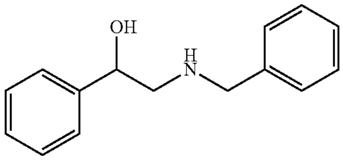
26
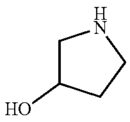
27
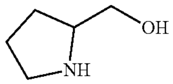
28
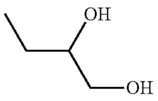
29
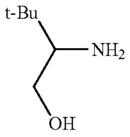
30
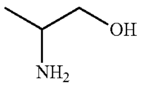
31
Alcohols
A solution of probe 3 (10.0 mM), chiral alcohols (32-33) (10.0 mM) and $LiO^tBu$ (20 mM) in 2.0 mL of tetrahydrofuran was stirred for 2 hours and subjected to CD (FIGS. 50-51) and UV analysis.

32

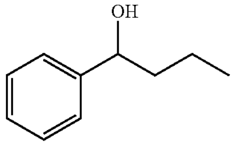

33

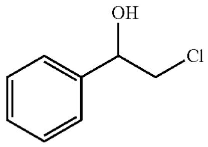

Amino Acids

A solution of probe 3 (5.0 mM), chiral amino acids (34-46 (shown below)) (5.0 mM) and $K_2CO_3$ (10.0 mM) in 2.0 mL of acetonitrile-water (4:1) mixture was stirred for 1 hour and subjected to CD (FIGS. 52-65) and UV analysis.

34

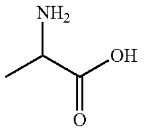

(Ala)

35

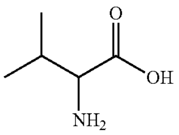

(Val)

36

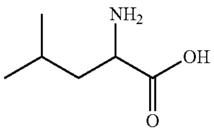

(Leu)

37

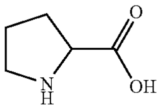

(Pro)

38

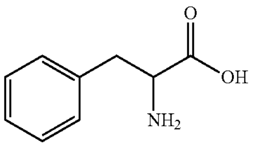

(Phe)

39

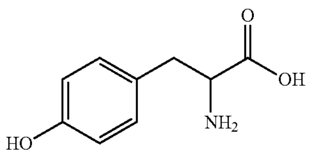

(Tyr)

-continued

40

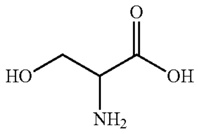

(Ser)

41

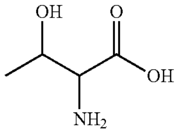

(Thr)

42

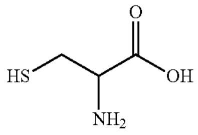

(Cys)

43

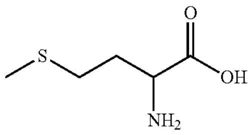

(Met)

44

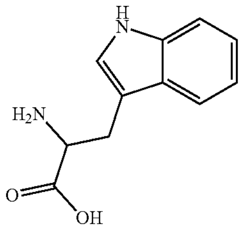

(Trp)

45

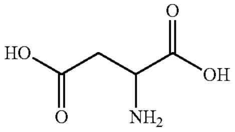

(Asp)

46

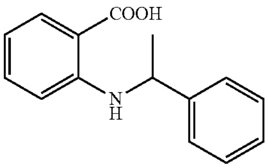

Example 7—Quantitative Sensing: Absolute Configuration, Enantiomeric Excess and Total Concentration The CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm and a scan rate of 400 nm/s.

Determination of the Concentration of (S)-1-(2-naphthyl)ethylamine Using Probe 1

Figure 66:
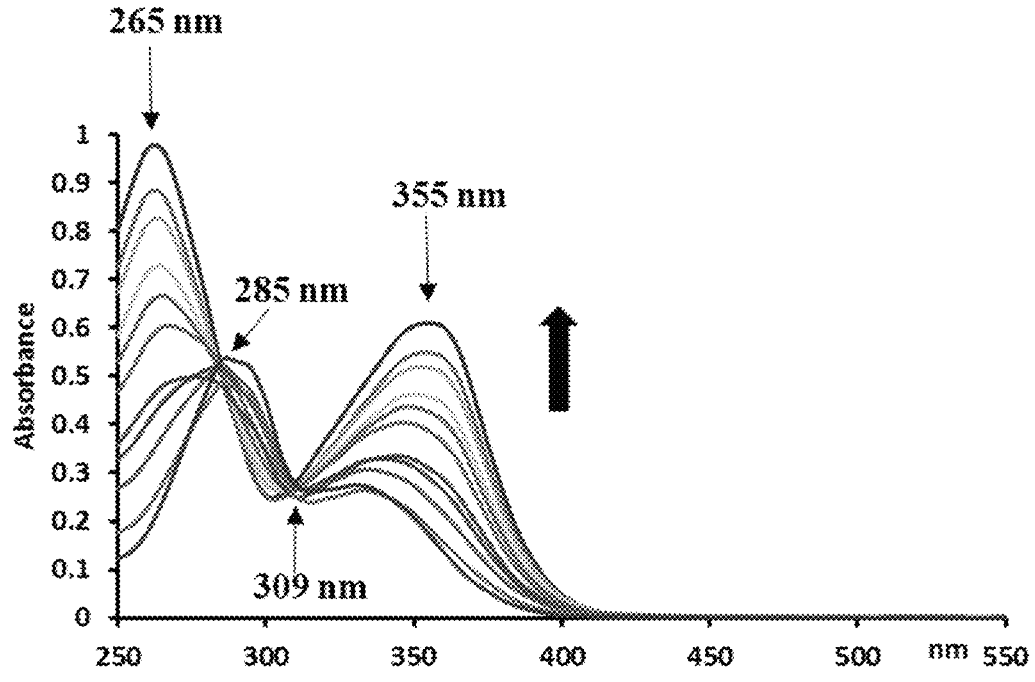
FIG. 66 is the UV spectra obtained from the reaction between probe 3 and varying amounts of (S)-1-phenylethylamine (10).
Figure 67:
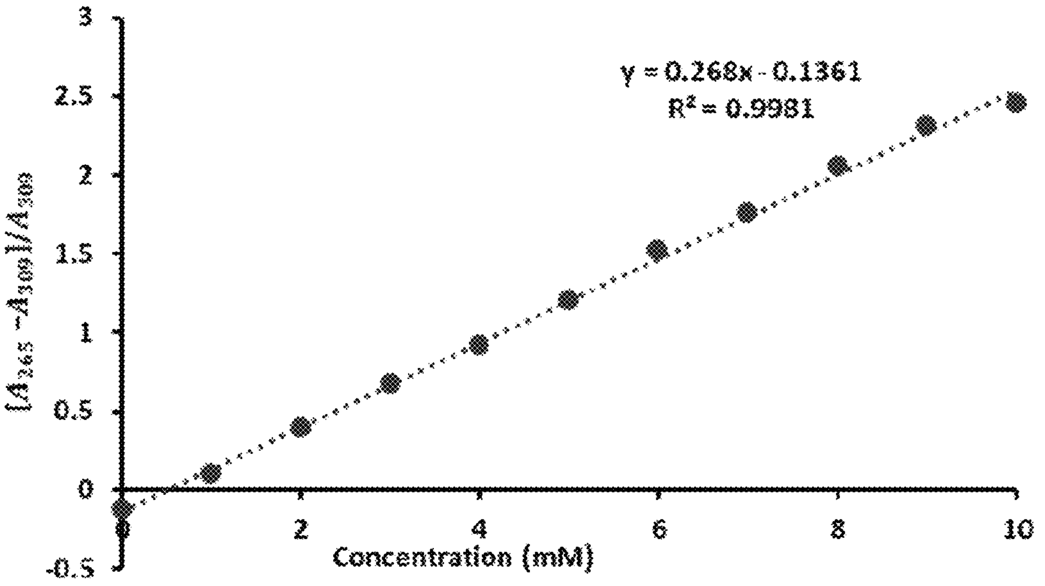
FIG. 67 is a graphical representation of the $$\frac{[A_{265} - A_{309}]}{A_{309}}$$

The change in the UV absorbance of probe 3 upon (S)-1-(2-naphthyl)ethylamine (10) sensing was analyzed. Probe 3 (10.0 mM) and 10 in varying concentrations (0, 1, 2, 3, 4, 5, 6, 7, 8, 9 and 10.0 mM) were dissolved in the presence of $Et_3N$ (10.0 mM) in 2.0 mL of chloroform. To 10 μL of this solution, chloroform (2.0 mL) was added and the mixture was subjected to UV analysis. The UV absorbance at 355 nm and 265 nm increased as the concentration of (S)-1-(2-naphthyl)ethylamine (10) changed from 0 to 10 μM (FIG. 66). Plotting and curve fitting of the UV absorbance change at 265 nm relative to 309 nm against the concentration (mM) of (S)-1-(2-naphthyl)ethylamine (10) gave a linear equation (FIG. 67). (y=0.268x−0.1361, $R^2$=0.9981).

Determination of the Enantiomeric Excess of 1-(2-naphthyl)ethylamine (10) Using Probe 3

A calibration curve was constructed using samples containing 1-(2-naphthyl)ethylamine (10) with varying enantiomeric composition. Probe 3 (10.0 mM) and 1-(2-naphthyl) ethylamine (10) (5.0 mM) with varying ee's (+100, +80, +60, +40, +20, 0, −20, −40, 60, −80, −100%) were dissolved in the presence of $Et_3N$ (10.0 mM) in 2.0 mL of chloroform. After 1 hour, CD analysis was carried out by diluting 25 μL of the reaction mixture with chloroform (2.0 mL) (FIG. 68). The CD amplitudes at 355 and 257 nm were plotted against the enantiomeric excess of 1-(2-naphthyl)ethylamine (10) (FIG. 69).

Simultaneous ee and Concentration Determination

Nine scalemic samples of (S)-1-(2-naphthyl)ethylamine (10) at varying concentrations in chloroform were prepared and subjected to simultaneous analysis of the concentration, enantiomeric excess and absolute configuration using probe 3. First, a UV spectrum was obtained as described above and the concentration was calculated using regression equation (Eq. 1) below. Then, a CD spectrum was obtained as described above. The relevant intensities were used with linear regression equations (Eq. 2) and (Eq. 3) to determine the enantiomeric excess (Table 3). The absolute configuration was determined using the sign of the Cotton effect. The calculated vs actual values of concentrations were plotted (FIG. 70).

$$\text{Using the ratio of, } y = \frac{[A_{265} - A_{309}]}{A_{309}};$$

$$x = \frac{(y + 0.1361)}{0.268} \quad \text{(Equation 1; x in mM)}$$

At 355 nm;

$$ee = \frac{\left(\frac{(mdeg \times 5)}{x} - 0.5075\right)}{0.3085} \quad \text{(Equation 2)}$$

At 422 nm;

$$ee = \frac{\left(\frac{(mdeg \times 5)}{x} + 2.0775\right)}{(-0.6456)} \quad \text{(Equation 3)}$$

TABLE 3

Concentration, ee and absolute configuration of samples of 1-(2-naphthyl)ethylamine (10) determined by the combined UV and CD responses of probe 3

| Sample composition | | | Sensing results | | | | |
|---|---|---|---|---|---|---|---|
| Abs. Config. | Concentration (μM) | % ee | Abs. Config. | Concentration by $\frac{[A_{265} - A_{309}]}{A_{309}}$ (μM) | % ee at 355 nm | % ee at 257 nm | Average % ee |
| R | 4.00 | 25.0 | R | 4.34 | 24.7 | 23.4 | 24.0 |
| R | 2.25 | 55.5 | R | 2.01 | 56.9 | 56.0 | 56.5 |
| S | 5.00 | 50.0 | S | 4.59 | 54.1 | 54.7 | 54.4 |
| R | 9.20 | 8.0 | R | 9.29 | 11.1 | 11.9 | 11.5 |
| S | 2.50 | 33.3 | S | 2.70 | 35.5 | 36.6 | 36.0 |
| R | 7.00 | 42.8 | R | 6.55 | 46.6 | 47.1 | 46.8 |
| S | 8.00 | 37.5 | S | 7.78 | 41.7 | 43.5 | 42.6 |
| S | 9.75 | 79.0 | S | 9.54 | 84.7 | 81.3 | 83.0 |
| S | 1.25 | 60.0 | S | 1.14 | 52.5 | 56.5 | 54.5 |

Example 8—Chiroptical Sensing of Crude Reaction Mixtures of the Asymmetric Reduction of N-Methyl-1-Phenylethan-1-Imine All commercially available reagents and solvents were used without further purification. $^1$H NMR spectra were obtained at 400 MHz and $^{13}$C NMR were obtained at 100 MHz. N-Boc protected asymmetric reduction products were purified by flash column chromatography on silica gel (particle size=40-60 μm). The enantiomeric ratio was determined by chiral HPLC.

The CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.1 s, a data interval of 1.00 nm and a scan rate of 600 nm/min.

Because of the UV and CD absorption of the iridium catalyst and other starting materials, ratiometric reaction analysis with the absorption at 265 nm was not possible. Therefore a calibration curves of signals above 300 nm was used.

UV Calibration Curve of the Reference (S)-N-methyl-1-phenylethylamine (17) Using Probe 3

The change in the UV absorbance of probe 3 upon (S)-N-methyl-1-phenylethylamine (17) sensing was analyzed. Probe 3 (10.0 mM) and (S)-N-methyl-1-phenylethylamine (17) in varying concentrations (0, 1, 2, 3, 4, 5, 6, 7, 8, 9 and 10.0 mM) were dissolved in the presence of $Et_3N$ (10.0 mM) in 2.0 mL of chloroform. To 10 μL of this solution, chloroform (2.0 mL) was added and the mixture was subjected to UV analysis (FIG. 71). The UV absorbance at 392 nm increased as the concentration of (S)-N-methyl-1-phenylethylamine (17) changed from 0 to 10 M. Plotting and curve fitting of the UV absorbance at 392 nm against the concentration (mM) of (S)-N-methyl-1-phenylethylamine (17) gave a linear equation (FIG. 72). (y=0.0092x+0.0122).

Determination of the enantiomeric excess of the reference (S)-N-methyl-1-phenylethylamine (17) using probe 3

A calibration curve was constructed using samples containing (S)-N-methyl-1-phenylethylamine (17) with varying enantiomeric composition. Probe 3 (10.0 mM) and (S)-N-Methyl-1-phenylethylamine (17) (5.0 mM) with varying ee's (+100, +80, +60, +40, +20, 0, −20, 40, −60, −80, −100%) were dissolved in the presence of $Et_3N$ (10.0 mM) in 2.0 mL of chloroform. After 1 hour, CD analysis was carried out by diluting 40 μL of the reaction mixture with chloroform (2.0 mL) (FIG. 73). The CD amplitudes at 376 nm were plotted against the enantiomeric excess of (S)-N-methyl-1-phenylethylamine (17) (FIG. 74).

Asymmetric reduction of N-methyl-1-phenylethan-1-imine (48) and Subsequent Analysis Scheme 11: Synthesis of N-methyl-1-phenylethan-1-imine

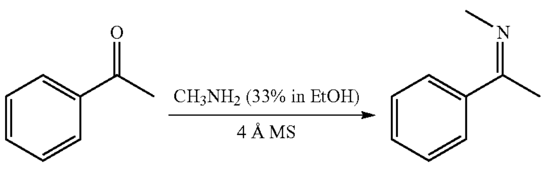

48

N-Methyl-1-phenylethan-1-imine (48) was synthesized via a modified literature procedure (Wakchaure et al., "Disulfonimide-Catalyzed Asymmetric Reduction of N-Alkyl Imines," *Angew. Chem. Int. Ed.* 54:11852-11856 (2015), which is hereby incorporated by reference in its entirety). Acetophenone (1.0 g, 8.32 mmol) was added to a solution of $CH_3NH_2$ (33% in EtOH, 5 ml) with activated 4 Å molecular sieves (250 mg/1 mmol) and the reaction was allowed to complete without stirring. Concentration of the reaction mixture in vacuo afforded 1.1 g (97%, 8.2 mmol) of a colorless oil which was used without further purification.

Ir-Ligand Catalyzed Enantioselective Hydrogenation of Imine

Bis(1,5-cyclooctadiene)diiridium(I) dichloride ([Ir(cod)$Cl]_2$) (12.4 mg, 0.02 mmol) was added to the ligand (0.04 mmol) (49-53) in dichloromethane and stirred for 30 minutes. N-Methyl-1-phenylethan-1-imine (48) (100 mg, 0.75 mmol) and the preformed metal-ligand complex (0.04 mmol) were mixed in dichloromethane:methanol (8:1) (9 mL) and stirred overnight under 15 bar $H_2$ pressure.

Scheme 12: Asymmetric reduction of N-methyl-1-phenylethan-1-imine (48)

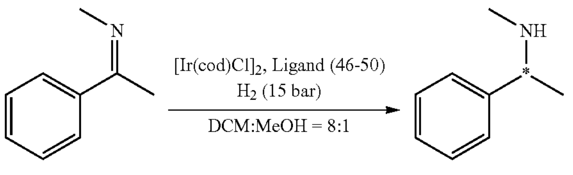

48

49

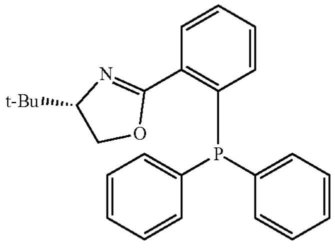

(S)-t-Bu-PHOX

50

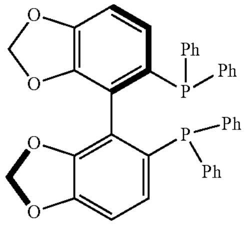

(R)-SEGPHOS

51

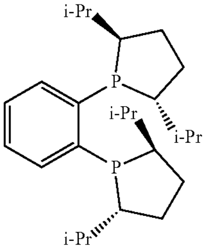

(R,R)-i-Pr-DUPHOS

52

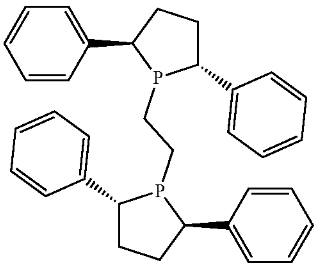

(R,R)-Ph-BPE

-continued

53

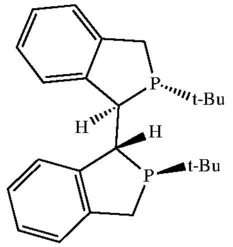

(1R,1'R,2S,2'S)-DuanPhos

Ir-Ligand Catalyzed Enantioselective Hydrogenation of Imine

Bis(1,5-cyclooctadiene)diiridium (I) dichloride ([Ir(cod) Cl]$_2$) (12.4 mg, 0.02 mmol) was added to the ligand (0.04 mmol) (49-53) in dichloromethane and stirred for 30 minutes. N-Methyl-1-phenylethan-1-imine (48) (100 mg, 0.75 mmol) and the preformed metal-ligand complex (0.04 mmol) were mixed in dichloromethane:methanol (8:1) (9 mL) and stirred overnight under 15 bar $H_2$ pressure.

Simultaneous ee and Concentration Determination of the Crude Reaction Mixture To 200 μL of the crude reaction mixture, 4-chloro-3-nitrocoumarin (3) (10.0 mM), and $Et_3N$ (10.0 mM) were added in 2.0 mL of chloroform and stirred for 1 hour. Then, 40 μL of this solution were diluted with chloroform (2.0 mL) and subjected to CD analysis to determine the absolute configuration based on the sign of the Cotton effect and the enantiomeric excess based on the CD amplitude. Another aliquot of 10 μL of the sensing solution was diluted with chloroform (2.0 mL) and subjected to UV analysis to determine the conversion (Table 4).

Using the absorbance measured at 392 nm = $y$ $$x = \frac{(y + 0.0122)}{0.0092} \quad \text{(Equation 4; x in mM)}$$

At 392 nm;

$$ee = \frac{\left(\frac{(mdeg \times 5)}{x} - 0.3586\right)}{0.126} \quad \text{(Equation 5)}$$

TABLE 4

Enantiomeric excess and conversion of the asymmetric hydrogenation of N-methyl-1-phenylethan-1-imine (48)

| | Catalyst | | Traditional analysis | | | Chiroptical sensing | |
|---|---|---|---|---|---|---|---|
| Ligand | Loading (mol %) | Time (h) | Abs. Config. | % ee by HPLC | Conv. (%) (by $^1H$ NMR) | Abs. Config. | % ee by CD at 376 nm | Conv. (%) UV at 392 nm |
| 49 | 5.00 | 18 | S | 55.8[a] | 99.9 | S | 59.8 | 96.0 |
| 50 | 5.00 | 18 | R | 16.3[a] | 99.9 | R | 14.3 | 99.9 |
| 51 | 5.00 | 18 | R | 31.0[a] | 99.9 | R | 32.2 | 99.1 |
| 52 | 5.00 | 18 | R | 31.4[a] | 99.9 | R | 25.8 | 98.0 |
| 53 | 5.00 | 18 | S | 16.3[a] | 92.0 | S | 14.2 | 96.3 |

TABLE 4-continued

Enantiomeric excess and conversion of the asymmetric hydrogenation of N-methyl-1-phenylethan-1-imine (48)

| Ligand | Catalyst Loading (mol %) | Time (h) | Traditional analysis Abs. Config. | % ee by HPLC | Conv. (%) (by $^1H$ NMR) | Chiroptical sensing Abs. Config. | % ee by CD at 376 nm | Conv. (%) UV at 392 nm |
|---|---|---|---|---|---|---|---|---|
| 49 | 2.50 | 1 | S | 46.2[b] | 51.1 | S | 47.8 | 53.9 |
| 49 | 3.25 | 1 | S | 57.3[b] | 63.3 | S | 54.5 | 68.4 |

Conv. = conversion

[a] S,S-Whelk-O: Hexane:IPA = 99:1, flow rate = 1.0 mL/min, UV = 214 nm, $t_R$ = 8.6 min (major) and $t_R$ = 9.6 min (minor).

[b] R,R-Whelk-O, Phenomenex ® Lux 5 μm Amylose-2 (connected in series): Hexane:IPA = 99:1, flow rate = 0.8 mL/min, UV = 214 nm, $t_R$ = 17.9 min (minor) and $t_R$ = 19.9 min (major).

HPLC Analysis

A portion of the crude reaction mixture was filtered through a cotton plug and di-tert-butyl dicarbonate was added to the filtrate. Due to the presence of methanol in the reaction mixture, di-tert-butyl dicarbonate was used in excess (3 equivalents) and the reaction was allowed to run for 5 hours. Then the reaction mixture was concentrated and purified via flash column chromatography on silica using 10%-40% dichloromethane in hexanes to afford a colorless oil of N-Boc-N-methyl-1-phenylethylamine. The enantiomeric excess of N-Boc-N-methyl-1-phenylethylamine was determined by chiral HPLC on an S,S-Whelk-O 1 column unless otherwise noted (FIG. 76). Mobile phase: hexanes: IPA=99:1, flow rate=1.0 mL/min, UV=214 nm, $t_R$=8.6 min (major) and $t_R$=9.6 min (minor).

Synthesis of racemic N-Boc-N-methyl-1-phenylethylamine: (±)—N-methyl-1-phenylethylamine (0.74 mmol, 100 mg) and di-tert-butyl dicarbonate (0.74 mmol, 161.4 mg) were stirred in dichloromethane for 3 hours. Purification by flash column chromatography (20% 60% dichloromethane in hexanes) afforded 170 mg (98%, 0.72 mmol) of a colorless oil. The HPLC is shown in FIG. 75.

$^1H$ NMR of the N-Boc-N-methyl-1-phenylethylamine (400 MHz, $CD_3CN$): δ=7.36 (dd, J=8.0, 6.7 Hz, 2H), 7.32-7.21 (m, 3H), 5.44-5.28 (m, 1H), 2.58 (s, 3H), 1.48 (d, J=7.1 Hz, 3H), 1.45 (s, 9H).

4-Chlorocoumarin (1): A single crystal was obtained by slow evaporation of a solution of 1 in chloroform. Single crystal X-ray analysis was performed at 100 K using a Siemens platform diffractometer with graphite monochromated Mo-Kα radiation (λ=0.71073 Å). Data were integrated and corrected using the APEX 3 program. The structures were solved by direct methods and refined with full-matrix least square analysis using SHELX-97-2 software. Non-hydrogen atoms were refined with anisotropic displacement parameter. Crystal data: $C_9H_5ClO_2$, M=180.58, prism, 0.32×0.27×0.07 mm$^3$, monoclinic space group, $P2_1/n$, a=7.0745(13), b=12.671(2), c=8.9875(17) Å, V=751.2(2) Å$^3$, Z=4.

4-Bromocoumarin (2): A single crystal was obtained by slow evaporation of a solution of 2 in chloroform. Single crystal X-ray analysis was performed at 100 K using a Siemens platform diffractometer with graphite monochromated Mo-Kα radiation (λ=0.71073 Å). Data were integrated and corrected using the APEX 3 program. The structures were solved by direct methods and refined with full-matrix least square analysis using SHELX-97-2 software. Non-hydrogen atoms were refined with anisotropic displacement parameter. Crystal data: $C_9H_5BrO_2$, M=225.03, prism, 0.19×0.10×0.08 $mm^3$, monoclinic space group, $P2_1/n$, a=7.1649(9), b=12.9828(16), c=9.0176(11) Å, V=783.24(17) $Å^3$, Z=4.

4-Iodo-3-nitrocoumarin (5): A single crystal was obtained by slow evaporation of a solution of 5 in chloroform. Single crystal X-ray analysis was performed at 100 K using a Siemens platform diffractometer with graphite monochromated Mo-Kα radiation (λ=0.71073 Å). Data were integrated and corrected using the APEX 3 program. The structures were solved by direct methods and refined with full-matrix least square analysis using SHELX-97-2 software. Non-hydrogen atoms were refined with anisotropic displacement parameter. Crystal data: $C_9H_4INO_4$, M=317.03, prism, 0.24×0.17×0.09 $mm^3$, monoclinic space group, Cc, a=14.714(1), b=8.0151(5), c=9.2491(6) Å, V=955.80(11) $Å^3$, Z=4.

(S)-3-Nitro-4-((1-phenylethyl)amino) coumarin (7): A single crystal was obtained by slow evaporation of a solution of 7 in 50% chloroform in hexanes. Single crystal X-ray analysis was performed at 100 K using a Siemens platform diffractometer with graphite monochromated Mo-Kα radiation (λ=0.71073 Å). Data were integrated and corrected using the APEX 3 program. The structures were solved by direct methods and refined with full-matrix least square analysis using SHELX-97-2 software. Non-hydrogen atoms were refined with anisotropic displacement parameter. Crystal data: $C_{17}H_{14}N_2O_4$, M=310.30, prism, 0.46×0.41×0.34 $mm^3$, triclinic space group, P1, a=7.4195(3), b=7.5034(3), c=15.0658(7) Å, V=716.64(5) $Å^3$, Z=2.

(R)-3-Nitro-4-(N,α-dimethylbenzyl)amino) coumarin: A single crystal was obtained by slow evaporation of a solution of (R)-3-nitro-4-(N,α-dimethylbenzyl)amino) coumarin in 50% hexanes in ethyl acetate. Single crystal X-ray analysis was performed at 100 K using a Siemens platform diffractometer with graphite monochromated Mo-Kα radiation (λ=0.71073 Å). Data were integrated and corrected using the APEX 3 program. The structures were solved by direct methods and refined with full-matrix least square analysis using SHELX-97-2 software. Non-hydrogen atoms were refined with anisotropic displacement parameter. Crystal data: $C_{18}H_{16}N_2O_4$, M=324.33, prism, 0.22×0.19×0.09 $mm^3$, monoclinicspace group, $P2_1$, a=6.4366(9), b=6.6366(10), c=18.111(3) Å, V=765.5 (2) $Å^3$, Z=2.

Example 10—Sensors 56-66 Carrying a Fluoroarene, Arylsulfonyl Chloride or Phosphorus Chloride Moiety Sensors 56, 60, 64 and 66 were commercially available. Sensors 57 (Smith, C. R. & RajanBabu, T. V., "Efficient, Selective, and Green: Catalyst Tuning for Highly Enantioselective Reactions of Ethylene," *Org. Lett.* 8:1657-1659 (2008), which is hereby incorporated by reference in its entirety), 59 (Voropai et al., *Zh Obshch Khim.* 55:65-73 (1985), which is hereby incorporated by reference in its entirety, and 65 (Goldstein, H. & Giddey, A., "Nitration of m- and p-Fluorobenzoic Acids," *Helv. Chim. Acta,* 37:2083-2088 (1954), which is hereby incorporated by reference in its entirety) were prepared as described in the literature.

56

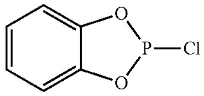

-continued

57

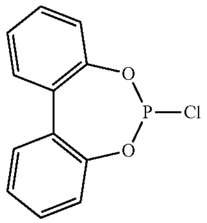

58

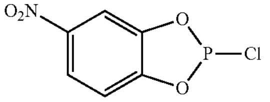

59

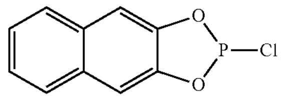

60

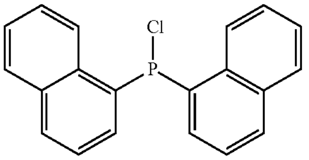

61

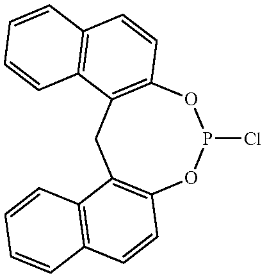

62

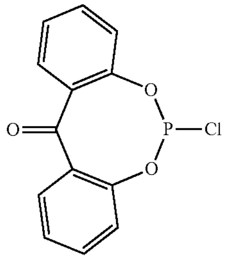

63

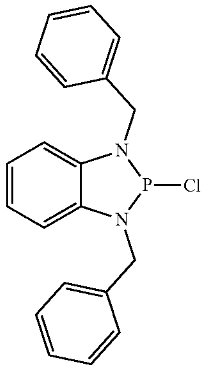

-continued

64

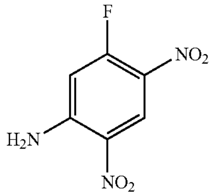

65

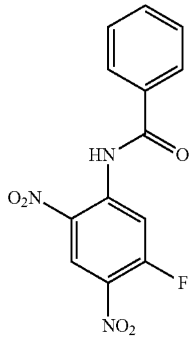

66

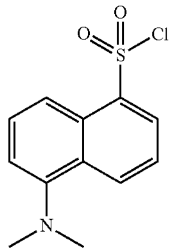

General Procedure for the Synthesis of Chlorophosphites and Chlorodiazaphosphites A 25-mL two-necked round-bottomed flask equipped with a magnetic stirring bar, reflux condenser with nitrogen inlet and a rubber septum was flame-dried and purged with nitrogen. The flask was charged with 1,1'-methylenebis (naphthalen-2-ol) (900 mg, 3.0 mmol) and phosphorus trichloride (2.51 mL, 28.8 mmol) under a strong stream of nitrogen. N-Methyl-2-pyrrolidinone (5 mol %) was added and the rubber septa was replaced with a glass stopper. All joints were greased and the reaction mixture was refluxed at 92° C.; for 2 hours. After cooling, the reaction mixture was transferred to a 100 mL single-necked round-bottomed flask and the remaining $PCl_3$ was removed under reduced pressure and the trace amounts of $PCl_3$ were further azeotropically evaporated with dry toluene (3×20 mL). The resulting colorless solid was directly used for chirality sensing of alcohols without purification.

2-Chloro-5-nitrobenzo[d][1,3,2]dioxaphosphole (58)

58

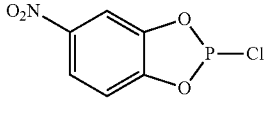

Compound 58 was obtained as a colorless oil in 89% yield (584 mg, 2.67 mmol) from 4-nitrobenzene-1,2-diol (465 mg, 3.0 mmol) and phosphorus trichloride (2.51 mL, 28.8 mmol) in the presence of 5 mol % NMP by following the general procedure described above. $R_f$=0.2 (hexanes/EtOAc, 8:2); $^1$H NMR (400 MHz, Chloroform-d) δ=8.15 (dd, J=8.6, 2.6 Hz, 1H), 8.13 (d, J=2.6 Hz, 1H), 7.37 (d, J=8.6 Hz, 1H); $^{13}$C NMR (100 MHz, Chloroform-d) δ=149.5 (d, $J_{C-P}$=8.0 Hz), 145.1 (d, $J_{C-P}$=8.0 Hz), 144.7, 121.2, 113.8, 110.4.

8-Chloro-16H-dinaphtho[2,1-d:1',2'-g][1,3,2]dioxaphosphocine (61)

61

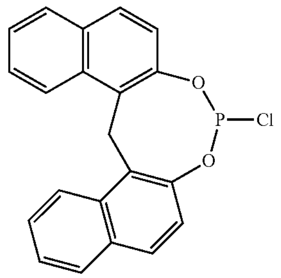

Compound 61 was obtained as a colorless solid in 95% yield (1.037 g, 2.85 mmol) from 1,1'-methylenebis(naphthalen-2-ol) (900 mg, 3.0 mmol) and phosphorus trichloride (2.51 mL, 28.8 mmol) in the presence of 5 mol % NMP by following the general procedure described above. $R_f$=0.5 (hexanes/EtOAc, 8:2); $^1$H NMR (400 MHz, Chloroform-d) δ=8.26 (d, J=8.4 Hz, 2H), 7.86 (d, J=8.4 Hz, 2H), 7.78 (d, J=8.5 Hz, 2H), 7.57 (ddd, J=8.4, 8.4, 1.6 Hz, 2H), 7.47 (ddd, J=8.4, 8.4, 1.6 Hz, 2H), 7.29 (d, J=8.5 Hz, 2H), 5.17 (d, J=16.0 Hz, 1H), 4.53 (d, J=16.0 Hz, 1H); $^{13}$C NMR (100 MHz, Chloroform-d) δ=148.1 (d, $J_{C-P}$=4.1 Hz), 132.7, 132.1, 129.1, 129.0, 127.3, 125.3, 125.0 (d, $J_{C-P}$=4.1 Hz), 123.6, 122.1, 24.6.

6-Chloro-12H-dibenzo[d,g][1,3,2]dioxaphosphocin-12-one (62)

62

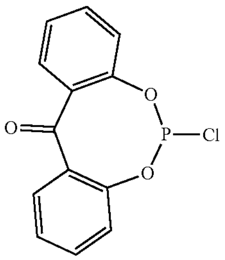

Compound 4 was obtained as a colorless oil in 94% yield (783 mg, 2.82 mmol) from bis(2-hydroxyphenyl)methanone (642 mg, 3.0 mmol) and phosphorus trichloride (2.51 mL, 28.8 mmol) in the presence of 5 mol % NMP by following the general procedure described above. $R_f$=0.5 (hexanes/EtOAc, 8:2); $^1$H NMR (400 MHz, Chloroform-d) δ=7.66 (dd, J=7.8, 1.6 Hz, 2H), 7.22 (dd, J=7.8, 7.8 Hz, 2H), 7.07 (dd, J=7.8, 7.9 Hz, 2H), 6.98 (d, J=7.8, 1.6 Hz, 2H); 13C NMR (100 MHz, Chloroform-d) δ=147.1 (d, $J_{C-P}$=8.0 Hz), 130.3, 129.1 (d, $J_{C-P}$=8.0 Hz), 126.6, 123.6, 118.8, 114.4 (d, $J_{C-P}$=12.0 Hz).

1,3-Dibenzyl-2-chloro-2,3-dihydro-1H-benzo[d][1,3,2]diazaphosphole (63)

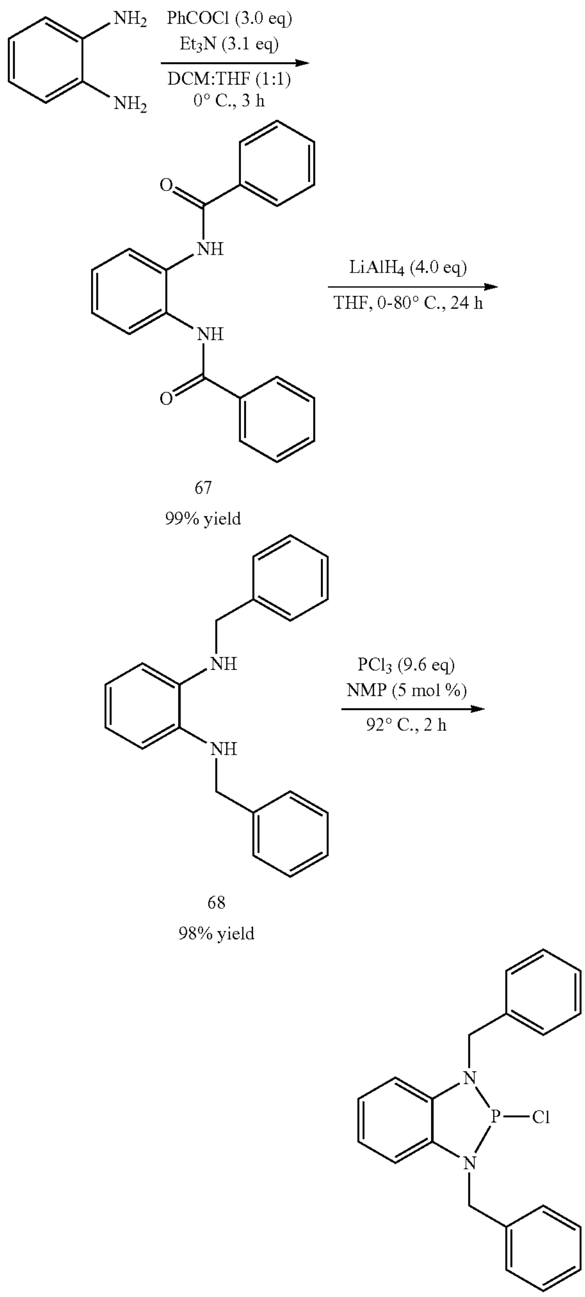

Compounds 67 and 68 were prepared following the literature (Jois, Y. H. R. & Gibson, H. W., "Synthesis of 2-cyano-1,3-dibenzoyl-2,3-dihydrobenzimidazole: A Novel Reissert Compound From Benzimidazole," *J. Org. Chem.* 56:865-867 (1991); Cetinkaya et al., "Synthesis and Structures of 1,3,1',3'-tetrabenzyl-2,2'-biimidazolidinylidenes (Electron-Rich Alkenes), Their Animal Intermediates and Their Degradation Products,". *J Chem. Soc. Perkin Trans.* 1. 13:2047-2054 (1998), which are hereby incorporated by reference in their entirety). Compound 63 was obtained as a pale yellow solid in 96% yield (1.013 g, 2.87 mmol) from $N^1$,$N^2$-dibenzylbenzene-1,2-diamine, 68, (865 mg, 3.0 mmol) and phosphorus trichloride (2.51 mL, 28.8 mmol) in the presence of 5 mol % NMP by following the general procedure described above. $R_f$=0.2 (hexanes/EtOAc, 8:2); $^1$H NMR (400 MHz, Chloroform-d) δ=7.46-7.40 (m, 4H), 7.40-7.30 (m, 6H), 7.01-6.95 (m, 2H), 6.93-6.87 (m, 2H), 4.92 (d, (d, $J_{H-P}$=12.1 Hz, 4H); $^{13}$C NMR (100 MHz, Chloroform-d) δ=137.2 (d, $J_{C-P}$=10.5 Hz), 135.9 (d, $J_{C-P}$=7.1 Hz), 129.0, 128.3 (d, $J_{C-P}$=1.3 Hz), 128.2, 121.6, 111.5 (d, $J_{C-P}$=1.3 Hz), 48.1 (d, $J_{C-P}$=17.7 Hz).

General CD Sensing Information

The CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation.

Sensor 63

Alcohols

A solution of probe 63 (25.0 mM), chiral alcohols (32, 33, 69-73) (20.0 mM) and DIPEA (40.0 mM) in 1.0 mL of chloroform was stirred for 2 hours and subjected to CD analysis (FIGS. 77-83).

32

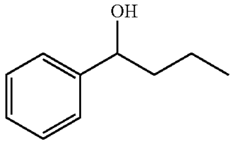

33

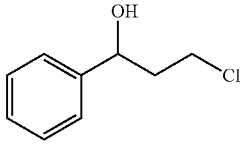

69

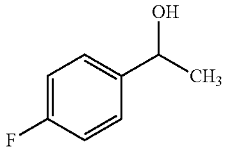

70

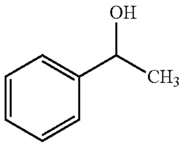

*trans*-71

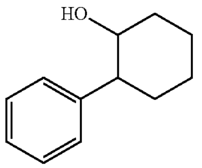

-continued

72

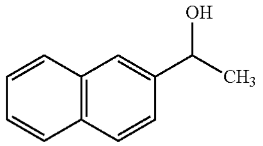

73

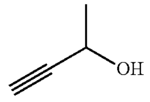

Amines

A solution of probe 63 (25.0 mM), chiral amines (8, 9, 12, 17, 76) (20.0 mM) and DIPEA (40.0 mM) in 1.0 mL of chloroform was stirred for 2 hours and subjected to CD analysis (FIGS. 84-88).

8

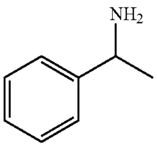

9

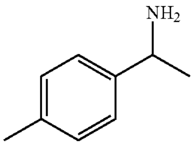

12

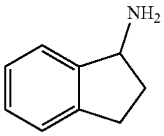

17

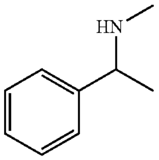

76

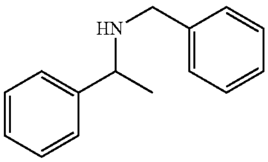

Amino Alcohols

A solution of probe 63 (33.0 mM), chiral amino alcohols (20, 21, 23, 25, 27, 77) (13.3 mM) and DIPEA (53.3 mM) in 1.5 mL of chloroform was stirred for 2 hours and subjected to CD analysis (FIGS. 89-94).

*anti*-20

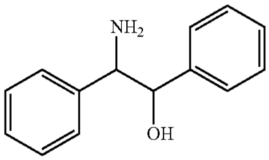

*syn*-21

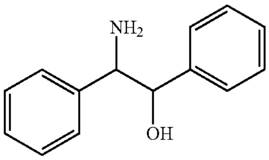

23

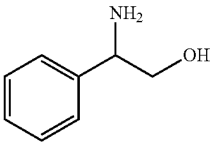

*anti*-25

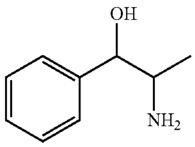

27

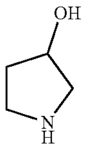

*trans*-77

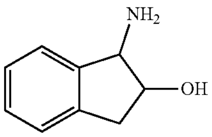

Hydroxy Acids

A solution of probe 63 (33.0 mM), hydroxyl acids (78-80) (13.3 mM) and DIPEA (39.9 mM) in 1.5 mL of chloroform was stirred for 2 hours and subjected to CD analysis (FIGS. 95-97).

78

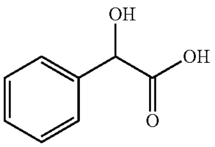

79

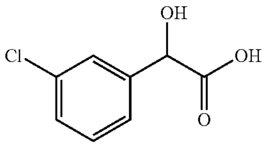

-continued

80

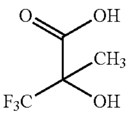

Hydroxy Amides and Hydroxy Esters

A solution of probe 63 (25.0 mM), chiral hydroxy amide (81) or chiral hydroxy ester (82) (20.0 mM) and DIPEA (40.0 mM) in 1.0 mL of chloroform was stirred for 2 hours and subjected to CD analysis (FIGS. 98-99).

*anti*-81

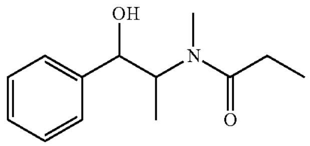

82

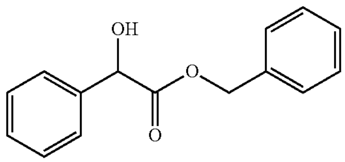

Sensor 56

Alcohols

A solution of probe 56 (25.0 mM), chiral alcohols (32, 33, 69-75) (20.0 mM) and DIPEA (40.0 mM) in 1.0 mL of chloroform was stirred for 2 hours and subjected to CD analysis (FIGS. 100-108).

32

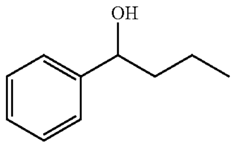

33

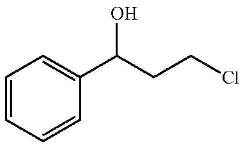

69

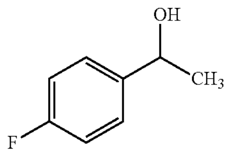

70

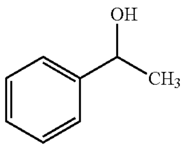

-continued

71

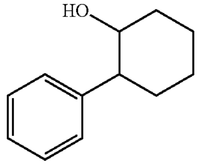

72

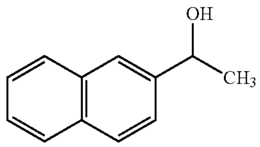

73

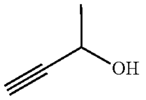

(+/-)-menthol-74

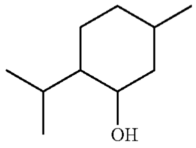

75

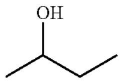

Amines

A solution of probe 56 (25.0 mM), chiral amines (8, 76) (20.0 mM) and DIPEA (40.0 mM) in 1.0 mL of chloroform was stirred for 2 hours and subjected to CD analysis (FIGS. 109-110).

8

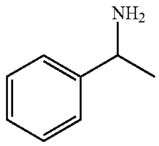

76

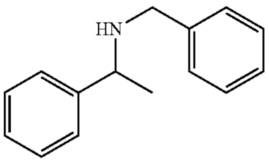

Hydroxy Amides

A solution of probe 56 (25.0 mM), chiral hydroxy amide (81) (20.0 mM) and DIPEA (40.0 mM) in 1.0 mL of chloroform was stirred for 2 hours and subjected to CD analysis (FIG. 111).

Sensor 57

Alcohols

A solution of probe 57 (25.0 mM), chiral alcohol (32) (20.0 mM) and DIPEA (40.0 mM) in 1.0 mL of chloroform was stirred for 2 hours and subjected to CD analysis (FIG. 112).

32

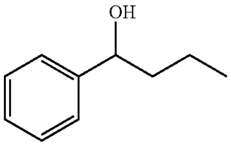

Sensor 58

Alcohols

A solution of probe 58 (25.0 mM), chiral alcohol (32) (20.0 mM) and DIPEA (40.0 mM) in 1.0 mL of chloroform was stirred for 2 hours and subjected to CD analysis (FIG. 113).

32

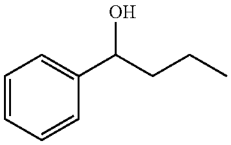

Sensor 59

Alcohols

A solution of probe 59 (25.0 mM), chiral alcohol (32) (20.0 mM) and DIPEA (40.0 mM) in 1.0 mL of chloroform was stirred for 2 hours and subjected to CD analysis (FIG. 114).

32

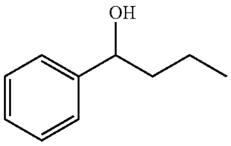

Sensor 60

Amines

A solution of probe 60 (25.0 mM), chiral amines (8, 17) (20.0 mM) and DIPEA (40.0 mM) in 1.0 mL of chloroform was stirred for 2 hours and subjected to CD analysis (FIGS. 115-116).

8

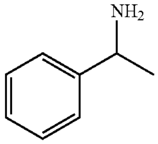

17

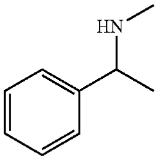

Sensor 61

Amines

A solution of probe 61 (25.0 mM), chiral amines (8, 76) (20.0 mM) and DIPEA (40.0 mM) in 1.0 mL of chloroform was stirred for 2 hours and subjected to CD analysis (FIGS. 117-118).

8

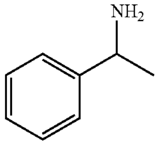

76

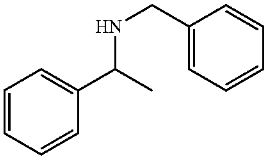

Amines

A solution of probe 62 (25.0 mM), chiral amines (8, 76) (20.0 mM) and DIPEA (40.0 mM) in 1.0 mL of chloroform was stirred for 2 hours and subjected to CD analysis (FIGS. 119-120).

8

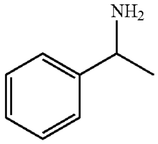

76

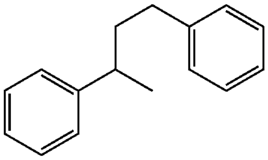

Sensor 64

Amines

A solution of probe 64 (10.0 mM), chiral amine (8) (10.0 mM) and $Et_3N$ (20.0 mM) in 2.0 mL of acetonitrile was stirred for 2 hours and subjected to CD analysis (FIG. 121).

8

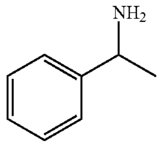

Amino Acids

A solution of probe 64 (10.0 mM), chiral amino acid (38) (10.0 mM) and $K_2CO_3$ (40.0 mM) in 2.0 mL of acetonitrile-water (4:1) mixture was stirred for 2 hours and subjected to CD analysis (FIG. 122).

38 (Phe)

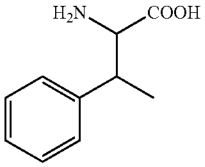

Sensor 65

Amines

A solution of probe 65 (10.0 mM), chiral amine (8) (10.0 mM) and $Et_3N$ (20.0 mM) in 2.0 mL of acetonitrile was stirred for 2 hours and subjected to CD analysis (FIG. 123).

8

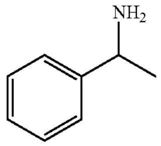

Amino Acids

A solution of probe 65 (10.0 mM), chiral amino acid (38) (10.0 mM) and $K_2CO_3$ (40.0 mM) in 2.0 mL of acetonitrile-water (4:1) mixture was stirred for 2 hours and subjected to CD analysis (FIG. 124).

38 (Phe)

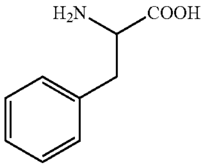

Sensor 66

Amines

A solution of probe 66 (25.0 mM), chiral amine (8, 10) (20.0 mM) and $Et_3N$ (40.0 mM) in 1.0 mL of acetonitrile was stirred for 2 hours and subjected to CD analysis (FIGS. 125-126).

8

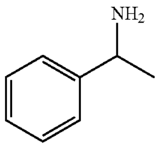

10

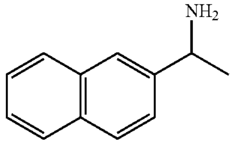

Amino Acids

A solution of probe 66 (10.0 mM), chiral amino acid (40) (10.0 mM) and $K_2CO_3$ (40.0 mM) in 2.0 mL of acetonitrile-water (4:1) mixture was stirred for 2 hours and subjected to CD analysis (FIG. 127).

40 (Ser)

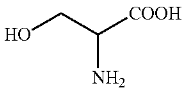

Example 11—UV Analysis

General Information

UV spectra were collected with an average scanning time of 0.0125 s, a data interval of 5.00 nm and a scan rate of 400 nm/s using a quartz cuvette (1 cm path length).

Sensor 63

A solution of probe 63 (25.0 mM), chiral alcohol 32 (20.0 mM) and DIPEA (40.0 mM) in 1.0 mL of chloroform was stirred for 2 hours and subjected to UV analysis (FIG. 128).

32

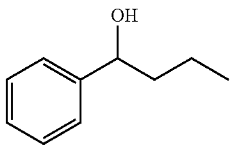

Sensor 57

A solution of probe 57 (25.0 mM), chiral alcohol 32 (20.0 mM) and DIPEA (40.0 mM) in 1.0 mL of chloroform was stirred for 2 hours and subjected to UV analysis (FIG. 129).

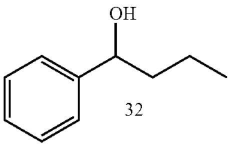

32

Sensor 56

A solution of probe 56 (25.0 mM), chiral alcohol 72 (20.0 mM) and DIPEA (40.0 mM) in 1.0 mL of chloroform was stirred for 2 hours and subjected to UV analysis (FIG. 130).

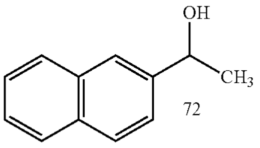

72

Example 12—Further Evaluation of Sensor 65

Amino Acids

The utility of probe 65 was further tested with additional amino acids, amines and amino alcohols. For the sensing of some amino acids, sodium borate buffer (0.25 M) was prepared using boric acid and sodium hydroxide in distilled water. The pH was adjusted to 8.5 using 5 M NaOH.

To a solution of probe 65 (25 mM in ACN, 480 μL) was added alanine (34) (25 mM in water, 400 μL), $K_2CO_3$ (1 M, 20 μL), and ACN was used to dilute the total volume to 2.0 mL. The reaction mixture was stirred for 3 hours and CD measurements were taken by diluting 40 μL of this mixture with 2.0 mL ACN (FIG. 131).

To a solution of probe 65 (25 mM in ACN, 480 μL) was added valine (35) (25 mM in water, 400 μL), $K_2CO_3$ (1 M, 20 μL), and ACN was used to dilute the total volume to 2.0 mL. The reaction mixture was stirred for 3 hours and CD measurements were taken by diluting 40 μL of this mixture with 2.0 mL ACN (FIG. 132).

To a solution of probe 65 (25 mM in ACN, 480 μL) was added leucine (36) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 62 μL of this mixture with 2.0 mL ACN (FIG. 133).

To a solution of probe 65 (25 mM in ACN, 480 μL) was added proline (37) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 64 μL of this mixture with 2.0 mL ACN (FIG. 134).

To a solution of probe 65 (25 mM in ACN, 480 μL) was added phenylalanine (38) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 64 μL of this mixture with 2.0 mL ACN (FIG. 135).

Tyrosine (39) (25 mM) was dissolved in 1.0 mL water by the addition of $K_2CO_3$ (1 M, 75 μL). To a solution of probe 65 (25 mM in DMSO, 480 μL) was added the tyrosine solution (25 mM, 400 μL) and DMSO was used to dilute the total volume to 2.0 mL. The reaction mixture was stirred for 3 hours and CD measurements were taken by diluting 50 μL of this reaction mixture with 2.0 mL ACN (FIG. 136).

To a solution of probe 65 (25 mM in ACN, 480 μL) was added serine (40) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 60 μL of this mixture with 2.0 mL ACN (FIG. 137).

To a solution of probe 65 (25 mM in ACN, 480 μL) was added threonine (41) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 60 μL of this mixture with 2.0 mL ACN (FIG. 138).

To a solution of probe 65 (25 mM in DMSO, 480 μL) was added cysteine (42) (25 mM in pH 8.5 sodium borate buffer 0.25 M, 400 μL) and the mixture was diluted to 2 mL with DMSO. The reaction mixture was stirred for 3 hours and CD measurements were taken by diluting 30 μL of this mixture with 2.0 mL ACN (FIG. 139).

To a solution of probe 65 (25 mM in ACN, 480 μL) was added methionine (43) (25 mM in water, 400 μL), $K_2CO_3$ (1 M, 20 μL), and ACN was used to dilute the total volume to 2.0 mL. The reaction mixture was stirred for 3 hours and CD measurements were taken by diluting 62 μL of this mixture with 2.0 mL ACN (FIG. 140).

To a solution of probe 65 (25 mM in ACN, 480 μL) was added tryptophan (44) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 55 μL of this mixture with 2.0 mL ACN (FIG. 141).

To a solution of probe 65 (25 mM in ACN, 480 μL) was added aspartic acid (45) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 62 μL of this mixture with 2.0 mL ACN (FIG. 142).

To a solution of probe 65 (25 mM in ACN, 480 μL) was added histidine (83) (25 mM in water, 400 μL), $K_2CO_3$ (1 M, 20 μL), and ACN was used to dilute the total volume to 2.0 mL. The reaction mixture was stirred for 3 hours and CD measurements were taken by diluting 40 μL of this mixture with 2.0 mL ACN (FIG. 143).

To a solution of probe 65 (25 mM in ACN, 480 μL) was added glutamic acid (84) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 73 μL of this mixture with 2.0 mL ACN (FIG. 144).

To a solution of probe 65 (25 mM in ACN, 480 μL) was added glutamine (85) (25 mM in pH 8.5 sodium borate buffer 0.25 M, 400 μL) and the mixture was diluted with 1120 μL of ACN and 500 μL water. The reaction mixture was stirred for 3 hours and CD measurements were taken by diluting 60 μL of this mixture with 2.0 mL ACN (FIG. 145).

To a solution of probe 65 (25 mM in DMSO, 480 μL) was added asparagine (86) (25 mM in pH 8.5 sodium borate buffer 0.25 M, 400 μL) and DMSO was used to dilute the total volume to 2.0 mL. The reaction mixture was stirred for 3 hours and CD measurements were taken by diluting 20 μL of this mixture with 2.0 mL ACN (FIG. 146).

To a solution of probe 65 (25 mM in DMSO, 480 μL) was added isoleucine (87) (25 mM in pH 8.5 sodium borate buffer 0.25 M, 400 μL) and DMSO was used to dilute the total volume to 2.0 mL. The reaction mixture was stirred for 3 hours and CD measurements were taken by diluting 50 μL of this mixture with 2.0 mL ACN (FIG. 147).

To a solution of probe 65 (25 mM in DMSO, 480 μL) was added lysine monohydrochloride (88) (25 mM in water, 400 μL), $K_2CO_3$ (1 M, 30 μL) and the mixture was diluted to 4 mL with DMSO. The reaction mixture was stirred for 3 hours and CD measurements were taken by diluting 62 μL of this mixture with 2.0 mL ACN (FIG. 148).

To a solution of probe 65 (25 mM in DMSO, 480 μL) was added arginine (89) (25 mM in water, 400 μL) and the mixture was diluted to 2 mL with DMSO. The reaction mixture was stirred for 3 hours and CD measurements were taken by diluting 62 μL of this mixture with 2.0 mL ACN (FIG. 149).

Amines

A solution of probe 65 (20.0 mM in chloroform), chiral amines (9-11, 16, 17, 19, 90) (20.0 mM in chloroform) and $Et_3N$ (40.0 mM) in 1.0 mL of chloroform was stirred for 2 hours. CD analysis was performed after dilution to the final concentration with chloroform as indicated in the figure description (FIGS. 150-156).

Amino Alcohols

A solution of probe 65 (20.0 mM in chloroform), chiral amino alcohols (21-22, 27) (20.0 mM in chloroform) and $Et_3N$ (40.0 mM) in 1.0 mL of chloroform was stirred for 2 hours. CD analysis was performed after dilution to the final concentration with chloroform as indicated in the figure descriptions (FIGS. 157-159).

MS Analysis of Probe 65

ESI-MS analysis of the probe 65 (4.8 mM) in the presence of pH 8.5 sodium borate buffer (40 mM) in 2.5 mL of ACN:buffer:water (4:1:1.25) mixture was performed. The reaction was diluted to 4.9 mL using 1.25 mL ACN and 1.15 mL water. A 5.0 μL aliquot of this mixture was diluted to 2 mL with ACN and subjected to ESI-MS analysis (FIG. 160)

MS Analysis of the Reaction Between (R)-aspartic acid (45) and Probe 65

ESI-MS analysis of the reaction between (R)-aspartic acid (45) (4 mM) and probe 65 (4.8 mM) in the presence of pH 8.5 sodium borate buffer (40 mM) in 2.5 mL of ACN:buffer: water (4:1) was performed. After 3 hours, the reaction mixture was acidified with 1 M formic acid (20 μL) and diluted to 10 mL using water and ACN (1:1). An 8.0 μL aliquot of this mixture was diluted to 2 mL with water for ESI-MS analysis (FIG. 161).

MS Analysis of the Reaction Between (R)-1-(2-naphthylethylamine) (10) and Probe 65

ESI-MS analysis of the reaction between (R)-1-(2-naphthylethylamine) (10) (20 mM) and probe 65 (24 mM) in the presence of $Et_3N$ (20 mM) in 1 mL of chloroform was performed. After 3 hours, the reaction mixture was acidified with 2 equivalents of formic acid and extracted with water and ethyl acetate. The organic layer was dried over $Na_2SO_4$, and the filtrate was concentrated and dissolved in 10 mL ACN. To this solution were added 2 equivalents of formic acid. An 8.0 μL aliquot of this mixture was diluted with 2 mL of ACN for ESI-MS analysis (FIG. 162).

MS Analysis of the Reaction Between (R)-2-pyrrolidinol (27) and Probe 65

ESI-MS analysis of the reaction between (R)-2-pyrrolidinol (27) (20 mM) and probe 65 (20 mM) in the presence of $Et_3N$ (20 mM) in 1 mL of chloroform was performed. After 3 hours, the reaction mixture was acidified with 2 equivalents of formic acid and extracted with water and ethyl acetate. The organic layer was dried over $Na_2SO_4$, concentrated and the filtrate was dissolved in 10 ml ACN. To this solution were added 2 equivalents of formic acid. An 8.0 μL aliquot of this mixture was diluted with 2 mL of ACN for ESI-MS analysis (FIG. 163).

UV Analysis

The change in the UV absorbance of probe 65 upon addition of (R)-1-(2-naphthyl)ethylamine (10) sensing was analyzed. A solution of probe 65 (20.0 mM) and (R)-1-(2-naphthyl)ethylamine (10) (20.0 mM) in the presence of $Et_3N$ (40.0 mM) in 1.0 mL of chloroform was stirred for 2 hours and subjected to UV analysis by diluting 2.5 μL of the reaction mixture with chloroform (2.0 mL) (FIG. 164).

Scheme 13: Reactin between probe 65 and (R)-1-(2-naphthyl)ethylamine (10)

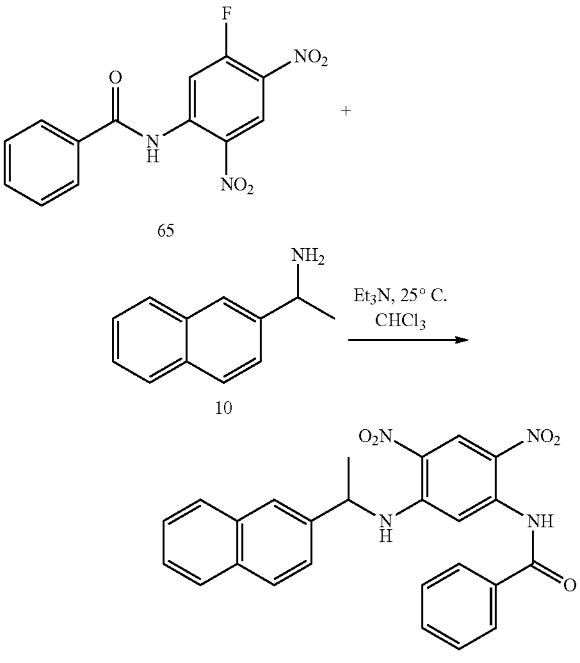

65

10

The change in the UV absorbance of probe 65 upon (S)-1-phenylethylamine (8) sensing was analyzed. A solution of probe 1 (20.0 mM), (S)-1-phenylethylamine (8) (20.0 mM) and $Et_3N$ (40.0 mM) in 1.0 mL of chloroform was stirred for 2 hours. UV analysis was carried out by diluting 2.5 μL of the reaction mixture with chloroform (2.0 mL) (FIG. 165).

Scheme 14: Reaction between probe 65 and (S)-1-phenylethylamine (8)

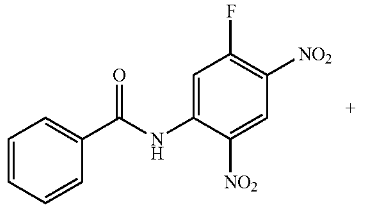

65

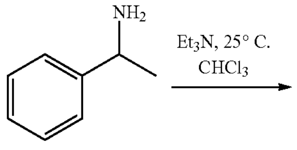

8

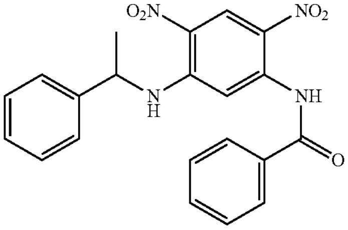

Concentration vs UV Absorbance

The change in the UV absorbance of probe 65 upon (R)-1-phenylethylamine (8) sensing was studied. Probe 65 (20.0 mM) and (R)-1-phenylethylamine (8) in varying concentrations (0.0, 5.0, 10.0, 15.0 and 20.0 mM) were dissolved in the presence of $Et_3N$ (20.0 mM) in 1.0 mL of chloroform. The mixture was stirred for 3 hours. To 2.5 μL of this solution, chloroform (2.0 mL) was added and the mixture was subjected to UV analysis (FIG. 166). The UV absorbance at 318 nm increased as the concentration of (R)-1-phenylethylamine (8) changed from 0.0 to 20.0 mM (FIG. 167).

Concentration vs CD output

The change in the CD amplitude of probe 65 upon (R)-1-phenylethylamine (8) sensing was analyzed. Probe 65 (20.0 mM) and (R)-1-phenylethylamine (8) in varying concentrations (0.0, 5.0, 10.0, 15.0 and 20.0 mM) were dissolved in the presence of $Et_3N$ (20.0 mM) in 1.0 mL of chloroform. The solution was stirred for 3 hours. To 10 μL of this solution, chloroform (2.0 mL) was added and the mixture was subjected to CD analysis (FIG. 168). The CD absorbance at 371 and 254 nm increased linearly as the concentration of (R)-1-phenylethylamine (8) changed from 0.0 to 20.0 mM (FIG. 169).

Quantitative Sensing: Absolute Configuration, Enantiomeric Excess and Total Concentration The CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm and a scan rate of 400 nm/s. An aspartic acid (45) stock solution (0.025 M) was prepared in 0.25 M pH 8.5 sodium borate buffer (prepared from $K_3BO_3$ and NaOH). A probe 65 stock solution was prepared in ACN.

Calibration Curve for Concentration Analysis of (R)-aspartic acid Using Probe 65

The change in the UV absorbance of probe 65 upon (R)-aspartic acid (45) sensing was analyzed. Probe 65 (4.8 mM) and (R)-aspartic acid (45) in varying concentrations (0.0, 0.4, 0.8, 1.2, 1.6, 2.0, 2.4, 2.8, 3.2, 3.6 and 4.0 mM) were dissolved in 2.5 mL of ACN:buffer:water (4:1:1.25). After 3 hours, the reactions were diluted using 1.25 ml of ACN and 1.15 ml of water. To 40 μL of this solution, ACN (2.0 mL) was added and the mixture was subjected to UV analysis (FIG. 170). The UV absorbance at 315 nm increased as the original concentration of (R)-aspartic acid (45) varied from 0.0 to 4.0 mM. Plotting and curve fitting of the UV absorbance change at 315 nm against the concentration (mM) of (R)-aspartic acid gave a polynomial equation. ($y=-0.0056x^3+0.031x^2+0.0391x+0.4298$, $R^2=0.9941$) (FIG. 171).

Calibration Curve for Enantiomeric Excess (ee) analysis of aspartic Acid (45) Using Probe 65

A calibration curve was constructed using samples containing aspartic acid with varying enantiomeric composition. Probe 65 (4.8 mM) and aspartic acid (45) (4.0 mM) with varying ee's (+100, +80, +60, +40, +20, 0, −20, −40, −60, −80, −100%) were dissolved in 2.5 mL of an ACN:buffer: water (1:1:1.25) mixture. After 3 hours, the reactions were diluted using 1.25 ml of ACN and 1.15 ml of water. CD analysis was carried out by diluting 90 μL aliquots with ACN (2.0 mL) (FIG. 172). The CD amplitudes at 320 nm were plotted against the enantiomeric excess of aspartic acid (FIG. 173).

Simultaneous ee and Concentration Determination

Nine scalemic samples of aspartic acid (45) at varying concentrations in ACN were prepared and subjected to simultaneous analysis of the concentration, enantiomeric excess and absolute configuration using probe 65. First, a UV spectrum was obtained as described above and the concentration was calculated using regression equation obtained above (FIG. 172). Then, a CD spectrum was obtained as described above. The relevant intensities were used with the linear regression equation obtained above (FIG. 173) to determine the enantiomeric excess. The absolute configuration was determined using the sign of the Cotton effect (Table 5).

TABLE 5

Concentration, ee and absolute configuration of samples of aspartic acid (45) determined by the combined UV and CD responses of probe 65

| Sample composition | | | Sensing results | | |
|---|---|---|---|---|---|
| Abs. Config. | Concentration (mM) | % ee | Abs. Config. | Concentration at 315 nm (mM) | % ee at 320 nm |
| S | 2.50 | 64.0 | S | 2.50 | 60.2 |
| R | 3.00 | 60.0 | R | 3.09 | 59.0 |
| S | 3.25 | 56.0 | S | 3.28 | 58.1 |
| R | 3.50 | 40.0 | R | 3.50 | 43.5 |
| S | 3.75 | 30.7 | S | 3.78 | 35.1 |
| R | 4.00 | 20.0 | R | 4.27 | 23.4 |
| S | 4.00 | 50.0 | S | 4.27 | 51.2 |
| S | 2.00 | 80.0 | S | 1.73 | 76.5 |
| S | 4.00 | 90.0 | S | 3.46 | 85.6 |
| R | 2.50 | 96.0 | R | 2.31 | 98.6 |

Example 13—Probe 63 in the Analysis of 1-phenylethanol (70)

Calibration Curve for Concentration Analysis of 1-phenylethanol (70) Using Probe 63

The change in the UV absorbance of probe 63 upon (R)-1-phenylethanol (70) sensing was analyzed. Probe 63 (25.0 mM) and (R)-1-phenylethanol (70) in varying concentrations (0, 2, 4, 6, 8, 10, 12, 14, 16, 18 and 20.0 mM) were dissolved in the presence of DIPEA (40.0 mM) in 1.0 mL of chloroform under inert atmosphere and the solution was stirred for 2 hours. An aliquot of 10 µL was diluted with chloroform (2.0 mL) and the mixture was subjected to UV analysis (FIG. 174). The UV absorbance at 300 nm increased as the concentration of (R)-1-phenylethanol (70) in the original samples changed from 0 to 20 mM. The UV absorbance change at 300.0 nm was plotted against concentration (mM) of (R)-1-phenylethanol (70) (FIG. 175).

A calibration curve was constructed using samples containing 1-phenylethanol (70) with varying enantiomeric composition. Probe 63 (25.0 mM) and 1-phenylethanol (70) (20.0 mM) with varying ee's (+100, +80, +60, +40, +20, 0, −20, −40, −60, −80, −100%) were dissolved in the presence of DIPEA (40.0 mM) in 1.0 mL of chloroform. After 2 hours, CD analysis was carried out by diluting 30 µL of the reaction mixture with chloroform (2.0 mL) (FIG. 176). A plot of the CD amplitudes at 300 nm versus sample % ee was constructed (FIG. 177).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An analytical method comprising:

providing a sample containing a chiral analyte that can exist in stereoisomeric forms;

providing an achiral probe selected from the group consisting of coumarin-derived Michael acceptors, dinitrofluoroarenes and analogs thereof, arylsulfonyl chlorides and analogs thereof, arylchlorophosphines and analogs thereof, aryl halophosphites, and halodiazaphosphites;

contacting the sample with the probe under conditions to permit covalent binding of the probe to the analyte; and performing a first spectroscopic analysis using one of circular dichroism (CD), optical rotatory dispersion and polarimetry, and/or a second spectroscopic analysis using one of ultraviolet (UV) spectroscopy and fluorescence spectroscopy to obtain, based on any covalent binding that occurs during said contacting, one or more of an absolute configuration of the analyte in the sample, concentration of the analyte in the sample, and an enantiomeric composition of the analyte in the sample.

2. The analytical method of claim 1, wherein the probe is a coumarin-derived Michael acceptor of Formula I:

I

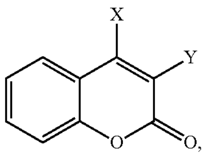

wherein:

Y is hydrogen or an electron withdrawing group selected from the group consisting of —$CF_3$, —C(O)$R_a$, —$SO_2R_a$, —CN, and —$NO_2$; wherein each $R_a$ is independently selected from the group consisting of —H, -alkyl, —O-alkyl, —N-alkyl, -alkenyl, -alkynyl, -aryl, —O-aryl, —N-aryl, -heteroaryl, —O-heteroaryl, —N-heteroaryl, -cycloalkyl, —O-cycloalkyl, —N-cycloalkyl, -heterocycloalkyl, —O-heterocycloalkyl, and —N-heterocycloalkyl; and X is a leaving group selected from a halogen, —$OR_b$, —OC(O)$R_b$, —OS(O)$_2R_b$, —S(O)$_2$—O—$R_b$, —$N_2^+$, —$N^+(R_b)_3$, —$S^+(R_b)_2$, and —$P^+(R_b)_3$; wherein each $R_b$ is independently selected from the group consisting of -alkyl, —O-alkyl, —N-alkyl, -alkenyl, -alkynyl, perfluoroalkyl, -perfluoroalkenyl, -perfluoroalkynyl, -aryl, perfluoroaryl, —O-aryl, —N-aryl, —O-perfluoroaryl, —N-perfluoroaryl, -heteroaryl, —O-heteroaryl, —N-heteroaryl, -cycloalkyl, —O-cycloalkyl, —N-cycloalkyl, -heterocycloalkyl, —O-heterocycloalkyl, and —N-heterocycloalkyl.

3. The analytical method of claim 2, wherein the probe is a coumarin-derived Michael acceptor selected from the group consisting of:

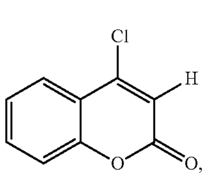 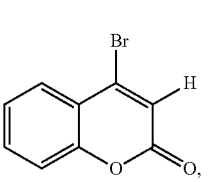

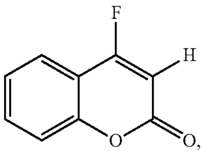 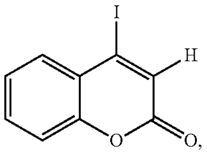

-continued

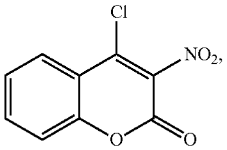

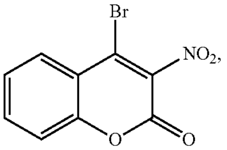

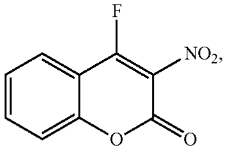

and

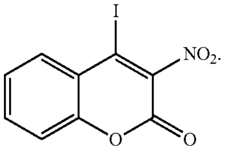

4. The analytical method of claim 2, wherein the probe is a coumarin-derived Michael acceptor and the analyte is an amino acid or an amino alcohol, or comprises one or more functional groups selected from the group consisting of amines, carboxylic acids, hydroxy acids, and thiols.

5. The analytical method of claim 1, wherein the probe is a dinitrofluoroarene or analog thereof of Formula II:

II

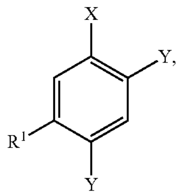

wherein:

each Y is independently selected from the group consisting of —$NO_2$, —CN, —C(O)$R_a$, and —$SO_2R_a$, wherein each $R_a$ is independently selected from the group consisting of —H, -alkyl, —O-alkyl, —N-alkyl, -alkenyl, -alkynyl, -perfluoroalkyl, -aryl, -perfluoroaryl, —O-aryl, —N-aryl, -heteroaryl, —O-heteroaryl, —N-heteroaryl, -cycloalkyl, —O-cycloalkyl, —N-cycloalkyl, -heterocycloalkyl, —O-heterocycloalkyl, and —N-heterocycloalkyl;

X is a leaving group selected from halogen, —$OR_b$, —OC(O)$R_b$, —OS$(O)_2R_b$, —S$(O)_2$—O—$R_b$, —$N_2^+$, —$N^+(R_b)_3$, —$S^+(R_b)_2$, and —$P^+(R_b)_3$; wherein each $R_b$ is independently selected from the group consisting of -alkyl, —O-alkyl, —N-alkyl, -alkenyl, -alkynyl, -perfluoroalkyl, -perfluoroalkenyl, -perfluoroalkynyl, -aryl, -perfluoroaryl, —O-aryl, —N-aryl, -heteroaryl, —O-heteroaryl, —N-heteroaryl, -cycloalkyl, —O-cycloalkyl, —N-cycloalkyl, -heterocycloalkyl, —O-heterocycloalkyl, and —N-heterocycloalkyl; and $R^1$ is selected from the group consisting of —$NH_2$, —NHC(O)$CH_2$Ar, —NHC(O)Ar, -hydrogen, -alkyl, —O-alkyl, —N-alkyl, -alkenyl, -alkynyl, -aryl, —O-aryl, —N-aryl, -heteroaryl, —O-heteroaryl, —N-heteroaryl, -cycloalkyl, —O-cycloalkyl, —N-cycloalkyl, -heterocycloalkyl, —O-heterocycloalkyl, —N-heterocycloalkyl, —CN, —C(O)$R_c$, —$CO_2R_c$, —$SO_2R_c$, —C(O)NH$R_c$, —S-alkyl, —S-aryl, and —S-heteroaryl;

wherein:

each $R_c$ is independently -Ar, -alkyl, or —$CH_2$Ar; and each Ar is independently an aryl, heteroaryl, cycloalkyl, heterocycloalkyl, perfluoroalkyl, or perfluoroaryl.

6. The analytical method of claim 5, wherein the probe is a dinitroflourarene selected from:

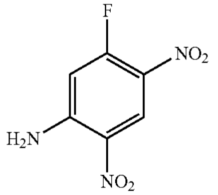

and

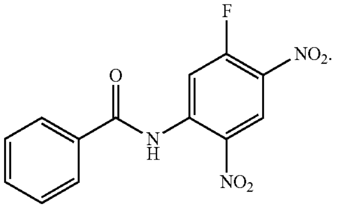

7. The analytical method of claim 1, wherein the probe is an arylsulfonyl chloride or analog thereof of Formula III:

III

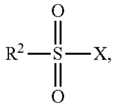

wherein:

X is selected from the group consisting of -halogen, —O-aryl, —O-heteroaryl, —O-cycloalkyl, —O-heterocycloalkyl, —O-alkyl, —O-perfluoroalkyl, —O-perfluoroaryl, —N-aryl, —N-heteroaryl, —N-cycloalkyl, —N-heterocycloalkyl, —N-alkyl, —N-perfluoroalkyl, —N-perfluoroaryl, —N(Ar)$SO_2$Ar, —NH$SO_2$Ar, and —NHAr; and $R^2$ is an aryl or heteroaryl, wherein the aryl or heteroaryl is optionally substituted with one or more groups selected from-alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —N$R_c$C(O)$R_c$, —$NO_2$, —CN, -halogen, and —$SO_2R_c$, wherein each $R_c$ is independently Ar, alkyl, or $CH_2$Ar;

wherein each Ar is independently an aryl or heteroaryl.

8. The analytical method of claim 7, wherein the probe is the arylsulfonyl chloride:

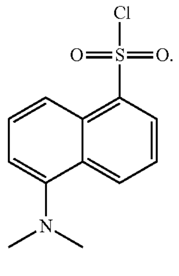 [SMILES: CN(C)c1cccc2c(S(=O)(=O)Cl)cccc12]

9. The analytical method of claim 1, wherein the probe is an arylchlorophosphine or analog thereof of Formula IV:

IV

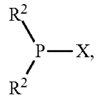

wherein:

X is selected from the group consisting of -halogen, —O-aryl, —O-heteroaryl, —O-cycloalkyl, —O-heterocycloalkyl, —O-alkyl, —O-perfluoroalkyl, and —O-perfluoroaryl; and each $R^2$ is independently an aryl or heteroaryl, wherein the aryl or heteroaryl is optionally substituted with one or more groups selected from-alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each $R_c$ is independently Ar, alkyl, or $CH_2$Ar and Ar is an aryl or heteroaryl.

10. The analytical method of claim 9, wherein the probe is the arylchlorophosphine:

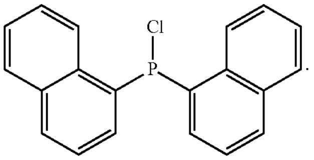 [SMILES: ClP(c1cccc2ccccc12)c1cccc2ccccc12]

11. The analytical method of claim 1, wherein the probe is an aryl halophosphite of Formula V:

V

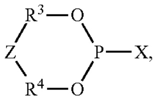

wherein:

X is a halogen; and (i) $R^3$ and $R^4$ are each independently an aryl or heteroaryl, wherein the aryl or heteroaryl is optionally substituted with one or more groups selected from-alkyl, —O-alkyl, —N-alkyl, -alkenyl, -alkynyl, —O-aryl, —O-perfluoroaryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each $R_c$ is independently Ar, alkyl, or $CH_2$Ar and Ar is an aryl or heteroaryl; and Z is selected from the group consisting of a bond, —C(O)—, —O—, —$NR_d$—, —S—, and —$CH_2$—, wherein $R_a$ is H, alkyl, aryl, or heteroaryl; or (ii) $R^3$ and $R^4$, together with the carbon atoms to which they are attached, form a monocyclic or bicyclic ring system selected from the group consisting of cycloalkyl, heterocycloalkyl, aryl, and heteroaryl, wherein the ring system is optionally substituted with one or more groups selected from-alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O)$R_c$, —$NO_2$, —CN, -halogen, and —$SO_2R_c$, wherein each Re is independently Ar, alkyl, or $CH_2$Ar and Ar is an aryl or heteroaryl; and Z is absent.

12. The analytical method of claim 11, wherein the probe is an aryl chlorophosphite selected from the group consisting of:

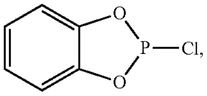

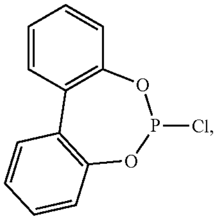

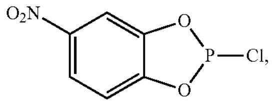

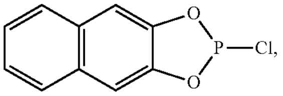

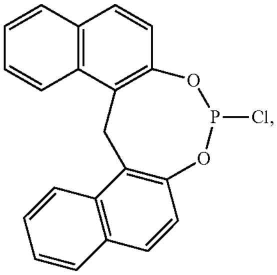

and

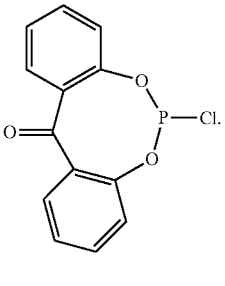

13. The analytical method of claim 1, wherein the probe is a halodiazaphosphite of Formula VI:

VI

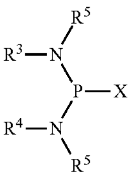

wherein:

X is a halogen;

$R^3$ and $R^4$ are each independently -aryl or -heteroaryl, wherein the aryl or heteroaryl is optionally substituted with one or more groups selected from-alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —$NR_c$C(O) $R_c$, —$NO_2$, —CN, -halogen, and —$SO_2R_c$, wherein each $R_c$ is independently Ar, alkyl, or $CH_2$Ar and Ar is an aryl or heteroaryl; or $R^3$ and $R^4$, together with the carbon atoms to which they are attached, form a monocyclic or bicyclic ring system selected from the group consisting of cycloalkyl, heterocycloalkyl, aryl, and heteroaryl, wherein the ring system is optionally substituted with one or more groups selected from-alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —N$R_c$C(O)$R_c$, —$NO_2$, —CN, -halogen, and —$SO_2R_c$, wherein each $R_c$ is independently Ar, alkyl, or $CH_2Ar$ and Ar is an aryl or heteroaryl; and each $R^5$ is independently selected from-alkyl, -aryl, —$CH_2$-aryl, —$CH_2$-heteroaryl, -cycloalkyl, -heterocycloalkyl, and -heteroaryl, wherein the alkyl, aryl, $CH_2$-aryl, $CH_2$-heteroaryl, cycloalkyl, heterocycloalkyl, or heteroaryl is optionally substituted with one or more groups selected from-alkyl, —O-alkyl, —N-alkyl, -alkenyl, -alkynyl, —O-aryl, —O-heteroaryl, —N-aryl, —N-heteroaryl, -aryl, —C(O)$R_c$, —$CO_2R_c$, —O—C(O)$R_c$, —NHC(O)$R_c$, —N$R_c$C(O)$R_c$, —$NO_2$, —CN, -halogen, and —$SO_2R_c$, wherein each $R_c$ is independently Ar, alkyl, or $CH_2Ar$ and Ar is an aryl or heteroaryl.

14. The analytical method of claim 13, wherein the probe is the chlorodiazaphosphite:

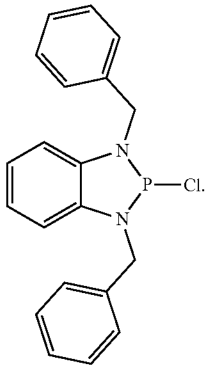 [SMILES: ClP1N(Cc2ccccc2)c2ccccc2N1Cc1ccccc1]

15. The analytical method of claim 1, wherein the analyte is an amino acid or an amino alcohol, or comprises one or more functional groups selected from the group consisting of primary amines, secondary amines, alcohols, carboxylic acids, hydroxy acids, thiols, and amides.

16. The analytical method of claim 1, wherein the analyte is an amino acid comprising a functionalized side chain or an unprotected amino acid.

17. The analytical method of claim 1, wherein said contacting is carried out in one or more solvents selected from aqueous solvents, protic solvents, and aprotic solvents.

18. The analytical method of claim 1, wherein said contacting is carried out in air.

19. The analytical method of claim 1, wherein said contacting is carried out for about 1 to about 300 minutes.

20. The analytical method of claim 1, wherein said contacting is carried out at a temperature range of 23±3° C. and a relative humidity range of 38±5%.

21. The analytical method of claim 1, wherein said contacting is carried out at a temperature that is below about 25° C. or between about 50° C. to about 100° C.

22. The analytical method of claim 1, wherein the probe is a dinitrofluoroarene or analog thereof, an arylsulfonyl chloride or analog thereof, an arylchlorophosphine or analog thereof, an aryl halophosphite, or a halodiazaphosphite, and the analyte is selected from the group consisting of alcohols, amino acids, amino alcohols, amines, carboxylic acids, hydroxy acids, thiols, amides, and combinations thereof.

23. The analytical method of claim 1, wherein two or three of (i)-(iii) are obtained:

(i) the absolute configuration of the analyte in the sample;

(ii) the concentration of the analyte in the sample; and iii) the enantiomeric composition of the analyte in the sample.

24. The analytical method of claim 23, wherein all of (i)-(iii) are obtained.

25. The analytical method of claim 1, wherein performing the first spectroscopic analysis is carried out using circular dichroism (CD), and performing the second spectroscopic analysis is carried out using ultraviolet (UV) spectroscopy.

* * * * *